US007517652B2

(12) United States Patent
Whitney et al.

(10) Patent No.: US 7,517,652 B2
(45) Date of Patent: Apr. 14, 2009

(54) METHODS OF DIAGNOSING TUMORS USING THE G-PROTEIN COUPLED RECEPTOR (GPCR), RAI-3

(75) Inventors: Gena S. Whitney, Lawrenceville, NJ (US); Gregory Opiteck, Montreal (CA); Leah Ann Garulacan, King of Prussia, PA (US); Chandra S. Ramanathan, Ringoes, NJ (US); Murray McKinnon, Washington Crossing, PA (US); John N. Feder, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/809,905

(22) Filed: May 31, 2007

(65) Prior Publication Data

US 2007/0259373 A1    Nov. 8, 2007

Related U.S. Application Data

(63) Continuation of application No. 10/600,816, filed on Jun. 20, 2003, now abandoned.

(60) Provisional application No. 60/407,006, filed on Aug. 29, 2002, provisional application No. 60/390,850, filed on Jun. 20, 2002.

(51) Int. Cl.
*C12Q 1/68* (2006.01)
*C07H 21/04* (2006.01)

(52) U.S. Cl. ............... 435/6; 536/24.31; 536/24.33

(58) Field of Classification Search ............... None
See application file for complete search history.

(56) References Cited

U.S. PATENT DOCUMENTS

| 5,618,717 | A | 4/1997 | Wei et al. |
|---|---|---|---|
| 6,150,502 | A | 11/2000 | Strachan |
| 6,573,095 | B1 | 6/2003 | Strachan |
| 6,812,339 | B1 * | 11/2004 | Venter et al. ............... 536/24.31 |
| 2003/0068636 | A1 * | 4/2003 | Veiby ............................ 435/6 |
| 2003/0113798 | A1 * | 6/2003 | Burmer et al. ............... 435/7.1 |
| 2003/0180747 | A1 | 9/2003 | Hruban et al. |
| 2005/0282165 | A1 | 12/2005 | Terret |

FOREIGN PATENT DOCUMENTS

| EP | 1 074 617 | 2/2001 |
|---|---|---|
| WO | WO 99/55865 | 11/1999 |
| WO | WO 00/69884 | 11/2000 |
| WO | WO 01/07612 | 2/2001 |
| WO | WO 01/42467 A2 | 6/2001 |
| WO | WO 01/57270 | 8/2001 |
| WO | WO 01/57271 | 8/2001 |
| WO | WO 01/57273 | 8/2001 |
| WO | WO 01/57274 | 8/2001 |
| WO | WO 01/57275 | 8/2001 |
| WO | WO 01/57276 | 8/2001 |
| WO | WO 01/57277 | 8/2001 |
| WO | WO 01/57278 | 8/2001 |
| WO | WO 01/86003 | 11/2001 |
| WO | WO 01/90357 | 11/2001 |
| WO | WO 02/00677 | 1/2002 |
| WO | WO 02/061087 | 8/2002 |
| WO | WO 03/000012 | 1/2003 |
| WO | WO 03/025138 | 3/2003 |

OTHER PUBLICATIONS

Aggarwal, Bharat B., "Apoptosis and Nuclear Factor-κB: A Tale of Association and Dissociation", Biochem. Pharmacol., vol. 60, pp. 1033-1039 (2000).
Baldi, et al., "Critical Role for Lysines 21 and 22 in Signal-induced, Ubiquitin-mediated Proteolysis of IκB-α", vol. 271, pp. 376-379 (1996).
Baeuerle, et al., "NF-κB: Ten Years After", Cell. vol. 87, pp. 13-20 (1996).
Milligan, et al., "Chimaeric Gα proteins: their potential use in drug discovery", TIPS, vol. 20, pp. 118-124 (1999).
Morriss-Kay, et al., "Embryonic development and pattern formation", Faseb J., vol. 10, pp. 961-968 (1996).
Nagahata, et al, "Identification of RA13 as a therapeutic target for breast cancer", Endocrine-Rel. Cancer, vol. 12, pp. 65-73 (2005).
Needleman, et al., "A General Method Applicable to the Search for Similarities in the Amino Acid Sequence of Two Proteins", J. Mol. Biol., vol. 48, pp. 443-453 (1970).

(Continued)

*Primary Examiner*—Ruixiang Li
(74) *Attorney, Agent, or Firm*—Stephen C. D'Amico

(57) ABSTRACT

The present invention describes a G-protein coupled receptor (GPCR) family member newly identified as being modified, e.g., phosphorylated, and associated with tyrosine phosphorylated activation complexes, following exposure of cells to smoke from tobacco burning substances, namely, cigarette smoke. This GPCR protein is RAI-3, which was first found to be phosphorylated in cells treated with cigarette smoke and to be associated with other proteins activated in cigarette smoke treated cells by virtue of the present invention. Because cigarette smoke is considered to be a major causative factor of chronic obstructive pulmonary disease (COPD) and disorders and conditions related thereto, the RAI-3 protein is newly provided as a cellular drug target for screening, discovering, and identifying modulators for the treatment and/or prevention of COPD and its related disorders and conditions, such as emphysema and chronic bronchitis. In accordance with the present invention RAI-3 modulators, e.g., agonists and antagonists, can be used as therapeutics in the treatment of COPD and numerous other diseases and disorders that are associated with regulation of NF-κB and/or its associated or interacting signaling molecules. This invention further provides SNPs of RAI-3, e.g., for determining COPD association in individuals.

2 Claims, 45 Drawing Sheets
(6 of 45 Drawing Sheet(s) Filed in Color)

OTHER PUBLICATIONS

Offermanns, et al., "Gα$_{15}$ and Gα$_{16}$ Couple a Wide Variety of Receptors to Phospholipase C", J. Biol. Chem., vol. 270(25), pp. 15175-15180 (1995).

Pierce, et al., "Seven-Transmembrane Receptors", Nature Revs. Molec. Cell. Biol., vol. 3, pp. 639-650 (2002).

Robbins, et al., "Localisation of the GPRC5B receptor in the rat brain and spinal cord", Molec. Brain Res., vol. 106, pp. 136-144 (2002).

Robbins, et al., Molecular Cloning and Characterization of Two Novel Retinoic Acid-Inducible Orphan G-Protein-Coupled Receptors (GPRC5B and GPRC5C), Genomics, vol. 67, pp. 8-18 (2000).

Roff, et al., "Role of IκBα Ubiquitination in Signal-induced Activation of NF-κB in Vivo", J. Biol. Chem., vol. 271(13), pp. 7844-7850 (1996).

Sacks, et al., "Retinoic Acid Inhibition of a Head and Neck Multicellular Tumor Spheroid Model", Head Neck, vol. 11, pp. 219-225 (1989).

Siebenlist, et al., "Structure, Regulation and Function of NF-κB", Ann. Rev. Cell Biol., vol. 10, pp. 405-455 (1994).

Silverman, et al., "NF-κB signaling pathways in mammalian and insect innate immunity", Genes Develop., vol. 15, pp. 2321-2342 (2001).

Simon, et al., "Diversity of G Proteins in Signal Transduction", Science, vol. 252, pp. 802-808 (1991).

Strebel, et al., "Characterization of Foot-and-Mouth Disease Virus Gene Products with Antisera Against Bacterially Synthesized Fusion Proteins", J. Virol, pp. 983-991 (1986).

Horn, et al., "G protein-coupled receptors in silico", J. Mol. Med., vol. 76, pp. 464-468 (1998).

Howard, et al., "Orphan G-protein-coupled receptors and natural ligand discovery", vol. 22, pp. 132-140 (2001).

Hubbard, et al., "Activation of NF-κB-dependent gene expression by silica in lungs of luciferase reporter mice", Am. J. Physiol. Lung Cell Mol. Physiol., vol. 282, pp. L968-L975 (2002).

Johnson, et al., "The G-Protein Family and Their Interaction with Receptors", Endocrine Rev., vol. 10(3), pp. 317-331 (1989).

Knappik, et al., "Fully Synthetic Human Combinatorial Antibody Libraries (HuCAL) Based on Modular Consensus Frameworks and CDRs Randomized with Trinucleotides", J. Mol. Biol., vol. 296, pp. 57-86 (2000).

Kobilka, et al., "Cloning, Sequencing, and Expression of the Gene Coding for the Human Platelet α$_2$-Adrenergic Receptor", Science, vol. 238, pp. 650-656 (1987).

Kobilka, et al., "cDNA for the human β$_2$-adrenergic receptor: A protein with multiple membrane-spanning domains and encoded by a gene whose chromosomal location is shared with that of the receptor for platelet-derived growth factor", PNAS, vol. 84, pp. 46-50 (1987).

Kohler, et al., "Continuous cultures of fused cells secreting antibody of predefined specificity", Nature, vol. 256, pp. 495-497 (1975).

Leurs, et al., "Agonist-independent regulation of constitutively active G-protein-coupled receptors", TIBS, vol. 23, pp. 418-422 (1998).

Leurs, et al., "Constitutive activity of G protein coupled receptors and drug action", Pharmaceutica Acta Helvetiae, vol. 74, pp. 327-331 (2000).

Love, et al., "Vitamin A, differentiation and cancer", Curr. Opin. Cell Biol., vol. 6, pp. 825-831 (1994).

International Human Genome Sequencing Consortium, "Initial sequencing and analysis of the human genome", Nature, vol. 409, pp. 860-921 (2001).

Massaro, et al., "Retinoic acid treatment partially rescues failed septation in rats and in mice", Am. J. Physiol. Lung Cell Mol. Physiol., vol. 278, pp. L955-L960 (2000).

Milligan, et al., "G$_{16}$ as a universal G protein adapter: implications for agonist screening strategies", TIPS, vol. 17, pp. 235-237 (1996).

NCBI Entrez Accession No. gi|13651786, NCBI Annotation Project, Jul. 16, 2001.

NCBI Entrez Accession No. gi|21779963; Cafferata, E.G. et al., Jul. 15, 2002.

NCBI Entrez Accession No. gi|33733830, Strachan, L., Aug. 17, 2003.

Cheng, Y. et al., "Molecular Cloning and Characterization of a Novel Retinoic Acid-inducible Gene That Encodes a Putative G Protein-coupled Receptor", The Journal of Biological Chemistry, vol. 273, No. 52, pp. 35008-35015 (1998).

Robbins, M.J. et al., "Molecular Cloning and Characterization of Two Novel Retinoic Acid-Inducible Orphan G-Protein-Coupled Receptors (GPRC5B and GPRC5C)", Genomics, vol. 67, pp. 8-18 (2000).

NCBI Entrez Accession No. gi|NP_003970, Robbins, M.J. et al., Dec. 20, 2003.

NCBI Entrez Accession No. gi|4063890, Cheng, Y. et al., Dec. 29, 1998.

NCBI Entrez Accession No. gi|11435926, NCBI Annotation Project, Feb. 10, 2001.

Sueoka, et al., "Molecular Pathogenesis of Interstitial Pneumonitis with TNF-α Transgenic Mice", Cytokine, vol. 10(2), pp. 124-131 (1998).

Takeyama, et al, "Oxidative Stress Causes Mucin Synthesis Via Transactivation of Epidermal Growth Factor Receptor: Role of Neurtophils", J. Immunol., vol. 164, pp. 1546-1552 (2000).

Thornberry, et al., "Caspases: Enemies Within", Science, vol. 281, pp. 1312-1316 (1998).

Valen, et al., "Nuclear Factor Kappa-B and the Heart", J. Amer. Coll. Cardiology, vol. 38(2), pp. 307-314 (2001).

Venter, et al., "The Sequence of the Human Genome", Science, vol. 291, pp. 1304-1351 (2001).

Weil, et al., "Regulation of IκBβ Degradation", J. Biol. Chem., vol. 272(15), pp. 9942-9949 (1997).

Whiteside, et al., "I kappa B epsilon, a novel member of the IκB family, controls RelA and cRel NF-κB activity", Embo J., vol. 16(5), pp. 1413-1426 (1997).

Wu, et al., "Integrative Genomics Revealed RA13 Is a Cell Growth-promoting Gene and a Novel P53 Transcriptional Target", J. Biol. Chem., vol. 280(13), pp. 12935-12943 (2005).

Zlokarnik, et al., "Quantitation of Transcription and Clonal Selection of Single Living Cells with β-Lactamase as Reporter", Science, vol. 279, pp. 84-88 (1998).

NCBI Entrez Accession No. NM_003979 (gi:63252917), Wu, et al., Sep. 24, 2005.

NCBI Entrez Accession No. NM_014707 (gi:7662279), Han, et al., Mar. 19, 2006.

NCBI Entrez Accession No. NM-058176 (gi:17158038), Han, et al., Mar. 19, 2006.

NCBI Entrez Accession No. NM_058177 (gi:17158040), Han, et al., Mar. 19, 2006.

Chen, et al., "Constitutive receptor systems for drug discovery", J. Pharmacol Toxicol, vol. 42, pp. 199-206 (1999).

Cheng, et al., "Molecular Cloning and Characterization of a Novel Retinoic Acid-inducible Gene That Encodes a Putative G Protein-coupled Receptor", J. Biol. Chem., vol. 273(52), pp. 35008-35015 (1998).

Christman, et al., "The Role of Nuclear Factor-κ B in Pulmonary Diseases", Chest, vol. 117, pp. 1482-1487 (2000).

Civelli, Olivier, "Functional genomics: the search for novel neurotransmitters and neuropeptides", FEBS Letters, vol. 430, pp. 55-58 (1998).

Day, et al., "Bleomycin upregulates expression of γ-glutamylcysteine synthetase in pulmonary artery endothelial cells", Am. J. Physiol. Lung Cell Mol. Physiol., vol. 282, pp. L1349-L1357 (2002).

deLigt, et al., "Inverse agonism at G protein-coupled receptors: (patho) physiological relevance and implications for drug discovery", British J. Pharmacol, vol. 130, pp. 1-12 (2000).

Feng, et al., "HIV-1 Entry Cofactor: Functional cDNA Cloning of a Seven-Transmembrane, G Protein-Coupled Receptor", Science, vol. 272, pp. 872-877 (1996).

Finco, et al., "Inducible phosphorylation of IκBα is not sufficient for its dissociation from NF-κB and is inhibited by protease inhibitors", PNAS, vol. 91, pp. 11884-11888 (1994).

Geysen, et al., "Use of peptide synthesis to probe viral antigens for epitopes to a resolution of a single amino acid", PNAS, vol. 81, pp. 3998-4002 (1984).

Ghosh, et al., "NF-κB and Rel Proteins: Evolutionarily Conserved Mediators of Immune Responses", Annu. Rev. Immunol., vol. 16, pp. 225-260 (1998).

Guijarro, et al., "Transcription factor-κB (NF-κB) and renal disease", Kidney Int'l, vol. 59, pp. 415-424 (2001).

Gurujeyalakshmi, et al., "Taurine and Niacin Block Lung Injury and Fibrosis by Down-Regulating Bleomycin-Induced Activation of Transcription Nuclear Factor—κB in Mice", J. Pharm. Exper. Ther., vol. 293(1), pp. 82-90 (2000).

Hinuma, et al., "The quest for novel bioactive peptides utilizing orphan seven-transmembrane-domain receptors", J. Mol. Med., vol. 77, pp. 495-504 (1999).

Horn, et al., "The Interaction of Class B G Protein-Coupled Receptors with their Hormones", Receptors Channels, vol. 5, pp. 305-314 (1998).

Baldwin, Albert S., "The NF-κB And IκB Proteins: New Discoveries and Insights", Annu. Rev. Immunol., vol. 14, pp. 649-681 (1996).

Baldwin, Albert S., "Control of oncogenesis and cancer therapy resistance by the transcription factor NF-κB", J. Clin. Invest., vol. 107(3), pp. 241-246 (2001).

Baldwin, Albert S., Jr., "The transcription factor NF-κB and human disease", J. Clin. Invest., vol. 107(1), pp. 3-6 (2001).

Basu, et al., "The DNA-Dependent Protein Kinase Participates in the Activation of NFκB Following DNA Damage", Biochem. Biophysical Res. Comm., vol. 247, pp. 79-83 (1998).

Baud, et al., "Signal transduction by tumor necrosis factor and its relatives", Trends Cell Biol., vol. 11(9), pp. 372-377 (2001).

Blahos, et al, "A Novel Site on the Gα-protein That Recognizes Heptahelical Receptors", vol. 275(5), pp. 3262-3269 (2001).

Bockaert, et al., "G Protein-Coupled Receptors: Dominant Players in Cell-Cell Communication", Int. Rev. Cyt., vol. 212, pp. 63-132 (2002).

Brauner-Osborne, et al., "Sequence and Expresion Pattern of a Novel Human Orphan G-Protein-Coupled Receptor, GPRC5B, a Family C Receptor with a Short Amino-Terminal Domain", Genomics, vol. 65, pp. 121-128 (2000).

Brauner-Osborne, et al., "Cloning and characterization of a human orphan family C G-protein coupled receptor GPRC5D", Biochimica Biophysica Acta, vol. 1518, pp. 237-248 (2001).

Brown, et al., "Control of IκB-α Proteolysis by Site-Specific, Signal-Induced Phosphorylation", Science, vol. 267, pp. 1485-1488 (1995).

Bunzow, et al., "Cloning and expression of a rat $D_{22}$ dopamine receptor cDNA", Nature, vol. 336, pp. 783-787 (1998).

Cafferata, et al., "Identification by Differential Display of a mRNA Specifically Induced by 12-O-Tetradecanoylphorbol-13-Acetate (TPA) in T84 Human Colon Carcinoma Cells", Cellular Molec. Biol., vol. 42(5), pp. 797-804 (1996).

Chalmers, et al., "The Use of Constitutively Active GPCRs In Drug Discovery and Functional Genomics", Nature Reviews, vol. 1, pp. 599-608 (2002).

Chen, et al., "Use of Constitutive G Protein-Coupled Activity for Drug Discovery", Molec. Pharm., vol. 57, pp. 125-134 (2000).

Tao, et al., "Identification of the Retinoic Acid-Inducible Gprc5a As a New Lung Tumor Suppressor Gene", JNCI, vol. 99 (22), pp. 1668-1682 (2007).

* cited by examiner

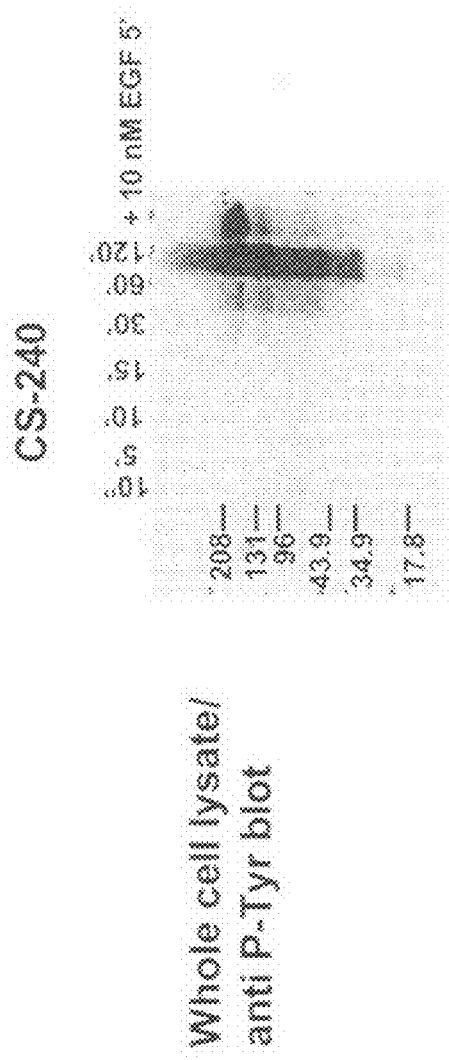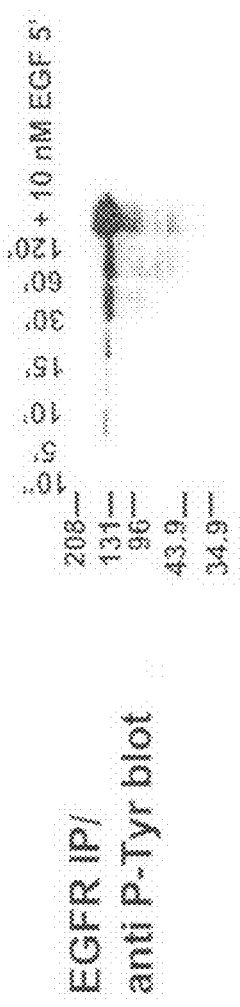
FIG. 1A Whole cell lysate/ anti P-Tyr blot
FIG. 1B EGFR IP/ anti P-Tyr blot
CS240 = 240 cigarettes/ 500 ml RPMI = ~ 5 cigarettes/ 10 ml Whole Cell Lysate Immunoprecipitation for Phosphotyrosine Whole cell lysate Without Immunoprecipitation

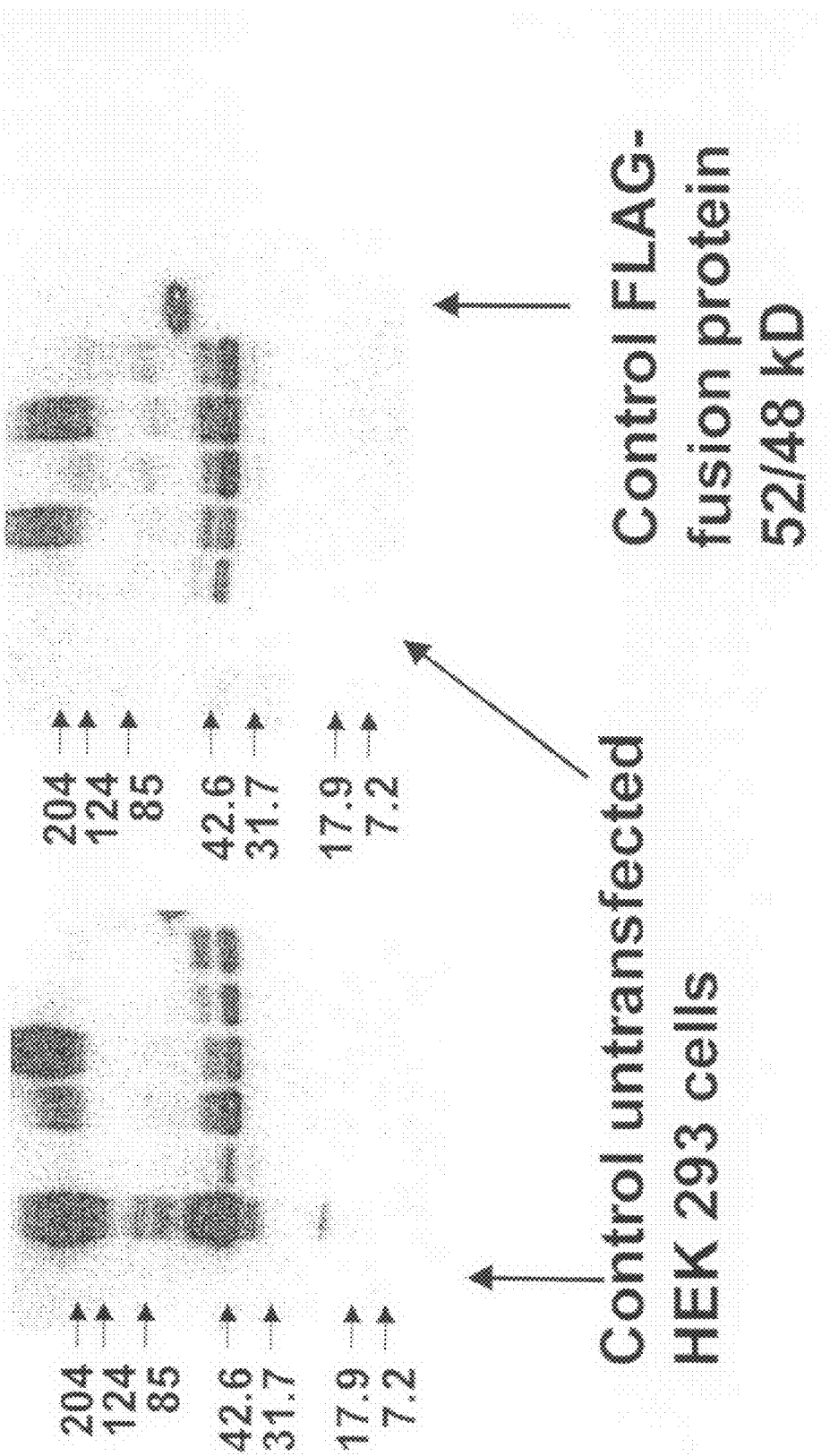

FIG. 10A

```
   1 ataacagcat gaagtgccgt ggaactggaa taggcgtgtc ctctccctcg accctccccc
  61 tccttgtccc tctgctcacc cctcgctcgt tccctccctc cggcgagggc cgcctttata
 121 acaactgctc agagtgcgag ggcgggatag ctgtccaagg tctcccccag cactgaggag
 181 ctcgcctgct gccctcttgc gcgcgggaag cagcaccaag ttcacggcca acgccttggc
 241 actagggtcc agaatggcta caacagtccc tgatggttgc cgcaatggcc tgaaatccaa
 301 gtactacaga ctttgtgata aggctgaagc ttggggcatc gtcctagaaa cggtggccac
 361 agccggggtt gtgacctcgg tggccttcat gctcactctc ccgatcctcg tctgcaaggt
 421 gcaggactcc aacaggcgaa aaatgctgcc tactcagttt ctcttcctcc tgggtgtgtt
 481 gggcatcttt ggcctcacct tcgccttcat catcggactg gacgggagca cagggcccac
 541 acgcttcttc ctctttggga tcctcttttc catctgcttc tcctgcctgc tggctcatgc
 601 tgtcagtctg accaagctcg tccgggggag gaagcccctt tccctgttgg tgattctggg
 661 tctggccgtg ggcttcagcc tagtccagga tgttatcgct attgaatata ttgtcctgac
 721 catgaatagg accaacgtca atgtcttttc tgagctttcc gctcctcgtc gcaatgaaga
 781 ctttgtcctc ctgctcacct acgtcctctt cttgatggcg ctgaccttcc tcatgtcctc
 841 cttcaccttc tgtggttcct tcacgggctg gaagagacat ggggcccaca tctacctcac
 901 gatgctcctc tccattgcca tctggtggc ctggatcacc ctgctcatgc ttcctgactt
 961 tgaccgcagg tgggatgaca ccatcctcag ctccgccttg gctgccaatg gctgggtgtt
1021 cctgttggct tatgttagtc ccgagttttg gctgctcaca aagcaacgaa acccatgga
1081 ttatcctgtt gaggatgctt tctgtaaacc tcaactcgtg aagaagagct atggtgtgga
1141 gaacagagcc tactctcaag aggaaatcac tcaaggtttt gaagagacag gggacacgct
1201 ctatgccccc tattccacac attttcagct gcagaaccag cctccccaaa aggaattctc
1261 catcccacgg gcccacgctt ggccgagccc ttacaaagac tatgaagtaa agaaagaggg
1321 cagctaactc tgtcctgaag agtgggacaa atgcagccgg cggcagatc tagcgggagc
1381 tcaaagggat gtgggcgaaa tcttgagtct tctgagaaaa ctgtacaaga cactacggga
1441 acagtttgcc tccctcccag cctcaaccac aattcttcca tgctggggct gatgtgggct
1501 agtaagactc cagttcttag aggcgctgta gtattttttt tttttgtct catcctttgg
1561 atacttcttt taagtgggag tctcaggcaa ctcaagttta gaccttact cttttgttt
1621 gttttttgaa acaggatctt gctctgtcac ccaggcttga gtgcagtggt gcgatcacag
1681 cccagtgcag cctcgaccac ctgtgctcaa gcaatcctcc catctccatc tcccaaagtg
1741 ctgggatgac aggcgtgagc cacagctccc agcctaggcc cttaatcttg ctgttatttt
1801 ccatggacta aggtctggt catctgagct cacgctggct cacacagctc tagggcctg
1861 ctcctctaac tcacagtggg ttttgtgagg ctctgtggcc cagagcagac ctgcatatct
1921 gagcaaaaat agcaaaagcc tctctcagcc cactggcctg aatctacact ggaagccaac
1981 ttgctggcac ccccgctccc caaccttct tgcctgggta ggagaggcta aagatcaccc
2041 taaatttact catctctcta gtgctgcctc acattgggcc tcagcagctc cccagcacca
```

FIG. 10B

```
2101 attcacaggt caccectctc ttcttgcact gtccccaaac ttgctgtcaa ttccgagatc
2161 taatctcccc ctacgctctg ccaggaattc tttcagacct cactagcaca agcccggttg
2221 ctccttgtca ggagaatttg tagatcattc tcacttcaaa ttcctggggc tgatacttct
2281 ctcatcttgc accccaacct ctgtaaatag atttaccgca tttacggctg cattctgtaa
2341 gtgggcatgg tctcctaatg gaggagtgtt cattgtataa taagttattc acctgagtat
2401 gcaataaaga tgtggtggcc actctttcat ggtggtggca gcaaaaaaaa aaaaaa
```

FIG. 11A

```
  1 MATTVPDGCR NGLKSKYYRL CDKAEAWGIV LETVATAGVV TSVAFMLTLP ILVCKVQDSN
 61 RRKMLPTQFL FLLGVLGIFG LTFAFIIGLD GSTGPTRFFL FGILFSICFS CLLAHAVSLT
121 KLVRGRKPLS LLVILGLAVG FSLVQDVIAI EYIVLTMNRT NVNVFSELSA PRRNEDFVLL
181 LTYVLFLMAL TFLMSSFTFC GSFTGWKRHG AHIYLTMLLS IAIWVAWITL LMLPDFDRRW
241 DDTILSSALA ANGWVFLLAY VSPEFWLLTK QRNPMDYPVE DAFCKPQLVK KSYGVENRAY
301 SQEEITQGFE ETGDTLYAPY STHFQLQNQP PQKEFSIPRA HAWPSPYKDY EVKKEGS
```

FIG. 11B

```
   1 ataacagcatgaagtgccgtggaactggaataggcgtgtcctctccctcgaccctccccc    60

61 tccttgtccctctgctcacccctcgctcgttccctccctccggcgagggccgcctttata   120

121 acaactgctcagagtgcgagggcgggatagctgtccaaggtctcccccagcactgaggag   180

181 ctcgcctgctgccctcttgcgcgcgggaagcagcaccaagttcacggccaacgccttggc   240

241 actagggtccagaatggctacaacagtccctgatggttgccgcaatggcctgaaatccaa   300
   1                 M  A  T  T  V  P  D  G  C  R  N  G  L  K  S  K    16

301 gtactacagactttgtgataaggctgaagcttggggcatcgtcctagaaacggtggccac   360
  17  Y  Y  R  L  C  D  K  A  E  A  W  G  I  V  L  E  T  V  A  T    36

361 agccggggttgtgacctcggtggccttcatgctcactctcccgatcctcgtctgcaaggt   420
  37  A  G  V  V  T  S  V  A  F  M  L  T  L  P  I  L  V  C  K  V    56

421 gcaggactccaacaggcgaaaaatgctgcctactcagtttctcttcctcctgggtgtgtt   480
  57  Q  D  S  N  R  R  K  M  L  P  T  Q  F  L  F  L  L  G  V  L    76

481 gggcatctttggcctcaccttcgccttcatcatcggactggacgggagcacagggcccac   540
  77  G  I  F  G  L  T  F  A  F  I  I  G  L  D  G  S  T  G  P  T    96

541 acgcttcttcctctttgggatcctcttttccatctgcttctcctgcctgctggctcatgc   600
  97  R  F  F  L  F  G  I  L  F  S  I  C  F  S  C  L  L  A  H  A   116

601 tgtcagtctgaccaagctcgtccgggggaggaagccccttccctgttggtgattctggg   660
 117  V  S  L  T  K  L  V  R  G  R  K  P  L  S  L  L  V  I  L  G   136

661 tctggccgtgggcttcagcctagtccaggatgttatcgctattaatatattgtcctgac   720
 137  L  A  V  G  F  S  L  V  Q  D  V  I  A  I  E  Y  I  V  L  T   156

721 catgaataggaccaacgtcaatgtcttttctgagctttccgctcctcgtcgcaatgaaga   780
 157  M  N  R  T  N  V  N  V  F  S  E  L  S  A  P  R  R  N  E  D   176

781 ctttgtcctcctgctcacctacgtcctcttcttgatggcgctgaccttcctcatgtcctc   840
 177  F  V  L  L  L  T  Y  V  L  F  L  M  A  L  T  F  L  M  S  S   196

841 cttcaccttctgtggttccttcacgggctggaagagacatggggcccacatctacctcac   900
 197  F  T  F  C  G  S  F  T  G  W  K  R  H  G  A  H  I  Y  L  T   216

901 gatgctcctctccattgccatctgggtggcctggatcaccctgctcatgcttcctgactt   960
 217  M  L  L  S  I  A  I  W  V  A  W  I  T  L  L  M  L  P  D  F   236

961 tgaccgcaggtgggatgacaccatcctcagctccgccttggctgccaatggctgggtgtt  1020
 237  D  R  R  W  D  D  T  I  L  S  S  A  L  A  A  N  G  W  V  F   256

1021 cctgttggcttatgttagtcccgagttttggctgctcacaaagcaacgaaacccatgga  1080
 257  L  L  A  Y  V  S  P  E  F  W  L  L  T  K  Q  R  N  P  M  D   276

1081 ttatcctgttgaggatgctttctgtaaacctcaactcgtgaagaagagctatggtgtgga  1140
 277  Y  P  V  E  D  A  F  C  K  P  Q  L  V  K  K  S  Y  G  V  E   296

1141 gaacagagcctactctcaagaggaaatcactcaaggttttgaagagacaggggacacgct  1200
 297  N  R  A  Y  S  Q  E  E  I  T  Q  G  F  E  E  T  G  D  T  L   316
```

FIG. 11C

```
1201 ctatgcccccctattccacacattttcagctgcagaaccagcctccccaaaaggaattctc 1260
317   Y  A  P  Y  S  T  H  F  Q  L  Q  N  Q  P  P  Q  K  E  F  S  336

1261 catcccacgggcccacgcttggccgagcccttacaaagactatgaagtaaagaaagaggg 1320
337   I  P  R  A  H  A  W  P  S  P  Y  K  D  Y  E  V  K  K  E  G  356

1321 cagctaactctgtcctgaagagtgggacaaatgcagccgggcggcagatctagcgggagc 1380
357   S                                                            357

1381 tcaaagggatgtgggcgaaatcttgagtcttctgagaaaactgtacaagacactacggga 1440

1441 acagtttgcctccctcccagcctcaaccacaattcttccatgctggggctgatgtgggct 1500

1501 agtaagactccagttcttagaggcgctgtagtattttttttttttgtctcatcctttgg 1560

1561 atacttcttttaagtgggagtctcaggcaactcaagtttagacccttactcttttgttt 1620

1621 gttttttgaaacaggatcttgctctgtcacccaggcttgagtgcagtggtgcgatcacag 1680

1681 cccagtgcagcctcgaccacctgtgctcaagcaatcctcccatctccatctcccaaagtg 1740

1741 ctgggatgacaggcgtgagccacagctcccagcctaggcccttaatcttgctgttatttt 1800

1801 ccatggactaaaggtctggtcatctgagctcacgctggctcacacagctctaggggcctg 1860

1861 ctcctctaactcacagtgggttttgtgaggctctgtggcccagagcagacctgcatatct 1920

1921 gagcaaaaatagcaaaagcctctctcagcccactggcctgaatctacactggaagccaac 1980

1981 ttgctggcaccccgctccccaacccttcttgcctgggtaggagaggctaaagatcaccc 2040

2041 taaatttactcatctctctagtgctgcctcacattgggcctcagcagctccccagcacca 2100

2101 attcacaggtcacccctctcttcttgcactgtccccaaacttgctgtcaattccgagatc 2160

2161 taatctccccctacgctctgccaggaattctttcagacctcactagcacaagcccggttg 2220

2221 ctccttgtcaggagaatttgtagatcattctcacttcaaattcctggggctgatacttct 2280

2281 ctcatcttgcacccaacctctgtaaatagattaccgcatttacggctgcattctgtaa 2340

2341 gtgggcatggtctcctaatggaggagtgttcattgtataataagttattcacctgagtat 2400

2401 gcaataaagatgtggtggccactctttcatggtggtggcagcaaaaaaaaaaaaaaaa 2456
```

```
GPCR5D_HUMAN   ------------------------------------MYKDCIESTGD.YFLLCDAEGPWGI
GPCR5D_MOUSE   ------------------------------------MYEDCVKSTED.YYLFCDNEGPWAI
RAI3_HUMAN     ----------------------------MATTVPDGCRNGLKSKYYRLCDKAEAWGI
GPRC5B_HUMAN   MFVASERKMRAHQVLTFLL...LFVITSVASENASTSRGCGLDLLPQYVSLCDLDAIWGI
GPRC5C_HUMAN   --------MAIHKALVMCLGLPLFLFPG.AWAQGHVPPGCSQGLNPLYYNLCDRSGAWGI

GPCR5D_HUMAN   ILESLAILGIVVTLLLLAFLFLMRKIQDCSQWNVLPTQLLFLLSVLGLFGLAFAFIIEL
GPCR5D_MOUSE   VLESLAVIGIVVTLLLLAFLFLMRKVQDCSQWNVLPTQFLFLLAVLGLFGLTFAFIIQL
RAI3_HUMAN     VLETVATAGVVTSVAFMLTLPILVCKVQDSNRRKMLPTQFLFLLGVLGIFGLTFAFIIGL
GPRC5B_HUMAN   VMEAVAGAGALITLLLMLILLVRLPFIKEKEKKSPVGLHFLFLLGTLGLFGLTFAFIIQE
GPRC5C_HUMAN   VLEAVAGAGIVTTFVLTLILVASLPFVQDTKKRSLLGTQVFFLLGTLGLFCLVFACVVKP

GPCR5D_HUMAN   NQQTAPVRYFLFGVLFALCFSCLLAHASNLVKLVR.GCVSFSWTTILCIAIGCSLLQIII
GPCR5D_MOUSE   NHQTAPVRYFLFGVLFAICFSCLLAHASNLVKLVR.GRVSFCWTTILFIAIGVSLLQTII
RAI3_HUMAN     DGSTCPTRFFLFGILFSICFSCLLAHAVSLTKLVR.GRKPLSLLVILGLAVGFSLVQDVI
GPRC5B_HUMAN   DETICSVRRFLWGVLFALCFSCLLSQAWRVRRLVRHGTGPAGW.QLVGLALCLMLVQVII
GPRC5C_HUMAN   DFSTCASRRFLFGVLFAICFSCLAAHVFALNFLARKNHGPRGW.VIFTVALLLTLVEVII
Variant HUMAN RAI3                                G  (SNP S/G)

GPCR5D_HUMAN   ATEYVTLIMTRG..........MMFVNMTPCQL.NVDFVVLLVYVLFLMALTFF.VSKA
GPCR5D_MOUSE   ATEYVTLIMTRG..........LMFEHMTPYQL.NVDFVCLLIYVLFLMALTFF.VSKA
RAI3_HUMAN     ATEYIVLTMNRT..........NVNVFSELSAPRR.NEDFVLLLTYVLFLMALTFL.MSSF
GPRC5B_HUMAN   AVEWLVLTVLR...DTRP............ACAYEPMDFVMALIYDMVLLV.VTLGLALF
GPRC5C_HUMAN   NTEWLITLVRGSGEGGPQGNSSAGWAVASPCAVANMDFVMALIYVMLLLGAFLG.AWP

GPCR5D_HUMAN   TFCGPCENWKQHGRLIFITVLFSIIIWVVWISMLLRGNPQFQRQPQWDDPVVCIALVTNA
GPCR5D_MOUSE   TFCGPCENWKQHGRLIFAIVLVSIIIWVVWISMLLRGNPQLQRQPHWDDPAVICIGLVTNA
RAI3_HUMAN     TFCGSFTGWKRHGAHIYLTMLLSIAIWVAWITLLML..PDFDRR..WDDTILSSALAANG
GPRC5B_HUMAN   TLCGKFKRWKLNGAFLLITAFLSVLIWVAWMTMYLFGNVKLQQGDAWNDPTLAITLAASG
GPRC5C_HUMAN   ALCGRYKRWRKHGVFVLLITATSVAIWVVWIVMYTYGN.KQHNSPTWDDPTLAIALAANA

GPCR5D_HUMAN   WVFLLLYIVPELCILYRSCR.QE.....CPLQGNACPVTAYQHSFQ.....VENQELSRA
GPCR5D_MOUSE   WVFLLIYITPELSILYRSCR.QE.....CPTQGNVCQVPVYQRSFR.....MDTQEPTRE
RAI3_HUMAN     WVFLLAYVSPEFWLLTKQRNPMD.....YPVEDAFCKPQLVKKSYG.....VENRAYSQE
GPRC5B_HUMAN   WVFVIFHAIPET.HCTLLPALQENTPNYFDTSQPRMRETAFEEDVQLPRAYMENKAFSMD
GPRC5C_HUMAN   WAFVLFYVIPEVSQVTKSSPEQSYQGDMYPTRCVGY.ETILKEQ.KGQSMFVENKAFSMD

GPCR5D_HUMAN   RDSDGAEE..DVALTSYGTPIQPQTVDPTQECFIPQAKLSPQQDAGGV~~~~~~~~~~~~
GPCR5D_MOUSE   C~~~~~~~~~~~~~~~~~~~~~~~~~~~~~~~~~~~~~~~~~~~~~~~~~~~~~~~~~
RAI3_HUMAN     EITQGFEETGDTLYAPYSTHFQLQNQPPQKEFSIPRAHAWPSPYKDYEVKKEGS~~~~~~
GPRC5B_HUMAN   E.HNAALRTAGFPNGSLGKRPSGSLGKRPSAPFRSNVYQPTEMAV...VLNGGTIPTAPP
GPRC5C_HUMAN   E.PVAAKRPVS.PY.......SGYNGQ.....LLTSVYQPTEMALMHKVPSEGAYDIILP
Variant HUMAN  R  (SNP Q/R)
RAI3

GPCR5D_HUMAN   ~~~~~~~~~~~~~~~~~~~~~~~~~~~~~~~~~~~~~~~~~~~~~~~~~~~
GPCR5D_MOUSE   ~~~~~~~~~~~~~~~~~~~~~~~~~~~~~~~~~~~~~~~~~~~~~~~~~~~
RAI3_HUMAN     ~~~~~~~~~~~~~~~~~~~~~~~~~~~~~~~~~~~~~~~~~~~~~~~~~~~
GPRC5B_HUMAN   SHTGRHLW~~~~~~~~~~~~~~~~~~~~~~~~~~~~~~~~~~~~~~~~~~~
GPRC5C_HUMAN   RATANSQVMGSANSTLRAEDMYSAQSHQAATPPKDGKNSQVFRNPYVWD
```

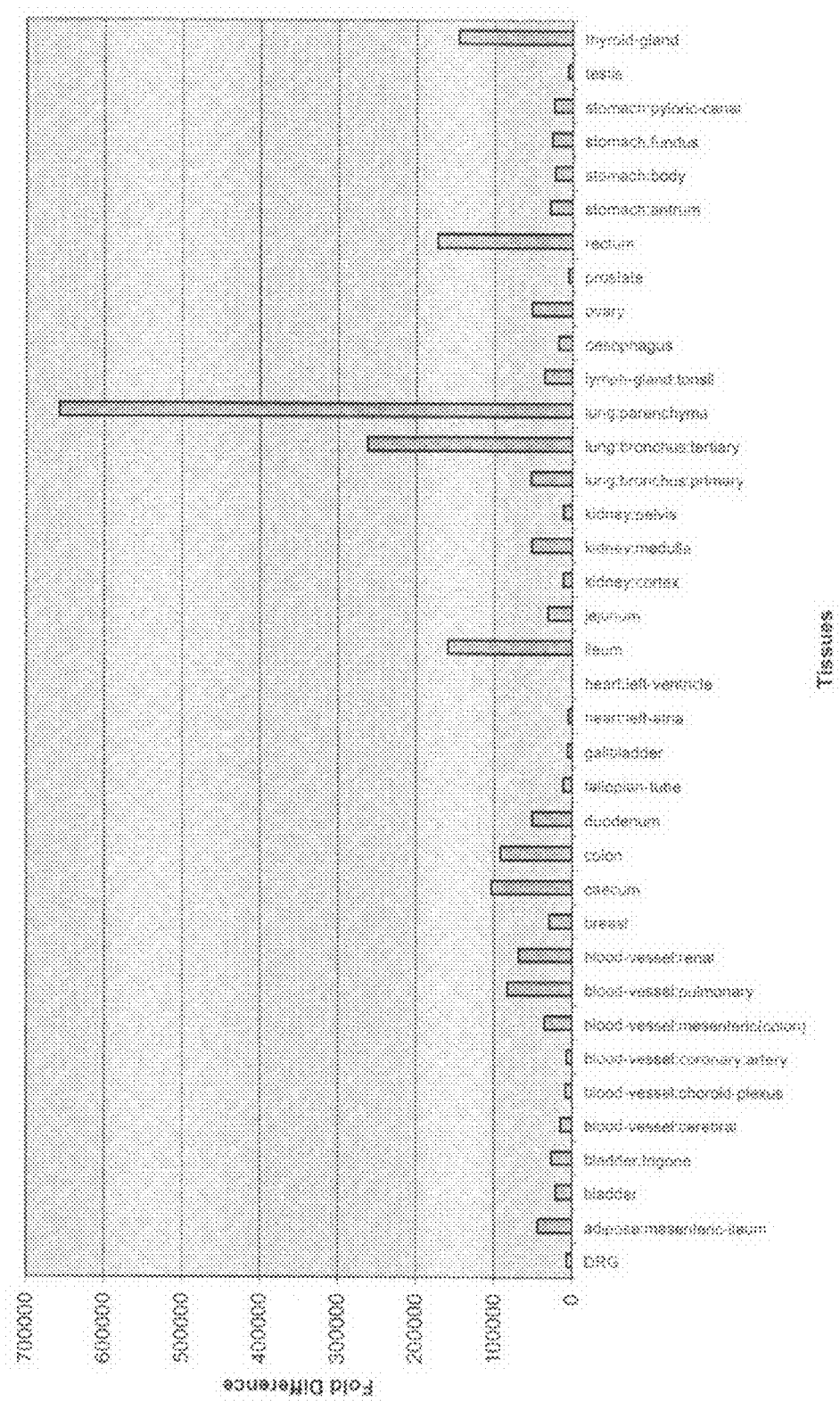

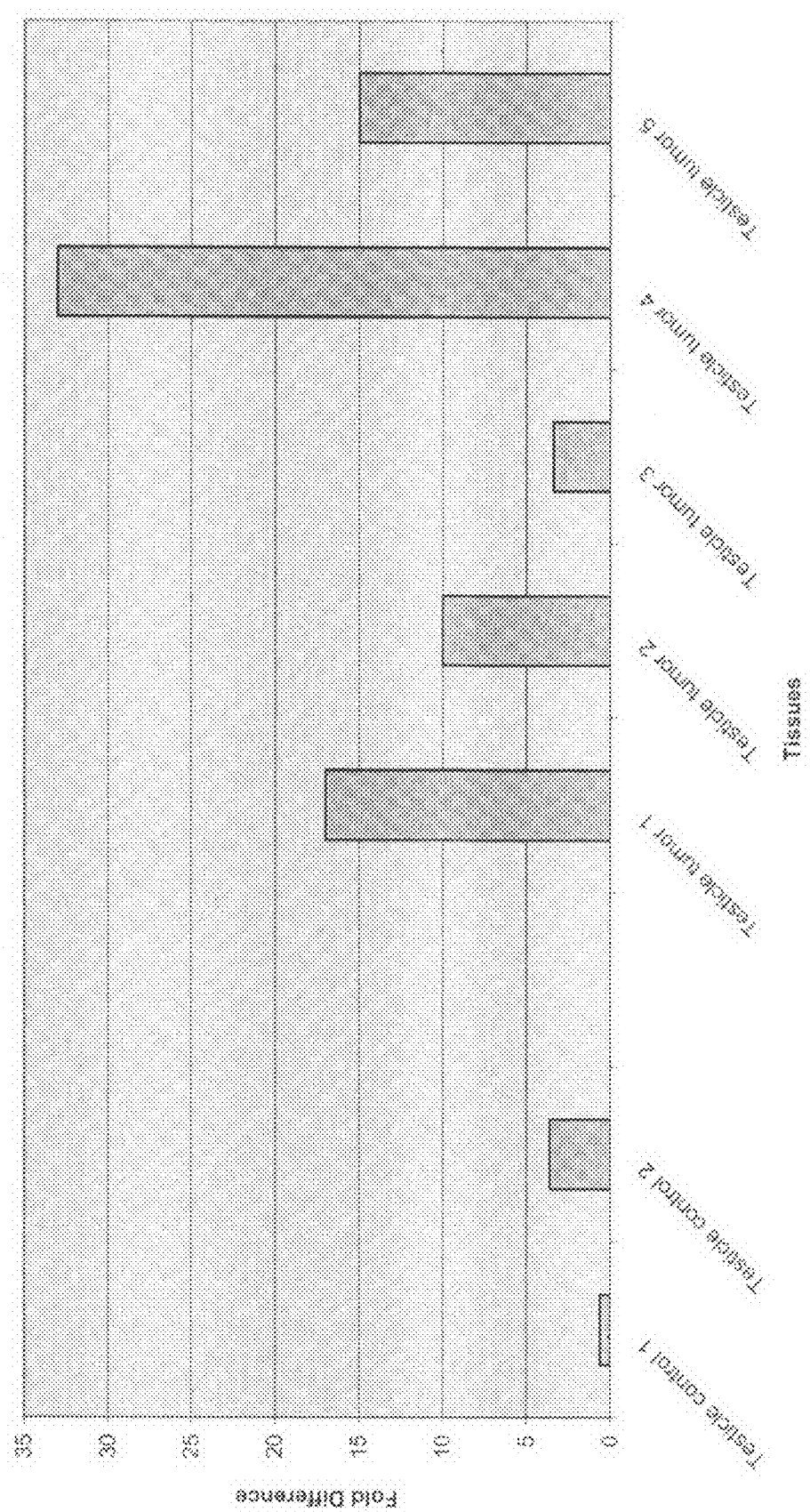

FIG. 19A

```
GPCR5D_HUMAN          NQQTAPVRYFLFGVLFALCFSCLLAHAS N LVKLVRGCVSFSWTTILCIAIGCSLLQIII
GPCR5D_MOUSE          NHQTAPVRYFLFGVLFAICFSCLLAHAS N LVKLVRGRVSFCWTTILFIAIGVSLLQTII
RAI3_HUMAN            DGSTGPTRFFLFGILFSICFSCLLAHAV S LTKLVRGRKPLSLLVILGLAVGFSLVQDVI
RAI3_MOUSE            DGATGPTRFFLFGVLFAICFSCLLAHAF N LIKLVRGRKPLSWLVILSLAVGFSLVQDVI
RAI3_RAT              DRATGPTRFFLFGVLFALCFSCLLAHAF N LIKLVRGRKPLSWLVILSLAVGFSLVQDVI
RAI3_COW              NGGTGPTRFFLFGVLFALCFSCLLVHAF N LTKLVRGRQPLSMLVMLGLALGFSLVQDII
RAI3_HUMAN            DGSTGPTRFFLFGILFSICFSCLLAHAV G LTKLVRGRKPLSLLVILGLAVGFSLVQDVI
(w/SNP S/G)
```

FIG. 19B

```
GPCR5D_HUMAN          RDS D GAEE..DVALTSYGTPIQPQTVDPTQECFIPQAKLSPQQDAGGV~~~~~~~~~~~~~
GPCR5D_MOUSE          C~~~~~~~~~~~~~~~~~~~~~~~~~~~~~~~~~~~~~~~~~~~~~~~~~~~~~~~~~~
RAI3_HUMAN            EIT Q GFEETGDTLYAPYSTHFQLQNQPPQKEFSIPRAHAWPSPYKDYEVKKEGS~~~~~~
RAI3_MOUSE            EIT Q GL.EMGDTLYAPYSTHFQLQNH..QKDFSIPRAQAPASPYNDYEGRKGDS
RAI3_HUMAN            EIT R GFEETGDTLYAPYSTHFQLQNQPPQKEFSIPRAHAWPSPYKDYEVKKEGS~~~~~~
(w/SNP Q/R)
```

FIG. 20

```
HUMAN:    6  PDGCRNGLKSKYYRLCDKAEAWGIVLETVATAGVVTSVAFMLTLPILVCKVQDSNRRKML  65
             P GCR+ L S+Y+RLCD AE WGI LET A  G  V  VA M  L L+CKVQDSN+RKML
MOUSE:  124  PSGCRSDLDSRYHRLCDLAEGWGIALETLAAVGAVATVACMFALVFLICKVQDSNKRKML  303

G
HUMAN:   66  PTQFLFLLGVLGIFGLTFAFIIGLDGSTGPTRFFLFGILFSICFSCLLAHAVSLTKLVRG  125
             P QFLFLLGVLG+FGLTFAFII LDG+TGPTRFFLFG+LF+ICFSCLLAHA +L KLVRG
MOUSE:  304  PAQFLFLLGVLGVFGLTFAFIIKLDGATGPTRFFLFGVLFAICFSCLLAHAFNLIKLVRG  483

A
HUMAN:  126  RKPLSLLVILGLAVGFSLVQDVIAIEYIVLTMNRTNVNVFSELSAPRRNEDFVLLLTYVL  185
             RKPLS LVIL LAVGFSLVQDVIAIEY+VLTMNRTNVNVFSEL APRRNEDFV+LL YVL
MOUSE:  484  RKPLSWLVILSLAVGFSLVQDVIAIEYLVLTMNRTNVNVFSELPAPRRNEDFVMLLIYVL  663

CHO NFAT Ga15 Control (Fluorescence)

CHO NFAT Ga15 RAI-3 (Fluorescence)

CHO NFAT Ga15

CHO NFAT Ga15 + T/P

CHO NFAT Ga15 oGPCR
Intermediate

CHO NFAT Ga15 oGPCR
High

FIG. 25A

```
  1  ataacagcatgaagtgccgtggaactggaataggcgtgtcctctccctcgaccctccccc    60

61  tccttgtccctctgctcacccctcgctcgttccctccctccggcgagggccncctttata   120

121  acaactgctcagagtgcgagggcgggatagctgtccaaggtctcccccagcactgaggag   180

181  ctcgcctgctgccctcttgcgcgcgggaagcagcaccaagttcacggccaacgccttggc   240

241  actagggtccagaatggctacaacagtccctgatggttgccgcaatggcctgaaatccaa   300
  1                M  A  T  T  V  P  D  G  C  R  N  G  L  K  S  K    16

301  gtactacagactttgtgataaggctgaagcttggggcatcgtcctagaaacggtggccac   360
 17   Y  Y  R  L  C  D  K  A  E  A  W  G  I  V  L  E  T  V  A  T    36

361  agcnggggttgtgacctcggtggccttcatgctcactctcccgatcctcgtctgcaaggt   420
 37   A  G  V  V  T  S  V  A  F  M  L  T  L  P  I  L  V  C  K  V    56

421  gcaggactccaacaggcgaaaaatgctgcctactcagtttctcttcctcctgggtgtgtt   480
 57   Q  D  S  N  R  R  K  M  L  P  T  Q  F  L  F  L  L  G  V  L    76

481  gggcatctttggcctcaccttcgccttcatnatcggactggagggagcacagggcccac   540
 77   G  I  F  G  L  T  F  A  F  I  I  G  L  D  G  S  T  G  P  T    96

541  acgcttcttcctctttgggatcctcttttccatctgcttctcctgcctgctggctcatgc   600
 97   R  F  F  L  F  G  I  L  F  S  I  C  F  S  C  L  L  A  H  A   116

601  tgtcngtctgaccaagctcgtccgggggaggaagccccttccctgttggtgattctggg   660
117   V  X  L  T  K  L  V  R  G  R  K  P  L  S  L  L  V  I  L  G   136

661  tctggccgtgggcttcagcctagtccaggatgttatcgctattgaatatattgtcctgac   720
137   L  A  V  G  F  S  L  V  Q  D  V  I  A  I  E  Y  I  V  L  T   156

721  catgaataggaccaacgtcaatgtcttttctgagctttccgctcctcgtcgcaatgaaga   780
157   M  N  R  T  N  V  N  V  F  S  E  L  S  A  P  R  R  N  E  D   176

781  ctttgtcctcctgctcncctacgtcctcttcttgatggcgctgaccttcctcatgtcctc   840
177   F  V  L  L  X  Y  V  L  F  L  M  A  L  T  F  L  M  S  S     196
```

FIG. 25B

```
 841  cttcaccttctgtggttccttcacgggctggaagagacatggggcccacatctacctcac   900
 197   F  T  F  C  G  S  F  T  G  W  K  R  H  G  A  H  I  Y  L  T  216

901  gatgctcctctccattgccatctgggtggcctggatcaccctgctcatgcttcctgactt   960
 217   M  L  L  S  I  A  I  W  V  A  W  I  T  L  L  M  L  P  D  F  236

961  tgaccgcaggtgggatgacaccatcctcagctccgccttggctgccaatggctgggtgtt  1020
 237   D  R  R  W  D  D  T  I  L  S  S  A  L  A  A  N  G  W  V  F  256

1021  cctgttggcttatgttagtcccgagttttggctgctcacaaagcaacgaaaccccatgga  1080
 257   L  L  A  Y  V  S  P  E  F  W  L  L  T  K  Q  R  N  P  M  D  276

1081  ttatcctgttgaggatgctttctgtaaaccncaactcgtgaagaagagctatggtgtgga  1140
 277   Y  P  V  E  D  A  F  C  K  P  Q  L  V  K  K  S  Y  G  V  E  296

1141  gaacagagcctactctcaagaggaaatcactcnaggttttgaagagacaggggacacgct  1200
 297   N  R  A  Y  S  Q  E  E  I  T  X  G  F  E  E  T  G  D  T  L  316

1201  ctatgccccctattccacacattttcagctgcagaaccagcctccccaaaaggaattctc  1260
 317   Y  A  P  Y  S  T  H  F  Q  L  Q  N  Q  P  P  Q  K  E  F  S  336

1261  catcccacgggcccacgcttggccgagcccttacaaagactatgaagtaaagaaagaggg  1320
 337   I  P  R  A  H  A  W  P  S  P  Y  K  D  Y  E  V  K  K  E  G  356

1321  cagctaactctgtcctgaagagtgggacaaatgcagccgggcggcagatctagcgggagc  1380
 357   S                                                            357

1381  tcaaagggatgtgggcgaaatcttgagtcttctgagaaaactgtacaagacactacggga  1440

1441  acagtttgcctccctcccagcctcaaccacaattcttccatgctggggctgatgtgggct  1500

1501  agtaagactccagttcttagaggcgctgtagtatttttttttttttgtctcatcctttgg  1560

1561  atacttcttttaagtgggagtctcaggcaactcaagtttagacccttactcttttttgttt  1620

1621  gttttttgaaacaggatcttgctctgtcacccaggcttgagtgcagtggtgcgatcacag  1680
```

FIG. 25C

```
1681  cccagtgcagcctcgaccacctgtgctcaagcaatcctcccatctccatctcccaaagtg  1740

1741  ctgggatgacaggcgtgagccacagctcccagcctaggcccttaatcttgctgttatttt  1800

1801  ccatggactaaaggtctggtcatctgagctcacgctggctcacacagctctaggggcctg  1860

1861  ctcctctaactcacagtgggttttgtgaggctctgtggcccagagcagacctgcatatct  1920

1921  gagcaaaaatagcaaaagcctctctcagcccactggcctgaatctacactggaagccaac  1980

1981  ttgctggcaccccgctccccaacccttcttgcctgggtaggagaggctaaagatcaccc   2040

2041  taaatttactcatctctctagtgctgcctcacattgggcctcagcagctccccagcacca  2100

2101  attcacaggtcacccctctcttcttgcactgtccccaaacttgctgtcaattccgagatc  2160

2161  taatctcccctacgctctgccaggaattctttcagacctcactagcacaagcccggttg   2220

2221  ctccttgtcaggagaatttgtagatcattctcacttcaaattcctggggctgatacttct  2280

2281  ctcatcttgcaccccaacctctgtaaatagatttaccgcatttacggctgcattctgtaa  2340

2341  gtgggcatggtctcctaatggaggagtgttcattgtataataagttattcacctgagtat  2400

2401  gcaataaagatgtggtggccactctttcatggtggtggcagcaaaaaaaaaaaaaa      2456
```

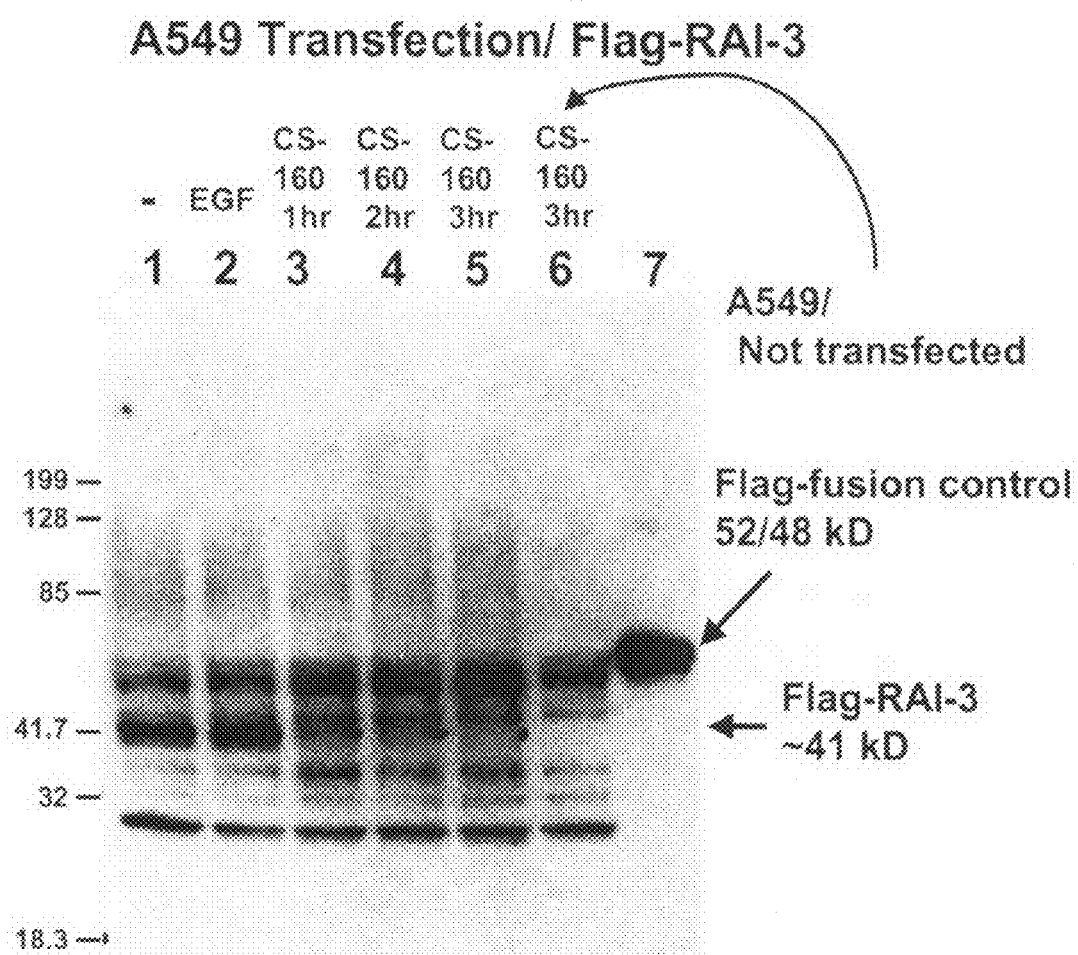

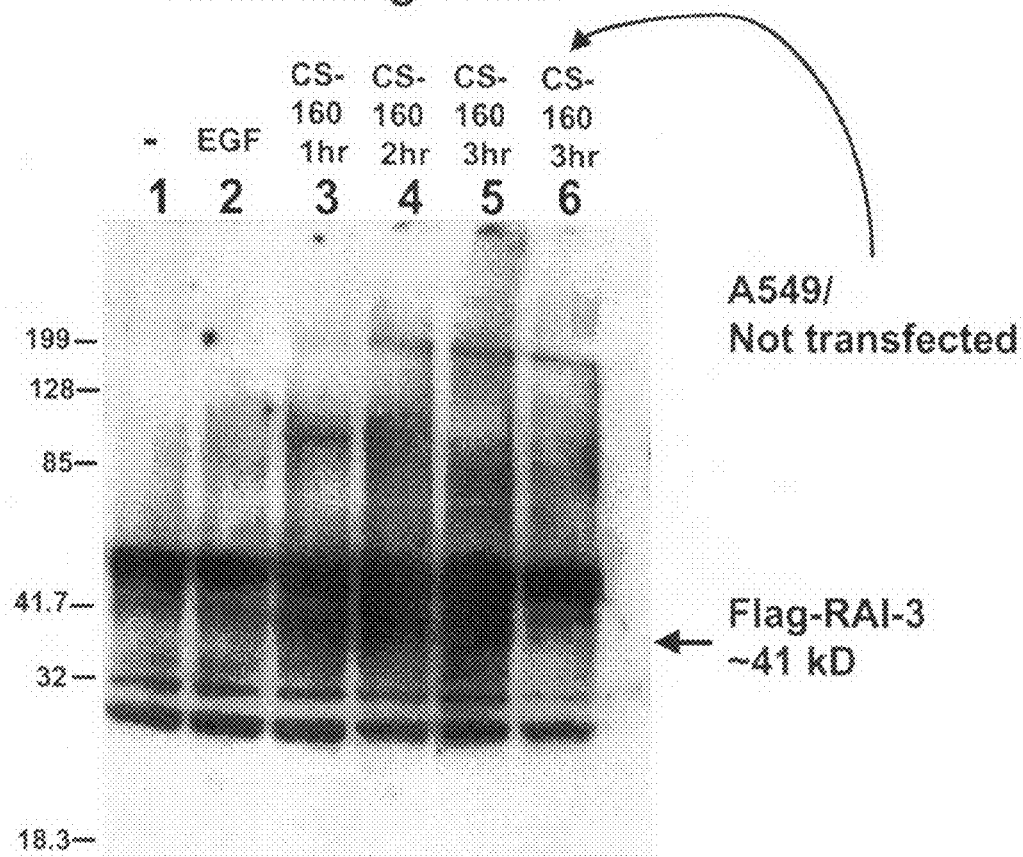

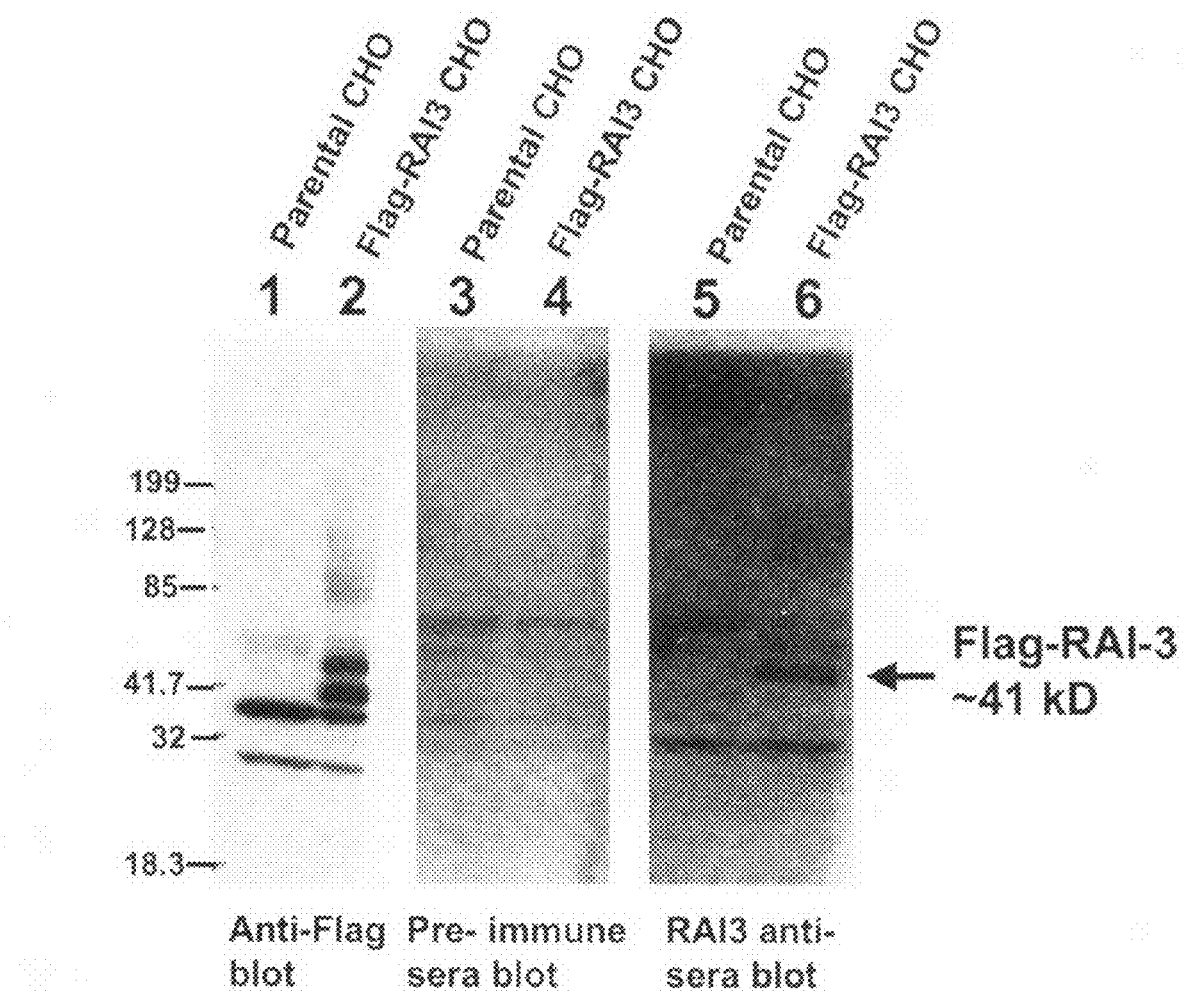

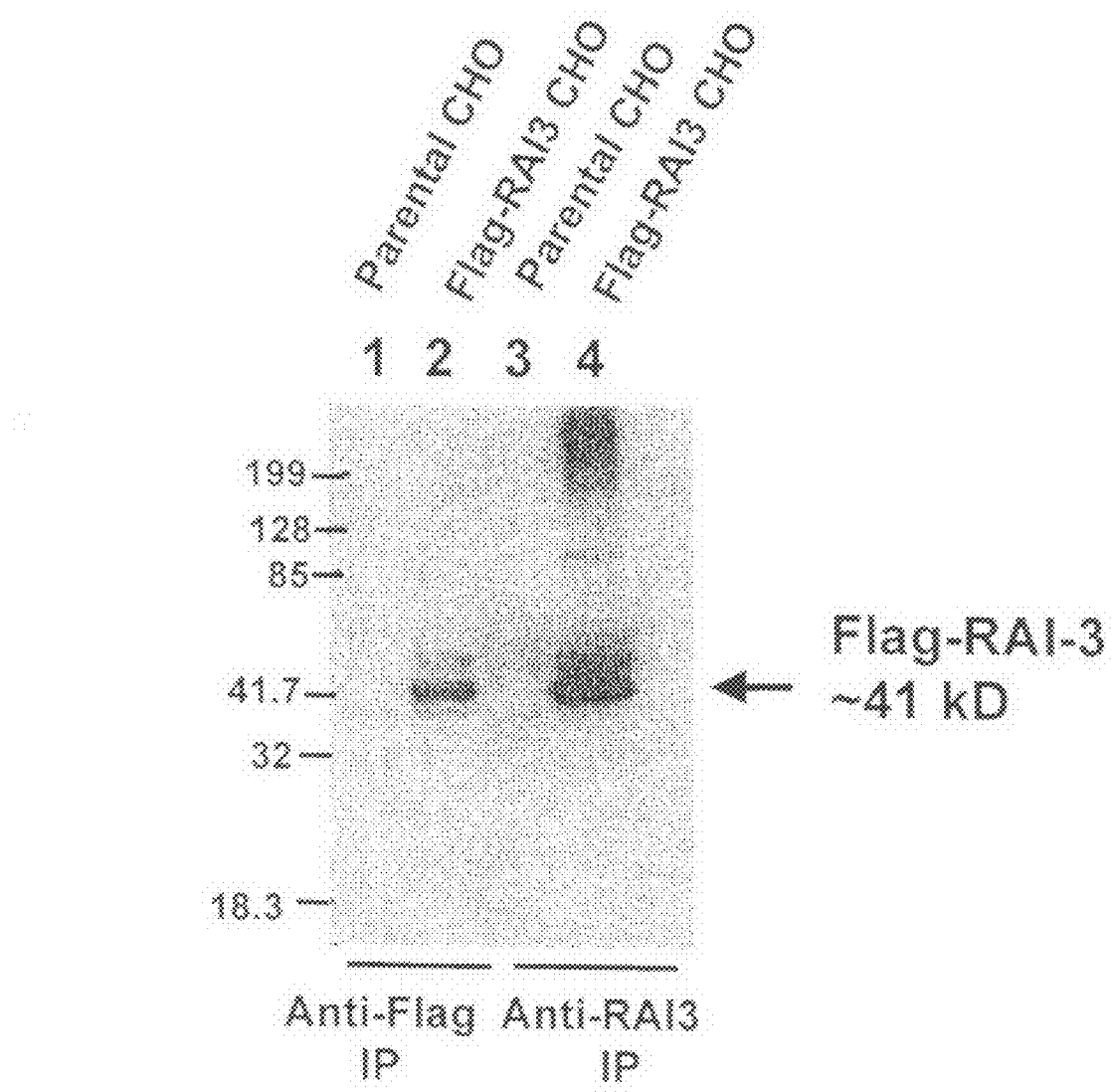

FIG. 33
A. Normal Lung Tissue
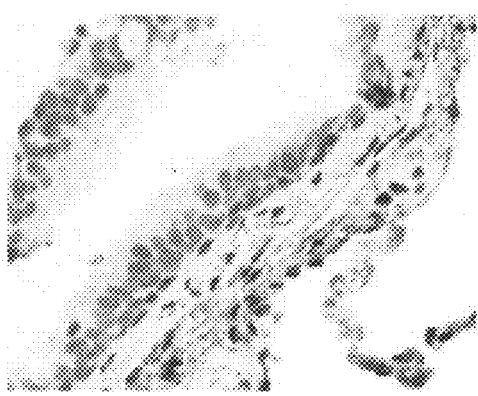
Respiratory Epithelium, Normal Lung
B. Normal Lung Tissue
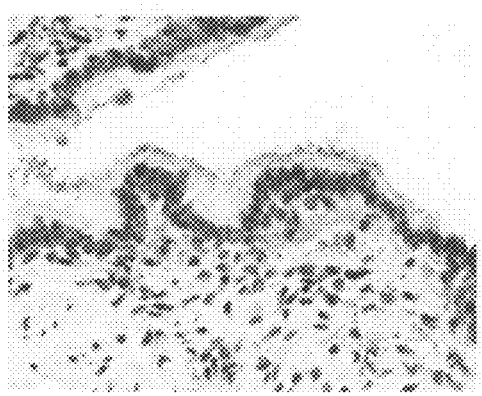
Respiratory Epithelium, Normal Lung
C. Emphysema, Human Lung Tissue
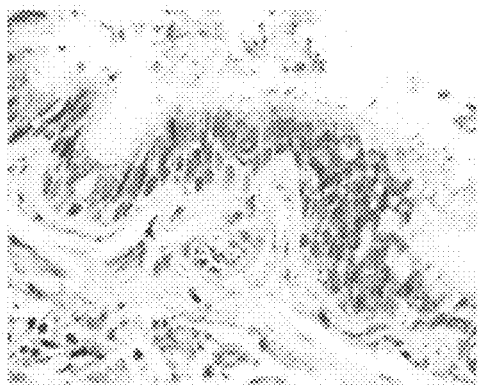
Respiratory Epithelium, Emphysema FIG. 34
A. Chronic Bronchitis, Human Lung Tissue
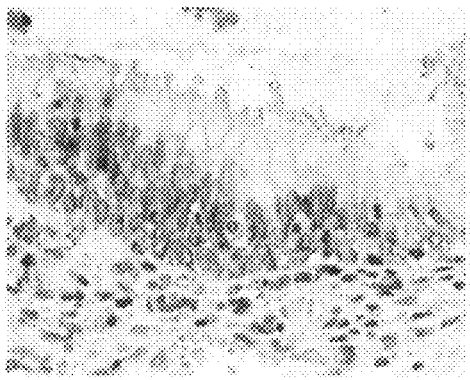
Respiratory Epithelium, Bronchitis
B. Chronic Bronchitis, Human Lung Tissue
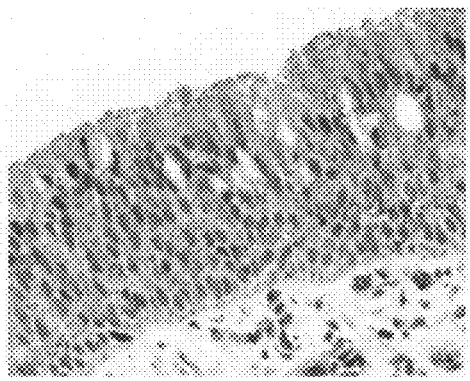
Respiratory Epithelium, Bronchitis
C. Chronic Bronchitis, Human Lung Tissue
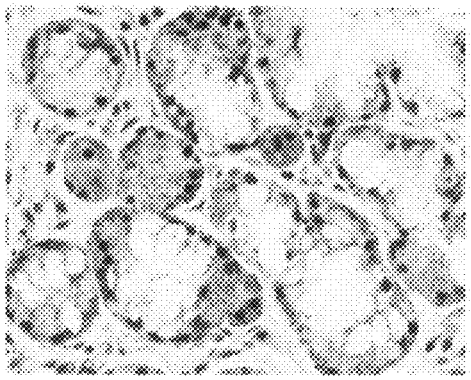
Seromucous Glands, Bronchitis
D. Chronic Bronchitis, Human Lung Tissue
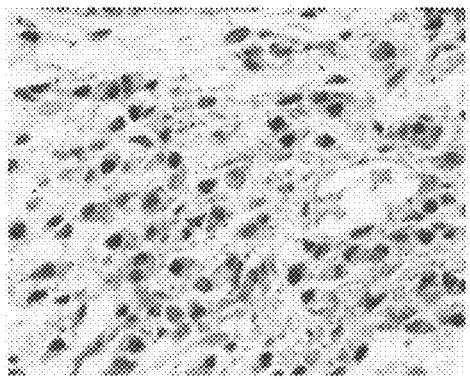
Mucosal Inflammation, Bronchitis

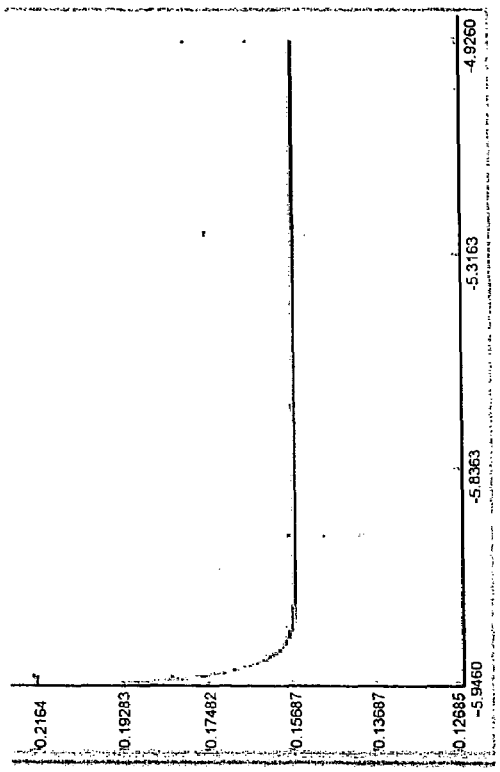
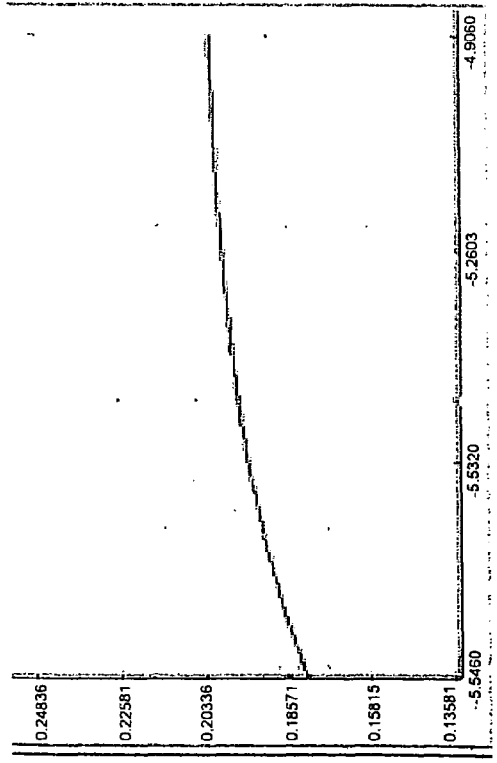
FIG. 35

METHODS OF DIAGNOSING TUMORS USING THE G-PROTEIN COUPLED RECEPTOR (GPCR), RAI-3

This application is a continuation application of non-provisional application U.S. Ser. No. 10/600,816, filed Jun. 20, 2003, abandoned, which claims benefit to provisional application U.S. Ser. No. 60/390,850 filed Jun. 20, 2002; and to provisional application U.S. Ser. No. 60/407,006, filed Aug. 29, 2002, under 35 U.S.C. 119(e). The entire teachings of the referenced applications are incorporated herein by reference.

FIELD OF THE INVENTION

The present invention relates to the identification of drug targets, and modulators thereof, for the treatment of chronic obstructive pulmonary disease (COPD) and COPD related disorders and conditions, such as emphysema and chronic bronchitis, as well as for the treatment of other diseases and disorders related to the regulation and/or mediation of the NF-κB pathway and components thereof. In particular, this invention relates to the new discovery that the RAI-3 protein, a member of the G-protein coupled receptor (GPCR) superfamily, is associated with the development of COPD and COPD related disorders and conditions. The invention further relates to modulators of the RAI-3 protein and their use in methods of treating not only COPD, but also a variety of other diseases and conditions that are affected or mediated by NF-κB regulation.

BACKGROUND OF THE INVENTION

Many medically significant biological processes that are mediated by proteins participating in signal transduction pathways involving G-proteins and/or second messengers, e.g., cAMP, have been established (Lefkowitz, 1991, *Nature*, 351:353-354). These proteins are often referred to as proteins participating in pathways with G-proteins or PPG proteins. Some examples of these proteins include the G protein-coupled receptors (GPCR), such as those for adrenergic agents and dopamine (B. K. Kobilka et al., 1987, *Proc. Natl. Acad. Sci. USA*, 84:46-50; B. K. Kobilka et al., 1987, *Science*, 238:650-656; and J. R. Bunzow et al., 1988, *Nature*, 336:783-787), G-proteins themselves, effector proteins, e.g., phospholipase C, adenylate cyclase and phosphodiesterase and actuator proteins, e.g., protein kinase A and protein kinase C (M. I. Simon et al., 1991, *Science*, 252:802-8).

For example, in one form of signal transduction, the effect of hormone binding results in activation of the enzyme adenylate cyclase inside the cell. Enzyme activation by hormones is dependent on the presence of the nucleotide GTP, where GTP also influences hormone binding. A G-protein binds the hormone receptors to adenylate cyclase. The G-protein has further been shown to exchange GTP for bound GDP when activated by hormone receptors. The GTP-carrying form of the G-protein then binds to an activated adenylate cyclase. Hydrolysis of GTP to GDP, catalyzed by the G-protein itself, returns the G-protein to its basal, inactive form. Thus, the G-protein serves a dual role—as an intermediate that relays the signal from receptor to effector, and as a "clock" that controls the duration of the signal.

The membrane protein gene superfamily of G-protein coupled receptors (GPCRs) has been characterized as having seven putative transmembrane domains. The domains are believed to represent transmembrane α-helices connected by extracellular or cytoplasmic loops. GPCRs include a wide range of biologically active receptors, such as hormone, viral, growth factor, and neuronal receptors.

GPCRs are further characterized as having seven conserved hydrophobic stretches of about 20 to 30 amino acids, connecting at least eight divergent hydrophilic loops. The G-protein coupled receptor family includes, for example, the following types of receptors: dopamine, calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant and cytomegalovirus receptors, etc.

Most GPCRs have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some GPCRs. Most GPCRs contain potential phosphorylation sites within the third cytoplasmic loop and/or the carboxyl terminus. For several GPCRs, such as the β-adrenoreceptor, phosphorylation by protein kinase A and/or specific receptor kinases mediates receptor desensitization.

For some receptors, the ligand binding sites of GPCRs are believed to comprise a hydrophilic socket formed by the transmembrane domains of several GPCRs. This socket is surrounded by hydrophobic residues of the GPCRs. The hydrophilic side of each GPCR transmembrane helix is postulated to face inward and form the polar ligand-binding site. TM3 has been implicated in several GPCRs as having a ligand-binding site, which includes the TM3 aspartate residue. In addition, serines within TM5, a TM6 asparagine and phenylalanines or tyrosines within TM6 or TM7 are also implicated in ligand binding.

GPCRs can be intracellularly coupled by heterotrimeric G-proteins to various intracellular enzymes, signal transduction pathways and molecules, ion channels and transporters (see, e.g., Johnson et al., 1989, *Endocrin. Rev.*, 10:317-331). Different G-protein β-subunits preferentially stimulate particular effectors to modulate various biological functions in a cell. Phosphorylation of cytoplasmic residues of GPCRs have been identified as an important mechanism for the regulation of G-protein coupling of some GPCRs. GPCRs are found in numerous sites within a mammalian host.

GPCRs are one of the largest receptor superfamilies known. These receptors are biologically important and malfunction of these receptors results in diseases such as Alzheimer's, Parkinson, diabetes, dwarfism, color blindness, retinitis pigmentosa, asthma and others. GPCRs are also involved in depression, schizophrenia, sleeplessness, hypertension, anxiety, stress, renal failure and in several other cardiovascular, metabolic, neural, oncological and immune disorders (F. Horn and G. Vriend, 1998, *J. Mol. Med.*, 76:464-468). They have also been shown to play a role in HIV infection (Y. Feng et al., 1996, *Science*, 272: 872-877).

As mentioned above, the structure of GPCRs comprises seven transmembrane helices that are connected by loops. The N-terminus is always extracellular and C-terminus is intracellular. GPCRs are involved in signal transduction. The signal is typically received at the extracellular N-terminus side. The signal can be an endogenous ligand, a chemical moiety, another type of extracellular signal, and even light. This signal is then transduced through the membrane to the cytosolic side where a heterotrimeric G-protein is activated which in turn elicits a response (F. Horn et al., 1998, *Recept. and Chann.*, 5: 305-314).

Modulators, e.g., ligands, agonists and antagonists, for GPCRs are utilized for preventative and therapeutic purposes to treat various diseases, disorders and/or conditions. The present invention has achieved the identification of a particular GPCR, newly linked by this invention to chronic obstructive pulmonary disease (COPD) and COPD-related disorders and conditions. This COPD-related GPCR, as described herein and newly associated with COPD, provides a new target for drug discovery and treatments effective against COPD and disorders and conditions related thereto. In addition, modulators of this COPD-related GPCR have been newly found in accordance with the present invention and as described herein to affect transcriptional mediators and signaling molecules, thereby providing new agents for treating not only COPD, but also other diseases and conditions affected by regulation of these transcriptional mediators, components of pathways related thereto and/or cell signaling components.

Chronic obstructive pulmonary disease (COPD), which encompasses both chronic bronchitis and emphysema, is one of the most common respiratory conditions of adults in the developed world. COPD poses an enormous burden to society both in terms of direct cost to healthcare services and indirect costs to society, primarily through loss of productivity. In the Western world, COPD is the fourth most common cause of death and it claims the lives of over 119,000 Americans annually. Approximately eighty to ninety percent of COPD patients have smoked and/or do smoke cigarettes.

The definition of COPD that is recognized by both the American Thoracic Society and the European Respiratory Society is a disorder characterized by reduced maximal expiratory flow and slow forced emptying of the lungs—features that do not change markedly over several months. This limitation in airflow is only minimally reversible with bronchodilators. The respiratory disease emphysema is defined pathologically as a condition in which there is permanent destructive enlargement of the air spaces distal to the terminal bronchioles without obvious fibrosis. Chronic bronchitis is defined clinically by the presence of chronic bronchial secretions, enough to cause expectoration, occurring on most days for a minimum of three months of the year for two consecutive years. The pathological basis of chronic bronchitis is mucus hypersecretion secondary to hypertrophy of the glandular elements of the bronchial mucosa. Patients with COPD have features of both conditions, although one of the conditions may be more prominent than the other.

Chronic bronchitis only really became recognized as a distinct disease, rather than as a set of symptoms, in the late 1950's. The great 'British Smogs' of the 1950's precipitated the deaths of many patients from respiratory failure. There is little doubt that at the present time, the most important risk factor in the development of COPD is smoking of tobacco burning products, in particular, cigarette smoking. Because approximately 80 to 90% of COPD cases are caused by smoking, a smoker is ten times more likely than a nonsmoker to die of COPD. According to the World Health Organization, 75% of deaths from COPD that occur in developed countries are directly related to smoking tobacco.

The effects of smoke from tobacco burning products, such as cigarette smoke, on the lungs are manifold. Cigarette smoke has been found to attract inflammatory cells into the lungs and stimulates the release of the proteolytic enzyme elastase from these cells. Elastase, in turn, breaks down elastin, a normal structural component of lung tissue. Normally, however, the lung is protected from the destructive effect of elastase by an inhibitor, alpha-1 antitrypsin (AAT). One effect of cigarette smoke is to attract more cells and stimulate the release of more elastase. The development of COPD, and in particular emphysema, is thought to be due, in part, to the imbalance between the destructive elastase and the protective AAT.

Not all people who smoke develop COPD; and not all patients with COPD are smokers, or have smoked in the past (although 85% to 90% of COPD patients have smoked or are smoking). There seems to be a varying susceptibility to lung damage due to cigarette smoke within the general population. Only a proportion of smokers (maybe only 10-15%) or former smokers show a rate of decline of lung function over the years that is fast enough to result in the severe impairment that is typical of patients who present with breathlessness due to COPD. Unfortunately, these types of former smokers do not improve after they stop smoking. By the time these subjects are symptomatic with breathlessness, they will have already had severe impairment of lung function. Cessation of smoking at this stage may extend their life expectancy, but may not improve their symptoms.

Another well established risk factor for COPD is a deficiency of the protective protease inhibitor, alpha-1 antitrypsin (AAT), which is produced in the liver. The risk factor relates to an inherited autosomal recessive (designated PiZZ) disorder which is fairly rare in the general gene pool. The incidence of homozygous births is about 1 in 3000 live births. As such, AAT deficiency accounts for probably less than 5% of all cases of COPD. The onset of AAT deficiency emphysema generally occurs between the ages of 20 to 40 years and is characterized by shortness of breath and decreased exercise capacity. Blood screening is used if the trait is suspected and can determine if a person is a carrier, or is AAT-deficient. If children are diagnosed as being AAT-deficient through blood screening, they may undergo a liver transplant.

Low levels of AAT allow the uninhibited action of elastase on the lung parenchyma, thereby giving rise to destruction of the alveoli and the eventual development of emphysema rather than chronic bronchitis. The pattern of emphysema in AAT deficiency differs slightly from that of smoking-induced pure emphysema in that AAT deficiency produces panlobular emphysema affecting predominantly the lower lung fields, while smoking-induced emphysema is usually centrilobular affecting the upper lung fields initially.

The quality of life for a person suffering from COPD diminishes as the disease progresses. People with COPD may eventually require supplemental oxygen and may have to rely on mechanical respiratory assistance. A recent American Lung Association survey revealed that about half of all COPD patients (i.e., 51%) indicate that their condition limits their ability to work. It also limits them in normal physical exertion (70%), household chores (56%), social activities (53%), sleeping (50%), and family activities (46%).

None of the existing medications for COPD have been shown to modify the long-term decline in lung function that is the hallmark of this disease. Therefore, pharmacotherapy for COPD is used to decrease symptoms and/or complications. Bronchodilator medications are central to the symptomatic management of COPD. Additional treatment includes antibodies, oxygen therapy, and systemic glucocorticosteroids. The efficacy of inhaled glucocorticosteroids is currently under study. Chronic treatment with steroids is avoided because of an unfavorable benefit-to-risk ratio. Lung transplantation is being performed in increasing numbers and may be an option for people who suffer from severe emphysema. In addition, lung volume reduction surgery has shown promise and is being performed with increasing frequency. However, a recent study found that emphysema patients who have severe lung obstruction with either limited ability to exchange gas when breathing, or damage that is evenly distributed throughout their lungs, are at high risk of death from the foregoing procedures. Treatments for AAT deficiency emphysema, including AAT replacement therapy and gene therapy, are currently being evaluated.

Because of the magnitude of the health and health care problems that correlate with COPD and COPD related conditions and disorders, both at the level of the patient and the patient's care by the medical community, it is clear that new drug target molecules, as well as alternative drugs and treatments, are sorely needed to combat and counteract this disease. As discussed above, the present therapies are sometimes only palliative, and do not satisfactorily treat, reduce, ameliorate, or eliminate all of the debilitating effects of COPD.

In addition, as described herein, it is newly recognized that the prevalent use of tobacco burning materials and substances, such as cigarettes and cigars, generates smoke-related cellular products, e.g., proteins and peptides, which are major causative factors for COPD. Therefore, identifying the proteins, signal transduction pathways and components thereof that are activated and/or modified when cells are exposed to smoke from tobacco burning products can be key to identifying new drug targets for the treatment of COPD. The present invention newly provides previously unrecognized sources and targets for new anti-COPD drugs and compounds useful in profoundly needed treatments and therapies for COPD and COPD related diseases, which can benefit vast numbers of COPD patients and sufferers.

In their diverse cellular roles, GPCRs can also be involved in cell suicide, or programmed cell death, during the lifetime of a multicellular organism. Programmed cell death or apoptosis occurs during a number of events in the organism's life cycle, such as for example, in the development of an embryo, during the course of an immunological response, or in the demise of cancerous cells after drug treatment, among others. The final outcome of cell survival versus apoptosis is dependent on the balance of two counteracting events, namely, the onset and speed of caspase cascade activation (essentially a protease chain reaction), and the delivery of anti-apoptotic factors which block the caspase activity (B. B. Aggarwal, 2000, *Biochem. Pharmacol.*, 60:1033-1039; N. A. Thornberry and Y. Lazebnik, 1998, *Science*, 281:1312-1316).

The production of anti-apoptotic proteins is controlled by the transcriptional factor complex NF-κB. For example, exposure of cells to the protein tumor necrosis factor (TNF) can signal both cell death and survival, an event playing a major role in the regulation of immunological and inflammatory responses (S. Ghosh et al., 1998, *Annu. Rev. Immunol.*, 16:225-260; N. Silverman and T. Maniatis, 2001, *Genes and Dev.*, 15:2321-2342; and V. Baud and M. Karin, 2001, *Trends Cell Biol.*, 11:372-377). The anti-apoptotic activity of NF-κB is also crucial to oncogenesis and to chemo- and radio-resistance in cancer (A. S. Baldwin, 2001, *J. Clin. Invest.*, 107: 241-246).

Nuclear Factor-κB (NF-κB), is composed of dimeric complexes of p50 (NF-κB1) or p52 (NF-κB2) that are usually associated with members of the Rel family (p65, c-Rel, Rel B) which have potent transactivation domains. Different combinations of NF-κB/Rel proteins bind to distinct κB sites to regulate the transcription of different genes. Early work involving NF-κB suggested that its expression was limited to specific cell types, particularly in stimulating the transcription of genes encoding kappa immunoglobulins in B lymphocytes. However, it has been discovered that NF-κB is, in fact, present and inducible in many, if not all, cell types and that it acts as an intracellular messenger capable of playing a broad role in gene regulation as a mediator of inducible signal transduction. Specifically, it has been demonstrated that NF-κB plays a central role in the regulation of intercellular signals in many cell types. For example, NF-κB has been shown to positively regulate the human beta-interferon (beta-IFN) gene in many, if not all, cell types. Moreover, NF-κB has also been shown to serve the important function of acting as an intracellular transducer of external influences.

The transcription factor NF-κB is sequestered in an inactive form in the cytoplasm as a complex with its inhibitor, IκB; the most prominent member of the class of IκB inhibitors is IκBα. A number of factors are known to serve the role of stimulators of NF-κB activity, such as, for example, tumor necrosis factor (TNF). After TNF exposure, the inhibitor is phosphorylated and proteolytically removed, thus releasing NF-κB into the nucleus and allowing its transcriptional activity. Numerous genes are up-regulated by this transcription factor, among them IκBα. The newly synthesized IκBα protein inhibits NF-κB, effectively shutting down further transcriptional activation of its downstream effectors.

However, as mentioned above, the IκBα protein may only inhibit NF-κB in the absence of IκBα stimuli, such as TNF stimulation, for example. Other agents that are known to stimulate NF-κB release, and thus NF-κB activity, are bacterial lipopolysaccharide, extracellular polypeptides, chemical agents, such as phorbol esters, which stimulate intracellular phosphokinases, inflammatory cytokines, IL-1, oxidative and fluid mechanical stresses, and Ionizing Radiation (S. Basu et al., 1998, *Biochem. Biophys. Res. Commun.*, 247(1):79-83). Therefore, as a general rule, the stronger the insulting stimulus, the stronger the resulting NF-κB activation, and the higher the level of IκBα transcription. As a consequence, measuring the level of IκBα RNA can be used as a marker for anti-apoptotic events, and indirectly, for the onset and strength of pro-apoptotic events.

SUMMARY OF THE INVENTION

The present invention relates to the identification of proteins and their component peptides that are activated when cells are exposed to smoke from tobacco burning products, particularly, cigarette smoke. Since cigarette smoke is the major causative factor for COPD, this invention has provided an innovative means of newly identifying proteins, signal transduction pathways and components thereof that are activated and/or modified when cells are exposed to cigarette smoke (or smoke resulting from the burning of other tobacco-containing substances). According to the present invention, the identification of such proteins, pathways and pathway components is a critical advancement to discovering and identifying new drug targets for the treatment of COPD and COPD related diseases, disorders and conditions, as newly described herein. Further, the identification of such proteins and the proteins with which they interact or regulate allows for the detection and discovery of modulators, e.g., agonists and/or antagonists, of protein targets that can have therapeutic efficacy in the treatment of a variety of diseases and disorders that are associated with downstream signaling and messenger events that are affected by target protein modulation.

In accordance with this invention, proteomics methods were utilized to isolate cigarette smoke-inducible tyrosine phosphorylated proteins (activation complexes) from airway epithelial cells. By means of this technique, the RAI-3 protein, a member of the G-protein coupled receptor superfamily, has been newly identified as being tyrosine phosphorylated, and/or as being associated/complexed with tyrosine phosphorylated proteins, only in those cells that had been exposed to cigarette smoke. As described herein, cellular peptides were identified and characterized using proteomics methodologies to allow the first determination that RAI-3 protein activation and/or modification results from smoke exposure to cells. According to this invention and the findings related thereto, RAI-3 can serve as a drug target for COPD and COPD related diseases and conditions. In addition, RAI-3 can be utilized as described herein to identify and/or screen for modulators, e.g., agonists or antagonists, for use in methods and compositions for the prevention and treatment of COPD. It is to be understood that throughout this disclosure, the present invention relates to methods and compositions suitable for the prevention, treatment and therapeutic intervention of COPD as well as COPD related diseases, disorders and conditions. The RAI-3 protein is also provided as a target for drug development in the field of oncology to treat a variety of cancers, tumors and malignancies.

It is an aspect of this invention to provide novel peptides and polypeptides which are modified in, e.g., by phosphorylation, and isolated from, cells exposed to smoke resulting from the burning of tobacco containing substances, namely cigarettes. More specifically, the GPCR protein RAI-3 has been newly identified as being associated with cellular responses to exposure to cigarette smoke. Thus, the RAI-3 protein and its peptides can serve as drug targets for the prevention and treatment of COPD.

It is another aspect of the present invention to provide modulators of the RAI-3 protein and RAI-3 peptide targets which can affect the function or activity of RAI-3 in a cell in which RAI-3 function or activity is to be modulated or affected. In addition, modulators of RAI-3 can affect downstream systems and molecules that are regulated by, or which interact with, RAI-3 in the cell. Modulators of RAI-3 include compounds, antibodies, antisense reagents, siRNA reagents, materials, agents, drugs, and the like, that antagonize, inhibit, reduce, block, suppress, diminish, decrease, or eliminate RAI-3 function and/or activity. Such compounds, antibodies, antisense reagents, siRNA reagents, materials, agents, drugs and the like can be collectively termed "antagonists". Alternatively, modulators of RAI-3 include compounds, antibodies, antisense reagents, siRNA reagents, materials, agents, drugs, and the like, that agonize, enhance, increase, augment, or amplify RAI-3 function in a cell. Such compounds, antibodies, antisense reagents, siRNA reagents, materials, agents, drugs and the like can be collectively termed "agonists".

Antagonists and agonists of the present invention include, for example, small molecules, large molecules, and antibodies directed against the RAI-3 protein or peptides thereof. Antagonists and agonists of the invention also include nucleotide sequences, such as antisense, siRNA reagents, and ribozyme molecules, and gene or regulatory sequence replacement constructs, that can be used to inhibit or enhance expression of the RAI-3 nucleic acid molecule, or oligomeric portions thereof, such as peptide encoding nucleic acid fragments.

Yet another aspect of this invention provides methods and compositions, including pharmaceutical compositions, for the treatment and/or prevention of COPD, or COPD related disorders and conditions. The compositions can comprise modulators of the RAI-3 protein, or peptides thereof. The modulators can be antagonists or agonists. Pharmaceutical compositions preferably comprising a pharmaceutically and/or physiologically acceptable diluent, excipient, or carrier (vehicle) are provided. The modulators can be employed alone, or in combination with other standard treatment regimens for lung-related diseases and/or conditions, e.g., emphysema. Such methods and compositions are capable of modulating the level of RAI-3 gene expression and/or the level of activity of the RAI-3 gene product or polypeptide. The methods include, for example, modulating the expression of the RAI-3 gene and/or the activity of the RAI-3 gene product, or modulating the expression of a gene or gene product that is regulated or controlled by RAI-3, effective for the treatment of COPD.

It is another aspect of the invention to provide screening methods for the identification of compounds, materials, substances, drugs, and agents that modulate the expression of the RAI-3 nucleic acid and/or the activity of the RAI-3 polypeptide. Such methods include, without limitation, assays that measure the effects of a test compound or agent on RAI-3 mRNA and/or gene product levels; assays that measure levels of RAI-3 activity or function; and assays that measure the levels or activities of molecules and/or systems that are regulated or mediated by RAI-3, or modulators of RAI-3, such as NF-κB and/or IκB, or E-selectin, for example.

It is another aspect of the present invention to provide the RAI-3 GPCR protein as a component of a cell signaling pathway in which it is involved in apoptotic events. Accordingly, downstream cellular events can be regulated via the activity of the RAI-3 protein using RAI-3 modulators, e.g., antagonists or agonists, such as antisense polynucleotides, polypeptides or low molecular weight chemicals to achieve a therapeutic effect in cancer, (e.g., lung cancer, breast cancer, stomach cancer, testicular cancer), autoimmune diseases, immunological disorders, renal diseases, ischemia-reperfusion injury, asthma, pulmonary fibrosis, cystic fibrosis and heart failure.

It is another aspect of this invention to provide RAI-3 polynucleotides and polypeptides, and fragments thereof, for treating, diagnosing, and/or ameliorating proliferative disorders, cancers, ischemia-reperfusion injury, heart failure, immunocompromised conditions, HIV infection, and renal diseases. According to the invention, RAI-3 polynucleotides and polypeptides, and fragments thereof, are useful for increasing NF-κB activity, increasing apoptotic events, and/or decreasing IκBα expression or activity levels.

It is another aspect of the present invention to provide antagonists directed against RAI-3 for treating, diagnosing, and/or ameliorating disorders, diseases and/or conditions including autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferation disorders, cancers, e.g., lung cancer, breast cancer, stomach cancer, testicular cancer, etc., HIV infection, and HIV propagation in cells infected with other viruses. According to the present invention, antagonists directed against RAI-3 are useful for decreasing NF-κB activity, decreasing apoptotic events, and/or increasing IκBα expression or activity levels.

In a further aspect of the present invention, agonists directed against RAI-3 are provided for treating, diagnosing, and/or ameliorating autoimmune disorders, disorders related to hyperimmune activity, hypercongenital conditions, birth defects, necrotic lesions, wounds, disorders related to aberrant signal transduction, immunocompromised conditions, HIV infection, proliferation disorders, and/or numerous types of cancers. According to the invention, agonists directed against RAI-3 are useful for increasing NF-κB activity, increasing apoptotic events, and/or decreasing IκBα expression or activity levels.

It is another aspect of this invention to provide RAI-3 polynucleotides and polypeptides, fragments thereof, and modulators thereof, for treating, diagnosing, and/or ameliorating ulcerative colitis, cerebral infarct, myocardial infarct, diabetic nephropathy, allergic rhinitis, Crohn's disease, atherosclerosis and rheumatoid arthritis.

It is another aspect of this invention to provide RAI-3 polynucleotides and polypeptides, fragments thereof, and modulators thereof, for treating, diagnosing, and/or ameliorating inflammatory/auto-immune disorders outside of the lung in addition to COPD.

It is another aspect of this invention to provide RAI-3 polynucleotides and polypeptides, fragments thereof, and modulators thereof, for treating, diagnosing, and/or ameliorating glioblastoma, pulmonary small cell undifferentiated carcinoma, carcinoma of the breast, colon, lung, ovary, pancreas, and prostate, and non-Hodgkin's lymphoma.

It is another aspect of this invention to provide RAI-3 polynucleotides and polypeptides, fragments thereof, and modulators thereof, for treating, diagnosing, and/or ameliorating pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

It is another aspect of this invention to provide RAI-3 polynucleotides and polypeptides, fragments thereof, and modulators thereof, for treating, diagnosing, and/or ameliorating pulmonary infections: pnemonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pnemonia (for example, as caused by *Mycobacterium tuberculosis*, etc.) mycoplasma pnemonia, fungal pnemonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, *Chlamydia* pneumonia, aspiration pneumonia, *Nocordia* sp. Infections, parasitic pnemonia (for example, as caused by *Strongyloides, Toxoplasma gondii*, etc.) necrotizing pnemonia, in addition to any other pulmonary disease and/or disorder (e.g., non-pneumonia) implicated by the causative agents listed above or elsewhere herein.

In another of its aspects, the present invention encompasses vectors or vector constructs, including expression vectors and cloning vectors, that contain the RAI-3 nucleic acid sequence, or peptide encoding portions of the RAI-3 nucleic acid sequence, or RAI-3 variants, for the expression of the RAI-3 nucleic acid molecule(s) in host organisms. The present invention also relates to host cells molecularly/genetically engineered to contain and/or express RAI-3 nucleic acid molecules. Such host cells which express RAI-3 polypeptides or peptides can be employed in screening assays as described herein, for example, to identify RAI-3 modulating compounds, and/or to assess the effect(s) of a variety of cell treatments and compounds on RAI-3 function or biological activity, which can include structural, biochemical, physiological, or biochemical functions in a cell. Further, host organisms that have been transformed with these nucleic acid molecules are also encompassed in the present invention, e.g., transgenic animals, particularly transgenic non-human animals, and particularly transgenic non-human mammals.

In another aspect of the present invention, methods are provided for regulating second messenger pathways and molecules therein by modulating RAI-3 function and/or activity. More particularly, the present invention affords the ability to regulate, modulate, or affect the activity of the NF-κB pathway and components thereof, e.g., IκB, by modulating, particularly by antagonizing, the function and/or activity of RAI-3. RAI-3 modulation can result in treatments for COPD, as well as for other diseases and disorders that are mediated by NF-κB and/or other molecules related thereto. Accordingly, the present invention further provides methods of treating diseases that are caused by, or are associated with, the NF-κB pathway and/or its components, preferably in which antagonist modulators of RAI-3 are employed to suppress, inhibit, or reduce the activity of the NF-κb pathway and/or its component molecules.

It is yet another aspect of the present invention to provide antisense nucleic acid molecules, and/or siRNA nucleic acid molecules, that specifically antagonize RAI-3 nucleic acid, e.g., by binding to mRNA of RAI-3, or RAI-3 peptides. Antisense molecules refer to nucleotide sequences, e.g., oligomers, and compositions containing nucleic acid sequences that are complementary to a specific DNA or RNA sequence, such as RAI-3 DNA or RNA sequences. In the case of siRNA, the specific DNA or RNA is preferably double stranded. Whether an antisense or siRNA molecule, the nucleic acid may be either a DNA, RNA, or DNA/RNA hybrid. The term "antisense strand" is used in reference to a nucleic acid strand that is complementary to the "sense" strand. Antisense (i.e., complementary) nucleic acid molecules include peptide nucleic acids ("PNAs"), as discussed below, and may be produced by any method, including synthesis or transcription. Once introduced into a cell, the complementary nucleotides combine with natural sequences produced by the cell to form duplexes, which block either transcription or translation of the RAI-3 mRNA or protein, respectively. The designation "negative" is sometimes used in reference to the antisense strand, and "positive" is sometimes used in reference to the sense strand.

PNAs are antisense molecules or anti-gene agents which comprise an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.*, 8:53-63). PNA may be pegylated to extend their life spans in the cell where they preferentially bind to complementary single stranded DNA and RNA.

An additional aspect of this invention pertains to the use of RAI-3 sequences and antibodies directed against the produced protein and peptides for diagnostic assessment of COPD, COPD-related disease states, or susceptibility to COPD and related disorders.

Another aspect of the present invention relates to a method of diagnosing, ameliorating, treating, reducing, eliminating, or preventing a disease, disorder, and/or condition affected by modulation of the G-protein coupled receptor protein RAI-3 in cells that express RAI-3, which involves providing a modulator, e.g., an agonist or antagonist, of RAI-3 in an amount effective to affect the function or activity of RAI-3, and/or to effect the function or activity of cellular molecules that are associated or correlated with modulated RAI-3 activity or function. In accordance with the present invention, the modulation of RAI-3 activity and/or function can occur in cells stimulated by a variety of stimuli, including cytokines, factors and chemokines, such as TNF-alpha, EGF, LPS, eotaxin, RANTES, smoke from tobacco burning materials such as cigarettes, and the like. In addition, the modulation of RAI-3 activity and/or function can occur as a result of cell exposure, interaction, or association with other molecules, such as, for example, cell adhesion molecules like I-CAM and E-selectin. Preferably, the cell stimulation, exposure, or interaction is associated with NF-κB activation. Examples of diseases, disorders, and/or conditions that can be diagnosed, ameliorated, treated, reduced, eliminated, or prevented by the methods of this invention, in which RAI-3 is modulated, include without limitation, COPD, the underlying symptoms of COPD, COPD-related disorders and/or conditions, autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, renal diseases, ischemia-reperfusion injury, heart disorders, disorders related to aberrant signal transduction, proliferation disorders, numerous types of cancers, such as lung cancer, stomach cancer, breast cancer, testicular cancer, etc., metastases, HIV infection, or HIV propagation in cells infected with other viruses, asthma, cystic fibrosis and pulmonary fibrosis.

Yet another aspect of the present invention provides a method for predicting the likelihood that an individual will be diagnosed as being at risk of developing COPD, a COPD-like disorder, or one or more of the underlying symptoms of COPD, upon exposure to cigarette smoke. The method comprises the steps of (a) obtaining a nucleic acid sample(s) from am individual to be assessed; and (b) determining the nucleotide present at one or more polymorphic position(s) of a gene of SEQ ID NO:2, wherein the one or more polymorphic position(s) is preferably selected from one or more of nucleotide positions 112, 364, 511, 523, 605, 797, 1111, or 1173 of SEQ ID NO:2 (see Tables 1 and 3 herein), and further wherein the presence of the alternative nucleotide at the one or more polymorphic position(s) as provided in Tables 1 and 3 indicates that the individual has a higher likelihood of being diagnosed as being at risk of developing COPD or a COPD-like disorder, or one or more of the underlying symptoms of COPD, compared to an individual having a reference allele at said polymorphic position(s).

In another of its aspects, the present invention relates to a method for predicting the likelihood that an individual will be diagnosed as being at risk of developing COPD, a COPD-like disorder, or one or more of the underlying symptoms of COPD upon exposure to cigarette smoke. The method comprises the steps of (a) obtaining a nucleic acid sample(s) from am individual to be assessed; and (b) determining the nucleotide present at one or more polymorphic position(s) of a gene of SEQ ID NO:2, wherein the one or more polymorphic position(s) is preferably selected from one or more of nucleotide positions 112, 364, 511, 523, 605, 797, 1111, or 1173 of SEQ ID NO:2 (see Tables 1 and 3 herein), and further wherein the presence of the alternative nucleotide at the one or more polymorphic position(s) as provided in Tables 1 and 3 indicates that the individual has a higher likelihood of being diagnosed as at risk of developing COPD, a COPD-like disorder, or one or more of the underlying symptoms of COPD, as compared to an individual having an alternate allele at the polymorphic position(s).

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of CRE response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are HEK cells.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, and further wherein said cells express the polypeptide at either low, moderate, or high levels.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said candidate compound is a small molecule, a peptide, or an antisense molecule.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said candidate compound is a small molecule, a peptide, or an antisense molecule, wherein said candidate compound is an agonist or antagonist.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said candidate compound is a small molecule, a peptide, or an antisense molecule.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said candidate compound is a small molecule, a peptide, or an antisense molecule, wherein said candidate compound is an agonist or antagonist.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said cells express beta lactamase at low, moderate, or high levels.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:3, or encoded by ATCC deposit RAI-3, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said cells express beta lactamase at low, moderate, or high levels.

The statement, "wherein said cells express beta lactamase at low, moderate, or high levels" is a reference to cells that either express beta lactamase at low, moderate, or high levels relative to the expression levels of a reference mRNA, gene, or protein; or a reference to the actual percentage of cells that express beta lactamase. In the latter example, high levels of expression would be achieved if the majority of cells were expressing beta lactamase, while low levels of expression would be achieved if only a subset of cells were expressing beta lactamase. Such cells may also express other proteins, such as the proteins of the present invention at low, moderate, or high levels as well.

Further aspects, features, and advantages of the present invention will be better appreciated upon a reading of the detailed description of the invention when considered in connection with the accompanying figures or drawings.

DESCRIPTION OF THE FIGURES

At least one Figure comprising this patent specification is executed in color. Copies of the patent with color Figure(s) will be provided by the U.S. Patent and Trademark Office upon request and payment of the necessary fee.

FIGS. 1A and 1B illustrate the results of Western Blot analysis of H292 lung airway epithelial cells (ATCC) using anti-phosphotyrosine (anti-Ptyr) antibodies. FIG. 1A illustrates the results of serum-starved H292 cells exposed to cigarette smoke bubbled medium (i.e., CS-240, the equivalent of 240 cigarettes per 500 ml of cell medium) for the periods of time shown (10 sec., 5 min., 10 min., 15 min., 30 min., 60 min., and 120 min.) and to EGF (10 nM) for 5 minutes. Whole cell lysates were obtained as described in the Examples herein, subjected to SDS-PAGE, transferred to PVDF membrane, and blotted with anti-Ptyr antibody conjugated to horse radish peroxidase (HRP). Molecular weight markers are shown in the left-most lane. FIG. 1B shows the results of immunoprecipitation of proteins from cigarette smoke-treated cell lysates, as described for FIG. 1A, using anti-EGFR antibody prior to SDS-PAGE and Western blotting analysis using anti-Ptyr antibody: For this experiment, 1.5 ml of cell lysate (~½ of a confluent T75 flask) was precleared twice with 50 µl of Protein A slurry with rotation at 4° C. Pre-cleared lysate was transferred to a new Eppendorf tube and 50 µl of Protein A and 2 µl of EGFR antisera (HER1/TWIB2 rabbit antisera to human EGFR) were added. After mixing for 1 hour at 4° C., the precleared lysate, Protein A and EGFR antisera were washed three times with Lysis buffer, one time with 1×PBS and aspirated "dry". Samples were subjected to SDS-PAGE and then transferred to nitrocellulose by standard western blotting techniques. The membranes were then blotted with the antiphosphotyrosine antibody HRP-Conjugated-4G10 #16-105 (Upstate Biotechnology, Inc. Lake Placid, N.Y.). (Example 1(C)).

FIG. 2A shows whole cell lysates from cigarette smoke-treated and control cells with no immunoprecipitation using anti-phosphotyrosine (anti-Ptyr) antibodies. FIG. 2B shows whole cell lysates from smoke treated and control cells following immunoprecipitation using anti-phosphotyrosine antibodies. Numerous phosphorylated proteins are observed in the smoke-treated cells after anti-Ptyr immunoprecipitation. Specifically, H292 lung airway epithelial cells were grown in complete RPMI media to confluence (approximately $3 \times 10^9$ cells in 24-500 cm² plates) and then serum-starved for 24 hours. The cells were then treated with CS-160 cigarette smoke-bubbled media (serum-free) for various times. CS-160 is equivalent to 160 cigarettes per 500 ml. After treatment, the cells were washed with ice-cold PBS and lysed in Lysis Buffer. The lysates were centrifuged and the supernatants recovered. Protein concentration was determined by a BCA assay. 10 µg of protein were run in each lane and blotted for anti-phosphotyrosine. (Example 1(D)). For immunoprecipitation of tyrosine phosphorylated proteins, cell lysates were first precleared and then incubated overnight at 4° C. with a 100 µg each of the five antibodies as described in Example 1(D). The bound proteins were incubated with a pre-washed cocktail of agarose beads conjugated to streptavidin, anti-mouse IgG and Protein G for two hours at 4° C. Precipitated immune complexes were then washed with lysis buffer including inhibitors, suspended in sample buffer, subjected to SDS-PAGE and then transferred to nitrocellulose by standard western blotting techniques. The membranes were then blotted with the antiphosphotyrosine antibody HRP-Conjugated-4G10 #16-105 (Upstate Biotechnology, Inc. Lake Placid, N.Y.).

In FIG. 7, A549, H292, BEAS-2B cell lines were seeded to confluency, starved for 24 hours, and then treated with 10 nM EGF for 30 minutes, 6 hours and 18 hours. RNA was harvested with the Rneasy Midi Kit (Qiagen, Hilden, Germany). The results show that RAI-3 mRNA expression is highest in H292 cells and does not show a clear induction in response to any treatment. RAI-3 expression is low in A549, BEAS-2B and Caco (colon, ATCC, Manassas, Va.) cells lines.

FIGS. 8A and 8B shows a characterization of RAI-3 stable cell lines and immunoprecipitation and Western Blotting as described in Example IJ herein. Controls included untransfected HEK293 cells (FIG. 8A) and a purified FLAG fusion protein (FIG. 8B).

FIGS. 10A and 10B present the full-length nucleotide sequence (2456 nucleotides) of human RAI-3 cDNA (RefSeq NM_003979), (SEQ ID NO:2).

FIGS. 11A-11C show the human RAI-3 polynucleotide and amino acid sequences. FIG. 11A shows the human RAI-3 amino acid sequence (357 amino acids), (SEQ ID NO:3), encoded by the RAI-3 nucleic acid sequence (SEQ ID NO:2) of FIGS. 10A and 10B. FIGS. 11B and 11C show the RAI-3 nucleic acid sequence (2456 nucleotides), (SEQ ID NO:2), and the encoded amino acid sequence of the RAI-3 polypeptide (SEQ ID NO:3). The RAI-3 peptide of SEQ ID NO:1 is underlined in FIG. 11C.

FIG. 12 presents a multiple sequence alignment of the human RAI-3 GPCR (RAI-3_HUMAN) amino acid sequence with four related GPCR amino acid sequences, namely, human GPCR5D (GPCR5D_HUMAN), (SEQ ID NO:4); murine GPCR5D (GPCR5D_MOUSE), (SEQ ID NO:5); human GPCR5B (GPCR5B_HUMAN), (SEQ ID NO:6); and human GPCR5C (GPCR5C_HUMAN), (SEQ ID NO:7). The GCG pileup program was used to generate the alignment. The blackened areas represent identical amino acid residues in more than half of the listed sequences and the gray highlighted areas represent similar amino acid residues.

FIG. 13 presents a multiple sequence alignment of the human RAI-3 GPCR amino acid sequence with other related GPCR sequences as described for FIG. 12. Non-synonymous SNPs are presented in double-underlined, italicized letters. The human RAI-3 amino acid sequence comprising the non-synonymous SNP (Ser/Gly) at amino acid position 118 (base A/G) is set forth in SEQ ID NO:8; and the human RAI-3 amino acid sequence comprising the non-synonymous SNP (Gln/Arg) at amino acid position 307 (base A/G) is set forth in SEQ ID NO:9.

(FIG. 14B and Example 3).

FIG. 15 shows the relative expression of RAI-3 in normal tissues, including various regions of the lung, as determined by quantitative PCR (Example 10). The high level of expression of RAI-3 in lung bronchus (tertiary) and lung parenchyma is particularly evident. For reference, primary lung airway tissue constitutes the trachea, while secondary lung tissue constitutes lobar tissue, both of which are major dissectible airways. Any airways which are distal to the primary and secondary airways, and which are greater than about 2 mm in diameter, are referred to as "tertiary". Quaternary refers to the smallest macroscopically dissectible bronchi of less than 2 mm in diameter. Such bronchi contain little or no macroscopically visible cartilage in their walls. More distal tissue comprises the parenchyma, which refers not only to alveoli, but also to very small bronchi and bronchioles, such as terminal and respiratory bronchioles.

FIG. 18 shows the results of quantitative PCR analysis in testicular tumors. (Example 10). Control testis tissue RNAs and testicular tumor RNAs were evaluated. It was demonstrated that testicular tumors (4 out of 5 samples) have elevated steady-state RAI-3 RNA levels.

FIGS. 19A and 19B show multiple amino acid sequence alignments of the SNP containing regions of human RAI-3 GPCR with RAI-3 sequences of other species and with other related GPCR sequences. The amino acids at the position of the SNPs are presented in larger, bold-faced type and are double underlined in all of the sequences. The human GPCR5D (GPCR5D_HUMAN) amino acid sequence is set forth in SEQ ID NO:4; the murine GPCR5D (GPCR5D_MOUSE) amino acid sequence is set forth in SEQ ID NO:5; the human RAI-3 amino acid sequence (RAI-3_HUMAN) is set forth in SEQ ID NO:3 (no SNPs); the human GPCR5D (GPCR5D_HUMAN) amino acid sequence as shown in FIG. 19A is set forth in SEQ ID NO:88; the mouse GPCR5D (GPCR5D_MOUSE) amino acid sequence as shown in FIG. 19A is set forth in SEQ ID NO:89; the mouse RAI-3 amino acid sequence (RAI-3_MOUSE) as shown in FIG. 19A is set forth in SEQ ID NO:10; the rat RAI-3 amino acid sequence (RAI-3_RAT) as shown in FIG. 19A is set forth in SEQ ID NO:11; the cow RAI-3 amino acid sequence (RAI-3_COW) as shown in FIG. 19A is set forth in SEQ ID NO:12; and the variant human RAI-3 amino acid sequence containing glycine at position 118 as a result of the Ser118Gly SNP, as shown in FIG. 19A, is set forth in SEQ ID NO:13. In FIG. 19B, the human GPCR5D (GPCR5D_HUMAN) amino acid sequence as shown in FIG. 19B is set forth in SEQ ID NO:90; the partial human RAI-3 amino acid sequence shown is set forth in SEQ ID NO:14 (no SNP); the variant human RAI-3 amino acid sequence containing arginine at position 307 as a result of the Glu307Arg SNP is set forth in SEQ ID NO:15; and the partial mouse RAI-3 sequence shown in FIG. 19B is set forth in SEQ ID NO:16.

FIG. 20 illustrates a comparison of the amino acid sequences of human RAI-3 and its murine RAI-3 orthologue. The alternative amino acids resulting from the missense SNPs in the RAI-3 nucleic acid sequence are shown in bold, double-underlining. Both the Ser118Gly and Thr182Ala SNPs occur at amino acid positions that are not conserved between the human and murine sequences. The Gln307Arg involves a conserved amino acid residue. The variant human RAI-3 amino acid sequence containing glycine at position 118 as a result of the Ser118Gly SNP is set forth in SEQ ID NO:13; the variant human RAI-3 amino acid sequence containing alanine at position 182 as a result of the Thr182Ala SNP is set forth in SEQ ID NO:17; and the variant human RAI-3 amino acid sequence containing arginine at position 307 as a result of the Gln307Arg SNP is set forth in SEQ ID NO:15.

FIG. 24A shows untransfected CHO/NFAT G alpha 15 cells prior to stimulation with 10 nM phorbol myristyl acetate (PMA) and 1 µM Thapsigargin/(− P/T). FIG. 24B shows CHO/NFAT-CRE cells after stimulation with 10 nM PMA and 1 µM Thapsigargin/(+ P/T). FIG. 24C shows CHO/NFAT G alpha 15 cells transfected with a representative orphan GPCR (oGPCR) and having an intermediate level of beta lactamase expression. FIG. 24D shows CHO/NFAT G alpha 15 cells transfected with a representative orphan GPCR (oGPCR) and having a high level of beta lactamase expression.

FIGS. 25A-25C presents the RAI-3 nucleic acid sequence and encoded amino acid sequence including polymorphic loci, e.g., single nucleotide polymorphisms (SNPs), at the designated positions in the sequence. The positions in the RAI-3 nucleic acid sequence comprising polymorphic loci are represented by an "n" (SEQ ID NO:18), wherein n includes the nucleotides as shown in Table 1; the amino acid changes related to the SNPs in the encoded RAI-3 amino acid sequence are designated with an "X" (SEQ ID NO:19), wherein X includes the amino acids as shown in Table 1. The underlined sequence (amino acids 340-353) in FIG. 25B represents the RAI-3 peptide of SEQ ID NO:1. Accordingly, the present invention is directed to a polynucleotide or a polypeptide comprising any combination of one or more of the polymorphisms according to those presented in FIGS. 25A-25C. The following Table 1 depicts the RAI-3 nucleic acid and amino acid sequences and various SNPs contained therein:

FIGS. 26A and 26B illustrate the results of Western Blot analysis of an A549 cell line (Human Lung Carcinoma CCL-185, American Type Culture Collection, Manassas, Va.) transiently transfected with a FLAG RAI-3 construct (described herein). Media on the cells was changed to serum-free and 48 hours port-transfection the cells were treated with cigarette smoke-bubbled media (i.e., CS-160, the equivalent of 160 cigarettes per 500 ml of cell medium) for the periods of time shown (1 hr., 2 hr., and 3 hr.) and with EGF (10 nM) for 5 minutes. Lysates were immuno-precipitated with 2 µg of anti-FLAG M2 antibody (Catalog # F-3165, Sigma, Saint Louis, Mo.) and 40 µl of Protein A. The Protein A/lysate/antibody mixture was washed, aspirated "dry", and 60 µl of 2×SDS-PAGE sample buffer was added. After heating at 95° C. for 10 minutes, the samples were loaded onto two 4-20% gradient gels, resolved by SDS-PAGE and transferred to nitrocellulose by standard Western Blotting techniques. The membranes were blotted/probed with either an anti-FLAG-HRP antibody (Sigma, Saint Louis, Mo., Catalog # A8592) as shown in FIG. 26A, or an anti-phosphotyrosine-HRP antibody (HRP-conjugated-4G10 antibody, #16-105, Upstate Biotechnology, Inc., Lake Placid, N.Y.) as shown in FIG. 26B. Lane 1 shows untreated A549/Flag-RAI-3, Lane 2 shows A549 cells transfected with Flag-RAI-3 plus EGF (10 nM) for 60 minutes, Lanes 3-5 show A549 cells transfected with Flag-RAI-3 treated with cigarette smoke-bubbled medium. Lane 6 shows untransfected A549 cells treated with cigarette smoke-bubbled medium and Lane 7 shows a control FLAG-fusion protein with a molecular weight of 52/48 kDa.

FIGS. 27A and 27B illustrate the results of a Western Blot analysis of a CHO/NFAT G alpha 15 cell line stably transfected with the pcDNA3.1/Flag-RAI-3 mammalian expression vector (Flag-RAI-3 CHO), as previously described and the results of a Western Blot analysis of the parental CHO cell line as a control. FIG. 27A illustrates the results of an anti-RAI-3 immunblot of lysates from ½ of a confluent T75 flask of either the stable Flag-RAI-3 CHO or parental cell line immuno-precipitated with 2 µg of anti-FLAG M2 antibody 5 (Catalog # F-316, Sigma, Saint Louis, Mo.) and 40 µl of Protein A. The Protein A/lysate/antibody mixture was washed, aspirated "dry", and 60 µl of 2×SDS-PAGE sample buffer was added. After heating at 95° C. for 10 minutes, the samples were loaded onto 4-20% gradient gels, resolved by SDS-PAGE and transferred to nitrocellulose by standard Western Blotting techniques. The membranes were blotted/probed with either an anti-FLAG-HRP antibody (Catalog # A8592, Sigma, Saint Louis, Mo.) at a 1:1000 dilution, a rabbit pre-immune antisera or rabbit RAI-3 anti-sera (GW7, Post Boost #4, production bleed) both at a 1:500 dilution. All samples were immunoprecipitated with an anti-Flag antibody. Lanes 1 and 2 show an anti-Flag blot of the Parental CHO and Flag-RAI-3 CHO, respectively. Lanes 3 and 4 show a rabbit pre-immune sera blot of the parental CHO cell line and Flag-RAI-3 CHO, respectively. Lanes 5 and 6 show a rabbit RAI-3 antisera blot of the parental CHO and Flag-RAI-3 CHO, respectively. FIG. 27B illustrates the results of an anti-Flag immunblot of lysates from ½ of a confluent T75 flask of either the stable Flag-RAI-3 CHO cell line or parental cell line immuno-precipitated with either 5 ul of rabbit RAI-3 antisera (GW7, Post Boost #4, production bleed antisera) and 40 µl of Protein A or 2 µg of anti-FLAG M2 antibody Catalog # F-3165 (Sigma, Saint Louis, Mo.) and 40 µl of Protein A. The Protein A/lysate/antibody mixture was washed, aspirated "dry", and 30 µl of 2×SDS-PAGE sample buffer was added. After heating at 95° C. for 10 minutes, the samples were loaded onto a 4-20% gradient gel, and resolved by SDS-PAGE and transferred to nitrocellulose by standard Western Blotting techniques. The membranes were blotted/probed with an anti-FLAG-HRP antibody (Sigma, Saint Louis, Mo., Catalog # A8592) at a 1:1000 dilution. All samples are immuno-blotted with an anti-FLAG-HRP antibody. Lanes 1 and 2 show the anti-Flag blot of the parental CHO and Flag-RAI-3 CHO cell lines immunoprecipitated 2 µg of anti-FLAG M2 antibody, respectively. Lanes 3 and 4 show the anti-Flag blot of the parental CHO and Flag-RAI-3 CHO cell lines immuno-precipitated with 5 ul of rabbit RAI-3 antisera (GW7, Post Boost #4, production bleed antisera).

FIG. 28A illustrates the results of Western Blot analysis of H292 lung airway epithelial cells (American Type Culture Collection (ATCC), Manassas, Va.) that were serum-starved for 24 hours and then treated with cigarette smoke-bubbled media (i.e., CS-160, the equivalent of 160 cigarettes per 500 ml of cell medium and CS-240) 3 hours. Lysates from ½ of a confluent T75 flask were immuno-precipitated with either a 4 ul of rabbit anti-EGFR (HER1 TW2, in-house) or 5 ul of rabbit RAI-3 and 40 µl of Protein A. The Protein A/lysate/antibody mixture was washed, aspirated "dry", and 30 µl of 2×SDS-PAGE sample buffer was added. After heating at 95° C. for 10 minutes, the samples were loaded onto a 4-20% gradient gel, resolved by SDS-PAGE and transferred to nitrocellulose by standard Western Blotting techniques. The membranes were blotted/probed with an anti-phosphotyrosine-HRP antibody (HRP-conjugated-4G10 antibody, #16-105, Upstate Biotechnology, Inc., Lake Placid, N.Y.). Lanes 1 and 4 show untreated H292s, Lanes 2 and 5 and show H292s treated 3 hours with cigarette smoke-bubbled medium, CS-160. Lanes 3 and 6 and show H292s treated 3 hours with cigarette smoke-bubbled medium, CS-240. Lanes 1-3 are immunoprecipitated with rabbit anti-EGFR and Lanes 4-6 are immunoprecipitated with rabbit anti-RAI-3. The membrane was blotted with an anti-phosphotyrosine-HRP antibody. FIG. 28B illustrate the results of Western Blot analysis of H292 lung airway epithelial cells (American Type Culture Collection (ATCC), Manassas, Va.) that were serum-starved for 24 hours and then treated with cigarette smoke-bubbled media. (i.e., CS-80, the equivalent of 80 cigarettes per 500 ml of cell medium, CS-160 and CS-240) for 3 hours. Lysates from ½ of a confluent T75 flask were immuno-precipitated with either 4 ul of rabbit anti-EGFR (HER1 TW2, in-house), 5 ul of rabbit pre-immune sera, or 5 ul of rabbit RAI-3 and 40 µl of Protein A. The Protein A/lysate/antibody mixture was washed, aspirated "dry", and 30 µl of 2×SDS-PAGE sample buffer was added. After heating at 95° C. for 10 minutes, the samples were loaded onto a 4-20% gradient gel, resolved by SDS-PAGE and transferred to nitrocellulose by standard Western Blotting techniques. The membranes were blotted/probed with an anti-phosphotyrosine-HRP antibody (HRP-conjugated-4G10 antibody, #16-105, Upstate Biotechnology, Inc., Lake Placid, N.Y.). Lanes 1, 4 and 7 show H292s treated 3 hours with cigarette smoke-bubbled medium, CS-80. Lanes 2, 5 and 8 show H292s treated 3 hours with cigarette smoke-bubbled medium, CS-160. Lanes 3, 6 and 9 show H292s treated 3 hours with cigarette smoke-bubbled medium, CS-240. Lanes 1-3 were immunoprecipitated with rabbit anti-EGFR. Lanes 4-6 were immunoprecipitated with rabbit pre-immune sera. Lanes 7-9 were immunoprecipitated with rabbit anti-RAI-3. The membrane was blotted with an anti-phosphotyrosine-HRP antibody.

K for 8 minutes at 4° C. to pellet. Cells were resuspended in 0.2 ml of binding buffer which was composed from DMEM (Gibco/BRL/Invitrogen Corporation, Carlsbad, Calif.) with a final concentration of 1% BSA (30% solution, Sigma-Aldrich Co. Saint Louis, Mo.) and 0.02% azide. Rabbit anti sera was added at a dilution of 1:250. The cells and antibody mixture was incubated for one hour on ice. The cells were centrifuged at 1.5 K for 8 minutes at 4° C. to pellet and washed twice with 10 ml of binding buffer and resuspended in a final volume of 0.2 ml of binding buffer containing the 2° antibody a Fluorescein (FITC)-conjugated AffiniPure F(ab')$_2$ Goat Anti-Rabbit IgG.at a dilution of 1:200 (Jackson Immunoreseach Laboratories, Inc, West Grove, Pa.). The cells and antibody mixture was incubated for 30 minutes on ice. The cells were centrifuged at 1.5 K for 8 minutes at 4° C. to pellet and washed twice with 10 ml of binding buffer and resuspended in a final volume of 0.5 ml of binding buffer for FACS analysis. The cells were analyzed on a Becton Dickenson FACSort using Cell Quest software (Becton-Dickenson, Franklin Lakes, N.J.). Cells were live gated and red/green color was compensated.

Figure 31:
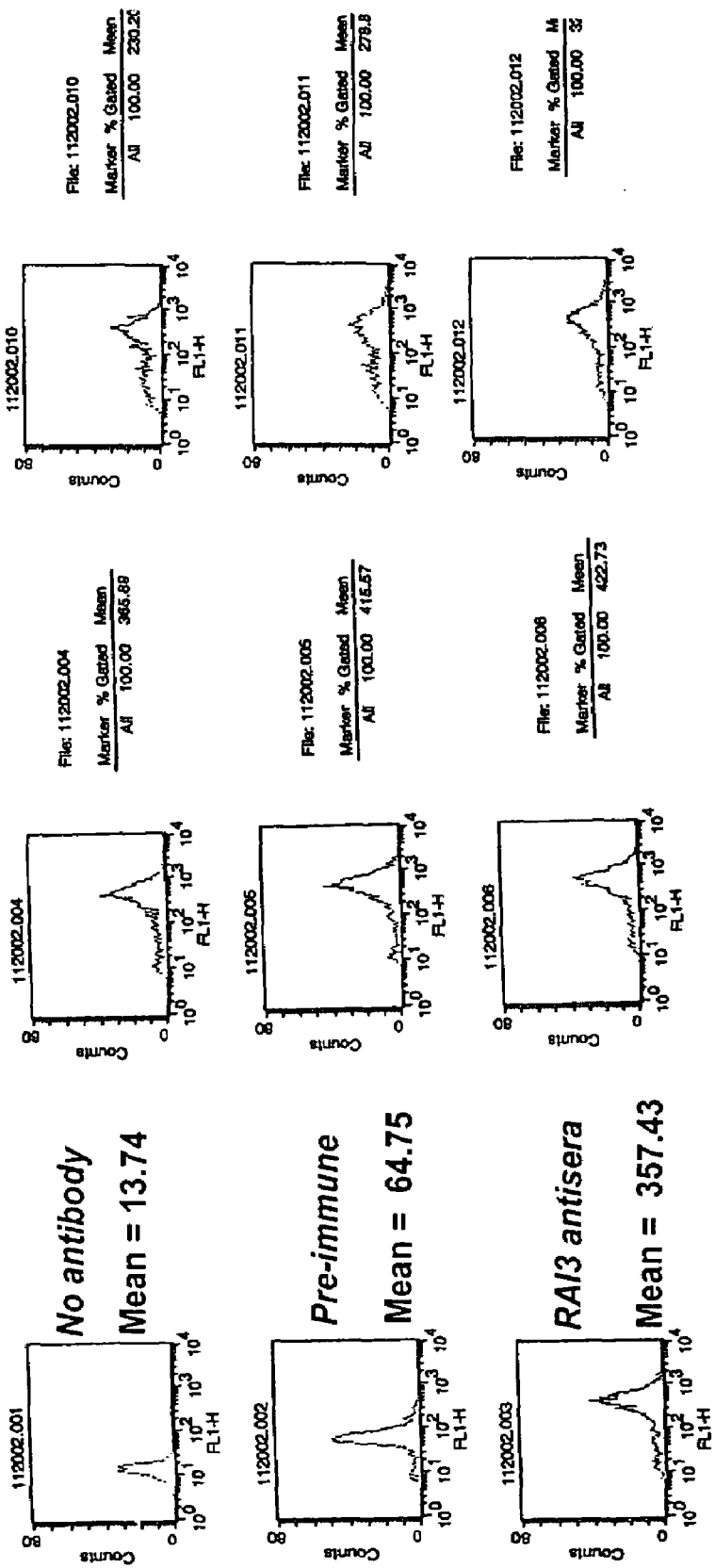

FIG. 31 illustrates the results of a FACs analysis of the H292 cell line transfected with the RAI-3 siRNA reagent 1864+1865 and controls. The most right column show the FACs analysis histogram of control H292 cells that were not transfected with Lipofectamine or siRNA. The top analysis figure show the mean signal when no antibody was added to the cells, the middle analysis figure shows the mean signal when the pre-immune antisera from the GW7 rabbit was added, and the bottom analysis figure shows the mean signal when the post boost #4 bleed of the rabbit RAI-3 antisera, GW7 was added. The middle column shows the FACs analysis histograms of control H292 cells that were transfected, in triplicate, with Lipofectamine 2000 alone without any siRNA. The most right column shows the histograms of H292 cells that were transfected, in triplicate, with the RAI-3 siRNA reagent 1864+1865. FACs analysis of H292 cells that were transfected, in triplicate, with control siRNA reagents (described in herein), showed an average mean greater than the controls. The day before transfection, ~2.5×10$^4$ H292 cells/well were seeded into 24 well-plates in RPMI media containing 10% fetal bovine serum, 20 mM Glutamine, 1% Penicillin-Streptomycin (Gibco/Invitrogen Corporation, Carlsbad, Calif.). On the day of the transfection, the cells were ~90% confluent and the media was replaced with RPMI media containing 10% fetal bovine serum and 20 mM Glutamine and no antibiotics. For each well, 4 ul of a 20 uM stock of the siRNA was diluted into 50 ul Opti-MEM (Gibco/Invitrogen Corporation, Carlsbad, Calif.). In a separate tube, 2 ul of Lipofectamine 2000 (Invitrogen Corp., Carlsbad, Calif.) was diluted into 50 ul of Opti-MEM. The diluted siRNA and the diluted Lipofectamine 2000 solutions were mixed and left at room temperature for 20 minutes. The mixture was then added to the cells containing media without antibiotics and incubated at 37° C., 5% CO2, for 24 hours. The transfections were done in triplicates. Cells (siRNA transfected as described above) from each well of the 24 well-culture plates (i.e., ~0.5×10$^5$ cells) were washed once with 1×PBS and then lifted from the plates with 0.5 ml of Cell Stripper (Cellgro/Mediatech, Herndon, Va.). 3 ml of 1×PBS was added to wash cells and then the cells were centrifuged at 1.5 K for 8 minutes at 4° C. to pellet. Cells were resuspended in 0.2 ml of binding buffer which is composed from DMEM (Gibco/BRL/Invitrogen Corporation, Carlsbad, Calif.) with a final concentration of 1% BSA (Sigma-Aldrich Co. Saint Louis, Mo.) and 0.02% azide. Rabbit anti sera was added at a dilution of 1:250. The cells and antibody mixture was incubated for one hour on ice. The cells were centrifuged at 1.5 K for 8 minutes at 4° C. to pellet, washed twice with 10 ml of binding buffer and resuspended in a final volume of 0.2 ml of binding buffer containing the 2° antibody a Fluorescein (FITC)-conjugated AffiniPure F(ab')$_2$ Goat Anti-Rabbit IgG.at a dilution of 1:200 (Jackson Immunoreseach Laboratories, Inc, West Grove, Pa.). The cells and antibody mixture was incubated for 30 minutes on ice. The cells were centrifuged at 1.5 K for 8 minutes at 4° C. to pellet washed twice with 10 ml of binding buffer and resuspended in a final volume of 0.5 ml of binding buffer for FACS analysis. The cells were analyzed on a Becton Dickenson FACSort using Cell Quest software (Becton-Dickenson, Franklin Lakes, N.J.). Cells were live gated and red/green color was compensated.

Figure 32:
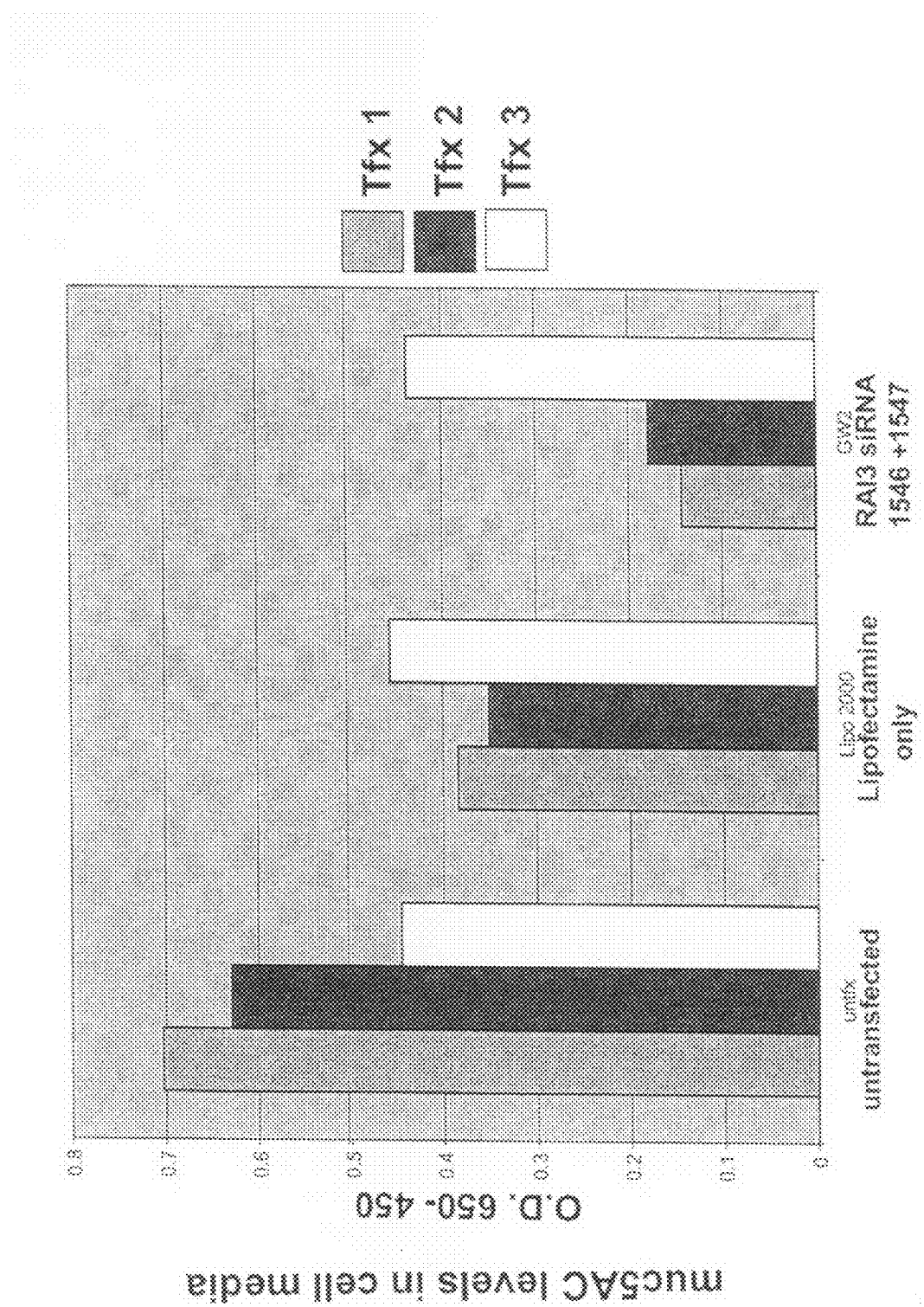

FIG. 32 illustrates the results of an ELISA assay detecting muc5AC protein levels in the supernatants of H292 cells transfected with the RAI-3 siRNA reagent 1864+1865 and exposed to cigarette smoke bubbled media, CS-10. Shown on the left are H292 cells that were untransfected, in triplicate, and exposed to cigarette smoke bubbled media, CS-10, for 72 hours. Shown in the middle, are H292 cells that were transfected with Lipofectamine 2000 alone without any siRNA, in triplicate, and exposed to cigarette smoke bubbled media, CS-10, for 72 hours. Shown on the left are H292 cells that were transfected with the RAI-3 siRNA reagent 1864+1865, in triplicate, and exposed to cigarette smoke bubbled media, CS-10, for 72 hours. Untransfected controls (in triplicate) receiving CS-10 media showed a 7.73 fold increase in the levels of muc5AC protein in the supernatant when compared to the supernatant of cells with only serum-free RPMI media (CS-10: average signal 0.5927, StDev 0.1326, serum-free media: average signal 0.0766, StDev 0.0339).

FIG. 33 shows the results of immunohistochemical (IHC) staining in human lung tissue using rabbit ant-RAI-3 antisera. Anti-RAI-3 antisera was generated using a synthesized peptide corresponding to amino acids 269-284 of SEQ ID NO:3 as described herein. Panel A shows RAI-3 staining in respiratory epithelium in normal lung isolated from a 78-year-old female at 40× magnification. Panel B shows RAI-3 staining in respiratory epithelium in normal lung isolated from a 47-year-old female at 40× magnification. Panel C shows RAI-3 staining in respiratory epithelium in emphysema lung isolated from a 57-year-old female at 40× magnification. The level of staining of RAI-3 in emphysema tissues is more pronounced as compared to the level of staining observed in normal lung tissue. The results are consistent with the putative role of RAI-3 in the pathobiology of cigarette smoke-related pulmonary disease.

FIG. 34 shows the results of immunohistochemical (IHC) staining in human lung tissue using rabbit ant-RAI-3 antisera. Anti-RAI-3 antisera was generated using a synthesized peptide corresponding to amino acids 269-284 of SEQ ID NO:3 as described herein. Panel A shows RAI-3 staining in respiratory epithelium in bronchitus lung isolated from a 56-year-old male at 40× magnification. Panel B shows RAI-3 staining in respiratory epithelium in bronchitus lung isolated from a 63-year-old male at 40× magnification. Panel C shows RAI-3 staining in seromucous glands in bronchitus lung isolated from a 63-year-old male at 40× magnification. Panel D shows RAI-3 staining in mucosal inflammation in bronchitus lung isolated from a 63-year-old male at 40× magnification. The level of staining of RAI-3 in bronchitis, seromucous gland, and mucosal inflammation tissues is more pronounced as compared to the level of staining observed in normal lung tissue (compare Panels A and B in FIG. 33). The results are consistent with the putative role of RAI-3 in the pathobiology of cigarette smoke-related pulmonary disease.

Figure 6:
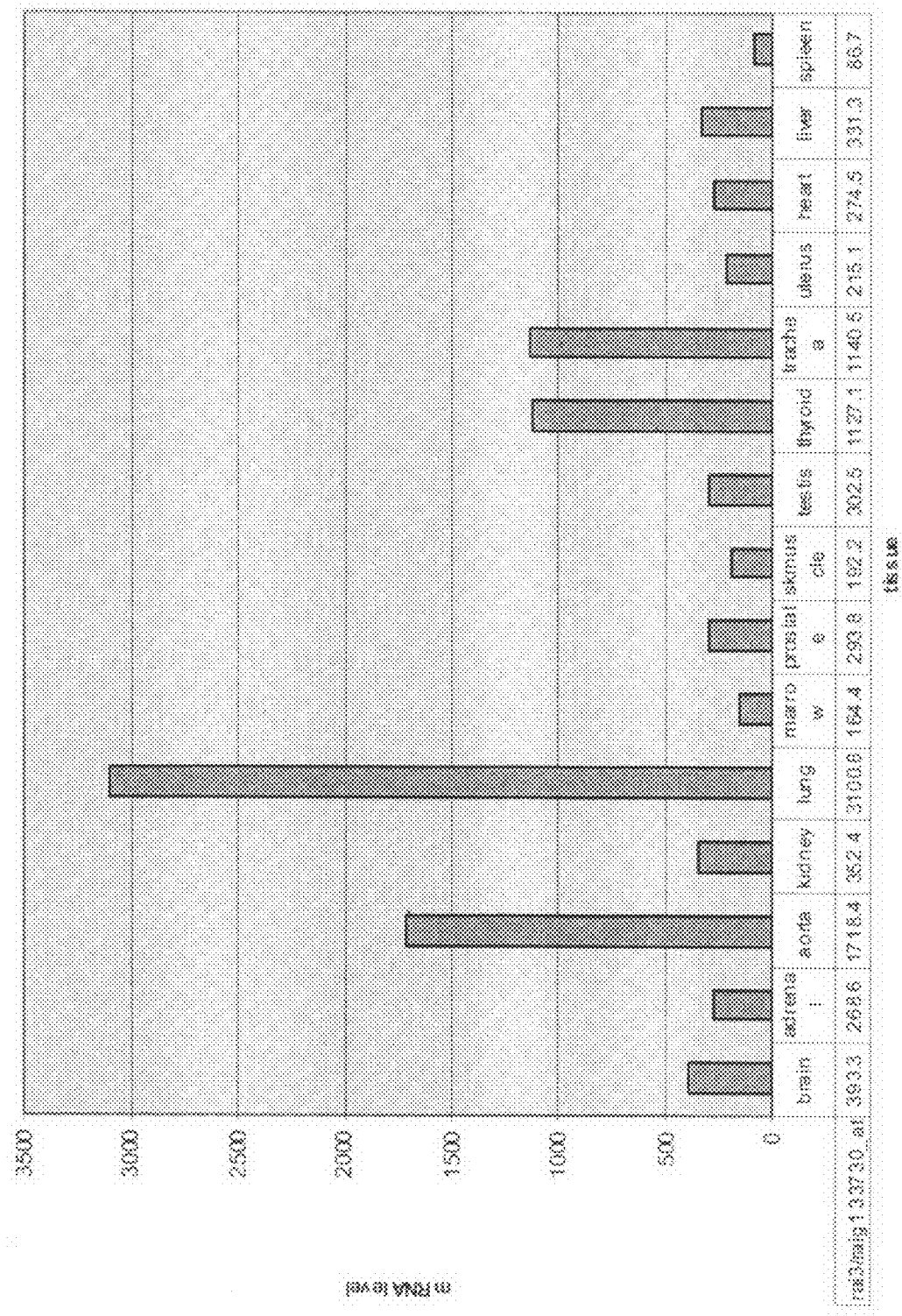
FIGS. 6 and 7 show the results gene chip experiments as described in Example 1(R) herein. The Affymetrix human U95v2 A, B, and C chips were probed with biotinylated in vitro transcription product prepared from sample mRNA obtained from the various tissues shown, per the manufacturer's instructions (see: *Protocol for Affymetrix Gene Chip Expression*). Hybridization, wash, and Phycoerythrin streptavidin staining were performed using the Affymetrix hybridization oven and fluidics workstation per the manufacturer's protocols (Chapter 6 of Affymetrix GeneChip Expression Analysis Manual, revision 2). Stained chips were scanned on the Affymetrix GeneChip scanner, and data were analyzed using the Affymetrix GeneChip software to determine the specifically hybridizing signal for each gene. The results represent the average of standard deviation (SD) of 3 replicates. The results in FIG. 6 show that RAI-3 relative message level is highest in the lung, followed by the aorta, trachea and thyroid. Expression levels in the other tissues tested is low.
Figure 7:
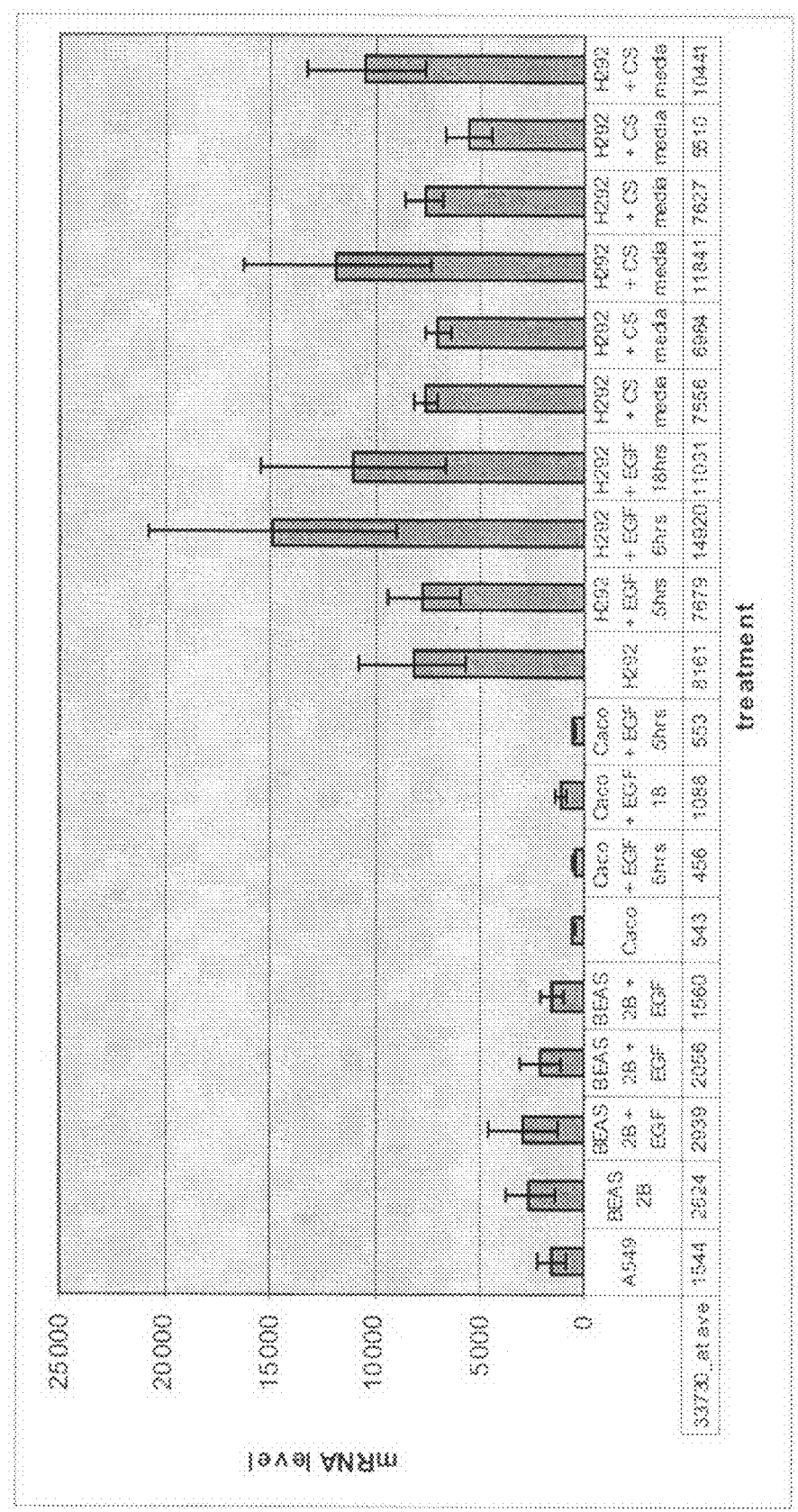

FIG. 35 shows the β-lactamase concentration response curve obtained from the UHTSS system for Compound 1 that was identified by screening the RAI-3 polypeptide for modulators (Panel A). Panel B shows the β-lactamase concentration response curve obtained from the UHTSS system for Compound 1 against another G-protein coupled receptor, HGPRBMY7. The constitutive level of activity of the RAI-3 expressing cell lines was matched to the level of constitutive activity for HGPRBMY7 for all data points. The data demonstrates that Compound 1 is a selective modulator of RAI-3.

lated RAI-3 protein has been newly found to be associated with the exposure of cells to cigarette smoke. Because of its first identification as a protein whose expression and modification are linked to smoke exposure of cells, and thus to COPD as described herein, RAI-3 emerges by virtue of the present invention as a new target for use in identifying RAI-3 modulators, e.g., drugs, compounds, or biological agents, and the like, for the treatment and prevention of COPD and COPD related diseases, disorders and conditions. Because RAI-3 was found to be expressed primarily in lung tissue (FIG. 6), it is an especially appealing target for the identification and screening of drugs for the treatment and prevention of COPD.

TABLE 1

| ID | Position in RAI-3 Nucleic Acid Sequence (cDNA) in FIGS. 25A-C | Corresponding Nucleotides in FIGS. 25A-C (wt nt/variant nt*) | Amino Acid/ Position in RAI-3 Amino Acid Sequence in FIGS. 25A-C | Corresponding Amino Acid in FIGS. 25A-C (wt aa/variant aa**) |
|---|---|---|---|---|
| RAI-3-s1 | 112 | g/a | | |
| RAI-3-s2 | 364 | c/t | 37 (Ala37Ala) | Ala/Ala |
| RAI-3-s3 | 511 | c/t | | |
| RAI-3-s4 | 523 | c/t | | |
| RAI-3-s5 | 797 | a/g | 182 (Thr182Ala) | Thr/Ala |
| RAI-3-s6 | 605 (dbSNP rs850932¥) | a/g | 118 (Ser118Gly) | Ser/Gly |
| RAI-3-s8 | 1111 | t/c | 286 (Pro286Pro) | Pro/Pro |
| RAI-3-s9 | 1173 | a/g | 307 (Gln307Arg) | Gln/Arg |

*wild-type nucleotide/variant nucleotide
**wild-type amino acid/variant amino acid
¥The Ser118Gly missense SNP was identified as rs850932 in the NCBI SNP database (NCBI dbSNP).

DETAILED DESCRIPTION OF THE INVENTION

The present invention describes the identification of proteins and their component peptides that are activated and/or modified when cells are exposed to smoke resulting from the burning of tobacco containing products and substances, namely cigarette smoke. Since cigarette smoke is the major causative factor for COPD, identifying the proteins and signal transduction pathways that are activated and/or modified when cells are exposed to cigarette smoke is newly provided as a critical aspect of identifying new drug targets for the treatment of COPD as described herein. In accordance with this invention, proteomics methods were designed and used to isolate cigarette smoke-inducible tyrosine phosphorylated proteins (activation complexes) from airway epithelial cells exposed to smoke. (Examples 1D-1F).

This strategy was employed based on the following non-limiting hypothesis according to this invention: Exposure to smoke induces oxidative stress, inhibits phosphatases, activates Src and transactivates EGFR, and potentially other receptor tyrosine kinases. This activation contributes to the transcription of mucin and cytokine genes which, in turn, contribute to the cause and symptoms of COPD. Compounds that are able to inhibit this activation, e.g., by affecting cellular proteins and/or peptides that are induced, activated and/or modified following cigarette smoke exposure, are thus reasoned to be useful as drugs for treating COPD.

In accordance with the present invention, the RAI-3 protein, a member of the G-protein coupled receptor superfamily, was newly identified among the various proteins found to be tyrosine phosphorylated (or associated/complexed with tyrosine phosphorylated proteins) only in cells that had been exposed to cigarette smoke. As described herein, phosphory- Briefly, to achieve the identification of proteins having a strong link to the exposure of cells to cigarette smoke, and thus a link to COPD, airway epithelial cells (lung cells) were treated both with and without cigarette smoke-bubbled media. (Examples 1A and 1B). Whole cell lysates were harvested and the proteins therein purified using anti-phosphotyrosine antibodies. The purified phosphorylated proteins were then proteolyzed together and the polypeptide fragments so created were identified by packed capillary HPLC coupled to tandem mass spectrometry. (Examples 1D and 3E). Data were searched, and peptides identified, using the SEQUEST algorithm as further described herein. Approximately 350 proteins were identified as being tyrosine phosphorylated (or associated with tyrosine phosphorylated proteins) only in those cells that had been exposed to cigarette smoke (treated cells). Included among the 350 identified proteins were a variety of signaling molecules, components of the epidermal growth factor receptor (EGFR) pathway, and RAI-3. The proteins found to be present in the treated versus the untreated samples were compared to identify those proteins that were activated by the cigarette smoke treatment, either exclusively or preferentially. Using this technique, certain peptides corresponding to the amino acid sequence of the RAI-3 (Retinoic Acid Induced 3) protein were isolated and the peptides were used in the determination of RAI-3 as a target protein for COPD treatment and prevention.

The gene encoding RAI-3, (formerly known as RAIG1), was reported in connection with studies performed to identify retinoic acid-regulated genes from a human oral squamous carcinoma cell line. (Y. Cheng and R. Lotan, 1998, "Molecular cloning and characterization of a novel retinoic acid-inducible gene that encodes a putative G protein-coupled receptor", *J. Biol. Chem.*, 273:35008-15). In their studies, Cheng and Lotan used differential display to identify retinoic acid-regulated genes from a human oral squamous carcinoma cell line to better understand the mechanisms through which retinoids suppress carcinogenesis. A cDNA corresponding to a retinoic acid-induced gene was named RAIG1. Subsequently, RAIG1 was renamed "RAI-3", as it is now known. Synonyms for RAI-3 include RAI-3; Retinoic Acid Induced 3; RAIG1; raig1 and GPRC5A.

According to Cheng and Lotan, RAI-3 expression was induced in cells subjected to all-trans-retinoic acid (ATRA) rapidly and in a dose-dependent manner. The levels of RAI-3 mRNA in different cancer cells varied greatly, with no correlation between the expression levels and the type of cancer cells. RAI-3 was also nonspecifically expressed in several normal human tissues, with the highest expression levels found in fetal and adult lung. Northern blot analysis detected two RAI-3 transcripts of 2.4 and 6.8 kb, which were surmised to result from the alternative use of different polyadenylation sites. (Cheng and Lotan, 1998, Ibid.).

The approved UCLA/HGNC/HUGO Human Gene Nomenclature database symbol is RAI-3 (retinoic acid induced 3), which corresponds to RefSeq NM_003979 (NCBI Database), which is 2456 bases in length (RAI-3 sequences: FIGS. 10A and 10B and FIGS. 11B and 11C), (SEQ ID NO:2).

The human RAI-3 polynucleotide sequence encodes a deduced protein of 357 amino acids in length (SEQ ID NO:3), with a calculated molecular mass of 40,256 Da. RAI-3 contains 7 predicted transmembrane domains, which is a signature motif of the G protein-coupled receptor superfamily, and a potential N-linked glycosylation site. Using a combination of radiation hybrid mapping and YAC contig mapping, the RAI-3 gene was localized to 12p13-p12.3, between markers D12S358 and D12S847. (Cheng and Lotan, 1998, Ibid.).

RAI-3 is a member of the GPCR Class C Family of Metabotropic glutamate/pheromone GPCRs and defined a new group in Class C, Group 5. Group 5 GPCR family members are most homologous to Class C GPCRs, although topographically they are more similar to the Class A GPCRs which have short extracellular amino terminal domains, rather than to the very long extracellular amino terminal domains of the Class C GPCRs. Since the time that RAI-3 was cloned, three new members of the group, GPRC5B, GPRC5C and GPRC5D have all been cloned by bioinformatics methods (H. Brauner-Osborne et al., 2000, *Genomics*, 65:121-128; M. J. Robbins et al., 2000, *Genomics*, 67:8-18; H. Brauner-Osborne et al., 2001, *Biochim Biophys Acta*, 1518:237-248).

Figure 9A:
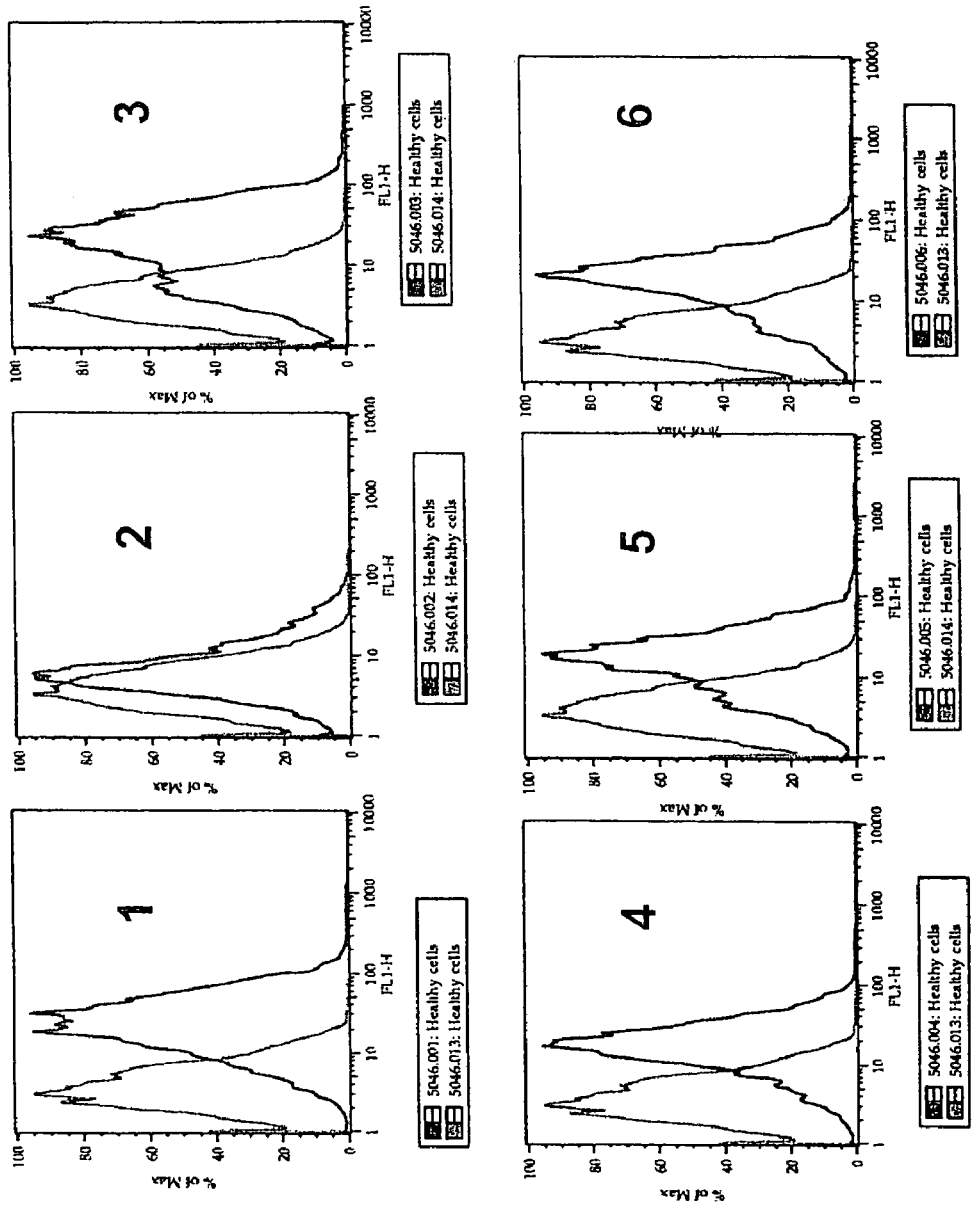
FIGS. 9A and 9B show a characterization of RAI-3 stable cell lines by FACS analysis as described in Example IK herein.
Figure 9B:
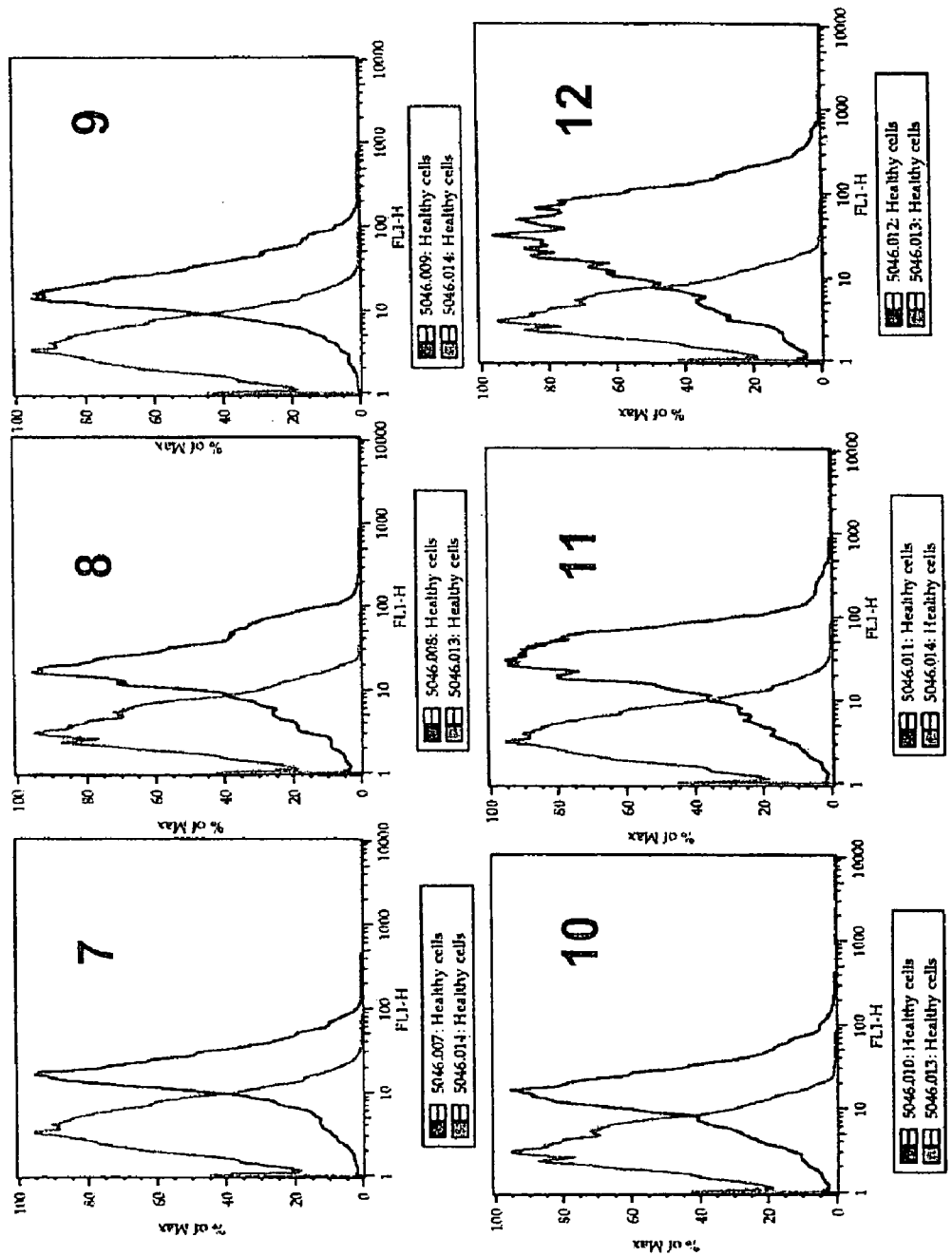

The GCG pileup program was used to generate a multiple sequence alignment of RAI-3 with other Class C, Group 5 family members (FIG. 9). The percentage identities and similarities between RAI-3 and other Class C, Group 5 family members were generated using the general method of S. B. Needleman and C. D. Wunsch. (1970, "A general method applicable to the search for similarities in the amino acid sequence of two proteins", *J. Mol. Biol.*, 48(3):443-53) and are shown in Table 2. Specifically, the GAP global alignment program in GCG was used to calculate the percent identity and similarity values presented in Table 2. The following GAP program parameters were used to obtain the values: gap creation penalty: 6; and gap extension penalty: 2.

TABLE 2

Sequence Similarity/Identity of Human RAI-3 with Other GPCR Class C, Group 5 Family Members

|  | Identity (%) | Similarity (%) |
| --- | --- | --- |
| Human RAI-3 vs Human GPCR5B | 37.791 | 46.512 |
| Human RAI-3 vs Human GPCR5C | 40.510 | 49.858 |
| Human RAI-3 vs Human GPCR5D | 45.455 | 53.079 |
| Human RAI-3 vs Mouse GPCR5D | 46.959 | 55.405 |

As can be seen from Table 2, human RAI-3 is most similar to GPCR5D (45% sequence identity with human GPCR5D and 47% sequence identity with murine GPCR5D) and to GPRC5C (41% sequence identity).

In accordance with an embodiment of the present invention, proteomics methods (i.e., a combination of biochemistry and analytical chemistry techniques) were used to test a premise according to the present invention that certain proteins would become phosphorylated directly or indirectly (e.g., by associating with already-phosphorylated proteins, or with proteins that became phosphorylated) as a result of exposure of epithelial airway cells with solubilized cigarette smoke (Examples 1A-1F). This premise was based upon observations that the oxidative stressing of these cells by solubilized cigarette smoke and by other agents (e.g., *J. Immunol.*, 2000, 164(3):1546-1552) contributed to an increase in the transcription of mucin and cytokine genes, and that the concomitant translations of these transcripts contributed to the cause(s) and underlying symptoms of COPD. Thus, cellular proteins induced, activated and/or modified by exposure to cigarette smoke, or smoke from other tobacco burning materials, would make good candidate targets for the diagnosis, screening, prognosis and treatment of the cause(s) and symptoms of COPD. Thus, using proteomics methods and a series of replicate experiments and evaluation, a set of proteins was identified, one of which was the RAI-3 protein. The discovery of RAI-3 following cigarette smoke exposure of airways cells supported the premise that certain proteins were indeed tyrosine phosphorylated directly, or indirectly by associating with other proteins that were already phosphorylated, or that became phosphorylated, following treatment of epithelial airway cells with solubilized cigarette smoke.

As a protein that by itself is a candidate for activating genes that cause the symptoms and/or the effects of COPD, or for playing a more indirect role in such gene activation, RAI-3, and peptides thereof, are thus provided as pivotal targets for treating and/or preventing COPD according to this invention. In addition, modification and/or activation of RAI-3 following cellular exposure to cigarette smoke can serve directly to cause or maintain the effects of COPD, and/or its symptoms.

Figure 5:
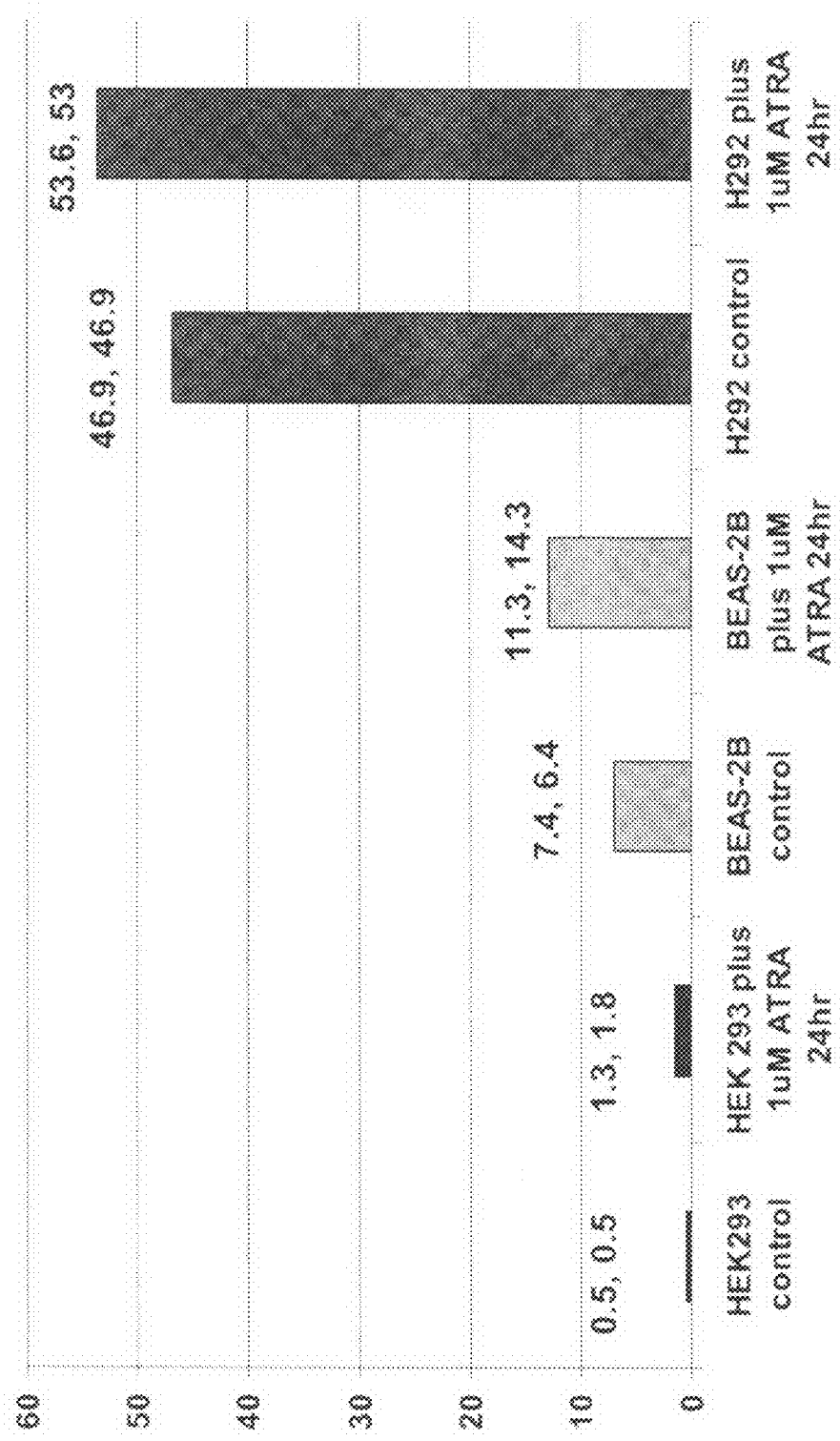
FIG. 5 shows the results of treating cells (HEK 293, BEAS-2B, and H292) with all-trans retinoic acid (ATRA), (1 µM), for 24 hours as described in Examples 1N and 1O herein. Transcription of RAI-3 mRNA is induced relative to control cells that were not treated with ATRA. Data are expressed as a fold increase over a reference tissue or cell type. Duplicate data values are shown above the bars.

The RAI-3 protein is also regulated by all-trans-retinoic acid (ATRA), as RAI-3 mRNA levels were found to increase in response to ATRA (Example 1(M) and FIG. 5). Because RAI-3 is a member of the GPCR protein family, its induction by ATRA indicates that the effects of retinoids, e.g., ATRA, and GPCR signal transduction pathways are linked or associated. Thus, RAI-3 could further play a role in mediating the effects of ATRA on embryogenesis, differentiation and tumorigenesis. (L. J. Gudas, 1994, *Curr. Opin. Cell Biol.*, 6:825-831; G. M. Morriss-Kay and N. Sokolova, 1996, *FASEB J.*, 10:961-968; M. B. Sporn et al., 1994, The Retinoids: Biology, Chemistry and Medicine, 2nd Ed., Raven Press, New York, N.Y.). Experiments in which rats displaying characteristics of human and experimental emphysema were treated with ATRA resulted in a reversal of the adverse changes to the lungs (G. D. Massaro et al., 2000, *Am J Physiol Lung Cell Mol Physiol.*, 278(5):L955-L960). Because RAI-3 mRNA levels are increased in response to ATRA in animal models of emphysema, RAI-3 is a candidate protein for involvement in regenerating lung tissue and elasticity in the treatment of COPD and emphysema, particularly in response to ATRA treatment of lung related diseases.

Further, RAI-3 may also be involved in processes that reverse malignant transformation, in view of RAI-3 mRNA levels being increased in response to ATRA. Retinoids, such as ATRA, have been shown to be able to reverse malignant transformation in several chemoprevention trials. More specifically, retinoids have been shown to suppress oral premalignant leukopakia lesions and decrease the incidence of second primary tumors in head and neck cancer patients (P. G. Sacks et al., 1989, *Head Neck*, 11(3):219-25). Thus, modulators of RAI-3, such as agonist compounds, can be considered to be efficacious in enhancing the reversal of lung deterioration and disease, as well as in enhancing the reversal of malignant transformation. Accordingly, uses of RAI-3 modulators, e.g., agonists and/or antagonists, encompass treatments for COPD and COPD related disorders, as well as for cancers, e.g., lung cancer, breast cancer, stomach cancer, testicular cancer, etc., as well as malignancies, so as to result in reduction, amelioration, reversal, or elimination of a disease, disorder or condition associated with RAI-3 activity and/or function.

In one embodiment of the present invention the RAI-3 nucleic acid and/or amino acid sequences, or a fragment thereof, e.g., oligomers or peptides, can be used to diagnose or screen for COPD, or COPD related diseases or disorders, for example, by assaying for over- or under-expression of the RAI-3 protein or RAI-3 peptides, as is further described herein. Expression of RAI-3 in individuals having COPD or a COPD related disorder, or in those individuals suspected of having COPD or a COPD related disorder, can be assessed by identifying mutations in the RAI-3 protein or in mRNA levels. As discussed further herein, an RAI-3 polypeptide or peptide is useful for screening compounds that affect the activity or function of the RAI-3 protein as a target for compounds that are suitable for use in treatments and therapies for COPD or COPD related conditions, diseases and disorders.

Additional evidence that RAI-3 is involved in the cellular response to cigarrette smoke demonstrates that RAI-3 is tyrosine phosphorylated in response to cigarette smoke, but not in response to EGF (see FIG. 26A). The results also demonstrate that endogenous RAI-3 protein in H292 cell lines is tyrosine phosphorylated or associated with tyrosine phosphorylated proteins in the H292 cell line in response to cigarette smoke (see FIG. 26B). The blot in FIG. 26B is a result of an immunoprecipitation using anti-flag antibodies and blotting the gel with an anti-phosphotyrosine secondary antibody.

Specifically, a transient transfection of a A549 cell line with a Flag-RAI-3 construct (described herein) shows that an anti-flag immunoprecipitate containing the recombinant Flag-RAI-3 protein is tyrosine phosphorylated in response a 1 to 3 hour exposure to cigarette smoke-bubbled media, CS-160 (FIG. 26A and FIG. 26B). The blot in FIG. 26A is a result of an immunoprecipitation using anti-flag antibodies and blotting the gel with an anti-flag secondary antibody. CS-160 for 3 hours is equivalent to the dose that was used in the initial Proteomics experiments that led to the identification of RAI-3 as being a component of a cigarette smoke-induced tyrosine phosphorylated complex. These results also show that EGF does not appear to cause tyrosine phosphorylation of the recombinant FLAG-RAI-3 protein in this experiment.

The latter results were confirmed to be specific to RAI-3 by generating anti-RAI-3 antibodies and repeating the blots with the anti-RAI-3 antibody (see FIGS. 27A and 27B).

Rabbit anti-RAI-3 polyclonal antibody was generated by immunizing mice with an RAI-3 protein antigen (MS2-RAI-3 fusion protein as described herein). The rabbit RAI-3 antisera was able to recognize a protein of the predicted molecular weight of 41 kDa in a lysate of a stable Flag-RAI-3 CHO cell line (previously described) when immunoprecipitated with an anti-Flag antibody (FIG. 27A). The rabbit RAI-3 antisera was able to immunoprecipitate a protein the predicted molecular weight from a lysate of a stable a stable Flag-RAI-3 CHO cell line and detected with an anti-Flag-HRP antibody (FIG. 27B). In addition to detecting a protein of the predicted molecular weight, the detection with an anti-Flag antibody of the rabbit RAI-3 antisera immunoprecipitate of the Flag-RAI-3 CHO cell line, showed a smear of high molecular weight bands. This is consistent with the observations that HEK293 extracts over-expressing a c-myc-GPRC5B receptor (RAI-3, aka GPRC5A, family member) when probed with rabbit anti-GPRC5B showed, in addition to the expected MW of 68 kDa, higher molecular weight bands that potentially represent GPRC5B dimers (at approximately 130 kDa) or higher molecular weight protein aggregates (Brain Res Mol Brain Res. 2002 Oct. 15;106(1-2):136-44. Localisation of the GPRC5B receptor in the rat brain and spinal cord. Robbins M J, Charles K J, Harrison D C, Pangalos Minn.).

Figure 28A:
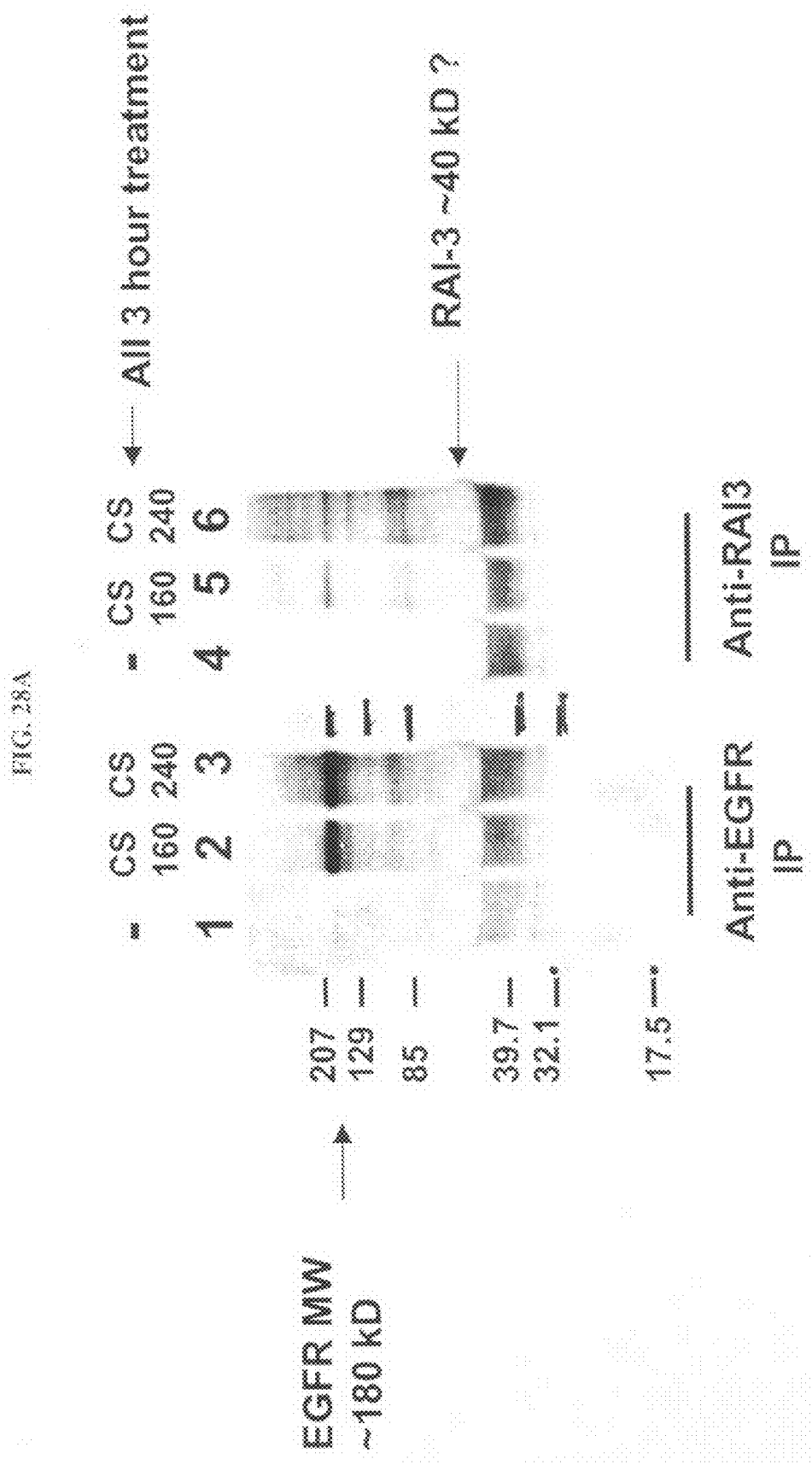
FIGS. 28A and 28B illustrate the results of a Western Blot analysis of the H292 cell line immunoprecipitated with either anti-EGFR, rabbit pre-immune sera or rabbit anti-RAI-3 and immunoblotted with an anti-phosphotyrosine antibody.
Figure 28B:
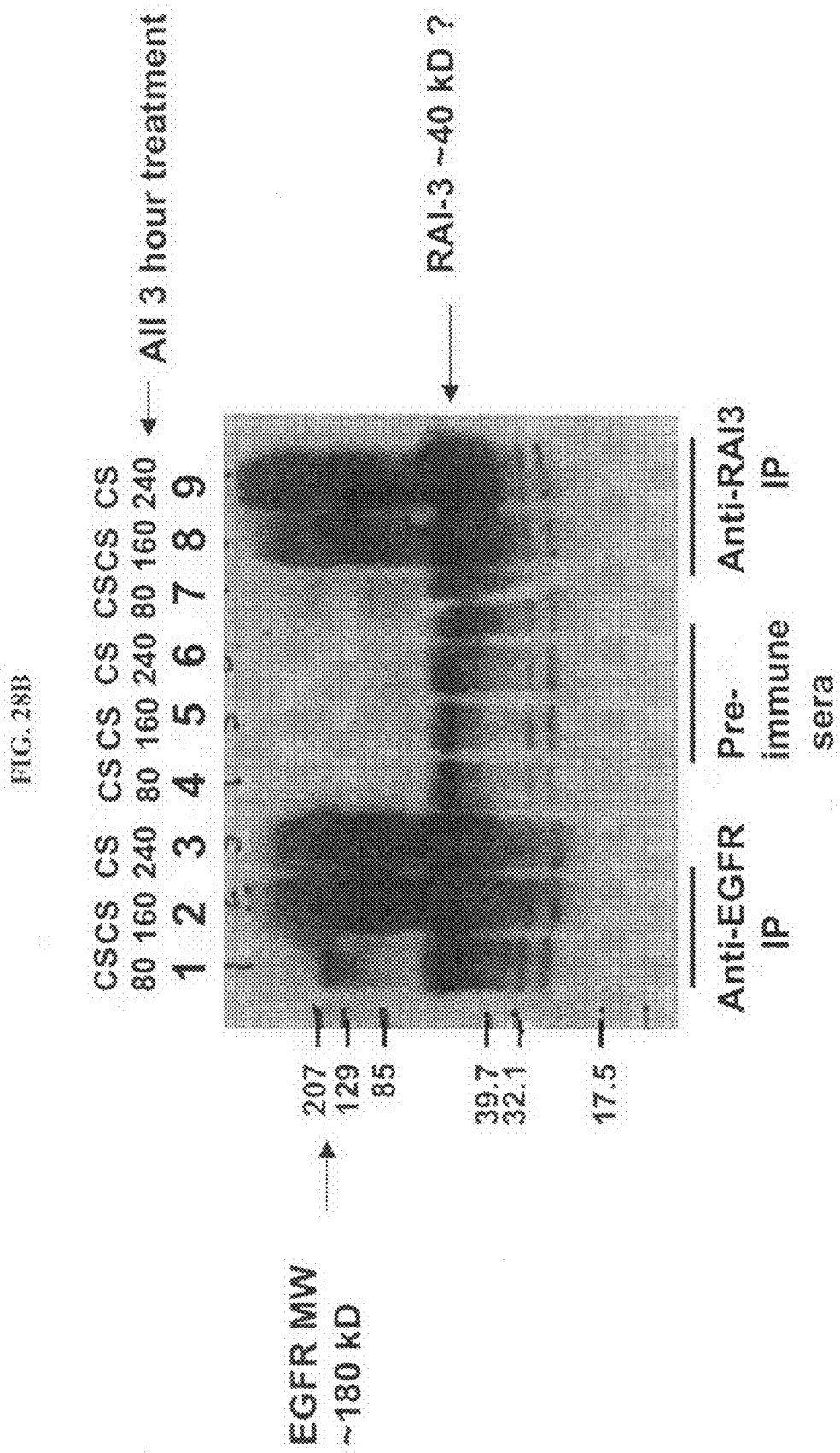

Further confirmation that RAI-3 is a component of a cigarette smoke-induced tyrosine phosphorylated complex, several additional experiments demonstrated that rabbit RAI-3 antisera can immunoprecipitate tyrosine phosphorylated proteins in response to exposure cigarette smoke-bubbled media (see FIGS. 28A and 28B). H292 lung airway epithelial cells were serum-starved for 24 hours and then exposed to various dilutions cigarette smoke-bubbled media (FIG. 28A and FIG. 28B) for three hours. The cells were lysed and immunoprecipitated with either anti-EGFR antibody, rabbit pre-immune antisera or rabbit RAI-3 antisera. There was a clear dose response of increasing tyrosine phosphorylation with increasing concentrations of cigarette smoke-bubbled media. Comparing the bands in the anti-EGFR antibody immunoprecipitate to the bands in the rabbit RAI-3 antisera immunopreciptate, demonstrated that the banding pattern was clearly different between the two antibodies. Although there appear to be some bands of the same MW, it is clear that the banding pattern is different. The ~180 kDa MW band in the anti-EGFR antibody immunoprecipitate is EGFR as determined by blotting with an anti-EGFR antibody (data not shown). The band at ~40 kDa in the rabbit RAI-3 antisera immunopreciptate is believed to be RAI-3, although blotting with the rabbit RAI-3 antisera did not give clear results in this experiment (data not shown).

Figure 29:
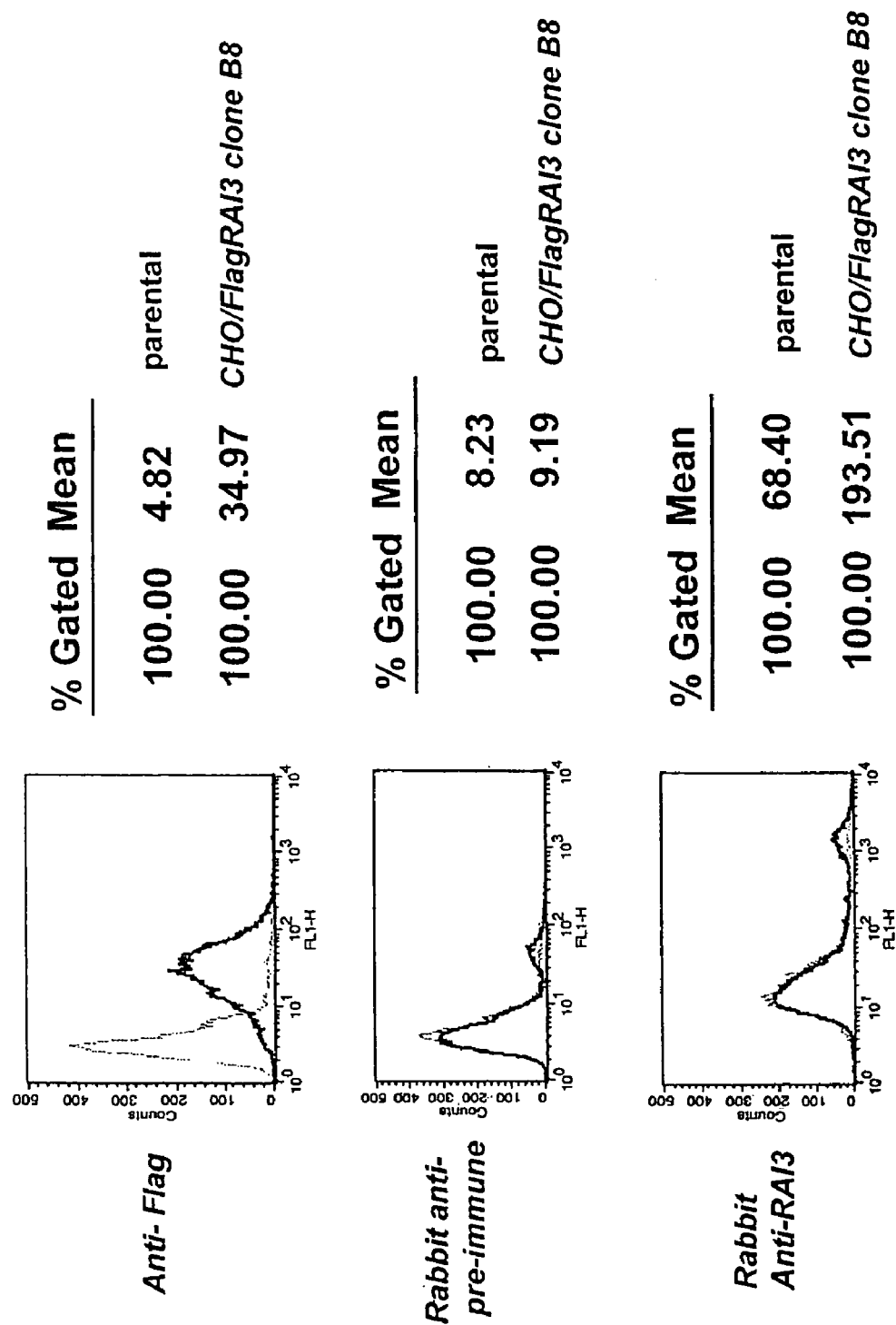
FIG. 29 illustrates the results of a FACs analysis comparing the stably expressing Flag-RAI-3 CHO cell line, clone B8, to the parental CHO cell line. The top panel shows a FACs analysis histogram comparing the stably expressing Flag-RAI-3 CHO cell line, clone B8, to the parental CHO cell line using an HRP-conjugated anti-FLAG. The middle panel shows a FACs analysis histogram comparing the stably expressing Flag-RAI-3 CHO cell line, clone B8, to the parental CHO cell line using the pre-immune antisera from the GW7 rabbit. The lower panel shows a FACs analysis histogram comparing the stably expressing Flag-RAI-3 CHO cell line, clone B8, to the parental CHO cell line using a post boost #4 bleed of the rabbit antisera, GW7. Cells from the confluent 100 mM cell culture plates (or equivalent), i.e., ~2×10$^6$ cells, were washed once with 1×PBS and then lifted from the plates with 2-3 ml of Cell Stripper (Cellgro/Mediatech, Herndon, Va.). 15 ml of 1×PBS was added to wash cells and then the cells were centrifuged at 1.5 K for 8 minutes at 4° C. to pellet. Cells were resuspended in 0.2 ml of binding buffer which is composed from DMEM (Gibco/BRL/Invitrogen Corporation, Carlsbad, Calif.) with a final concentration of 1% BSA (30% solution, Sigma-Aldrich Co. Saint Louis, Mo.) and 0.02% azide. Anti-FLAG FITC (Sigma, Saint Louis, Mo.; Catalog #F4049) was added at a dilution of 1:400 or rabbit anti sera was added at a dilution of 1:250. The cells and antibody mixture were incubated for one hour on ice. The cells incubated with the rabbit antisera were centrifuged at 1.5 K for 8 minutes at 4° C. to pellet and washed twice with 10 ml of binding buffer and resuspended in a final volume of 0.2 ml of binding buffer containing the 2° antibody a Fluorescein (FITC)-conjugated AffiniPure F(ab')$_2$ Goat Anti-Rabbit IgG.at a dilution of 1:200 (Jackson Immunoreseach Laboratories, Inc, West Grove, Pa.). The cells and antibody mixture were incubated for 30 minutes on ice. The cells were centrifuged at 1.5 K for 8 minutes at 4° C. to pellet and washed twice with 10 ml of binding buffer and resuspended in a final volume of 0.5 ml of binding buffer for FACS analysis. The cells were analyzed on a Becton Dickenson FACSort using Cell Quest software (Becton-Dickenson, Franklin Lakes, N.J.). Cells were live gated and red/green color was compensated.

Additional characterization of the anti-RAI-3 antisera demonstrated that it can recognize recombinant Flag-RAI-3 expressed in a stable CHO cell line (see FIG. 29).

Specifically, polyclonal rabbit antisera, GW7, was raised against an almost full length RAI-3 fusion protein antigen expressed in bacteria (as discussed herein). A post boost #4 bleed of the rabbit antisera, GW7, could recognize Flag-RAI-3 expressed in the stable CHO cell line, clone B8, by FACs analysis (see FIG. 29). The parental CHO line and the stable CHO cell line, clone B8, expressing the Flag-RAI-3 recombinant protein were compared using an HRP-conjugated anti-FLAG antibody and a post boost #4 bleed of the rabbit antisera, GW7. Using the HRP-conjugated anti-FLAG antibody and gating 100%, the mean signal of the parental cell line was 4.82 and the mean signal of the stable Flag-RAI-3 CHO cell line, clone B8, was 34.97. The anti-FLAG signal detecting the Flag-RAI-3 protein on the surface of the stable CHO cell line was 7-fold over background. Using the pre-immune antisera from the GW7 rabbit, and gating 100%, the mean signal of the parental cell line was 8.23 and the mean signal of the stable Flag-RAI-3 CHO cell line, B8, was 9.19. Clearly, there was no signal over background in the rabbit GW7 pre-immune antisera against the Flag-RAI-3 CHO cell line, clone B8. Using a post boost #4 bleed of the rabbit antisera, GW7, and gating 100%, the mean signal of the parental cell line was 68.40 and the mean signal of the stable Flag-RAI-3 CHO cell line, clone B8, was 193.51. Although there appears to be a higher background signal against the parental CHO cell line with the post boost #4 bleed of the rabbit antisera, GW7, the signal detecting the Flag-RAI-3 protein on the surface of the stable Flag-RAI-3 CHO cell line, clone B8, was 2.8-fold over background. Clearly, the post boost #4 bleed of the rabbit antisera, GW7, can detect the Flag-RAI-3 recombinant protein expressed at the surface in the Flag-RAI-3 CHO cell line, clone B8.

Additional results also demonstrate that the RAI-3 rabbit antisera can recognize endogenous RAI-3 on the surface of the airway epithelial cell lines A549 and H292.

Figure 30:
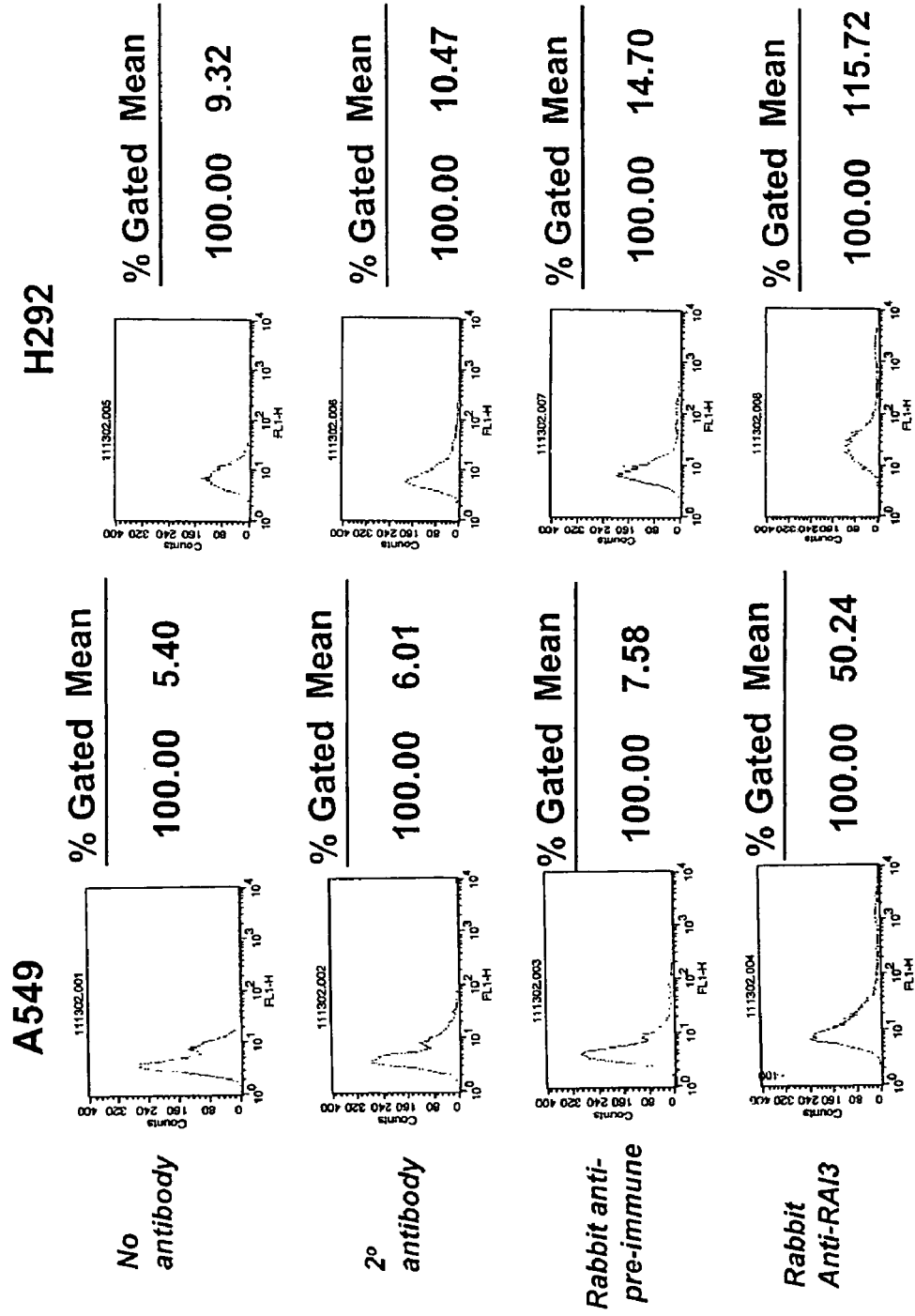
FIG. 30 illustrates the results of a FACs analysis comparing expression of the endogenous RAI-3 protein on the surface of the A549 and H292 cell lines. The top panels show results of a FACs analysis histogram without any antibody present. The second from top panels show the results of a FACs analysis histogram using the 2° antibody alone. The second from bottom panels show the results of a FACs analysis histogram using the pre-immune antisera from the GW7 rabbit. The bottom panels show the results of a FACs analysis histogram using the post boost #4 bleed of the rabbit antisera, GW7. Cells from the confluent 100 mM cell culture plates (or equivalent), i.e., ~2×10$^6$ cells, were washed once with 1×PBS and then lifted from the plates with 2-3 ml of Cell Stripper (Cellgro/Mediatech, Herndon, Va.). 15 ml of 1×PBS was added to wash cells and then the cells were centrifuged at 1.5

Specifically, the post boost #4 bleed of the rabbit antisera, GW7, could recognize endogenous RAI-3 on the surface of the airway epithelial cell lines, A549 and H292 by FACs analysis (see FIG. 30). FACs analysis of the A549 and H292 cell lines with no antibody present gave mean signals of 5.40 and 9.32, respectively. FACs analysis of the A549 and H292 cell lines using the 2° antibody alone gave mean signals of 6.01 and 10.47, respectively. FACs analysis of the A549 and H292 cell lines using the rabbit GW7 pre-immune antisera gave mean signals of 7.58 and 14.70, respectively. There was no signal over background in the rabbit GW7 pre-immune antisera detected on the airway epithelial cell lines, A549 and H292. FACs analysis of the A549 and H292 cell lines using the post boost #4 bleed of the rabbit antisera, GW7, gave mean signals of 50.24 and 115.72, respectively. Clearly, there was no signal over background in the rabbit GW7 pre-immune antisera detected on the airway epithelial cell lines, A549 and H292. The post boost #4 bleed of the rabbit antisera, GW7, gave a 6.6-fold increase in signal as compared to the rabbit GW7 pre-immune antisera on the A549 cell line. The post boost #4 bleed of the rabbit antisera, GW7, gave a 7.8-fold increase in signal as compared to the rabbit GW7 pre-immune antisera on the H292 cell line. Comparing the signals of the post boost #4 bleed of the rabbit antisera, GW7, on the A549 and H292 cell line shows that the H292 cell line has a 2.3 fold larger signal. This correlates well with Affychip data that shows that the H292 cell line expresses about twice as much RAI-3 mRNA as compared to the A549 cell line (data not shown).

In an effort to further assess the role of RAI-3, double stranded RNAi reagents were created to specifically inhibit transcription of the RAI-3 protein. Several experiments were performed to demonstrate that subjecting H292 cells with siRNA reagents 1864 and 1865 reduced levels of endogenopus RAI-3 protein (see FIG. 31). When the airway epithelial cell line, H292, was transfected with the RAI-3 siRNA reagent 1864+1865, there were reduced levels of endogenous RAI-3 protein expressed at the surface of the cell as detected by FACs analysis using the post boost #4 bleed of the rabbit RAI-3 antisera, GW7. Transfections of the H292 cell line were done in triplicate. FACs analysis of control H292 cells that were not transfected had a mean signal of 13.74 when no antibody was added, a mean signal of 64.74 when the pre-immune antisera from the GW7 rabbit was added, and mean signal of 357.43 when the post boost #4 bleed of the rabbit RAI-3 antisera, GW7 was added. FACs analysis of control H292 cells that were transfected, in triplicate, with Lipofectamine 2000 alone without any siRNA, had a average mean signal of 401.41 (StDev of 30.97). FACs analysis of H292 cells that were transfected, in triplicate, with the RAI-3 siRNA reagent 1864+1865, had a average mean signal of 278.22 (StDev of 47.83).

Consistent with the association of RAI-3 to the incidence of pulmonary disease, and in particular COPD, additional experiments were performed that demonstrate that H292 cells treated with cigarette-smoke bubble media are transfected with RAI-3 siRNA 1864+1865, the levels of muc5AC protein in the cell supernatant is significantly reduced when compared to untransfected or control transfected cells. (see FIG. 32).

Specifically, when the airway epithelial cell line, H292, was transfected with the RAI-3 siRNA reagent 1864+1865, there were reduced levels of muc5AC protein in the supernatent as detected by ELISA. H292 cells that were untransfected, in triplicate, and exposed to cigarette smoke bubbled media, CS-10, for 72 hours showed an average ELISA signal of 0.87 (StDev of 0.044). H292 cells that were transfected with Lipofectamine 2000 alone without any siRNA, in triplicate, and exposed to cigarette smoke bubbled media, CS-10, for 72 hours showed an average ELISA signal of 0.91 (StDev of 0.082). H292 cells that were transfected with the RAI-3 siRNA reagent 1864+1865, in triplicate, and exposed to cigarette smoke bubbled media, CS-10, for 72 hours showed an average ELISA signal of 0.206 (StDev of 0.063).

Immunohistochemical assays were also performed to further assess the expression pattern of RAI-3 and to identify any differential expression patterns in normal compared to diseased lung tissue. Polyclonal anti-RAI-3 antisera was generated from rabbits immunized against one of two peptides specific to RAI-3 (SEQ ID NO:91 and 92). Consistent with the putative role of RAI-3 in the pathobiology of cigarette smoke-related pulmonary disease, increases in staining were identified in samples of pulmonary emphysema and chronic bronchitis when compared to normal (disease-free) lungs as evident in the representative samples shown in FIGS. 33 and 34.

In addition, increased staining over normal tissue was observed in ulcerative colitis, cerebral infarct, myocardial infarct, diabetic nephropathy, allergic rhinitis, Crohn's disease, atherosclerosis and rheumatoid arthritis. These findings suggest a role for RAI-3 in inflammatory/auto-immune disorders outside of the lung in addition to COPD. The most noteworthy staining of malignancies was observed in malignant melanoma in which tumor cells stained moderately to strongly, and, in one sample, many moderately to strongly positive tumor-associated lymphocytes were identified. In addition, at least faintly positive staining was identified in glioblastoma, pulmonary small cell undifferentiated carcinoma, carcinoma of the breast, colon, lung, ovary, pancreas, and prostate, and in non-Hodgkin's lymphoma. Increased staining was also observed in benign prostatic hyperplasia.

RAI-3 Nucleic Acid and Variants

The RAI-3 nucleic acid molecule (SEQ ID NO:2) encodes the RAI-3 protein or polypeptide (SEQ ID NO:3) that is newly described by this invention as being involved in the development and/or persistence of COPD and COPD related diseases, disorders and conditions. Although RAI-3 has been shown to display sequence homology to members of the G-protein receptor family, this protein has not previously been shown to be associated with, or linked to, cellular exposure to cigarette smoke, with COPD, or with COPD related diseases, disorders and conditions. An RAI-3 nucleic acid molecule or an RAI-3 nucleic acid or polynucleotide can also refer to fragments and/or degenerate variants of nucleic acid sequences, including naturally occurring variants or mutant alleles thereof. Such fragments include, for example, nucleic acid sequences that encode portions of the RAI-3 protein that correspond to functional domains of the protein. In particular, an RAI-3 fragment, or peptide, as determined by the proteomics methods of the present invention is further embraced by the present invention. More specifically an RAI-3 fragment of the present invention comprises a nucleic acid sequence of at least 42 nucleotides in length encoding an amino acid sequence having at least 14 amino acids in length, for example, the polynucleotide provided in SEQ ID NO:1.

In preferred embodiments, the present invention encompasses a polynucleotide lacking including the initiating start codon, in addition to, the resulting encoded polypeptide of RAI-3. Specifically, the present invention encompasses the polynucleotide corresponding to nucleotides 251 thru 1324 of SEQ ID NO:2, and the polypeptide corresponding to amino acids 1 thru 357 of SEQ ID NO:3. Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of RAI-3. Specifically, the present invention encompasses the polynucleotide corresponding to nucleotides 254 thru 1324 of SEQ ID NO:2, and the polypeptide corresponding to amino acids 2 thru 357 of SEQ ID NO:3. Also encompassed are recombinant vectors comprising said encoding sequence, and host cells comprising said vector.

Although RAI-3 displays sequence and structural homology to members of the GPCR family of proteins (Table 2), as known in the art, it is also known in the art that proteins displaying such homologies can have significant differences in function, activity and molecular interactions within the cell, as well as differences in tissue expression. As such, it is acknowledged in the art that nucleic acid molecules and the proteins encoded by those molecules sharing these homologies can still represent diverse, distinct and unique nucleic acids and proteins, respectively.

An RAI-3 nucleic acid molecule as described herein can comprise the following sequences: (a) the DNA sequence of RAI-3 as shown in FIGS. 10A and 10B and 11B and 11C, and SEQ ID NO:2; (b) any nucleic acid sequence that encodes the amino acid sequence of RAI-3 of SEQ ID NO:3 and FIGS. 11A-11C; (c) any nucleic acid sequence that hybridizes to the complement of nucleic acid sequence that encodes the amino acid sequence of SEQ ID NO:3, or FIGS. 11A-11C under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (see, e.g., F. M. Ausubel et al., eds., 1989, *Current Protocols in Molecular Biology*, Vol. I, Green Publishing Associates, Inc., and John Wiley & sons, Inc., New York, at p. 2.10.3); or (d) any nucleic acid sequence that hybridizes to the complement of the nucleic acid sequences that encode the amino acid sequence of SEQ ID NO:3 or FIGS. 11A-11C under less stringent conditions, such as moderately stringent conditions, e.g., washing in 0.2×SSC/0.1% SDS at 42° C. (F. M. Ausubel et al., 1989, supra), and which encodes a gene product functionally equivalent to an RAI-3 gene product encoded by the nucleic acid sequence depicted in FIGS. 10A and 10B and 11B and 11C (SEQ ID NO:2). "Functionally equivalent" as used herein refers to any protein capable of exhibiting a substantially similar in vivo or in vitro activity as the RAI-3 gene product encoded by the RAI-3 nucleic acid molecule described herein, e.g., modulation of second messenger molecules involved in COPD or related diseases and conditions, or direct causative effects associated with COPD or related diseases and conditions.

As used herein, the term "RAI-3 nucleic acid molecule" or "RAI-3 nucleic acid" can also refer to fragments and/or degenerate variants of the nucleic acid sequences of (a) through (d) above, including naturally occurring variants or mutant alleles thereof. Such fragments include, for example, nucleic acid sequences that encode portions of the RAI-3 protein that correspond to functional domains of the protein. In addition, RAI-3 nucleic acid molecules can include isolated nucleic acids, preferably DNA molecules, that hybridize under highly stringent or moderately stringent hybridization conditions to at least about 6, preferably at least about 12, more preferably at least about 18, and most preferably about 42 consecutive nucleotides of the nucleic acid sequences of (a) through (d), as described above.

The terms "stringent conditions" or "stringency" refer to the conditions for hybridization as defined by nucleic acid composition, salt, and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (for example, formamide, dextran sulfate and/or polyethylene glycol) and reaction temperature (within a range of from about 5° C. below the melting temperature of the probe to about 20° C.-25° C. below the melting temperature). One or more factors may be varied to generate conditions, either low or high stringency that are different from, but equivalent to, the aforementioned conditions.

As will be understood by those of skill in the art, the stringency of hybridization can be altered in order to identify or detect identical or related polynucleotide sequences. As will be further appreciated by the skilled practitioner, the melting temperature, $T_m$, can be approximated by the formulas that are well known in the art, depending on a number of parameters, such as the length of the hybrid or probe in number of nucleotides, or hybridization buffer ingredients and conditions (see, for example, T. Maniatis et al., *Molecular Cloning. A Laboratory Manual*, Cold Spring Harbor Laboratory, Cold Spring Harbor, N.Y., 1982; J. Sambrook et al., *Molecular Cloning. A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger, 1987, *Methods Enzymol.* 152:399-407; and A. R. Kimmel, 1987; *Methods of Enzymol.* 152:507-511).

As a general guide, $T_m$ decreases approximately 1° C.-1.5° C. with every 1% decrease in sequence homology in an aqueous solution containing 100 mM NaCl. Also, in general, the stability of a hybrid is a function of ionic strength and temperature. Typically, the hybridization reaction is initially performed under conditions of low stringency, followed by washes of varying, but higher stringency. Reference to hybridization stringency, for example, high, moderate, or low stringency, typically relates to such washing conditions. It is to be understood that the low, moderate and high stringency hybridization or washing conditions can be varied using a variety of ingredients, buffers and temperatures well known to and practiced by the skilled artisan.

RAI-3 nucleic acid molecules can also include nucleic acids, preferably DNA molecules, that hybridize to, and are therefore complements of, the nucleic acid sequences of (a) through (d), as set forth above. Such hybridization conditions may be highly stringent or moderately stringent, as described above. In those instances in which the nucleic acid molecules are deoxyoligonucleotides ("oligos"), highly stringent conditions may include, e.g., washing in 6×SSC/0.05% sodium pyrophosphate at 37° C. (for 14-base oligos), 48° C. (for 17-base oligos), 55° C. (for 20-base oligos), and 60° C. (for 23-base oligos).

As will be discussed further below, the nucleic acid molecules of the invention can encode or act as RAI-3 antisense molecules useful, for example, in RAI-3 gene regulation or as antisense primers in amplification reactions of RAI-3 nucleic acid sequences. Further, such sequences can be used as part of ribozyme and/or triple helix sequences, also useful for RAI-3 gene regulation. Still further, such molecules can be used as components of diagnostic methods whereby, for example, the presence of a particular RAI-3 allele or alternatively-spliced RAI-3 transcript responsible for causing or predisposing one to COPD, or to a disorder or condition related to COPD can be detected.

Moreover, due to the degeneracy of the genetic code, other DNA sequences that encode substantially the amino acid sequence of RAI-3 can be used in the practice of the present invention, e.g., for the cloning and expression of RAI-3 polypeptides. Such DNA sequences include those that are capable of hybridizing to RAI-3 nucleic acid under stringent (high or moderate) conditions, or that would be capable of hybridizing under stringent conditions but for the degeneracy of the genetic code. Typically, RAI-3 nucleic acids should exhibit at least about 80% overall sequence homology at the nucleotide level, more preferably at least about 85-90% overall homology and most preferably at least about 95% overall homology to the nucleic acid sequence of FIGS. 10A/10B and SEQ ID NO:2 (e.g., as determined by the CLUSTAL W algorithm using default parameters (J. D. Thompson et al., 1994, Nucleic Acids Research, 2(22):4673-4680).

Alternatively, the RAI-3 polypeptide should exhibit at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% overall homology to the RAI-3 amino acid sequence as depicted in FIGS. 11A-C and in SEQ ID NO:3 (e.g., as determined by the CLUSTAL W algorithm using default parameters (J. D. Thompson et al., 1994, Nucleic Acids Research, 2(22):4673-4680).

Those having skill in the art will know how to determine percent identity between/among sequences using, for example, algorithms such as those used in the GAP computer program (S. B. Needleman and C. D. Wunsch, 1970, "A general method applicable to the search for similarities in the amino acid sequence of two proteins", J. Mol. Biol., 48(3): 443-53) or based on the CLUSTALW computer program, mentioned above, or FASTDB, (Brutlag et al., 1990, Comp. App. Biosci., 6:237-245). Although the FASTDB algorithm typically does not consider internal non-matching deletions or additions in sequences, i.e., gaps, in its calculation, this can be corrected manually to avoid an overestimation of the % identity. GAP and CLUSTALW, however, do take sequence gaps into account in their identity calculations.

Also available to those having skill in this art are the BLAST and BLAST 2.0 algorithms (Altschul et al., 1977, Nuc. Acids Res., 25:3389-3402 and Altschul et al., 1990, J. Mol. Biol., 215:403-410). The BLASTN program for nucleic acid sequences uses as defaults a wordlength (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff & Henikoff, 1989, Proc. Natl. Acad. Sci., USA, 89:10915) uses alignments (B) of 50, expectation (E) of 10, M=5, N=4, and a comparison of both strands.

Altered RAI-3 nucleic acid sequences that can be used in accordance with the invention include deletions, additions or substitutions of different nucleotide residues resulting in a modified nucleic acid molecule, i.e., mutated or truncated, that encodes the same or a functionally equivalent RAI-3 gene product. The gene product itself may contain deletions, additions or substitutions of amino acid residues within the RAI-3 protein sequence, which result in a silent change, thus producing a functionally equivalent RAI-3 polypeptide. Such amino acid substitutions may be made on the basis of similarity in polarity, charge, solubility, hydrophobicity, hydrophilicity, and/or the amphipatic nature of the residues involved. For example, negatively-charged amino acids include aspartic acid and glutamic acid; positively-charged amino acids include lysine, arginine and histidine; amino acids with uncharged polar head groups having similar hydrophilicity values include the following: leucine, isoleucine, valine, glycine, alanine, asparagine, glutamine, serine, threonine, phenylalanine, tyrosine. A functionally equivalent RAI-3 polypeptide can include a polypeptide which displays the same type of biological activity (e.g., COPD related expression and/or modification) as the native RAI-3 protein, but not necessarily to the same extent.

The RAI-3 nucleic acid molecule or RAI-3 polynucleotide sequences can be engineered in order to alter the RAI-3 coding sequence for a variety of reasons, including but not limited to, alterations that modify processing and expression of the gene product. For example, mutations may be introduced using techniques which are well known in the art, e.g., site-directed mutagenesis, to insert new restriction sites, to alter glycosylation patterns, phosphorylation, etc. For example, in certain expression systems such as yeast, host cells may over-glycosylate the gene product. When using such expression systems, it may be preferable to alter the RAI-3 coding sequence to eliminate any N-linked glycosylation sites.

In another embodiment, an RAI-3 nucleic acid sequence, e.g., a modified RAI-3 nucleic acid, can be ligated to a heterologous protein-encoding sequence to encode a fusion protein. Preferably, the RAI-3 nucleic acid that encodes a polypeptide with an activity of an RAI-3 protein, or a fragment thereof, is linked, uninterrupted by stop codons and in frame, to a nucleotide sequence that encodes a heterologous protein or peptide. The fusion protein can be engineered to contain a cleavage site, located between the RAI-3 sequence and the heterologous protein sequence, so that the RAI-3 protein can be cleaved away from the heterologous moiety. Nucleic acid sequences encoding fusion proteins can include full length RAI-3 coding sequence, sequences encoding truncated RAI-3, sequences encoding mutated RAI-3, or sequences encoding peptide fragments of RAI-3. The RAI-3 nucleic acid molecules can also be used as hybridization probes for obtaining RAI-3 cDNAs or genomic RAI-3 DNA. In addition, RAI-3 nucleic acids can be used as primers in PCR amplification methods to isolate RAI-3 cDNAs and genomic DNA, e.g., from other species.

The RAI-3 gene sequence can also used to isolate mutant or variant RAI-3 gene alleles. Such mutant or variant alleles can be isolated from individuals either known or proposed to have a genotype related to COPD, COPD susceptibility, or COPD related disorders, conditions, or dysfunctions. Mutant or variant alleles and mutant or variant allele gene products can then be used in the screening, therapeutic and diagnostic systems described herein. In addition, such RAI-3 gene sequences can be used to detect RAI-3 gene regulatory (e.g., promoter) defects which can affect COPD or COPD related disorders.

Single nucleotide polymorphisms (SNPs) within the coding region of the human RAI-3 sequence are encompassed and described herein. Both non-synonymous and synonymous SNPs are included. Several SNPs are provided as follows:

Non-Synonymous SNPs in human RAI-3:
1) AA118: Ser/Gly (base A/G, wherein "A" represents the wild-type or reference RAI-3 nucleotide and "G" represents the variant or polymorphic nucleotide in the RAI-3 sequence) and
2) AA307: Gln/Arg (base A/G).

Synonymous SNPs in human RAI-3:
1) AA37: Ala/Ala (base C/T) and
2) AA286: Pro/Pro (base T/C).

The Ser118Gly SNP is located in the second cytoplasmic domain of the RAI-3 polypeptide sequence; Thr182Ala is located in the fifth transmembrane (TM5) domain of RAI-3; and Gln307Arg is located in the cytoplasmic tail.

FIG. 13 shows a multiple sequence alignment containing the human RAI-3 amino acid sequence identifying the non-synonymous SNPs in the RAI-3 coding region. Accordingly, an RAI-3 variant comprising a non-synonymous SNP at amino acid position 118 in the RAI-3 amino acid sequence is set forth in SEQ ID NO:8. All other sequences are as described for FIG. 12. An RAI-3 variant comprising a non-synonymous SNP at amino acid position 307 in the RAI-3 amino acid sequence is set forth in SEQ ID NO:9. Further, an RAI-3 variant comprising a synonymous SNP at amino acid position 37 in the RAI-3 amino acid sequence is set forth in SEQ ID NO:20; and an RAI-3 variant comprising a synonymous SNP at amino acid position 286 in the RAI-3 amino acid sequence is set forth in SEQ ID NO:21.

The S/G amino acid variation at position 118 of the human RAI-3 amino acid sequence, resulting from the a/g SNP at position 605 of the RAI-3 nucleic acid sequence, is present in the intracellular loop between the third and fourth transmembrane domains (TMs 3 and 4). This intracellular loop is functionally associated with G-protein coupling. The amino acid corresponding to this position is conserved in RAI-3 sequences from non-human species and also in human and mouse GPCR5D, a closely related sequence. (See FIG. 19A). In human RAI-3, the position 118 amino acid residue is a Serine (S), a hydrophilic residue. In the other sequences listed in the alignment shown in FIG. 19A, the amino acid at this position is an Asparagine (N), a basic residue. The non-synonymous SNP at position 118 in the human RAI-3 amino acid sequence corresponds to Glycine (G), which is neither as hydrophilic as Serine, nor as basic as Asparagine. Since this residue is present in the intracellular loop, any change in the hydrophilicity could have an effect on G-protein coupling.

This Q/R amino acid variation at position 307 of the human RAI-3 amino acid sequence, resulting from the a/g SNP at position 1173 of the RAI-3 nucleic acid sequence, is present in the C-terminus cytoplasmic tail of the protein. The C-terminus of GPCRs is typically associated with functions such as signal transduction and receptor trafficking. This residue is conserved in both human and mouse RAI-3 sequences (See FIG. 19B). The SNP in human RAI-3 is non-synonymous and it changes the residue at amino acid position 307 in the sequence from Glutamine (Q) to Arginine (R). This polymorphic variation might have functional effects on the signal transduction pathway or on the trafficking of the RAI-3 receptor protein.

SNPs that were identified in the RAI-3 coding sequence (e.g., RAI-3-s2, RAI-3-s6, RAI-3-s8 and RAI-3-s9) are set forth in Table 3. The columns of the Table provide (i) a flanking sequence of contiguous nucleotides within the RAI-3 nucleic acid sequence of SEQ ID NO:2 in which the wild-type RAI-3 nucleotide is in bold; (ii) the SNP-containing RAI-3 sequence of contiguous nucleotides within the RAI-3 nucleic acid sequence of SEQ ID NO:2 in which the SNP nucleotide is in bold and underlined; (iii) a listing of the base change of the wild-type base versus the SNP base; and a description of the location of the SNP (in FIGS. 25A-25C and SEQ ID NO:2). The corresponding SEQ ID NOS of the RAI-3 reference and SNP-containing nucleic acid sequences are shown below each sequence.

TABLE 3

| SNP # | RAI-3 Flanking Sequence | RAI-3 SNP-containing sequence | Base change | Location (FIGS. 25 A-C); (SEQ ID NO:2) |
|---|---|---|---|---|
| RAI-3-s2 | 5'-ctagaaacgg tggccacagc cggggttgtg acctcggtgg-3' (SEQ ID NO:22) | 5'-ctagaaacgg tggccacagc t_gggttgtg acctcggtgg-3' (SEQ ID NO:23) | c/t | BP 364 |
| RAI-3-s6 | 5'-tgcctgctgg ctcatgctgt cagtctgacc aagctcgtcc gggg-3' (SEQ ID NO:24) | 5'-tgcctgctgg ctcatgctgt cggtctgacc aagctcgtcc gggg-3' (SEQ ID NO:25) | a/g | BP 605 |
| RAI-3-s8 | 5'-tcctgttgag gatgctttct gtaaacctca actcgtgaag aagagctatg-3' (SEQ ID NO:26) | 5'-tcctgttgag gatgctttct gtaaacc_cca actcgtgaag aagagctatg-3' (SEQ ID NO:27) | t/c | BP 1111 |

TABLE 3-continued

| SNP # | RAI-3 Flanking Sequence | RAI-3 SNP-containing sequence | Base change | Location (FIGS. 25 A-C); (SEQ ID NO:2) |
|---|---|---|---|---|
| RAI-3-s95 | 5'-tctcaagagg aaatcactca aggttttgaa gagacagggg-3' (SEQ ID NO:28) | 5'-tctcaagagg aaatcactcg aggttttgaa gagacagggg-3' (SEQ ID NO:29) | a/g | BP 1173 |

In a related embodiment, the present invention relates to RAI-3 SNP discovery by DNA sequencing (e.g., Example 7). In this preferred aspect of the invention, the RAI-3 nucleic acid (gene) sequence was examined in 48 individuals, in which the coding region of the RAI-3 gene containing four exons was analyzed. The DNA analyzed comprised 36 Caucasian DNA samples from the Coriell Cell Repositories (Collingswood, N.J.), and as further described herein. Six SNPs were identified, including one missense SNP, as presented in Table 4.

TABLE 4

| SNP_ID | Location | Nucleotide Position | AA Position | Nature | Comments |
|---|---|---|---|---|---|
| RAI-3-s1 | EXON1 | 112 | | 5' UTR | |
| RAI-3-s7 | INTRON1 | | | intron | |
| RAI-3-s2 | EXON2 | 364 | 37 | silent (Ala/Ala) | |
| RAI-3-s3 | EXON2 | 511 | 86 | silent (Ile/Ile) | |
| RAI-3-s4 | EXON2 | 523 | 90 | silent (Asp/Asp) | |
| RAI-3-s5 | EXON2 | 797 | 182 | missense (Thr/Ala) | missense |

The RAI-3 SNPs as provided above, either alone or in combination, are useful as diagnostic tools, e.g., nucleic acid probes provided in a kit, for identifying individuals who are at risk for, or who are susceptible to, developing COPD or COPD related disorders, by way of nonlimiting example.

A cDNA of a mutant RAI-3 gene can be isolated, for example, by using PCR, a technique that is well known to those of skill in the art (see, e.g., U.S. Pat. No. 4,683,202). The first cDNA strand may be synthesized by hybridizing an oligo-dT oligonucleotide to mRNA isolated from tissue known or suspected to be expressed in an individual putatively carrying the mutant RAI-3 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known in the art. By comparing the DNA sequence of the mutant RAI-3 allele to that of the normal RAI-3 allele, the mutation(s) responsible for the loss or alteration of function of the mutant RAI-3 gene product can be ascertained.

Alternatively, a genomic library can be constructed using DNA obtained from an individual suspected of or known to carry the mutant RAI-3 allele, or a cDNA library can be constructed using RNA from tissue known, or suspected, to express the mutant RAI-3 allele. The normal RAI-3 gene, or any suitable fragment thereof, can then be labeled and used as a probe to identify the corresponding mutant RAI-3 allele in such libraries. Clones containing mutant RAI-3 gene sequences can then be purified and subjected to sequence analysis according to methods well known in the art.

In another aspect, an expression library can be constructed utilizing cDNA synthesized from, for example, RNA isolated from a tissue known or suspected to express a mutant RAI-3 allele in an individual suspected of or known to carry such a mutant allele. Gene products made by the putatively mutant tissue can be expressed and screened using standard antibody screening techniques in conjunction with antibodies raised against the normal RAI-3 gene product. For screening techniques, see, for example, Harlow, E. and Lane, eds., 1988, *Antibodies: A Laboratory Manual*, Cold Spring Harbor Press, Cold Spring Harbor.

In cases in which an RAI-3 mutation results in an expressed gene product with altered function (e.g., as a result of a missense or a frameshift mutation), a polyclonal set of anti-RAI-3 gene product antibodies are likely to cross-react with the mutant RAI-3 gene product. Library clones detected via their reaction with such labeled antibodies can be purified and subjected to sequence analysis according to methods well known to those of skill in the art.

Alternatively, the coding sequence of RAI-3 can be synthesized in whole or in part, using chemical methods well known in the art, based on the nucleic acid and/or amino acid sequences of the RAI-3 gene and protein, respectively. (See, for example, Caruthers et al., 1980, *Nuc. Acids Res. Symp. Ser.*, 7: 215-233; Crea and Horn, 1980, *Nuc. Acids Res.*, 9(10): 2331; Matteucci and Caruthers, 1980, *Tetrahedron Letters*, 21: 719; and Chow and Kempe, 1981, *Nuc. Acids Res.*, 9(12): 2807-2817). The invention encompasses (a) DNA vectors that contain any of the foregoing RAI-3 nucleic acids and/or their complements; (b) DNA expression vectors that contain any of the foregoing RAI-3 coding sequences operatively associated with a regulatory element that directs the expression of the coding sequences; and (c) genetically engineered host cells that contain any of the foregoing RAI-3 coding sequences operatively associated with a regulatory element that directs the expression of the coding sequences in the host cell. As used herein, regulatory elements include, but are not limited to, inducible and non-inducible promoters, enhancers, operators and other elements that drive and regulate expression, as known to those skilled in the art. Nonlimiting examples of such regulatory elements include the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The invention further relates to nucleic acid analogs, including but not limited to, peptide nucleic acid analogues, equivalent to the nucleic acid molecules described herein. "Equivalent" as used in this context refers to nucleic acid analogs that have the same primary base sequence as the RAI-3 nucleic acid molecules described above. Nucleic acid analogs and methods for the synthesis of nucleic acid analogs are well known to those of skill in the art. (See, e.g., Egholm, M. et al., 1993, *Nature*, 365:566-568; and Perry-O'Keefe, H. et al., 1996, *Proc. Natl. Acad. USA*, 93:14670-14675). Modulation of RAI-3: Methods, Compounds and Compositions Related Thereto In another embodiment, modulators of RAI-3 are particularly embraced by the present invention. Modulators can include any molecule, e.g., protein, peptide, oligopeptide, small organic molecule, chemical compound, polysaccharide, polynucleotide, etc., having the capability to directly or indirectly alter or modify the activity or function of the RAI-3 polypeptide. Candidate modulatory agents or compounds or materials can also encompass numerous chemical classes, though typically they are organic molecules, preferably small organic compounds, for example, without limitation, those having a molecular weight of more than 100 and less than about 10,000 daltons, preferably, less than about 2000 to 5000 daltons. Candidate modulatory compounds can comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

Modulatory agents or compounds can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents can also be subjected to directed or random chemical modifications, such as acylation, alkylation, esterification, amidification to produce structural analogs.

Modulators of RAI-3 as embraced by this invention can be antagonists, suppressors, inhibitors, or blockers of RAI-3, as such modulators can be efficacious in affecting smoke-induced activation and in reducing the symptoms underlying COPD. An antagonist is typically a molecule which, when bound to, or associated with, RAI-3 polypeptide, or a functional fragment thereof, decreases or inhibits the amount or duration of the biological or immunological activity of the RAI-3 polypeptide. Antagonists can include proteins, nucleic acids, carbohydrates, antibodies, or any other molecules that decrease or reduce the effect of an RAI-3 polypeptide. Antagonists typically, diminish, inhibit, block, decrease, reduce, suppress, or abolish the function or activity of an RAI-3 molecule. More specifically, modulators of RAI-3 can be efficacious in treating, ameliorating, or preventing chronic bronchitis, emphysema, the symptoms of chronic bronchitis, the symptoms of emphysema, in addition to increasing maximal expiratory flow of the lungs, increasing forced emptying of the lungs, increasing airflow of the lungs when used in conjunction with a bronchodilator, decreasing enlargement of the air spaces distal to the terminal bronchioles, decreasing bronchial secretions, decreasing mucus secretion in the lung, decreasing hypertrophy of the glandular elements of the bronchial mucosa, decreasing the level of elastase released into the lungs, increasing the level of alpha-1 antitrypsin (AAT) in the lungs, increasing the effectiveness of alpha-1 antitrypsin in the lungs in protecting the lung from elastase-dependent damage, and/or decreasing the number of inflammatory cells into the lungs. Indeed, since RAI-3 either directly or indirectly can affect mucus production, modulators of RAI-3 find utility in the treatment, amelioration, therapy, and/or prevention of cystic fibrosis.

In addition, modulators such as agonists or enhancers of RAI-3 function or activity are embraced by the present invention, particularly, for an RAI-3 target that is part of a reparative, reversing, and/or protective mechanism, which is induced following the exposure of cells to smoke, such as cigarette smoke, for example. Agonists typically are molecules which, when bound to, or associated with, an RAI-3 polypeptide, or a functional fragment thereof, increase, enhance, or prolong the duration of the effect of the RAI-3 polypeptide. Agonists may include proteins, peptides, nucleic acids, carbohydrates, or any other molecules that bind to and modulate the effect of the RAI-3 polypeptide. Agonists typically enhance, increase, or augment the function or activity of an RAI-3 molecule. As such, an agonist compound may be efficacious in enhancing the protective mechanism of RAI-3 in alleviating the symptoms of COPD. Another embodiment of the present invention encompasses screening methods and assays for the identification of compounds that modulate the expression of RAI-3 nucleic acid and/or the activity of the RAI-3 polypeptide or peptides of the invention, e.g., assays that measure RAI-3 mRNA and/or RAI-3 gene product levels, or assays that measure levels of RAI-3 activity, such as the ability of the RAI-3 protein, or modulators thereof, to regulate or modulate second messengers or other molecules, such as E-selectin, or a component of the NF-κB pathway, such as IκB.

In an embodiment of this invention, cellular and non-cellular assays can be used to identify compounds that interact with the RAI-3 gene and/or gene product, e.g., modulate the activity of the gene and/or bind to the gene product. Such cell-based assays are generally known, and in terms of the present invention, utilize cells, cell lines, or engineered cells or cell lines that express the RAI-3 gene product or RAI-3 peptide products. Illustratively, such methods comprise contacting a cell with a compound or agent that expresses an RAI-3 nucleic acid sequence, e.g., the RAI-3 gene; measuring the level of gene expression, gene product expression, or gene product activity, and comparing this level to the level of RAI-3 gene expression, gene product expression, or gene product activity produced by the cell in the absence of the compound or agent, such that if the level obtained in the presence of the compound differs from that obtained in its absence, a compound that modulates the expression of the RAI-3 gene and/or the synthesis, function, or activity of the gene product has been identified. Such assays can comprise subjecting the appropriate RAI-3-expressing cells to cigarette smoke in the presence of a candidate compound or agent to determine if the compound or agent prevents modification, e.g., phosphorylation, of RAI-3 in the cells, or complexation of RAI-3 with other proteins, following cigarette smoke treatment or cells, relative to control cells. A compound or agent that prevents phosphorylation of RAI-3, or its complexation with other cellular proteins, in the smoke-treated cells, relative to control cells, is identified as one which modulates the activity or function of RAI-3 in response to smoke exposure.

Screening assays and methods also comprise administering a compound or agent to a host organism, e.g., a transgenic animal that expresses a RAI-3 transgene or a mutant RAI-3 transgene, and measuring the level of RAI-3 gene (or nucleic acid) expression, gene product expression, or gene product activity. The measured expression level is compared to the level of RAI-3 gene expression, gene product expression, or gene product activity in a host that is not exposed to the compound or agent, such that if the level obtained when the host is exposed to the compound or agent differs from that obtained when the host is not exposed to the compound, a compound or agent that modulates the expression of the RAI-3 gene and/or the synthesis or activity of the RAI-3 gene products has been identified. In addition, the host organism harboring the RAI-3 gene and expressing RAI-3 protein can be exposed to cigarette smoke prior to performing the screening assays, e.g., employing lung cells or tissue.

The compounds identified by these methods include therapeutic compounds that can comprise pharmaceutical compositions and formulations to reduce or eliminate the symptoms or effects of COPD or COPD related disorders and conditions. Pharmaceutical formulations suitable for the treatment of COPD or COPD related disorders comprise at least one compound that inhibits or activates RAI-3 activity, in combination with a pharmaceutically acceptable carrier, diluent or excipient as further described herein.

In another embodiment, the present invention further provides a method of identifying a compound that modulates the biological activity of RAI-3, comprising (a) combining a candidate modulator compound with RAI-3 having the polypeptide sequence as set forth in SEQ ID NO:3, or with an RAI-3 peptide; and measuring an effect of the candidate modulator compound on the activity of RAI-3, or, if appropriate, on the activity of the RAI-3 peptide.

In view of the involvement of RAI-3 in the regulation of second messengers and cellular molecules, such as IκB and E-selectin, another embodiment of this invention further provides a method of identifying a compound that modulates the biological activity of an RAI-3 regulated or modified second messenger, cellular molecule, or a pathway or system that is associated with the RAI-3 regulated or modified second messenger. For example, the method comprises combining a candidate modulator compound with a host cell expressing RAI-3 (e.g., the RAI-3 amino acid sequence as set forth in SEQ ID NO:3, or fragments or portions thereof); and (b) measuring an effect of the candidate modulator compound on the activity of the expressed RAI-3, and/or on the RAI-3 regulated or modified second messenger or cellular molecule, e.g., IκB.

The invention further relates to a method of identifying a compound that modulates the biological activity of RAI-3. Such a compound can be used to affect RAI-3 function or activity in the cells of COPD sufferers, or those with COPD related diseases and conditions. The method comprises combining a candidate modulator compound with a host cell containing a vector in which RAI-3, or a peptide thereof, preferably a functional RAI-3 peptide, is expressed by the cell, and measuring an effect of the candidate modulator compound on the activity of the expressed RAI-3 or peptide thereof.

In another embodiment, the present invention embraces a method of screening for a compound that is capable of modulating the biological activity of RAI-3, comprising (a) providing a host cell in which RAI-3, or a peptide thereof, is expressed such as described herein; (b) determining the biological activity of RAI-3 in the absence of a modulator compound; (c) contacting the cell with the modulator compound; and (d) determining the biological activity of RAI-3 in the presence of the modulator compound. In this method, a difference between the activity of RAI-3 in the presence of the modulator compound and in the absence of the modulator compound indicates a modulating effect of the compound. Accordingly, the invention further relates to a compound that modulates the biological activity of human RAI-3, wherein the compound has been identified by the methods described herein.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

RAI-3 Modulation, NF-κB and Components Related Thereto

The regulation or modulation of the Nuclear Factor κB (NF-κB) pathway and/or components thereof, and/or cell signaling or transcriptional molecules by RAI-3 is also embraced by the present invention. As a transcriptional activator, NF-κB plays a central role in regulating the transcription of a number of genes, including those which encode proteins involved in inflammatory and immune responses. Representative examples of genes controlled by NF-κB include the cytokines tumor necrosis factor (TNF-α), IL-1β, IL-6, and IL-8; the adhesion molecules E-selectin and vascular cell adhesion molecule (VCAM)-1; and the enzyme nitric oxide (NO)-synthase (for reviews, see Siebenlist et al. *Annu. Rev. Cell Biol.* 10: 405-455, 1994; Bauerle and Baltimore, *Cell,* 87:13-20, 1997). Also, NF-κB has been shown to be induced by several stimuli, in addition to mediators of immune function, such as UV irradiation, growth factors, and viral infection.

The NF-κB transcription factor normally resides in the cytoplasm in unstimulated cells as an inactive complex with a member of the inhibitor κB (IκB) inhibitory protein family. The IκB class of proteins includes IκB-α, IκB-β, and IκB-ε—all of which contain ankyrin repeats for complexing with NF-κB (for review, see Whiteside et al., *EMBO J.* 16:1413-1426, 1997). In the case of IκB-α, the most carefully studied member of this class, stimulation of cells with agents which activate NF-κB-dependent gene transcription results in the phosphorylation of IκB-α at serine-32 and serine-36 (Brown et al. Science, 267:1485-1488, 1995).

IκB is a cytoplasmic protein that controls NF-κB activity by retaining NF-κB in the cytoplasm. IκB is phosphorylated by the IκB kinase (IKK), which has two isoforms, IKK-1 (or IκB kinase α, IKKα) and IKK-2 (or IκB kinase β, IKKβ). Upon phosphorylation of IκB by IKK, NF-κB is rapidly released into the cell and translocates to the nucleus where it binds to the promoters of many genes and up-regulates the transcription of pro-inflammatory genes. Inhibitors of IKK can block the phosphorylation of IκB and further downstream effects, specifically those associated with NF-κB transcription factors. Inhibition of NF-κB and/or its activation pathway provides a means for treating a wide range of diseases including autoimmune diseases, Alzheimer's disease, atherosclerosis, oncogenesis, and so forth. See, e.g., Baldwin, 1996, "The NF-κB and IκB Proteins: New Discoveries and Insights," *Annual Rev. Immunol., Vol.* 14:649-81; see also Christman et al., 2000, "Impact of Basic Research on Tomorrow's Medicine, The Role of Nuclear Factor-κB in Pulmonary Diseases," *Chest,* Vol. 117:1482-87.

Phosphorylation of IκB-α is critical for its subsequent ubiquitination and proteolysis, upon which NF-κB is released from complexing with IκB. NF-κB can then translocate into the nucleus and ultimately activate gene transcription (Finco et al., 1994, *Proc. Natl. Acad. Sci. USA*, 91:11884-11888; Baldi et al., 1996, *J. Biol. Chem.*, 271:376-379; and Roff et al., 1996, *J. Biol. Chem.*, 271:7844-7850). Substituting both serine-32 and serine-36 of IκB with alanine prevents signal-induced NF-κB activation and also results in an IκB (e.g. IκB-α), which is not phosphorylated, ubiquitinated, or proteolytically digested (Roff et al., Ibid.). Analogous serines have been identified in both IκB-β and IκB-ε, and phosphorylation at these residues appears to regulate the proteolytic degradation of these proteins by a mechanism similar to that of IκB-α (Weil et al., 1997, *J. Biol. Chem.*, 272:9942-9949; and Whiteside et al., 1997, *EMBO J.*, 16:1413-1426).

More particularly, upon phosphorylation, ubiquitination and degradation of IκB, NF-κB is released from the IκB/NF-κB complex and allowed to translocate from the cytoplasm to the nucleus and activate a number of genes, particularly those involved in inflammatory and immune responses. Since NF-κB is of significant importance in inflammation and immune responses, inhibition of IκB, for example, by inhibiting the signal-inducible phosphorylation of IκB, can be an important target in the treatment of inflammatory and immune system-related diseases and disorders. In accordance with this invention, modulation of IκB and/or NF-κB activation, particularly by RAI-3 or RAI-3 modulation, either directly or indirectly, can also be important in the treatment and/or the pathobiology of COPD, cancers, such as lung cancer, breast cancer, stomach cancer, testicular cancer, etc., malignancies and asthma.

In a particular embodiment related to the modulation of NF-κB via RAI-3 or RAI-3 modulation, and/or the modulation of other components of the cellular pathway that includes NF-κB via RAI-3 or RAI-3 modulation, the present invention embraces the treatment, therapy, amelioration and/or prevention of pulmonary fibrosis. Because the expression of many pro-inflammatory cytokines and chemokines, including TNF-alpha (α), are NF-κB dependent, it is expected that inhibitors of NF-κB function or activity would be efficacious in pulmonary fibrosis. TNF-α, among other pro-inflammatory factors, is believed to play an important role in driving the pathology of pulmonary fibrosis (e.g., N. Sueoka et al., 1998, *Cytokine*, 10:124-131). NF-κB has been shown to be activated in the lungs of affected animals in animal models of pulmonary fibrosis (see, e.g., G. Gurujeyalakshmi et al., 2000, *J. Pharmacol. Lung Cell Mol. Physiol.*, 293:82-90; and A. K. Hubbard et al., 2002, *Am. J. Physiol. Lung Cell Mol. Physiol.*, 282:L968-75). Moreover, oxidative stress responses are thought to play a role in pulmonary fibrosis and cellular glutathione (GSH) levels are important in regulating oxidative stress. Consistent with the role of NF-κB in disease, the expression of gamma-glutamylcysteine synthetase (gamma-GCS), which controls the key regulatory step in GSH synthesis and is up-regulated in animal models of pulmonary fibrosis, is also NF-κB dependent. (R. M. Day et al., 2002, *Am. J. Physiol. Lung Cell Mol. Physiol.*, 282:L1349-57).

In accordance with another particular, yet nonlimiting, embodiment of the present invention, RAI-3 modulation, i.e., the activity of RAI-3 antisense as described herein (FIGS. 14A and 14B and Example 2), produced an increase in the level of IκBα mRNA in cells. The up-regulation of IκBα due to the down-regulation of RAI-3 thus places this GPCR protein into a signaling pathway potentially involved in cellular apoptotic events. This affords the opportunity to regulate downstream events via the activity of the RAI-3 protein with modulators, such as antisense polynucleotides, polypeptides, or low molecular chemicals, for example, with the potential of achieving a therapeutic effect in cancer and/or autoimmune diseases, among others. In addition to cancer and immunological disorders, NF-kB has significant roles in other diseases (See, A. S. Baldwin, 2001, *J. Clin. Invest.*, 107:3-6). Also, NF-kB is a key factor in the pathophysiology of ischemia-reperfusion injury and heart failure (G. Valen et al., 2001, *J. Am. Coll. Cardiol.*, 38:307-14). Furthermore, NF-kB has been found to be activated in experimental renal disease (C. Guijarro and J. Egido, 2001, *Kidney Int.*, 59:415-425).

In other preferred embodiments of this invention in keeping with the above, RAI-3 polynucleotides and polypeptides, including fragments thereof, are useful for treating, diagnosing, and/or ameliorating proliferative disorders, cancers, (e.g., lung cancer, breast cancer, stomach cancer, testicular cancer, etc.), ischemia-reperfusion injury, heart failure, immunocompromised conditions, HIV infection, and renal diseases. Moreover, RAI-3 polynucleotides and polypeptides, including fragments thereof, are useful for increasing NF-κB activity, increasing apoptotic events, and/or decreasing IκBα expression or activity levels. Indeed, because many anti-apoptotic factors are NF-κB dependent, a modulator of RAI-3 which inhibits, suppresses, reduces, blocks, or antagonizes NF-κB activation can have applicability in lung cancer, for example, in view of the expression of RAI-3 in lung tissue as described and demonstrated herein. Accordingly the present invention encompasses a method of treating lung cancer involving the use of an RAI-3 modulator, e.g., as determined by the methods described herein, which inhibits NF-κB activation.

In still other preferred embodiments, antagonists directed against RAI-3 are useful for treating, diagnosing, and/or ameliorating the following disorders, diseases and/or conditions: autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferation disorders, cancers, (e.g., lung cancer, breast cancer, stomach cancer, testicular cancer, etc.), HIV infection, and HIV propagation in cells infected with other viruses. Moreover, antagonists directed against RAI-3 are useful for decreasing NF-κB activity, decreasing apoptotic events, and/or increasing IκBα expression or activity levels.

In additional preferred embodiments of the present invention, agonists directed against RAI-3 are useful for treating, diagnosing, and/or ameliorating autoimmune disorders, disorders related to hyperimmune activity, hypercongenital conditions, birth defects, necrotic lesions, wounds, disorders related to aberrant signal transduction, immunocompromised conditions, HIV infection, proliferation disorders, and/or cancers, such as lung cancer, breast cancer, stomach cancer, testicular cancer, ovarian cancer, cervical cancer, etc. In addition, agonists directed against RAI-3 are useful for increasing NF-κB activity, increasing apoptotic events, and/or decreasing IκBα expression or activity levels.

The RAI-3 Protein and Peptides, and Expression Thereof

The RAI-3 nucleic acid can be used to generate recombinant DNA molecules that direct the expression of the RAI-3 protein (polypeptide) or peptides thereof in appropriate host cells, including the full-length RAI-3 protein, functionally active or equivalent RAI-3 proteins and polypeptides, e.g., mutated, truncated or deleted forms of RAI-3, peptide fragments of RAI-3, or RAI-3 fusion proteins. A functionally equivalent RAI-3 polypeptide can include a polypeptide which displays the same type of biological activity (e.g., regulation or modulation of second messenger activity and/or function) as the native RAI-3 protein, but not necessarily to the same extent. Such recombinantly expressed RAI-3 molecules are useful in the various screening assays for determining modulators of RAI-3, particularly for treatments and therapies of COPD and COPD related disorders as described herein.

The amino acid sequence of the RAI-3 polypeptide is depicted in FIG. 11 and SEQ ID NO:3. Both the RAI-3 polypeptide and RAI-3 peptide sequences are useful as targets, and/or as immunogens to generate antibodies for the methods and compositions according to the present invention. The proteins and polypeptides of the invention include peptide fragments of RAI-3, peptides corresponding to one or more domains of the protein, mutated, truncated or deleted forms of the proteins and polypeptides, as well as RAI-3 fusion proteins; all of the aforementioned RAI-3 derivatives can be obtained by techniques well known in the art, given the RAI-3 nucleic acid and amino acid sequences as described herein. The RAI-3 protein and its peptides can also contain deletions, additions or substitutions of amino acid residues within the RAI-3 protein sequence, which can result in a silent change, thus producing a functionally equivalent RAI-3 polypeptide. Such amino acid substitutions can be made on the basis of similarity in polarity, charge, solubility, hydrophobicity, hydrophilicity, and/or the amphipatic nature of the residues involved. For example, negatively-charged amino acids include aspartic acid and glutamic acid; positively-charged amino acids include lysine, arginine and histidine; amino acids with uncharged polar head groups having similar hydrophilicity values include the following: leucine, isoleucine, valine, glycine, alanine, asparagine, glutamine, serine, threonine, phenylalanine, tyrosine.

The RAI-3 polypeptide should exhibit at least about 80% overall sequence identity at the amino acid level, more preferably at least about 85-90% overall identity and most preferably at least about 95% overall identity to the amino acid sequence of FIGS. 11A-11C and SEQ ID NOS:1 and/or 3 (e.g., as determined by the CLUSTAL W algorithm using default parameters (J. D. Thompson et al., 1994, *Nucleic Acids Research*, 2(22):4673-4680).

Alternatively, the RAI-3 polypeptide should exhibit at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% overall identity to the RAI-3 amino acid sequence as depicted in FIGS. 11A-C and in SEQ ID NO:3 (e.g., as determined by the CLUSTAL W algorithm using default parameters (J. D. Thompson et al., 1994, *Nucleic Acids Research*, 2(22):4673-4680).

Mutated or altered forms of the RAI-3 protein and peptides can be obtained using random mutagenesis techniques, site-directed mutagenesis techniques, or by chemical methods, e.g., protein synthesis techniques, as practiced in the art. Mutant RAI-3 protein or peptides can be engineered so that regions important for function are maintained, while variable residues are altered, e.g., by deletion or insertion of an amino acid residue(s) or by the substitution of one or more different amino acid residues. For example, conservative alterations at the variable positions of a polypeptide can be engineered to produce a mutant RAI-3 polypeptide that retains the function of RAI-3. Non-conservative alterations of variable regions can be engineered to alter RAI-3 function, if desired. Alternatively, in those cases where modification of function (either to increase or decrease function) is desired, deletion or non-conservative alterations of conserved regions of the RAI-3 polypeptide can be engineered.

In another aspect, fusion proteins containing RAI-3 amino acid sequences can also be obtained by techniques known in the art, including genetic engineering and chemical protein synthesis techniques. According to this aspect, RAI-3 fusion proteins are encoded by an isolated nucleic acid molecule comprising an RAI-3 nucleic acid that encodes a polypeptide with an activity of an RAI-3 protein, or a fragment thereof, linked in frame and uninterrupted by stop codons, to a nucleotide sequence that encodes a heterologous protein or peptide.

Fusion proteins include those that contain the full length RAI-3 amino acid sequence, an RAI-3 peptide sequence, e.g., encoding one or more functional domains, a mutant RAI-3 amino acid sequence, or a truncated RAI-3 amino acid sequence linked to an unrelated protein or polypeptide sequence. Such fusion proteins include, but are not limited to, Ig Fc fusions which stabilize the RAI-3 fusion protein and can prolong the half-life of the protein in vivo, or fusions to an enzyme, fluorescent protein or luminescent (chemiluminescent) protein that provides a marker function.

RAI-3 protein, peptides, and derivatives thereof, can be produced using genetic engineering techniques. Thus, in order to express a biologically active RAI-3 polypeptide by recombinant technology, a nucleic acid molecule coding for the polypeptide, or a functional equivalent thereof, is inserted into an appropriate expression vector, i.e., a vector which contains the necessary elements for the transcription and translation of the inserted coding sequence. More specifically, the RAI-3 nucleic acid is operatively associated with a regulatory nucleotide sequence containing transcriptional and/or translational regulatory information that controls expression of the RAI-3 nucleic acid in the host cell. The RAI-3 gene products so produced, as well as host cells, or cell lines transfected or transformed with recombinant RAI-3 expression vectors, can be used for a variety of purposes. These include, but are not limited to, generating antibodies (i.e., monoclonal or polyclonal) that bind to the RAI-3 protein or peptides, including those that competitively inhibit binding and thus "neutralize" RAI-3 activity, and the screening and selection of RAI-3 analogs, ligands, or interacting molecules.

In preferred embodiments, for example, RAI-3 transfected CHO/NFAT-CRE cell lines of the present invention, as described in Example 1(L), are useful for the identification of agonists and antagonists of the RAI-3 polypeptide. Representative uses of these cell lines include employing the cell lines in a method of identifying RAI-3 agonists and antagonists. Preferably, the cell lines are useful in a method for identifying a compound that modulates the biological activity of the RAI-3 polypeptide, comprising the steps of: (a) combining a candidate modulator compound with a host cell expressing the RAI-3 polypeptide having the sequence as set forth in SEQ ID NO:3; and (b) measuring an effect of the candidate modulator compound on the activity of the expressed RAI-3 polypeptide. Representative vectors expressing the RAI-3 polypeptide are referenced herein (e.g., pcDNA3.1 hygro™) or otherwise known in the art and as described in Example 1(L).

RAI-3 expressing cell lines are also useful in a method of screening for a compound that is capable of modulating the biological activity of RAI-3 polypeptide, comprising the steps of: (a) determining the biological activity of the RAI-3 polypeptide in the absence of a modulator compound; (b) contacting a host cell expression the RAI-3 polypeptide with the modulator compound; and (c) determining the biological activity of the RAI-3 polypeptide in the presence of the modulator compound; wherein a difference between the activity of the RAI-3 polypeptide in the presence of the modulator compound and in the absence of the modulator compound indicates a modulating effect of the compound. Additional uses for such RAI-3 cell lines are described herein or otherwise known in the art.

Methods that are well known to those skilled in the art are used to construct expression vectors containing the RAI-3 protein or peptide coding sequences and appropriate transcriptional and translational control elements and/or signals. These methods include in vitro recombinant DNA techniques, synthetic techniques and in vivo recombination/genetic recombination. See, for example, the techniques described in Maniatis et al., 1989, *Molecular Cloning, A Laboratory Manual*, Cold Spring Harbor Laboratory, N.Y. and Ausubel et al., 1989, *Current Protocols in Molecular Biology*, Greene Publishing Associates and Wiley Interscience, N.Y. See also, Sambrook et al., 1989, *Molecular Cloning, A Laboratory Manual*, Cold Spring Harbor Press, N.Y.

A variety of host-expression vector systems can be used to express the RAI-3 coding sequences. Such host-expression systems represent vehicles by which the coding sequences of interest can be produced and subsequently purified, but also represent cells which can, when transformed or transfected with the appropriate nucleotide coding sequences, exhibit the corresponding RAI-3 gene product(s) in situ and/or function in vivo. These hosts include, but are not limited to, microorganisms such as bacteria (e.g., *E. coli, B. subtilis*) transformed with recombinant bacteriophage DNA, plasmid DNA, or cosmid DNA expression vectors containing the RAI-3 coding sequences; yeast (e.g., *Saccharomyces, Pichia*) transformed with recombinant yeast expression vectors containing RAI-3 coding sequences; insect cell systems infected with recombinant virus expression vectors (e.g., baculovirus) containing RAI-3 coding sequences; plant cell systems infected with recombinant virus expression vectors (e.g., cauliflower mosaic virus (CaMV); tobacco mosaic virus (TMV)) or transformed with recombinant plasmid expression vectors (e.g., Ti plasmid) containing RAI-3 coding sequences; or mammalian cell systems, including human cells, (e.g., COS, CHO, BHK, 293, NIH/3T3) harboring recombinant expression constructs containing promoters derived from the genome of mammalian cells as described below.

The expression elements of these systems can vary in their strength and specificities. Depending on the host/vector system utilized, any of a number of suitable transcriptional and translational elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used; when cloning in insect cell systems, promoters such as the baculovirus polyhedrin promoter can be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) can be used; when cloning in mammalian cell systems, promoters derived from the genome of mammalian cells (e.g., metallothionein promoter) or from mammalian viruses (e.g., the adenovirus late promoter; the vaccinia virus 7.5K promoter) can be used; when generating cell lines that contain multiple copies of RAI-3 DNA, SV40-, BPV- and EBV-based vectors can be used with an appropriate selectable marker.

In bacterial systems, a number of expression vectors can be advantageously selected depending upon the use intended for the expressed RAI-3 polypeptide or peptide. For example, when large quantities of the RAI-3 polypeptide or peptide are to be produced, e.g., for the generation of antibodies or for the production of the RAI-3 gene product, vectors which direct the expression of high levels of fusion protein products that are readily purified may be desirable. Such vectors include, but are not limited to, the *E. coli* expression vector pUR278 (Ruther et al., 1983, *EMBO J.*, 2:1791), in which the RAI-3 coding sequence can be ligated into the vector in-frame with the lacZ coding region so that a hybrid RAI-3/lacZ protein is produced; pIN vectors (Inouye & Inouye, 1985, *Nucleic Acids Res.*, 13: 3101-3109; Van Heeke & Schuster, 1989, *J. Biol. Chem.*, 264: 5503-5509); and the like. pGEX vectors can also be used to express foreign polypeptides as fusion proteins with glutathione S-transferase (GST). In general, such fusion proteins are soluble and can easily be purified from lysed cells by affinity chromatography, e.g., adsorption to glutathione-agarose beads followed by elution in the presence of free glutathione. The pGEX vectors are designed to include thrombin or factor Xa protease cleavage sites so that the cloned polypeptide of interest can be released from the GST moiety. See also Booth et al., 1988, *Immunol. Lett.*, 19: 65-70; and Gardella et al., 1990, *J. Biol. Chem.*, 265: 15854-15859; Pritchett et al., 1989, *Biotechniques*, 7: 580.

In yeast, a number of vectors containing constitutive or inducible promoters are suitable for use. For a review, see *Current Protocols in Molecular Biology*, Vol. 2, 1988, Ed. Ausubel et al., Greene Publish. Assoc. & Wiley Interscience, Ch. 13; Grant et al., 1987, Expression and Secretion Vectors for Yeast, In: *Methods in Enzymology*, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, *Methods in Enzymology*, Eds. Berger & Kimmel, Acad. Press, N.Y., Vol. 152, pp. 673-684; and *The Molecular Biology of the Yeast Saccharomyces*, 1982, Cold Spring Harbor Press, Vols. I and II.

In an insect system, *Autographa californica* nuclear polyhedrosis virus (AcNPV) can be used as a vector to express foreign genes. The virus grows in *Spodoptera frugiperda* cells. RAI-3 encoding sequences can be cloned into non-essential regions (for example, the polyhedrin gene) of the virus and placed under the control of an AcNPV promoter (for example, the polyhedrin promoter). Successful insertion of the RAI-3 coding sequence results in inactivation of the polyhedrin gene and production of non-occluded recombinant virus (i.e., virus lacking the proteinaceous coat coded for by the polyhedrin gene). These recombinant viruses can then be used to infect *Spodoptera frugiperda* cells in which the inserted gene is expressed (see e.g., Smith et al., 1983, *J. Virol.*, 46: 584; Smith, U.S. Pat. No. 4,215,051).

In mammalian host cells, a number of virus-based expression systems can be employed. In cases where an adenovirus is used as an expression vector, the RAI-3 coding sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) results in a recombinant virus that is viable and capable of expressing RAI-3 in infected hosts (see, e.g., Logan & Shenk, 1984, *Proc. Natl. Acad. Sci. USA*, 81: 3655-3659). Alternatively, the vaccinia 7.5K promoter can be used (see, e.g., Mackett et al., 1982, *Proc. Natl. Acad. Sci. USA*, 79:

7415-7419; Mackett et al., 1984, *J. Virol.*, 49: 857-864; Panicali et al., 1982, *Proc. Natl. Acad. Sci. USA*, 79: 4927-4931).

Specific initiation signals may also be required for efficient translation of inserted RAI-3 coding sequences. These signals include the ATG initiation codon and adjacent sequences. In cases where the entire RAI-3 gene, including its own initiation codon and adjacent sequences, is inserted into the appropriate expression vector, no additional translational control signals may be needed. However, in cases where only a portion of the RAI-3 coding sequence is inserted, exogenous translational control signals, including the ATG initiation codon, are preferably provided. Furthermore, the initiation codon is preferably in phase with the reading frame of the RAI-3 coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.*, 153:516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can frequently be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include, but are not limited to, CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell lines such as, for example, CRL7030 and Hs578Bst, and the like.

For long-term, high-yield production of recombinant proteins, stable expression is preferred. For example, cell lines which stably express the RAI-3 polypeptide or peptide are engineered. Thus, rather than using expression vectors which contain viral origins of replication, host cells can be transformed with RAI-3 encoding nucleic acid molecules, e.g., DNA, controlled by appropriate expression control elements (e.g., promoter, enhancer, sequences, transcription terminators, polyadenylation sites, etc.), and at least one selectable marker. Following the introduction of the foreign DNA, engineered cells are allowed to grow for about 1-2 days in an enriched medium, and then are placed in selective medium. The selectable marker in the recombinant plasmid confers resistance to the selection medium and allows cells to stably integrate the plasmid into their chromosomes and grow to form foci which, in turn, can be cloned and expanded into cell lines. This method can advantageously be used to engineer cell lines which express cellular RAI-3 polypeptides or peptides. Such engineered cell lines are particularly useful in screening for RAI-3 analogs or ligands, or for determining compounds, molecules, and the like, which modulate RAI-3 expression or function.

In instances in which the mammalian cell is a human cell, human artificial chromosome (HAC) systems are among the expression systems by which RAI-3 nucleic acid sequences can be expressed (see, e.g., Harrington et al., 1997, *Nature Genetics*, 15: 345-355). RAI-3 gene products can also be expressed in transgenic animals, such as mice, rats, rabbits, guinea pigs, pigs, micro-pigs, sheep, goats, and non-human primates, e.g., baboons, monkeys, and chimpanzees. The term "transgenic" as used herein refers to animals expressing RAI-3 nucleic acid sequences from a different species (e.g., mice expressing human RAI-3 nucleic acid sequences), as well as animals that have been genetically engineered to over-express endogenous (i.e., same species) RAI-3 nucleic acid sequences, or animals that have been genetically engineered to no longer express endogenous RAI-3 nucleic acid sequences (i.e., "knock-out" animals), and their progeny.

Transgenic animals can be produced using techniques well known in the art, including, but not limited to, pronuclear microinjection (P. C. Hoppe and T. E. Wagner, 1989, U.S. Pat. No. 4,873,191); retrovirus mediated gene transfer into germ lines (Van der Putten et al., 1985, *Proc. Natl. Acad. Sci. USA*, 82: 6148-6152); gene targeting in embryonic stem cells (Thompson et al., 1989, *Cell*, 56: 313-321); electroporation of embryos (Lo, 1983, *Mol Cell. Biol.*, 3: 1803-1814); and sperm-mediated gene transfer (Lavitrano et al., 1989, *Cell*, 57: 717-723); etc. For a review of such techniques, see Gordon, 1989, Transgenic Animals, *Intl. Rev. Cytol.*, 115: 171-229. In addition, any technique known in the art can be used to produce transgenic animal clones containing an RAI-3 transgene, for example, nuclear transfer into enucleated oocytes of nuclei from cultured embryonic, fetal or adult cells at quiescence (Campbell et al., 1996, *Nature*, 380: 64-66; and Wilmut et al., 1997, *Nature*, 385: 810-813).

Host cells which contain the RAI-3 coding sequence and which preferably express a biologically active gene product can be identified by at least four general approaches: (a) DNA-DNA or DNA-RNA hybridization; (b) the presence or absence of "marker" gene functions; (c) assessing the level of transcription as measured by the expression of RAI-3 mRNA transcripts in the host cell; and (d) detection of the gene product as measured by immunoassay or by its biological activity.

In the first approach, the presence of the RAI-3 coding sequence inserted into the expression vector can be detected by DNA-DNA or DNA-RNA hybridization using probes comprising nucleotide sequences that are homologous to the RAI-3 coding sequence, respectively, or portions or derivatives thereof.

In the second approach, the recombinant expression vector/host system can be identified and selected based upon the presence or absence of certain "marker" gene functions. For example, if the RAI-3 coding sequence is inserted within a marker gene sequence of the vector, recombinants containing the RAI-3 coding sequence can be identified by the absence of the marker gene function. Alternatively, a marker gene can be placed in tandem with the RAI-3 sequence under the control of the same or a different promoter used to control the expression of the RAI-3 coding sequence. Expression of the marker in response to induction or selection indicates expression of the RAI-3 coding sequence.

Selectable markers include, for example, resistance to antibiotics, resistance to methotrexate, transformation phenotype, and occlusion body formation in baculovirus. In addition, thymidine kinase activity (M. Wigler et al., 1977, *Cell*, 11: 223) hypoxanthine-guanine phosphoribosyltransferase (Szybalska & Szybalski, 1962, *Proc. Natl. Acad. Sci. USA*, 48: 2026), and adenine phosphoribosyltransferase (Lowy et al., 1980, *Cell*, 22: 817) genes can be employed in tk⁻, hgprt⁻ or aprt⁻ cells, respectively. Also, anti-metabolite resistance can be used as the basis of selection for dhfr, which confers resistance to methotrexate (M. Wigler et al., 1980, *Proc. Natl. Acad. Sci. USA*, 77: 3567; O'Hare et al., 1981, *Proc. Natl. Acad. Sci. USA*, 78: 1527); gpt, which confers resistance to mycophenolic acid (Mulligan & Berg, 1981, *Proc. Natl. Acad. Sci. USA,* 78: 2072); neo, which confers resistance to the aminoglycoside G-418 (Colberre-Garapin, et al., 1981, *J. Mol. Biol.,* 150: 1); and hygro, which confers resistance to hygromycin (Santerre et al., 1984, *Gene,* 30: 147). Additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA,* 85: 8047); and ODC (ornithine decarboxylase) which confers resistance to the ornithine decarboxylase inhibitor, 2-(difluoromethyl)-DL-ornithine, DFMO (McConlogue, 1987, *in Current Communications in Molecular Biology,* Cold Spring Harbor Laboratory ed.).

In the third approach, transcriptional activity for the RAI-3 coding region can be assessed by hybridization assays. For example, RNA can be isolated and analyzed by Northern blot using a probe homologous to the RAI-3 coding sequence or particular portions thereof Alternatively, total nucleic acids of the host cell can be extracted and assayed for hybridization to such probes.

In the fourth approach, the expression of the RAI-3 protein or peptide product can be assessed immunologically, for example by Western blots, immunoassays such as radio-immunoprecipitation, enzyme-linked immunoassays and the like. The ultimate test of the success of the expression system, however, involves the detection of biologically active RAI-3 gene product. A number of assays can be used to detect RAI-3 activity, including but not limited to, binding assays and biological assays for RAI-3 activity.

Once a cell clone that produces high levels of a biologically active RAI-3 polypeptide is identified, the cloned cells can be expanded and used to produce large amounts of the polypeptide which can be purified using techniques well known in the art, including but not limited to, immunoaffinity purification using antibodies, immunoprecipitation, or chromatographic methods including high performance liquid chromatography (HPLC).

In instances in which the RAI-3 coding sequence is engineered to encode a cleavable fusion protein, purification can be readily accomplished using affinity purification techniques. For example, a collagenase cleavage recognition consensus sequence can be engineered between the carboxy terminus of RAI-3 and protein A. The resulting fusion protein can be purified using an IgG column that binds to the protein A moiety. Unfused RAI-3 can be released from the column by treatment with collagenase. Another example embraces the use of pGEX vectors that express foreign polypeptides as fusion proteins with glutathione S-transferase (GST). The fusion protein can be engineered with either thrombin or factor Xa cleavage sites between the cloned gene and the GST moiety. The fusion protein can be easily purified from cell extracts by adsorption to glutathione agarose beads, followed by elution in the presence of glutathione. In fact, any cleavage site or enzyme cleavage substrate can be engineered between the RAI-3 gene product sequence and a second peptide or protein that has a binding partner which can be used for purification, e.g., any antigen for which an immunoaffinity column can be prepared.

In addition, RAI-3 fusion proteins can be readily purified by utilizing an antibody specific for the fusion protein being expressed. For example, a system described by Janknecht et al. allows for the purification of non-denatured fusion proteins expressed in human cell lines (Janknecht, et al., 1991, *Proc. Natl. Acad. Sci. USA,* 88: 8972-8976). In this system, the gene of interest is subcloned into a vaccinia recombination plasmid such that the open reading frame of the gene is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Alternatively, RAI-3 protein and peptides can be produced using chemical methods to synthesize the RAI-3 amino acid sequences in whole or in part. For example, peptides can be synthesized by solid phase techniques, cleaved from the resin, and purified by preparative high performance liquid chromatography (see, e.g., Creighton, 1983, *Proteins: Structures And Molecular Principles,* W.H. Freeman and Co., N.Y., pp. 50-60). The composition of the synthetic peptides can be confirmed by amino acid analysis or sequencing (e.g., the Edman degradation procedure; see Creighton, 1983, *Proteins: Structures and Molecular Principles,* W.H. Freeman and Co., N.Y., pp. 34-49).

The RAI-3 protein, polypeptides and peptide fragments, mutated, truncated or deleted forms of RAI-3 and/or RAI-3 fusion products can be prepared for various uses, including but not limited to, the generation of antibodies (See, Example IO), as reagents in diagnostic assays, the identification of other cellular gene products associated with RAI-3 in the development or continuance of COPD or COPD related disorders, and as reagents in assays for screening for compounds for use in the treatment of COPD and COPD related diseases and disorders.

In a particular related embodiment, RAI-3 peptides, preferably the RAI-3 peptide of SEQ ID NO:1, can be used to identify individuals who are at risk for developing COPD or the underlying symptoms thereof. Such identification can be achieved by a variety of diagnostic or screening methods and assays as are known in the art. For example, antibodies specific for the RAI-3 peptide of SEQ ID NO:1 can be used in such assays, in addition to primers directed against the polynucleotide sequence that codes for the RAI-3 peptide. Primers are preferably obtained from the nucleic acid sequence encoding the RAI-3 polypeptide of SEQ ID NO:3; e.g., nucleotides 1271-1312 of SEQ ID NO:2, which encode the RAI-3 peptide of SEQ ID NO:1, namely, gcccacgcttggccgagcccttacaaagactatgaagtaaag (SEQ ID NO:30). Illustrative primers include, for example, the first 17 nucleotides of the RAI-3-encoding polynucleotide sequence of SEQ ID NO:2, i.e., gcccacgcttggccgag (sense primer), (SEQ ID NO:31); in addition to the antisense of the 3'-most sequence of the RAI-3-encoding polynucleotide, i.e., ctttacttcatagtctttg (antisense primer), (SEQ ID NO:32). In addition, degenerative sequences that encode the RAI-3 polypeptide are encompassed in this embodiment, for example, the degenerative nucleotide that codes for the RAI-3 peptide of SEQ ID NO:1, i.e., nucleotides 1271-1312 of SEQ ID NO:2): namely, gcncaygcntggccntcnccntayaargaytaygargtnaar, (SEQ ID NO:33), (wherein "n" equals A, G, C, or T; wherein "y" equals C or T, and wherein "r" equals A or G). Illustrative primers for this degenerative sequence include, for example, gcncaygcntggccntc (degenerative sense primer), (SEQ ID NO:34) and yttnacytcrtartcyttrtang (degenerative antisense primer), (SEQ ID NO:35), wherein n, y and r are as described above.

Functional Coupling of Human GPCR, RAI-3

In another of its embodiments, the present invention relates to functional coupling of the human RAI-3 GPCR. It has been reported that certain GPCRs exhibit a cDNA concentration-dependent constitutive activity through cAMP response element (CRE) luciferase reporters. (G. Chen et al., 1999, *J.*

*Pharmacol. Toxicol. Methods,* 42:199-206). In accordance with the present invention, functional coupling of RAI-3 to known GPCR second messenger pathways was demonstrated as described in Example 1(L) herein. Briefly, to this end, RAI-3 cDNA was PCR amplified and subcloned into the pcDNA3.1 Hygro™ mammalian expression vector, which was transfected into a CHO cell line wherein the RAI-3 polypeptide was expressed at high constitutive levels as described herein.

Figure 21:
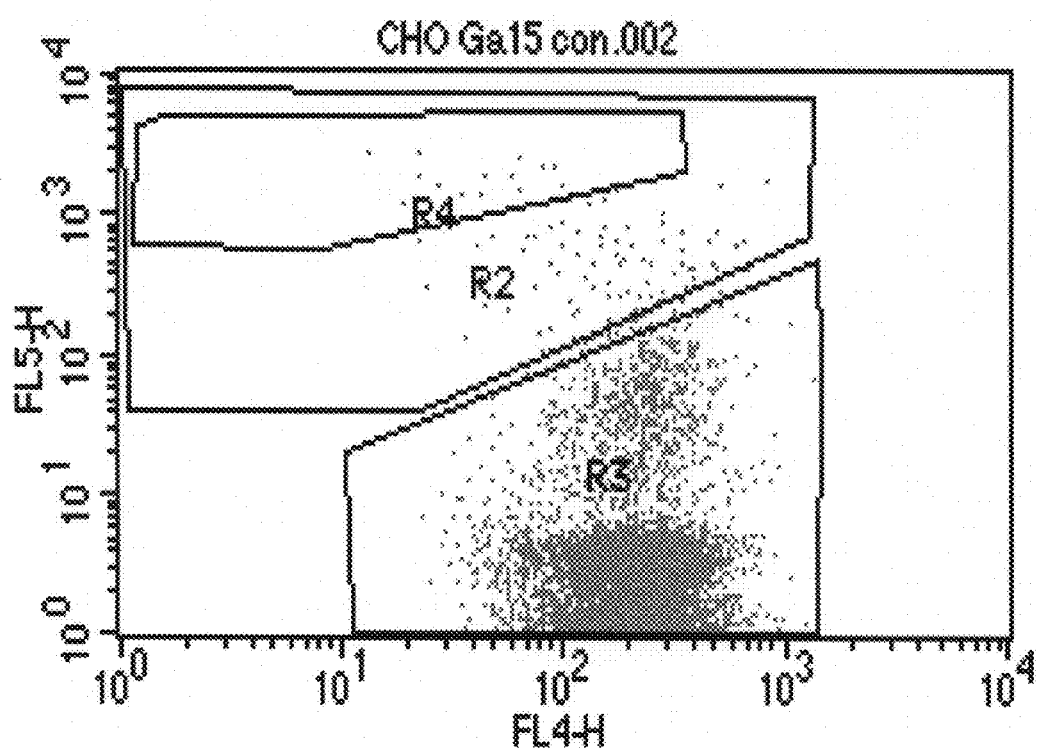
FIG. 21 depicts an untransfected CHO NFAT-G alpha 15 cell line FACS profile. "NFAT" is an acronym for "Nuclear Factor Activator of Transcription". CHO/NFAT-CRE cells, in the absence of the pcDNA3.1 Hygro™/RAI-3 mammalian expression vector transfection, were used as controls, as described herein. The cells were analyzed via FACS (Fluorescence Activated Cell Sorter) analysis according to their wavelength emission at 518 nM (Channel R3—Green Cells), and 447 nM (Channel R2—Blue Cells). As shown, the vast majority of cells emitted at 518 nM, with minimal emission observed at 447 nM. This is expected, since the NFAT response elements remain dormant in the absence of an activated G-protein dependent signal transduction pathway (e.g., a pathway mediated by Gq/11 or promiscuous G coupled receptors). As a result, the cell permeant, CCF2/AM™ (Aurora Biosciences; G. Zlokarnik et al., 1998, *Science*, 279:84-88) substrate remains intact and emits light at 518 nM.
Figure 22:
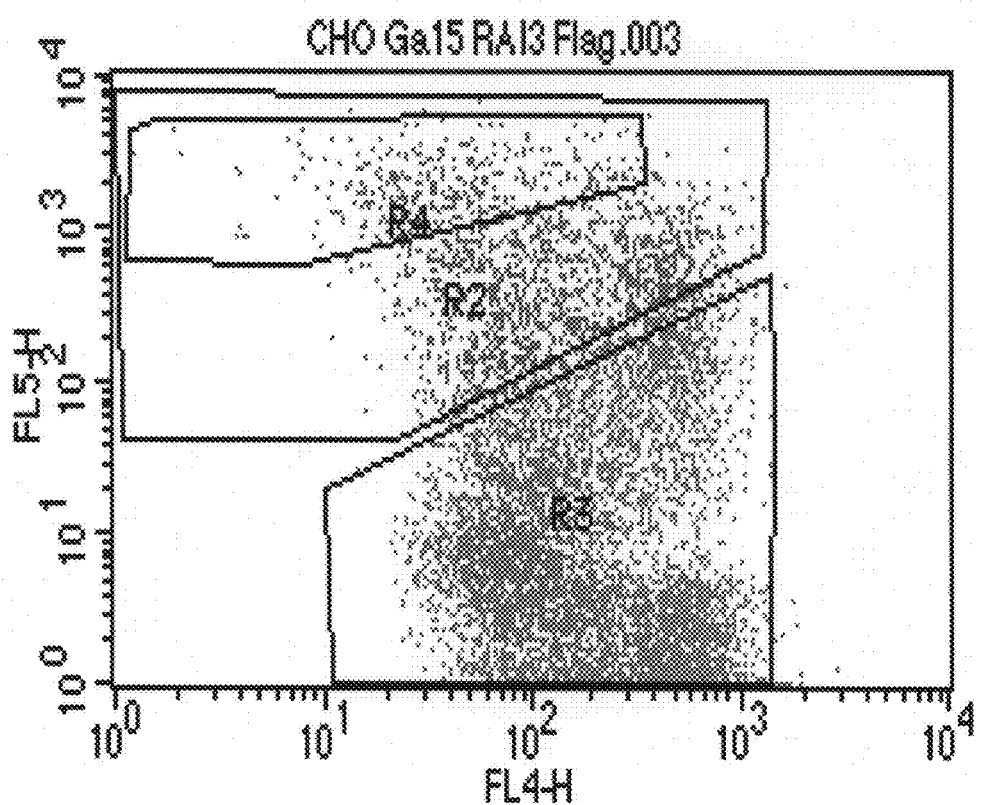
FIG. 22 demonstrates that overexpression of RAI-3 constitutively couples through the promiscuous G protein-(G alpha 15) coupled NFAT response element. CHO/NFAT G alpha 15 cell lines were transfected with the pcDNA3.1 Hygro™/RAI-3 mammalian expression vector, as described herein. The cells were analyzed via FACS according to their wavelength emission at 518 nM (Channel R3—Green Cells), and 447 nM (Channel R2—Blue Cells). As shown, overexpression of RAI-3 resulted in functional coupling, and subsequent activation, of beta lactamase gene expression, as evidenced by the significant number of cells with fluorescent emission at 447 nM relative to the non-transfected CHO/NFAT G alpha 15 cells used as control (see FIG. 23A).

To demonstrate functional coupling of the RAI-3 polypeptide as shown by example herein, i.e., Example 1(L), the ability of RAI-3 to couple to a G protein was examined by employing the promiscuous G protein, G alpha 15. Specific domains of alpha subunits of G proteins have been shown to control coupling to GPCRs (e.g., J. Blahos et al., 2001, *J. Biol. Chem.,* 275(5), 3262-3269). It has been shown that the extreme C-terminal 20 amino acids of either G alpha 15 or 16 confer the unique ability of these G proteins to couple to many GPCRs, including those that naturally do not stimulate phospholipase C (PLC), (J. Blahos et al., 2001, Ibid.). Indeed, both G alpha 15 and 16 have been shown to couple a wide variety of GPCRs to PLC activation of calcium mediated signaling pathways (including the NFAT-signaling pathway), (See, e.g., S. Offermanns and M. I. Simon, 1995, *J. Biol. Chem.,* 270(25):15175-15180). In brief, as described in Example 1(L) hereinbelow, to demonstrate that RAI-3 was functioning as a GPCR, the CHO/NFAT G alpha 15 cell line that contained only the integrated NFAT response element linked to the Beta-Lactamase reporter was transfected with a pcDNA3.1 Hygro™/RAI-3 construct. Analysis of the fluorescence emission from this stable pool showed that RAI-3 constitutively coupled to the NFAT-mediated second messenger pathways via G alpha 15 (FIGS. 20 and 21). The results are consistent with RAI-3 functioning as a GPCR in a manner analogous to that of the known G alpha 15 coupled receptors. Therefore, constitutive expression of RAI-3 in the CHO/NFAT G alpha 15 cell line leads to NFAT activation through accumulation of intracellular $Ca^{2+}$.

Accordingly, in preferred embodiments according to this invention, RAI-3 polynucleotides and polypeptides, including agonists, antagonists, and fragments thereof, are useful for modulating intracellular $Ca^{2+}$ levels, modulating $Ca^{2+}$-sensitive signaling pathways, and modulating NFAT element-associated signaling pathways via G alpha 15.

In additional preferred embodiments, the RAI-3 transfected CHO/NFAT G alpha 15 cell lines of the present invention are useful for the identification of agonists and antagonists of the RAI-3 polypeptide. Illustrative uses of such cell lines include methods of identifying RAI-3 agonists and antagonists. Preferably, an embodiment of the invention embraces a method of identifying a compound that modulates the biological activity of the RAI-3 polypeptide, comprising (a) combining a candidate modulator compound with a host cell expressing the RAI-3 polypeptide having the sequence as set forth in SEQ ID NO:3, or a fragment or portion thereof; and (b) measuring an effect of the candidate modulator compound on the activity of the expressed RAI-3 polypeptide. Representative vectors expressing the RAI-3 polypeptide are described herein, e.g., pcDNA3.1 Hygro™, or are otherwise known in the art.

The cell lines of the present invention are also useful in a method of screening for compounds that are capable of modulating the biological activity of the RAI-3 30 polypeptide, or a peptide thereof, comprising the steps of: (a) determining the biological activity of the RAI-3 polypeptide in the absence of a modulator compound; (b) contacting a host cell expressing the RAI-3 polypeptide with the modulator compound; and (c) determining the biological activity of the RAI-3 polypeptide in the presence of the modulator compound; wherein a difference between the activity of the RAI-3 polypeptide in the presence of the modulator compound and in the absence of the modulator compound indicates a modulating effect of the compound. Additional uses for such cell lines are described herein or otherwise known in the art.

Anti-RAI-3 Antibodies

The present invention also includes antibodies directed to the RAI-3 polypeptide and peptides, as well as methods for the production of such antibodies, including antibodies that specifically recognize one or more RAI-3 epitopes or epitopes of conserved RAI-3 variants, or peptide fragments of RAI-3. Antibodies can be generated against the RAI-3 polypeptide comprising, or alternatively, consisting of, an epitope of the polypeptide having an amino acid sequence of SEQ ID NO:1 or SEQ ID NO:3. Antibodies refer to intact molecules as well as fragments thereof, such as Fab, $F(ab')_2$, Fv, which are capable of binding to an epitopic or antigenic determinant. An antigenic determinant refers to that portion of a molecule that makes contact with a particular antibody (i.e., an epitope). The term "epitope" as used herein, refers to portions of a polypeptide having antigenic or immunogenic activity in an animal, preferably a mammal, and most preferably a human. An "immunogenic epitope" as used herein, refers to a portion of a protein that elicits an antibody response in an animal, as determined by any method known in the art, for example, by the methods for generating antibodies described herein. (See, for example, Geysen et al., 1983, *Proc. Natl. Acad. Sci. USA,* 81:3998-4002). The term "antigenic epitope" as used herein refers to a portion of a protein to which an antibody can immunospecifically bind to its antigen as determined by any method well known in the art, for example, by the immunoassays described herein. Immunospecific binding excludes non-specific binding, but does not necessarily exclude cross-reactivity with other antigens. Antigenic epitopes need not necessarily be immunogenic. Either the full-length protein or an antigenic peptide fragment can be used. Antibodies are preferably prepared from these regions or from discrete fragments in regions of the RAI-3 nucleic acid and protein sequences comprising an epitope.

Anti-RAI-3 antibodies can also be prepared from any region of the RAI-3 polypeptide or peptides thereof as described herein. Antibodies can be developed against the entire receptor or portions of the receptor, for example, the intracellular carboxy terminal domain, the amino terminal extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example. Also, when inactivation of the protein is desired, a preferred fragment generates the production of an antibody that diminishes or completely prevents ligand binding.

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 45 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof, as well as any combination of two, three, four, five or more of these antigenic epitopes. Antigenic epitopes are useful, for example, to raise antibodies, including monoclonal antibodies, that specifically bind the epitope. In addition, antigenic epitopes can be used as the target molecules in immunoassays. (See, for instance, Wilson et al., 1984, *Cell*, 37:767-778; and Sutcliffe et al., 1983, *Science*, 219:660-666). Such fragments as described herein are not to be construed, however, as encompassing any fragments which may be disclosed prior to the invention.

When the RAI-3 protein or a peptide portion of RAI-3 is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody. Specific binding or specifically binding refer to the interaction between a protein or peptide, i.e., the RAI-3 protein or an RAI-3 peptide, and a binding molecule, such as an agonist, an antagonist, or an antibody. The interaction is dependent upon the presence of a particular structure (i.e., an antigenic determinant or epitope) of the protein that is recognized by the binding molecule.

Similarly, immunogenic epitopes can be used, for example, to induce antibodies according to methods well known in the art. (See, for instance, Sutcliffe et al., supra; Wilson et al., supra; Chow et al., 1985, *Proc. Natl. Acad Sci. USA*, 82:910-914; and Bittle et al., 1985, *J. Gen. Virol.*, 66:2347-2354). Preferred immunogenic epitopes include the immunogenic epitopes disclosed herein, as well as any combination of two, three, four, five or more of these immunogenic epitopes.

The RAI-3 polypeptide comprising one or more immunogenic epitopes which elicit an antibody response can be introduced together with a carrier protein, such as albumin, to an animal system (such as rabbit or mouse). Alternatively, if the polypeptide is of sufficient length (e.g., at least about 25 amino acids), the polypeptide can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

An epitope-bearing RAI-3 polypeptide or peptide can be used to induce antibodies according to methods well known in the art including, but not limited to, in vivo immunization, in vitro immunization, and phage display methods. See, e. g., Sutcliffe et al., supra; Wilson et al., supra; and Bittle et al., supra). If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Epitope bearing RAI-3 polypeptide or peptides can also be synthesized as multiple antigen peptides (MAPs), first described by J. P. Tam et al., 1995, *Biomed. Pept., Proteins, Nucleic Acids*, 199, 1(3):123-32; and Calvo, et al., 1993, *J. Immunol.*, 150(4):1403-12), which are hereby incorporated by reference in their entirety herein. MAPs contain multiple copies of a specific peptide attached to a non-immunogenic lysine core. MAP peptides usually contain four or eight copies of the peptide, which are often referred to as MAP4 or MAP8 peptides. By way of non-limiting example, MAPs can be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers commercially available MAP resins, such as, for example, the Fmoc Resin 4 Branch and the Fmoc Resin 8 Branch which can be used to synthesize MAPs. Cleavage of MAPs from the resin is performed with standard trifloroacetic acid (TFA)-based cocktails known in the art. Purification of MAPs, except for desalting, is not generally necessary. MAP peptides can be used in immunizing vaccines which elicit antibodies that recognize both the MAP and the native protein from which the peptide was derived.

Epitope-bearing RAI-3 polypeptide and peptides thereof can also be incorporated into a coat protein of a virus, which can then be used as an immunogen or a vaccine with which to immunize animals, including humans, in order stimulate the production of anti-epitope antibodies. For example, the V3 loop of the gp120 glycoprotein of the human immunodeficiency virus type 1 (HIV-1) has been engineered to be expressed on the surface of rhinovirus. Immunization with rhinovirus displaying the V3 loop peptide yielded apparently effective mimics of the HIV-1 immunogens (as measured by their ability to be neutralized by anti-HIV-1 antibodies as well as by their ability to elicit the production of antibodies capable of neutralizing HIV-1 in cell culture). This techniques of using engineered viral particles as immunogens is described in more detail in Smith et al., 1997, *Behring Inst Mitt Feb*, (98):229-39; Smith et al., 1998, *J. Virol.*, 72:651-659; and Zhang et al., 1999, *Biol. Chem.*, 380:365-74), which are hereby incorporated by reference herein in their entireties.

Epitope bearing RAI-3 polypeptide and peptides thereof can be modified, for example, by the addition of amino acids at the amino- and/or carboxy-terminus of the peptide. Such modifications are performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, thus resulting in a stable loop structure of the epitope-bearing polypeptide under non-reducing conditions. Disulfide bonds can form between a cysteine residue added to the polypeptide and a cysteine residue of the naturally-occurring epitope, or between two cysteines which have both been added to the naturally-occurring epitope-bearing polypeptide. In addition, it is possible to modify one or more amino acid residues of the naturally-occurring epitope-bearing polypeptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing polypeptides contemplated by this invention include biotinylation.

For the production of antibodies in vivo, host animals, such as rabbits, rats, mice, sheep, or goats, are immunized with either free or carrier-coupled peptides or MAP peptides, for example, by intraperitoneal and/or intradermal injection. Injection material is typically an emulsion containing about 100 μg of peptide or carrier protein and Freund's adjuvant, or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal can be increased by selection of anti-peptide antibodies, e.g., by adsorption of the peptide onto a solid support and elution of the selected antibodies according to methods well known in the art.

As one having skill in the art will appreciate, and as discussed above, the RAI-3 polypeptide and peptides as described herein, which comprise an immunogenic or antigenic epitope, can be fused to other polypeptide sequences. For example, the polypeptides of the present invention can be fused with the constant domain of immunoglobulins (IgA, IgE, IgG, IgD, or IgM), or portions thereof, e.g., CH1, CH2, CH3, or any combination thereof, and portions thereof, or with albumin (including, but not limited to, recombinant human albumin, or fragments or variants thereof (see, e. g., U.S. Pat. No. 5,876,969; EP Patent No. 0 413 622; and U.S. Pat. No. 5,766,883, incorporated by reference in their entirety herein), thereby resulting in chimeric polypeptides. Such fusion proteins may facilitate purification and may increase half-life in vivo. This has been shown for chimeric proteins containing the first two domains of the human CD4-polypeptide and various domains of the constant regions of the heavy or light chains of mammalian immunoglobulins. See, e. g., Traunecker et al., 1988, *Nature*, 331:84-86).

Enhanced delivery of an antigen across the epithelial barrier to the immune system has been demonstrated for antigens (e.g., insulin) conjugated to an FcRn binding partner, such as IgG or Fc fragments (see, e.g., PCT publications WO 96/22024 and WO 99/04813). IgG fusion proteins that have a disulfide-linked dimeric structure due to the IgG portion disulfide bonds have also been found to be more efficient in binding and neutralizing other molecules than are monomeric polypeptides, or fragments thereof, alone. See, e.g., Fountoulakis et al., 1995, *J. Biochem.*, 270:3958-3964).

Nucleic acids encoding epitopes can also be recombined with a gene of interest as an epitope tag (e.g., a hemagglutinin ("HA") tag or Flag tag) to aid in detection and purification of the expressed polypeptide. For example, a system for the ready purification of non-denatured fusion proteins expressed in human cell lines has been described by Janknecht et al., (1991, *Proc. Natl. Acad. Sci. USA*, 88:8972-897). In this system, the gene of interest is subcloned into a vaccinia recombination plasmid such that the open reading frame of the gene is translationally fused to an amino-terminal tag having six histidine residues. The tag serves as a matrix binding domain for the fusion protein. Extracts from cells infected with the recombinant vaccinia virus are loaded onto an $Ni^{2+}$ nitriloacetic acid-agarose column and histidine-tagged proteins are selectively eluted with imidazole-containing buffers.

Additional fusion proteins of the invention can be generated by employing the techniques of gene-shuffling, motif-shuffling, exon-shuffling, and/or codon-shuffling (collectively referred to as "DNA shuffling"). DNA shuffling can be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., 1997, *Curr. Opinion Biotechnol.*, 8:724-33; Harayama, 1998, *Trends Biotechnol.*, 16(2):76-82; Hansson, et al., 1999, *J. Mol. Biol.*, 287:265-76; and Lorenzo and Blasco, 1998, *Biotechniques*, 24(2):308-313, the contents of each of which are hereby incorporated by reference in its entirety).

In one aspect, the alteration of a polynucleotide encoding the RAI-3 polypeptide or a fragment thereof can be achieved by DNA shuffling. DNA shuffling involves the assembly of two or more DNA segments by homologous or site-specific recombination to generate variation in the polynucleotide sequence. Alternatively, the RAI-3 polynucleotide, or its encoded polypeptide or peptides, can be altered by being subjected to random mutagenesis by error-prone PCR, random nucleotide insertion, or other methods, prior to recombination. In addition, one or more components, motifs, sections, parts, domains, fragments, etc., of a polynucleotide encoding the RAI-3 polypeptide can be recombined with one or more components, motifs, sections, parts, domains, fragments, etc. of one or more heterologous molecules.

A bispecific or bifunctional antibody is an artificial hybrid antibody having two different heavy/light chain pairs and two different binding sites. Bispecific antibodies can be produced by a variety of methods, including fusion of hybridomas or linking of Fab' fragments. (See, e. g., Songsivilai & Lachmann, 1990, *Clin. Exp. Immunol.*, 79:315-321; Kostelny et al., 1992, *J. Immunol.*, 148:1547 1553). In addition, bispecific antibodies can be formed as "diabodies" (See, Holliger et al., 1993, *Proc. Natl. Acad. Sci. USA*, 90:6444-6448), or "Janusins" (See, Traunecker et al., 1991, *EMBO J.*, 10:3655-3659 and Traunecker et al., 1992, *Int. J. Cancer Suppl.* 7:51-52-127).

Antibodies of the invention include the various types mentioned herein above, as well as anti-idiotypic (anti-Id) antibodies (including, e.g., anti-Id antibodies to antibodies of the invention), intracellularly made antibodies (i.e., intrabodies), and epitope-binding fragments of any of the above. The immunoglobulin molecules of the invention can be of any type (e.g., IgG, IgE, IgM, IgD, IgA and IgY), class or subclass (e.g., IgG1, IgG2, IgG3, IgG4, IgA1 and IgA2) of immunoglobulin molecule. A preferred immunoglobulin is of the IgG1 isotype. Other preferred antibody isotypes include the IgG2 and the IgG4 isotypes.

As is appreciated by the skilled practitioner, immunoglobulins can have both a heavy and a light chain. An array of IgG, IgE, IgM, IgD, IgA, and IgY heavy chains can be paired with a light chain of the kappa or lambda types. Most preferably, antibodies of the present invention are human antigen-binding antibodies and antibody fragments and include, but are not limited to, Fab, Fab' F(ab') 2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, and CH1, CH2, and CH3 domains. Also included in connection with the invention are antigen-binding fragments also comprising any combination of variable region(s) with a hinge region, and CH1, CH2, and CH3 domains. The antibodies of the invention can be from any animal origin including birds and mammals. Preferably, the antibodies are of human, murine (e. g., mouse and rat), donkey, sheep, rabbit, goat, guinea pig, camel, horse, or chicken origin. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described herein and, for example, in U.S. Pat. No. 5,939,598.

The antibodies of the present invention can be monospecific, bispecific, trispecific, or of greater multispecificity. Multispecific antibodies can be specific for different epitopes of the RAI-3 polypeptide, or can be specific for both an RAI-3 polypeptide and a heterologous epitope, such as a heterologous polypeptide or solid support material. (See, e.g., PCT publications WO 93/17715; WO 92/08802; WO 91/00360; WO 92/05793; Tutt et al., 1991, J. Immunol., 147:60-69; U.S. Pat. Nos. 4,474,893; 4,714,681; 4,925,648; 5,573,920; 5,601,819; and Kostelny et al., 1992, J. Immunol., 148:1547-1553).

Antibodies of the present invention can be described or specified in terms of the epitope(s) or portion(s) of the RAI-3 polypeptide which are recognized or specifically bound. The epitope(s) or polypeptide portion(s) can be specified, e.g., by N-terminal and C-terminal positions, by size in contiguous amino acid residues, or as presented in the sequences defined herein. Further included in accordance with the present invention are antibodies which bind to polypeptides encoded by polynucleotides which hybridize to the RAI-3 polynucleotide (SEQ ID NO:2) under stringent, or moderately stringent, hybridization conditions as described herein.

The antibodies of the invention (including molecules comprising, or alternatively consisting of, antibody fragments or variants thereof) can bind immunospecifically and/or preferentially to an RAI-3 polypeptide, an RAI-3 polypeptide fragment, or a variant RAI-3 protein. By way of non-limiting example, an antibody can be considered to bind to a first antigen preferentially if it binds to the first antigen with a dissociation constant (Kd) that is less than the antibody's Kd for the second antigen. In another non-limiting embodiment, an antibody can be considered to bind to a first antigen preferentially if it binds to the first antigen with an affinity that is at least one order of magnitude less than the antibody's Ka for the second antigen. In another non-limiting example, an antibody can be considered to bind to a first antigen preferentially if it binds to the first antigen with an affinity that is at least two orders of magnitude less than the antibody's Kd for the second antigen.

In another nonlimiting example, an antibody can be considered to bind to a first antigen preferentially if it binds to the first antigen with an off rate (koff) that is less than the antibody's koff for the second antigen. In a further nonlimiting example, an antibody can be considered to bind to a first antigen preferentially if it binds to the first antigen with an affinity that is at least one order of magnitude less than the antibody's koff for the second antigen. In yet a further non-limiting example, an antibody can be considered to bind to a first antigen preferentially if it binds to the first antigen with an affinity that is at least two orders of magnitude less than the antibody's koff for the second antigen.

Anti-RAI-3-antibodies of this invention can also be described or specified in terms of their binding affinity to the RAI-3 polypeptide or peptide thereof. Preferred binding affinities include those with a dissociation constant or Kd of less than $5\times10^{-2}$ M, $1\times10^{-2}$ M, $5\times10^{-3}$ M, $1\times10^{-3}$ M, $5\times10^{-4}$ M, or $1\times10^{-4}$ M. More preferred binding affinities include those with a dissociation constant or Kd less than $5\times10^{-5}$ M, $1\times10^{-5}$ M, $5\times10^{-6}$ M, $1\times10^{-6}$ M, $5\times10^{-7}$ M, $1\times10^{-7}$ M, $5\times10^{-8}$ M, or $1\times10^{-8}$ M. Even more preferred antibody binding affinities include those with a dissociation constant or Kd of less than $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $1\times10^{-12}$ M, $5\times10^{-13}$ M, $1\times10^{-13}$ M, $5\times10^{-14}$ M, $1\times10^{-14}$ M, $5\times10^{-15}$ M, or $1\times10^{-15}$ M.

More specifically, antibodies of the invention bind to the RAI-3 polypeptide, RAI-3 fragments, or variants thereof, with an off rate (koff) of less than or equal to about $5\times10^{-2}$ sec$^{-1}$, $1\times10^{-2}$ sec$^{-1}$, $5\times10^{-3}$ sec$^{-1}$, or $1\times10^{-3}$ sec$^{-1}$. More preferably, antibodies of the invention bind to the RAI-3 polypeptide, RAI-3 fragments, or variants thereof, with an off rate (koff) of less than or equal to about $5\times10^{-4}$ sec$^{-1}$, $1\times10^{-4}$ sec$^{-1}$, $5\times10^{-5}$ sec$^{-1}$, $1\times10^{-5}$ sec$^{-1}$, $5\times10^{-6}$ sec$^{-1}$, $1\times10^{-6}$ sec$^{-1}$, $5\times10^{-7}$ sec$^{-1}$, or $1\times10^{-7}$ sec$^{-1}$. In other aspects, antibodies of the invention bind to the RAI-3 polypeptide, RAI-3 fragments, or variants thereof with an on rate (kon) of greater than or equal to $1\times10^{3}$ M$^{-1}$ sec$^{-1}$, $5\times10^{3}$ M$^{-1}$ sec$^{-1}$, $1\times10^{4}$ M$^{-1}$ sec$^{-1}$, or $5\times10^{4}$ M$^{-1}$ sec$^{-1}$. More preferably, antibodies of the invention bind to the RAI-3 polypeptide, or RAI-3 fragments, or variants thereof with an on rate greater than or equal to $1\times10^{5}$ M$^{-1}$ sec$^{-1}$, $5\times10^{5}$ M$^{-1}$ sec$^{-1}$, $1\times10^{6}$ M$^{-1}$ sec$^{-1}$, $5\times10^{-6}$ M$^{-1}$ sec$^{-1}$, or $1\times10^{-7}$ M$^{-1}$ sec$^{-1}$.

The present invention also provides antibodies that competitively inhibit the binding of an antibody to an RAI-3 epitope as determined by any method known in the art for determining competitive binding, for example, the immunoassays as described herein. In preferred embodiments, the antibody competitively inhibits binding to an epitope by at least 95%, at least 90%, at least 85%, at least 80%, at least 75%, at least 70%, at least 60%, or at least 50%.

As mentioned above, antibodies of the present invention can act as agonists or antagonists of the RAI-3 polypeptide. For example, the invention includes antibodies which disrupt RAI-3 receptor/ligand interactions, or disrupt interactions of cellular molecules affected by RAI-3 following cell stimulation, either partially or fully. The invention includes both receptor-specific antibodies and ligand-specific antibodies. The invention also includes receptor-specific antibodies which do not prevent ligand binding, but do prevent receptor activation. Receptor activation (i.e., signaling) can be determined by techniques described herein or as otherwise known in the art. For example, receptor activation can be determined by detecting the phosphorylation (e.g., on tyrosine or serine/threonine) of the receptor or its substrate by immunoprecipitation followed by Western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in the absence of the antibody.

In an embodiment of the present invention, antibodies that immunospecifically bind to the RAI-3 protein, or to a fragment or variant thereof, comprise a polypeptide having the amino acid sequence of any one of the Ig heavy chains expressed by an anti-RAI-3 protein antibody-expressing cell line of the invention, and/or any one of the Ig light chains expressed by an anti-RAI-3 protein antibody-expressing cell line of the invention. In another embodiment of the present invention, antibodies that immunospecifically bind to the RAI-3 protein, or to a fragment or variant thereof, comprise a polypeptide having the amino acid sequence of any one of the $V_H$ domains of a heavy chain expressed by an anti-RAI-3 protein antibody-expressing cell line, and/or any one of the $V_L$ domains of a light chain expressed by an anti-RAI-3 protein antibody-expressing cell line. In preferred embodiments, antibodies of the present invention comprise the amino acid sequence of a $V_H$ domain and $V_L$ domain expressed by a single anti-RAI-3 protein antibody-expressing cell line. In alternative embodiments, antibodies of the present invention comprise the amino acid sequence of a $V_H$ domain and a $V_L$ domain expressed by two different anti-RAI-3 protein antibody-expressing cell lines. Molecules comprising, or alternatively consisting of, antibody fragments or variants of the $V_H$ and/or $V_L$ domains expressed by an anti-RAI-3 protein antibody-expressing cell line that immunospecifically bind to an RAI-3 protein are also encompassed by the invention, as are nucleic acid molecules encoding these $V_H$ and $V_L$ domains, molecules, fragments and/or variants.

The present invention also provides antibodies that immunospecifically bind to the RAI-3 polypeptide, or fragment or variant of the RAI-3 protein, wherein the antibodies comprise, or alternatively consist of, a polypeptide having an amino acid sequence of any one, two, three, or more of the $V_H$ CDRs contained in an Ig heavy chain expressed by one or more anti-RAI-3 protein antibody expressing cell lines. In particular, the invention provides antibodies that immunospecifically bind to the RAI-3 protein, comprising, or alternatively consisting of, a polypeptide having the amino acid sequence of a $V_H$ CDR1 contained in an Ig heavy chain expressed by one or more anti-RAI-3 protein antibody expressing cell lines. In another embodiment, antibodies that immunospecifically bind to the RAI-3 protein, comprise, or alternatively consist of, a polypeptide having the amino acid sequence of a $V_H$ CDR2 contained in a heavy chain expressed by one or more anti-RAI-3 protein antibody expressing cell lines. In a preferred embodiment, antibodies that immunospecifically bind to the RAI-3 protein, comprise, or alternatively consist of, a polypeptide having the amino acid sequence of a $V_H$ CDR3 contained in an Ig heavy chain expressed by one or more anti-RAI-3 protein antibody expressing cell lines of the invention. Molecules comprising, or alternatively consisting of, these antibodies, or antibody fragments or variants thereof, that immunospecifically bind to the RAI-3 protein or to an RAI-3 protein fragment or variant thereof are also encompassed by the invention, as are nucleic acid molecules encoding these anti-RAI-3 antibodies, molecules, fragments and/or variants.

The present invention also provides antibodies that immunospecifically bind to the RAI-3 polypeptide, or a fragment or variant of the RAI-3 protein, wherein the antibodies comprise, or alternatively consist of, a polypeptide having an amino acid sequence of any one, two, three, or more of the $V_L$ CDRs contained in an Ig heavy chain expressed by one or more anti-RAI-3 protein antibody expressing cell lines of the invention. In particular, the invention provides antibodies that immunospecifically bind to the RAI-3 protein, comprising, or alternatively consisting of, a polypeptide having the amino acid sequence of a $V_L$ CDR1 contained in an Ig heavy chain expressed by one or more anti-RAI-3 protein antibody-expressing cell lines of the invention. In another embodiment, antibodies that immunospecifically bind to the RAI-3 protein, comprise, or alternatively consist of, a polypeptide having the amino acid sequence of a $V_L$ CDR2 contained in an Ig heavy chain expressed by one or more anti-RAI-3 protein antibody-expressing cell lines of the invention. In a preferred embodiment, antibodies that immunospecifically bind to the RAI-3 protein, comprise, or alternatively consist of, a polypeptide having the amino acid sequence of a $V_L$ CDR3 contained in an Ig heavy chain expressed by one or more anti-RAI-3 protein antibody-expressing cell lines of the invention. Molecules comprising, or alternatively consisting of, these antibodies, or antibody fragments or variants thereof, that immunospecifically bind to the RAI-3 protein or to an RAI-3 protein fragment or variant thereof are also encompassed by the invention, as are nucleic acid molecules encoding these anti-RAI-3 antibodies, molecules, fragments and/or variants.

The present invention also provides antibodies (including molecules comprising, or alternatively consisting of, antibody fragments or variants) that immunospecifically bind to the RAI-3 protein or to an RAI-3 polypeptide fragment or variant, wherein the antibodies comprise, or alternatively consist of, one, two, three, or more $V_H$ CDRs, and one, two, three or more $V_L$ CDRs, as contained in an Ig heavy chain or light chain expressed by one or more anti-RAI-3 protein antibody-expressing cell lines of the invention. In particular, the invention provides antibodies that immunospecifically bind to the RAI-3 protein or to an RAI-3 polypeptide fragment or variant, wherein the antibodies comprise, or alternatively consist of, a $V_H$ CDR1 and a $V_L$ CDR1, a $V_H$ CDR1 and a $V_L$ CDR2, a $V_H$ CDR1 and a $V_L$ CDR3, a $V_H$ CDR2 and a $V_L$ CDR1, VH CDR2 and $V_L$ CDR2, a $V_H$ CDR2 and a $V_L$ CDR3, a $V_H$ CDR3 and a $V_H$ CDR1, a $V_H$ CDR3 and a $V_L$ CDR2, a $V_H$ CDR3 and a $V_L$ CDR3, or any combination thereof, of the $V_H$ CDRs and $V_L$ CDRs contained in an Ig heavy chain or Ig light chain expressed by one or more anti-RAI-3 protein antibody-expressing cell lines of the invention. In a preferred embodiment, one or more of these combinations are from a single anti-RAI-3 protein antibody-expressing cell line. Molecules comprising, or alternatively consisting of, fragments or variants of these antibodies that immunospecifically bind to the RAI-3 protein are also encompassed by the invention, as are nucleic acid molecules encoding these anti-RAI-3 antibodies, molecules, fragments or variants.

Also provided are nucleic acid molecules, generally isolated, encoding an antibody of the invention (including molecules comprising, or alternatively consisting of, antibody fragments or variants thereof). In a specific aspect, a nucleic acid molecule of the invention encodes an antibody (including molecules comprising, or alternatively consisting of, antibody fragments or variants thereof), comprising, or alternatively consisting of, a $V_H$ domain having an amino acid sequence of any one of the $V_H$ domains of an immunoglobulin heavy chain expressed by an anti-RAI-3 protein antibody-expressing cell line of the invention and a $V_L$ domain having an amino acid sequence of an immunoglobulin light chain expressed by an anti-RAI-3 protein antibody-expressing cell line of the invention. In another aspect, a nucleic acid molecule of the invention encodes an antibody (including molecules comprising, or alternatively consisting of, antibody fragments or variants thereof), comprising, or alternatively consisting of, a $V_H$ domain having an amino acid sequence of any one of the $V_H$ domains of an immunoglobulin heavy chain expressed by an anti-RAI-3 protein antibody-expressing cell line of the invention, or a $V_L$ domain having an amino acid sequence of a light chain expressed by an anti-RAI-3 protein antibody-expressing cell line of the invention. The present invention also provides antibodies that comprise, or alternatively consist of, variants (including derivatives) of the antibody molecules (e.g., the $V_H$ domains and/or $V_L$ domains) described herein, which antibodies immunospecifically bind to the RAI-3 protein or to a fragment or a variant thereof.

Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably the molecules are immunoglobulin molecules. Also, preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, relative to the reference $V_H$ domain, $V_H$ CDR1, $V_H$ CDR2, $V_H$ CDR3, $V_L$ domain, $V_L$ CDR1, $V_L$ CDR2, or $V_L$ CDR3 domain.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Alternatively, mutations can be introduced randomly along all or part of the coding sequence, such as by saturation mutagenesis. The resultant mutants can be screened for biological activity to identify mutants that retain activity. For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or to improve hybridoma antibody production. Alternatively, non-neutral missense mutations can alter an antibody's ability to bind antigen. The location of most silent and neutral missense mutations is likely to be in the framework regions, while the location of most non-neutral missense mutations is likely to be in the CDRs, although this is not an absolute requirement. One of skill in the art is able to design and test mutant molecules with desired properties, such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known and practiced in the art.

In a specific aspect, an antibody of the invention (including a molecule comprising, or alternatively consisting of, an antibody fragment or variant thereof), that immunospecifically binds to the RAI-3 protein or to fragments or variants thereof, comprises, or alternatively consists of, an amino acid sequence encoded by a nucleotide sequence that hybridizes to a nucleotide sequence that is complementary to that encoding one of the $V_H$ or $V_L$ domains expressed by one or more anti-RAI-3 protein antibody-expressing cell lines of the invention, preferably under stringent conditions, e.g., hybridization to filter-bound DNA in 6× sodium chloride/sodium citrate (SSC) at about 45° C. followed by one or more washes in 0.2×SSC/0.1% SDS at about 50-65° C., preferably under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structures and many of the same biological activities. Thus, in one aspect, an antibody (including a molecule comprising, or alternatively consisting of, an antibody fragment or variant thereof), that immunospecifically binds to the RAI-3 polypeptide, or to RAI-3 peptide fragments or variants, comprises, or alternatively consists of, a $V_H$ domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a $V_H$ domain of a heavy chain expressed by an anti-RAI-3 protein antibody-expressing cell line of the invention.

In another aspect, an antibody (including a molecule comprising, or alternatively consisting of, an antibody fragment or variant thereof), that immunospecifically binds to the RAI-3 protein or to RAI-3 fragments or variants, comprises, or alternatively consists of, a $V_L$ domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a $V_L$ domain of a light chain expressed by an anti-RAI-3 protein antibody-expressing cell line of the invention.

The present invention also provides antibodies (including molecules comprising, or alternatively consisting of, antibody fragments or variants thereof), that down-regulate the cell-surface expression of an RAI-3 protein, as determined by any method known in the art such as, for example, FACS analysis or immunofluorescence assays. By way of a non-limiting hypothesis, such down-regulation may be the result of antibody induced internalization of the RAI-3 protein. Such antibodies can comprise, or alternatively consist of, a portion (e.g., $V_H$ CDR1, $V_H$ CDR2, $V_H$ CDR3, $V_L$ CDR1, $V_L$ CDR2, or $V_L$ CDR3) of a $V_H$ or $V_L$ domain having an amino acid sequence of an antibody of the invention, or a fragment or variant thereof.

In another aspect, an antibody that down-regulates the cell-surface expression of the RAI-3 protein comprises, or alternatively consists of, a polypeptide having the amino acid sequence of a $V_H$ domain of an antibody of the invention, or a fragment or variant thereof and a $V_L$ domain of an antibody of the invention, or a fragment or variant thereof. In another aspect, an antibody that down-regulates the cell-surface expression of the RAI-3 protein comprises, or alternatively consists of, a polypeptide having the amino acid sequence of a $V_H$ domain and a $V_L$ domain from a single antibody (or scFv or Fab fragment) of the invention, or fragments or variants thereof. In another aspect, an antibody that down-regulates the cell-surface expression of the RAI-3 protein comprises, or alternatively consists of, a polypeptide having the amino acid sequence of a $V_H$ domain of an antibody of the invention, or a fragment or variant thereof. In another aspect, an antibody that down-regulates the cell-surface expression of the RAI-3 protein comprises, or alternatively consists of, a polypeptide having the amino acid sequence of a $V_L$ domain of an antibody of the invention, or a fragment or variant thereof.

In a preferred aspect, an antibody that down-regulates the cell-surface expression of the RAI-3 protein comprises, or alternatively consists of, a polypeptide having the amino acid sequence of a $V_H$ CDR3 of an antibody of the invention, or a fragment or variant thereof. In another preferred aspect, an antibody that down-regulates the cell-surface expression of the RAI-3 protein comprises, or alternatively consists of, a polypeptide having the amino acid sequence of a $V_L$ CDR3 of an antibody of the invention, or a fragment or variant thereof. Nucleic acid molecules encoding these antibodies are also encompassed by the invention.

In another preferred aspect, an antibody that enhances the activity of the RAI-3 protein, or a fragment or variant thereof, comprises, or alternatively consists of, a polypeptide having the amino acid sequence of a $V_L$ CDR3 of an antibody of the invention, or a fragment or variant thereof. Nucleic acid molecules encoding these antibodies are also encompassed by the invention.

In addition, as nonlimiting examples, anti-RAI-3 antibodies as described herein can be used to purify, detect, and target the RAI-3 polypeptide, including both in vitro and in vivo diagnostic, detection, screening, and/or therapeutic methods. For example, the antibodies can be used in immunoassays for qualitatively and quantitatively measuring levels of the RAI-3 protein in biological samples. (See, e.g., Harlow et al., *Antibodies: A Laboratory Manual*, Cold Spring Harbor Laboratory Press, 2nd Ed. 1988, which is incorporated by reference herein in its entirety). By way of another nonlimiting example, anti-RAI-3 antibodies can be administered to individuals as a form of passive immunization. Alternatively, antibodies of the present invention can be used for epitope mapping to identify the epitope(s) that are bound by one or more antibodies. Epitopes identified in this way can, in turn, for example, be used as vaccine candidates, i.e., to immunize an individual to elicit antibodies against the naturally-occurring forms of the RAI-3 protein.

As discussed in more detail below, anti-RAI-3 antibodies can be used either alone or in combination with other compositions. The antibodies can further be recombinantly fused to a heterologous polypeptide at the N- or C-terminus, or chemically conjugated (including covalent and non-covalent conjugations) to polypeptides or other compositions. For example, antibodies of the present invention can be recombinantly fused or conjugated to molecules that are useful as labels in detection assays and to effector molecules such as heterologous polypeptides, drugs, radionuclides, or toxins. See, e.g., PCT publications WO 92/08495; WO 91/14438; WO 89/12624; U.S. Pat. No. 5,314,995 and EP 396, 387.

The antibodies of the invention further include derivatives that are modified, i.e., by the covalent attachment of any type of molecule to the antibody. For example, without limitation, anti-RAI-3 antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. In addition, the derivative can contain one or more non-classical amino acids.

Anti-RAI-3 antibodies of the present invention can be generated by any suitable method known in the art. Polyclonal antibodies directed against an antigen or immunogen of interest can be produced by various procedures well known in the art. For example, the RAI-3 protein or an RAI-3 peptide can be administered to various host animals as elucidated above to induce the production of sera containing polyclonal antibodies specific for the antigen. Various adjuvants may be used to increase the immunological response, depending on the host species; adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art, including the use of hybridoma, recombinant and phage display technologies, or a combinatione thereof. For example, monoclonal antibodies can be produced using hybridoma techniques as known and practiced in the art and as taught, for example, in Harlow et al., Antibodies: A Laboratory Manual, (Cold Spring Harbor Laboratory Press, 2nd Ed. 1988; Hammerling, et al., In: Monoclonal Antibodies and T-Cell Hybridomas, Elsevier, N.Y., pages 563-681, 1981, the contents of which are incorporated herein by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a nonlimiting example, mice can be immunized with the RAI-3 polypeptide or a peptide thereof, or with a cell expressing the RAI-3 polypeptide or peptide. Once an immune response is detected, e.g., antibodies specific for the antigen are detected in the sera of immunized mice, the spleen is harvested and splenocytes are isolated. The splenocytes are then fused by well known techniques to any suitable myeloma cells, for example cells from cell line SP2/0 or P3X63-AG8.653 available from the ATCC. Hybridomas are selected and cloned by limiting dilution techniques. The hybridoma clones are then assayed by methods known in the art to determine and select those cells that secrete antibodies capable of binding to the RAI-3 protein, or to a portion of the RAI-3 protein. Ascites fluid, which generally contains high levels of antibodies, can be generated by immunizing mice with positive hybridoma clones.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of *Current Protocols in Immunology*, Coligan et al., Eds., 1994, John Wiley & Sons, NY, which is hereby incorporated by reference herein in its entirety. The source of B cells for transformation is commonly human peripheral blood, but B cells for transformation can also be obtained from other sources including, but not limited to, lymph node, tonsil, spleen, tumor tissue, and infected tissues. Tissues are generally prepared as single cell suspensions prior to EBV transformation. In addition, T cells that may be present in the B cell samples can be either physically removed or inactivated (e.g., by treatment with cyclosporin A). The removal of T cells is often advantageous, because T cells from individuals who are seropositive for anti-EBV antibodies can suppress B cell immortalization by EBV. In general, a sample containing human B cells is innoculated with EBV and cultured for 3-4 weeks. A typical source of EBV is the culture supernatant of the B95-8 cell line (ATCC; VR-1492). Physical signs of EBV transformation can generally be seen toward the end of the 3-4 week culture period.

By phase-contrast microscopy, transformed cells appear large, clear and "hairy"; they tend to aggregate in tight clusters of cells. Initially, EBV lines are generally polyclonal. However, over prolonged periods of cell culture, EBV lines can become monoclonal as a result of the selective outgrowth of particular B cell clones. Alternatively, polyclonal EBV transformed lines can be subcloned (e.g., by limiting dilution) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g., SPAM-8, SBC-H20, and CB-F7), and human cell lines (e.g., GM 1500, SKO-007, RPMI 8226, and KR-4). Thus, the present invention also includes a method of generating polyclonal or monoclonal human antibodies against polypeptides of the invention or fragments thereof, comprising EBV-transformation of human B cells.

Antibody fragments that recognize specific epitopes can be generated by known techniques. For example, Fab and F(ab')2 fragments of the invention can be produced by proteolytic cleavage of immunoglobulin molecules, using enzymes such as papain (to produce Fab fragments) or pepsin (to produce F (ab') 2 fragments). F(ab')2 fragments contain the variable region, the light chain constant region and the CH1 domain of the heavy chain.

Antibodies encompassed by the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest, i.e., the RAI-3 protein or fragment thereof, can be selected or identified with antigen, e.g., using labeled antigen or antigen bound or captured onto a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., 1995, *J. Immunol. Methods*, 182:41-50; Ames et al., 1995, *J. Immunol. Methods*, 184:177-186; Kettleborough et al., 1994, *Eur. J. Immunol.*, 24:952-958; Persic et al., 1997, *Gene*, 187:9-18; Burton et al., 1994, *Advances in Immunology*, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce single-chain Fvs and antibodies include those described in U.S. Pat. Nos. 4,946,778 and 5,258,498; Huston et al., 1991, *Methods in Enzymology*, 203:46-88; Shu et al., 1993, *Proc. Natl. Acad. Sci. USA*, 90:7995-7999; and Skerra et al., 1988, *Science*, 240:1038-1040. For some uses, including the in vivo use of antibodies in humans and in in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, 1985, *Science*, 229:1202; Oi et al., 1986, *BioTechniques*, 4:214; Gillies et al., 1989, *J. Immunol. Methods*, 125:191-202; and U.S. Pat. Nos. 5,807,715; 4,816,567; and 4,816,397, which are incorporated herein by reference in their entirety).

Humanized antibodies are antibody molecules from non-human species antibody that bind to the desired antigen and have one or more complementarity determining regions (CDRs) from the nonhuman species and framework regions from a human immunoglobulin molecule. Often, framework residues in the human framework regions are substituted with the corresponding residues from the CDR donor antibody to alter, and preferably to improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (See, e.g., Queen et al., U.S. Pat. No. 5,585,089; and Riechmann et al., 1988, *Nature*, 332:323, which are incorporated herein by reference in their entireties). Antibodies can be humanized using a variety of techniques known in the art, including, for example, CDR-grafting (EP 239,400; PCT publication WO 91/09967; U.S. Pat. Nos. 5,225,539; 5,530, 101; and 5,585,089); veneering or resurfacing (EP 592,106; EP 519,596; Padlan, 1991, *Molecular Immunology*, 28(4/5): 489-498; Studnicka et al., 1994, *Protein Engineering*, 7(6): 805-814; Roguska et al., 1994, *Proc. Natl. Acad Sci. USA*, 91:969-973; and chain shuffling (U.S. Pat. No. 5,565,332).

Completely human antibodies can be made by a variety of methods known in the art, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. Completely human antibodies are particularly desirable for therapeutic treatment of human patients, so as to avoid or alleviate immune reaction to foreign protein.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly, or by homologous recombination, into mouse embryonic stem cells. Alternatively, the human variable region, constant region, and diversity region may be introduced into mouse embryonic stem cells, in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Monoclonal antibodies directed against the antigen can be obtained from the immunized transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce useful human IgG, IgA, IgM and IgE antibodies. For an overview of the technology for producing human antibodies, see Lonberg and Huszar, 1995, *Intl. Rev.*

*Immunol.*, 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.) and Genpharm (San Jose, Calif.) can be engaged to provide human antibodies directed against a selected antigen using technology similar to the above described technologies.

In another aspect, completely human antibodies which recognize a selected epitope can be generated using a technique referred to as "guided selection". In this approach, a selected non-human monoclonal antibody, e.g., a mouse antibody, is used to guide the selection of a completely human antibody recognizing the same epitope. (Jespers et al., 1988, *BioTechnology*, 12:899-903).

Further, antibodies specific for the RAI-3 protein can, in turn, be utilized to generate anti-idiotypic antibodies that "mimic" the RAI-3 protein using techniques well known to those skilled in the art. (See, e.g., Greenspan and Bona, 1989, *FASEB J.*, 7(5):437-444 and Nissinoff, 1991, *J. Immunol.*, 147(8):2429-2438). For example, antibodies which bind to and competitively inhibit polypeptide multimerization and/or binding of the RAI-3 polypeptide to a ligand can be used to generate anti-idiotypic antibodies that "mimic" the polypeptide multimerization and/or binding domain and, as a consequence, bind to and neutralize the polypeptide and/or its ligand, e.g., in therapeutic regimens. Such neutralizing anti-idiotypes or Fab fragments of such anti-idiotypes can be used to neutralize polypeptide ligand. For example, such anti-idiotypic antibodies can be used to bind the RAI-3 polypeptide and/or to bind its ligands/receptors, and thereby activate or block its biological activity.

In another aspect, intrabodies are embraced. Intrabodies are antibodies, often scFvs, that are expressed from a recombinant nucleic acid molecule and are engineered to be retained intracellularly (e.g., retained in the cytoplasm, endoplasmic reticulum, or periplasm of the host cells). Intrabodies can be used, for example, to ablate the function of a protein to which the intrabody binds. The expression of intrabodies can also be regulated through the use of inducible promoters in the nucleic acid expression vector comprising nucleic acid encoding the intrabody. Intrabodies of the invention can be produced using methods known in the art, such as those disclosed and reviewed in Chen et al., 1994, *Hum. Gene Ther.*, 5:595-601; Marasco, W. A., 1997, *Gene Ther.*, 4:11-15; Rondon and Marasco, 1997, *Annu. Rev. Microbiol.*, 51:257-283; Proba et al., 1998, *J. Mol. Biol.*, 275:245-253; Cohen et al., 1998, *Oncogene*, 17:2445-2456; Ohage and Steipe, 1999, *J. Mol. Biol.*, 291:1119-1128; Ohage et al., 1999, *J. Mol. Biol.*, 291:1129-1134; Wirtz and Steipe, 1999, *Protein Sci.*, 8:2245-2250; Zhu et al., 1999, *J. Immunol. Methods*, 231:207-222.

XenoMouse Technology Antibodies in accordance with the invention are preferably prepared by the utilization of a transgenic mouse that has a substantial portion of the human antibody producing genome inserted, but that is rendered deficient in the production of endogenous murine antibodies (e.g., XenoMouse strains available from Abgenix Inc., Fremont, Calif.). Such mice are capable of producing human immunoglobulin molecules and antibodies and are virtually deficient in the production of murine immunoglobulin molecules and antibodies. Technologies utilized for achieving the same are disclosed in the patents, applications, and references disclosed herein.

The ability to clone and reconstruct megabase-sized human loci in YACs and to introduce them into the mouse germline provides a powerful approach to elucidating the functional components of very large or crudely mapped loci, as well as generating useful models of human disease. Furthermore, the utilization of such technology for substitution of mouse loci with their human equivalents can provide unique insights into the expression and regulation of human gene products during development, their communication with other systems, and their involvement in disease induction and progression. An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies, as well as their role in B cell development. Furthermore, such a strategy can provide an ideal source for the production of fully human monoclonal antibodies (Hu MAbs) an important milestone toward fulfilling the promise of antibody therapy in human disease.

Fully human antibodies are expected to minimize the immunogenic and allergic responses intrinsic to mouse or mouse-derivatized monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach toward the goal of producing fully human antibodies was to engineer mouse strains deficient in mouse antibody production to harbor large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human monoclonal antibodies with the desired specificity could be readily produced and selected.

This general strategy was demonstrated in connection with the generation of the first "XenoMouseT" strains as published in 1994. See Green et al., 1994, *Nature Genetics*, 7:13-21. The XenoMouse strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through the use of megabase-sized, germline configuration YAC fragments of the human heavy chain loci and kappa light chain loci, respectively, to produce XenoMouse mice. See Mendez et al., 1997, *Nature Genetics*, 15:146-156; Green and Jakobovits, 1998, *J. Exp. Med.*, 188: 483-495; and Green, 1999, *Journal of Immunological Methods*, 231:11-23, the disclosures of which are hereby incorporated herein by reference.

Human anti-mouse antibody (HAMA) responses have led the industry to prepare chimeric or otherwise humanized antibodies. While chimeric antibodies typically are comprised of a human constant region and a murine variable region, it is expected that certain human anti-chimeric antibody (HACA) responses will be observed, particularly in treatments involving chronic or multi-dose utilizations of the antibody. Thus, it is desirable to provide fully human antibodies against the RAI-3 protein or peptides in order to vitiate concerns and/or effects of HAMA or HACA responses.

Polypeptide antibodies of the invention can be chemically synthesized or produced through the use of recombinant expression systems. Accordingly, the invention further embraces polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, an antibody that specifically binds to the RAI-3 polypeptide having the amino acid sequence of SEQ ID NO:3.

Polynucleotides can be obtained, and the nucleotide sequence of the polynucleotides determined, by any method known in the art. For example, if the nucleotide sequence of the antibody is known, a polynucleotide encoding the antibody can be assembled from chemically synthesized oligonucleotides (e.g., as described in Kutmeier et al., 1994, *BioTechniques*, 17:242), which, briefly, involves the synthesis of overlapping oligonucleotides containing portions of the sequence encoding the antibody, the annealing and ligating of those oligonucleotides, and then the amplification of the ligated oligonucleotides by PCR.

Alternatively, a polynucleotide encoding an antibody can be generated from nucleic acid from a suitable source. If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library, or a cDNA library generated from, (or a nucleic acid, preferably poly A+ RNA, isolated from), any tissue or cells expressing the antibody, such as hybridoma cells selected to express an antibody of the invention by PCR amplification using synthetic primers hybridizable to the 3' and 5' ends of the sequence. Alternatively, cloning using an oligonucleotide probe specific for the particular gene sequence to identify, e.g., a cDNA clone from a cDNA library that encodes the antibody can be employed. Amplified nucleic acids generated by PCR can then be cloned into replicable cloning vectors using any method well known in the art.

Once the nucleotide sequence and corresponding amino acid sequence of the antibody are determined, the nucleotide sequence of the antibody can be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2nd Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate antibodies having a different amino acid sequence, for example, to create amino acid substitutions, deletions, and/or insertions.

In a specific embodiment, the amino acid sequence of the heavy and/or light chain variable domains can be inspected to identify the sequences of the CDRs by methods that are well known in the art, e.g., by comparison to known amino acid sequences of other heavy and light chain variable regions, to determine the regions of sequence hypervariability. Using routine recombinant DNA techniques, one or more of the CDRs can be inserted within framework regions, e.g., into human framework regions, to humanize a non-human antibody, as described supra. The framework regions can be naturally occurring or consensus framework regions, and preferably, are human framework regions (see, e.g., Chothia et al., 1998, *J. Mol. Biol.*, 278:457-479 for a listing of human framework regions).

Preferably, the polynucleotide generated by the combination of the framework regions and CDRs encodes an antibody that specifically binds to the RAI-3 protein. Also preferably, as discussed supra, one or more amino acid substitutions can be made within the framework regions; such amino acid substitutions are performed with the goal of improving binding of the antibody to its antigen. In addition, such methods can be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and are within the skill of the art.

For some uses, such as for in vitro affinity maturation of an anti-RAI-3 protein antibody of the invention, it is useful to express the $V_H$ and $V_L$ domains of the Ig heavy and light chains of one or more antibodies of the invention as single chain antibodies, or Fab fragments, in a phage display library using phage display methods as described supra. For example, the cDNAs encoding the $V_H$ and $V_L$ domains of one or more antibodies of the invention can be expressed in all possible combinations using a phage display library, thereby allowing for the selection of $V_H/V_L$ combinations that bind to the RAI-3 protein or peptides thereof with preferred binding characteristics such as improved affinity or improved off rates. In addition, $V_H$ and $V_L$ segments, particularly, the CDR regions of the $V_H$ and $V_L$ domains of one or more antibodies of the invention, can be mutated in vitro. Expression of $V_H$ and $V_L$ domains with "mutant" CDRs in a phage display library allows for the selection of $V_H/V_L$ combinations that bind to the RAI-3 protein, which is a receptor polypeptide, with preferred binding characteristics such as improved affinity or improved off rates.

In phage display methods, functional antibody domains are displayed on the surface of phage particles which carry the polynucleotide sequences encoding them. In particular, DNA sequences encoding the $V_H$ and $V_L$ domains are amplified from animal cDNA libraries (e.g., human or murine cDNA libraries of lymphoid tissues) or from synthetic cDNA libraries. The DNA encoding the $V_H$ and $V_L$ domains are joined together by an scFv linker by PCR and cloned into a phagemid vector (e.g., p CANTAB 6 or pComb 3 HSS). The vector is introduced into *E. coli* via electroporation and the *E. coli* is infected with helper phage. Phage used in these methods are typically filamentous phage, including fd and M13, and the $V_H$ and $V_L$ domains are usually recombinantly fused either to the phage gene III or gene VIII. Phage expressing an antigen binding domain that binds to an antigen of interest (i.e., the RAI-3 polypeptide or a fragment thereof) can be selected or identified with antigen, e.g., using labeled antigen or antigen bound or captured onto a solid surface or bead.

Recombinant expression of an anti-RAI-3 protein antibody of the invention, or a fragment, derivative, variant, or analog thereof (e.g., a heavy or light chain of an antibody, or a single chain antibody, of the invention) requires construction of an expression vector containing a polynucleotide that encodes the antibody. Once a polynucleotide encoding an anti-RAI-3 protein antibody molecule, or a heavy or light chain of an antibody, or portion thereof (preferably containing the heavy or light chain variable domain), of the invention has been obtained, the vector for the production of the antibody molecule can be produced by recombinant DNA technology using techniques well known in the art. Methods for preparing a protein by expressing a polynucleotide encoding an antibody are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus embraces replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., PCT publication WO 86/05807; PCT publication WO 89/01036; and U.S. Pat. No. 5,122,464) and the variable domain of the antibody can be cloned into such a vector for expression of the entire heavy or light chain.

Methods of constructing expression vectors; types of vectors; methods of transferring the expression vectors into host cells and culturing the cells to produce antibodies; use of selection markers and systems; and the like, involve conventional techniques, and have been described above with respect to RAI-3 protein expression. Such methods and the like are equally applicable for recombinant immunoglobulin protein expression and the production of anti-RAI-3 antibodies.

As one of its aspects, the invention includes host cells containing a polynucleotide encoding an anti-RAI-3 protein antibody, or a heavy or light chain thereof, or a single chain antibody of the invention, operably linked to a heterologous promoter. In preferred aspects for the expression of double-chained antibodies, vectors encoding both the heavy and light chains may be co-expressed in the host cell for expression of the entire immunoglobulin molecule, as detailed below.

The expression levels of an antibody molecule can be increased by vector amplification (for a review, see Bebbington and Hentschel, "The use of vectors based on gene amplification for the expression of cloned genes in mammalian cells in DNA cloning", Vol. 3. (Academic Press, New York, 1987). When a marker in the vector system expressing an antibody is amplifiable, an increase in the level of inhibitor present in the host cell culture increases the number of copies of the marker gene. Since the amplified region is associated with the antibody gene, production of the antibody will also increase (Crouse et al., 1983, *Mol. Cell. Biol.*, 3:257).

Vectors which use glutamine synthase (GS) or DHFR as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e. g. Chinese Hamster Ovary (CHO) cells) by providing additional inhibitor to prevent the functioning of the endogenous gene.

Vectors that express glutamine synthase as the selectable marker include, but are not limited to, the pEE6 expression vector described in Stephens and Cockett, 1989, *Nucl. Acids. Res.*, 17:7110. A glutamine synthase expression system and components thereof are detailed in PCT publications: WO87/04462; WO86/05807; WO89/01036; WO89/10404; and WO91/06657 which are incorporated by reference herein in their entireties. In addition, glutamine synthase expression vectors that can be used in accordance with the present invention are commercially available from suppliers, including, for example, Lonza Biologics, Inc. (Portsmouth, N.H.). The expression and production of monoclonal antibodies using a GS expression system in murine myeloma cells is described in Bebbington et al., 1992, *BioTechnology*, 10:169 and in Biblia and Robinson, 1995, *Biotechnol. Prog.*, 11:1, which are incorporated by reference herein in their entireties.

A host cell can be co-transfected with two expression vectors of the invention, the first vector encoding an Ig heavy chain derived polypeptide and the second vector encoding an Ig light chain derived polypeptide. The two vectors can contain identical selectable markers which enable equal expression of heavy and light chain polypeptides. Alternatively, a single vector can be used which encodes, and is capable of expressing, both the Ig heavy and light chain polypeptides. In such situations, the light chain should be placed before the heavy chain to avoid an excess of toxic free heavy chain (Proudfoot, 1986, *Nature*, 322:52; Kohler, 1980, *Proc. Natl. Acad. Sci. USA*, 77:2197). The coding sequences for the heavy and light chains can comprise cDNA or genomic DNA.

Once an anti-RAI-3 antibody molecule of the invention has been produced by an animal, chemically synthesized, or recombinantly expressed, it can be purified by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies that are recombinantly fused or chemically conjugated (including both covalently and non-covalently conjugated) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but can occur through linker sequences. The antibodies can be specific for RAI-3 antigens (or portions thereof, preferably at least 10, 20, 30, 40, 50, 60, 70, 80, 90 or 100 amino acids of the polypeptide). For example, antibodies can be used to target the RAI-3 polypeptide to particular cell types, either in vitro or in vivo, by fusing or conjugating RAI-3 to antibodies specific for particular cell surface receptors.

Figure 2B:
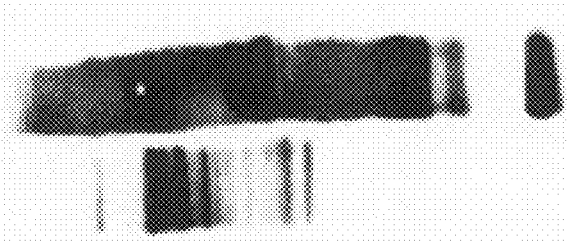
FIGS. 2A and 2B depict SDS-PAGE and Western Blot analysis of H292 cell lysates prepared from cells that had either been treated with cigarette smoke (CS-160) or not treated (Control, Serum Free Medium, SFM).
Figure 2A:
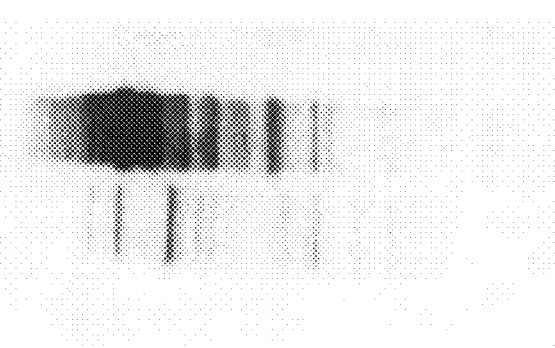

RAI-3 or anti-RAI-3 antibodies of the present invention (including fragments or variants thereof) can be fused to either the N-terminal or C-terminal end of a heterologous protein (e.g., immunoglobulin Fc polypeptide or human serum albumin polypeptide). Antibodies of the invention can also be fused to albumin (including, but not limited to, recombinant human serum albumin (see, e.g., U.S. Pat. No. 5,876, 969, issued Mar. 2, 1999; EP Patent 0 413 622; and U.S. Pat. No. 5,766,883, issued Jun. 16, 1998, incorporated herein by reference in their entirety), resulting in chimeric polypeptides. In a preferred aspect, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094, which is herein incorporated by reference in its entirety). In another preferred aspect, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 incorporated herein by reference in its entirety.

Polynucleotides encoding RAI-3 fusion proteins and antibodies thereto are also encompassed by the invention. Such fusion proteins can, for example, facilitate purification and can increase half-life in vivo. Antibodies fused or conjugated to the polypeptides of the present invention can also be used in in vitro immunoassays and purification methods using methods known in the art. See, e.g., Harbor et al., supra, and PCT publication WO 93/21232; EP 439, 095; Naramura et al., 1994, *Immunol. Lett.*, 39:91-99; U.S. Pat. No. 5,474,981; Gillies et al., 1992, *Proc. Natl. Acad. Sci. USA,* 89:1428-1432; Fell et al., 1991, *J. Immunol.*, 146:2446-2452, which are incorporated by reference herein in their entireties. For guidance, chimeric proteins having the first two domains of the human CD4 polypeptide and various domains of the constant regions of the heavy or light chains of mammalian immunoglobulins have been described. (EP 394,827; Traunecker et al., 1988, *Nature,* 331:84-86). RAI-3 polypeptide or peptide fused or conjugated to an antibody, or portion thereof, having disulfide-linked dimeric structures (due to the IgG), for example, can also be more efficient in binding and neutralizing other molecules, than the monomeric secreted protein or protein fragment alone. (Fountoulakis et al., 1995, *J. Biochem.*, 270:3958-3964).

The present invention further includes compositions comprising the RAI-3 polypeptide or peptides thereof fused or conjugated to antibody domains other than the variable region domain. For example, the polypeptides of the present invention can be fused or conjugated to an antibody Fc region, or portion thereof. The antibody portion fused to a polypeptide of the present invention can comprise the constant region, hinge region, CH1 domain, CH2 domain, CH3 domain, or any combination of whole domains or portions thereof. The polypeptides can also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating polypeptides to antibody portions are known in the art. (See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., 1991, *Proc. Natl. Acad. Sci. USA,* 88:10535-10539; Zheng et al., 1995, *J. Immunol.*, 154:5590-5600; and Vil et al., *Proc. Natl. Acad. Sci. USA,* 89:11337-11341, which are hereby incorporated by reference herein in their entireties).

In many cases, the Fc portion in a fusion protein is beneficial in therapy, diagnosis, and/or screening methods, and thus can result in, for example, improved pharmacokinetic properties. (EP A 232, 262). In drug discovery, for example, human proteins, such as hIL-5, have been fused with Fc portions for the purpose of high-throughput screening assays to identify antagonists of hIL-5. (See, Bennett et al., 1995, *J. Molecular Recognition,* 8:52-58; and Johanson et al., 1995, *J. Biol. Chem.*, 270:9459-9471). Alternatively, deleting the Fc portion after the fusion protein has been expressed, detected, and purified, may be desired. For example, the Fc portion may hinder therapy and diagnosis if the fusion protein is used as an antigen for immunizations.

Moreover, according to this invention, anti-RAI-3 antibodies or fragments thereof can be fused to marker sequences, such as a peptide, to facilitate their purification. In preferred embodiments, the marker amino acid sequence is a hexahistidine peptide, such as the tag provided in a pQE vector (QIAGEN, Inc., Chatsworth, Calif.), among others, many of which are commercially available. As described in Gentz et al., 1989, *Proc. Natl. Acad. Sci. USA,* 86:821-824, for instance, hexa histidine provides for convenient purification of the fusion protein. Other peptide tags useful for purification include, but are not limited to, the "HA" tag and the Flag tag, as previously described herein.

The present invention further encompasses antibodies or fragments thereof conjugated to a diagnostic or therapeutic agent. The antibodies can be used diagnostically, for example, to monitor the development or progression of a tumor as part of a clinical testing procedure, or to determine the efficacy of a given treatment regimen. Detection can be facilitated by coupling the antibody to a detectable substance. Nonlimiting examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker as known in the art) using techniques known in the art. (See, for example, U.S. Pat. No. 4,741,900 for metal ions which can be conjugated to antibodies for use as diagnostics according to the present invention).

Nonlimiting examples of suitable detectable enzymes include horseradish peroxidase, alkaline phosphatase, beta-galactosidase, or acetylcholinesterase; Nonlimiting examples of suitable prosthetic group complexes include streptavidin/biotin and avidin/biotin; nonlimiting examples of suitable fluorescent materials include umbelliferone, fluorescein, fluorescein isothiocyanate, rhodamine, dichlorotriazinylamine fluorescein, dansyl chloride or phycoerythrin; a nonlimiting example of a luminescent material includes luminol; nonlimiting examples of bioluminescent materials include luciferase, luciferin, and aequorin; and nonlimiting examples of suitable radioactive material include iodine ($^{125}$I, $^{131}$I), carbon ($^{14}$C), sulfur (3sus), tritium ($^{3}$H), indium ($^{111}$In and other radioactive isotopes of inidium), technetium ($^{99}$Tc, $^{99m}$Tc), thallium (20'Ti), gallium ($^{68}$Ga, $^{67}$Ga), palladium ($^{103}$Pd), molybdenum ($^{99}$Mo), xenon ($^{133}$Xe), fluorine ($^{19}$F), $^{153}$Sm, $^{177}$Lu, radioactive Gd, radioactive Pm, radioactive La, radioactive Yb, $^{166}$Ho, $^{90}$Y, radioactive Sc, radioactive Re, radioactive Re, $^{142}$Pr, $^{105}$Rh, and $^{97}$Ru.

In specific aspects, the RAI-$^{3}$ protein or a peptide portion thereof is attached to macrocyclic chelators useful for conjugating radiometal ions, including, but not limited to, $^{111}$In, $^{177}$Lu, $^{90}$Y, $^{166}$Ho, and $^{153}$Sm, to polypeptides. In a preferred aspect, the radiometal ion associated with the macrocyclic chelators attached to the RAI-3 protein or peptide is $^{111}$In. In another preferred aspect, the radiometal ion associated with the macrocyclic chelator attached to the RAI-3 protein or peptide is $^{90}$Y. In specific aspects, the macrocyclic chelator is 1,4,7,10-tetraazacyclododecane-N,N',N'',N'''-tetraacetic acid (DOTA). In other specific aspects, the DOTA is attached to the RAI-3 protein or peptide via a linker molecule.

Examples of linker molecules useful for conjugating DOTA to a polypeptide are commonly known in the art. (See, for example, DeNardo et al., 1998, *Clin. Cancer Res.,* 4(10): 2483-90; Peterson et al., 1999, *Bioconjug. Chem.,* 10(4):553-557; and Zimmerman et al, 1999, *Nucl. Med. Biol.,* 26(8): 943-950, which are hereby incorporated by reference in their entirety. In addition, U.S. Pat. Nos. 5,652,361 and 5,756,065, which disclose chelating agents that can be conjugated to antibodies and methods for making and using them, are hereby incorporated by reference in their entireties. Although U.S. Pat. Nos. 5,652,361 and 5,756,065 focus on conjugating chelating agents to antibodies, one skilled in the art can readily adapt the methods disclosed therein in order to conjugate chelating agents to other polypeptides. Antibodies can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating therapeutic moieties to antibodies are well known, see, e.g., Arnon et al., "Monoclonal Antibodies For Immunotargeting Of Drugs In Cancer Therapy", *In: Monoclonal Antibodies And Cancer Therapy,* Reisfeld et al. (eds.), pp. 243-56, Alan R. Liss, Inc., 1985; Hellstrom et al., "Antibodies For Drug Delivery", *In: Controlled Drug Delivery* (2nd Ed.), Robinson et al. (eds.), pp. 623-53, Marcel Deldcer, Inc., 1987; Thorpe, "Antibody Carriers Of Cytotoxic Agents In Cancer Therapy: A Review", *In: Monoclonal Antibodies '84: Biological And Clinical Applications,* Pinchera et al. (eds.), pp. 475-506, 1985; "Analysis, Results, And Future Prospective Of The Therapeutic Use Of Radiolabeled Antibody In Cancer Therapy", *In: Monoclonal Antibodies For Cancer Detection And Therapy,* Baldwin et al. (eds.), pp. 303-316, Academic Press, 1985; and Thorpe et al., 1982, "The Preparation And Cytotoxic Properties Of Antibody-Toxin Conjugates", *Immunol. Rev.,* 62:119-158. Alternatively, an antibody can be conjugated to a second antibody to form an antibody heteroconjugate, e.g., as described in U.S. Pat. No. 4,676,980 to Segal, which is incorporated herein by reference in its entirety. An antibody, i.e., an antibody specific for RAI-3, with or without a therapeutic moiety conjugated to it, and administered alone or in combination with cytotoxic factor(s) and/or cytokine(s), can be used as a therapeutic.

The antibodies of the invention can be utilized for immunophenotyping of cell lines and biological samples. The translation product of the RAI-3-encoding nucleic acid can be useful as cell specific marker(s), or more specifically, as cellular marker(s) that are differentially expressed at various stages of differentiation and/or maturation of particular cell types (e.g., in particular tissues). Monoclonal antibodies directed against a specific epitope, or combination of epitopes, allow for the screening of cellular populations expressing the marker. Various techniques utilizing monoclonal antibodies can be employed to screen for cellular populations expressing the marker(s), including magnetic separation using antibody-coated magnetic beads, "panning" with antibody(ies) attached to a solid matrix (i.e., tissue culture plate), and flow cytometry (See, e.g., U.S. Pat. No. 5,985,660; and Morrison et al., 1999, *Cell,* 96:737-749). The above techniques allow for the screening of particular populations of cells, such as might be found with cancers or malignancies (i.e., minimal residual disease (MRD), for example, in lung cancer patients) and "non-self" cells in transplantations to prevent graft-versus-host disease (GVHD).

Anti-RAI-3 antibodies according to this invention can be assayed for immunospecific binding by any method known in the art. The immunoassays which can be used include, but are not limited to, competitive and non-competitive assay systems using techniques such as BIAcore analysis, FACS (Fluorescence Activated Cell Sorter) analysis, immunofluorescence, immunocytochemistry, Western blots, radioimmunoassays, ELISA (enzyme linked immunosorbent assays), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few. Such assays are routine and well known and practiced in the art (see, e.g., Ausubel et al, eds, 1994, *Current Protocols in Molecular Biology,* Vol. 1, John Wiley & Sons, Inc., New York, which is incorporated by reference herein in its entirety). Nonlimiting, exemplary immunoassays are described briefly below.

Immunoprecipitation protocols generally comprise lysing a population of cells in a lysis buffer such as RIPA buffer (i.e., 1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate); adding the antibody of interest to the cell lysate; incubating for a period of time (e.g., 1 to 4 hours) at 4° C.; adding protein A and/or protein G sepharose beads to the cell lysate; incubating for about 60 minutes or more at 4° C.; washing the beads in lysis buffer; and resuspending the beads in SDS/sample buffer. The ability of the antibody of interest to immunoprecipitate a particular antigen can be assessed by, for example, Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols, see, e.g., Ausubel et al, eds, 1994, *Current Protocols in Molecular Biology,* Vol. 1, John Wiley & Sons, Inc., New York, at 10.16.1.

Western blot analysis generally comprises preparing protein samples; electrophoresis of the protein samples in a polyacrylamide gel (e.g., 8%-20% SDS PAGE depending on the molecular weight of the antigen); transferring the protein sample from the polyacrylamide gel to a solid support membrane such as nitrocellulose, PVDF or nylon; blocking the membrane in blocking solution (e.g., PBS with 3% BSA or nonfat milk); washing the membrane in washing buffer (e.g., PBS-Tween 20); blocking the membrane with primary antibody (the antibody of interest) diluted in blocking buffer; washing the membrane in washing buffer; blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer; washing the membrane in wash buffer; and detecting the presence of the antigen. One of skill in the art would be knowledgeable as to the parameters that can be modified to increase the signal detected and to reduce the background noise. For further discussion regarding Western blot protocols, see, e.g., Ausubel et al, eds, 1994, *Current Protocols in Molecular Biology,* Vol. 1, John Wiley & Sons, Inc., New York, at 10.8.1.

ELISAs comprise preparing antigen; coating the wells of a 96 well microtiter plate with antigen; adding to the wells the antibody of interest conjugated to a detectable compound such as an enzymatic substrate (e.g., horseradish peroxidase or alkaline phosphatase); incubating for a period of time; and detecting the presence of the antigen. In ELISAs, the antibody of interest does not have to be conjugated to a detectable compound; instead, a second antibody (which recognizes the antibody of interest) conjugated to a detectable compound can be added to the wells. Further, instead of coating the wells with antigen, the antibody can be first coated onto the well. In this case, a second antibody conjugated to a detectable compound can be added to the antibody-coated wells following the addition of the antigen of interest. One of skill in the art would be knowledgeable as to the parameters that can be modified to increase the signal detected, as well as other variations of ELISAs known in the art. For further discussion regarding ELISAs, see, e.g., Ausubel et al, eds, 1994, *Current Protocols in Molecular Biology*, Vol. 1, John Wiley & Sons, Inc., New York, at 11.2.1.

The binding affinity of an antibody to an antigen and the off-rate of an antibody-antigen interaction can be determined by competitive binding assays. One example of a competitive binding assay is a radioimmunoassay (RIA) involving the incubation of labeled antigen (e.g., $^3$H or $^{125}$I), or a fragment or variant thereof, with the antibody of interest in the presence of increasing amounts of labeled antigen, and the detection of the antibody bound to the labeled antigen. The affinity of the antibody of interest for the RAI-3 protein and the binding off rates can be determined from the data by Scatchard plot analysis. Competition with a second antibody can also be determined using RIAs. In this case, the RAI-3 protein is incubated with antibody of interest conjugated to a labeled compound (e.g., a compound labeled with $^3$H or $^{125}$I) in the presence of increasing amounts of an unlabeled second antibody. This kind of competitive assay between two antibodies, can also be used to determine if two antibodies bind to the same or to different epitopes of the same molecule.

In a preferred aspect, BIAcore kinetic analysis is used to determine the binding on and off rates of antibodies (including antibody fragments or variants thereof) to the RAI-3 protein, or fragments of the RAI-3 protein. Kinetic analysis comprises analyzing the binding and dissociation of antibodies from chips with immobilized RAI-3 protein on the chip surface.

Methods of Diagnosis of COPD and COPD Related Disorders and Diseases

The present invention also relates to methods and compositions for the diagnosis of COPD or COPD related disorders, diseases and conditions. Such methods comprise, for example, measuring expression of the RAI-3 gene, or peptide-encoding fragments thereof, in a patient sample, or detecting a mutation in the gene in the genome of an individual suspected of exhibiting COPD or COPD related dysfunction. RAI-3 nucleic acid molecules can also be used as diagnostic hybridization probes, or as primers, for diagnostic PCR analysis to identify RAI-3 gene mutations, allelic variations, or regulatory defects, such as defects in the expression of the gene, which can serve as indicators of susceptibility to COPD, or a lack thereof. Such diagnostic PCR analyses can be used to diagnose individuals with COPD associated mutation, allelic variation, or regulatory defects in the RAI-3 gene.

Diagnosis and Prognosis of COPD and COPD Related Disorders

Methods of the invention for the diagnosis, screening and/or prognosis of COPD and COPD related diseases, disorders and conditions can utilize reagents such as the RAI-3 nucleic acid molecule and sequences or antibodies directed against the RAI-3 protein or polypeptide, including peptide fragments thereof. Specifically, such reagents can be used, for example, for: (1) the detection of the presence of RAI-3 gene mutations, or the detection of either over- or under-expression of RAI-3 gene mRNA relative to the COPD state, or the qualitative or quantitative detection of alternatively-spliced forms of RAI-3 transcripts which may correlate with COPD or COPD related disorders or susceptibility to such disorders; and (2) the detection of either an over- or an under-abundance of the RAI-3 gene product relative to the COPD state or the presence of a modified (e.g., less than full length) RAI-3 gene product which correlates with COPD dysfunctional state or a progression toward such a state. In addition, such RAI-3 reagents can be used in methods for the screening, diagnosis and/or prognosis of non-COPD related diseases, disorders, and/or conditions, as described further herein, that are associated, for example, with NF-κB activation, with the activity or function of component molecules of the NF-κB pathway, or with other cell signaling molecules.

The methods described herein may be performed, for example, by utilizing pre-packaged diagnostic test kits comprising at least one specific RAI-3 nucleic acid or anti-RAI-3 antibody reagent described herein, which can be conveniently used, e.g., in clinical or laboratory settings, to screen and diagnose patients exhibiting COPD or COPD related conditions or symptoms related thereto, and to screen and identify those individuals exhibiting a predisposition or susceptibility to COPD or COPD related conditions.

For the detection of RAI-3 mutations, any nucleated cell can be used as a starting source for genomic nucleic acid; however, lung cells, e.g., epithelial airway cells, are preferred. For the detection of RAI-3 transcripts or RAI-3 gene products, any cell type or tissue in which the RAI-3 gene is expressed can be employed.

Detection of RAI-3 Nucleic Acid Molecules

Mutations or polymorphisms within the RAI-3 gene can be detected by utilizing a number of techniques. Nucleic acid from any nucleated cell can be used as the starting point for such assay techniques, and can be isolated according to standard nucleic acid preparation procedures which are well known to those of skill in the art.

Genomic DNA can be used in hybridization or amplification assays of biological samples to detect abnormalities involving the RAI-3 gene structure, including point mutations, insertions, deletions and chromosomal rearrangements. Such assays can include, but are not limited to, direct sequencing (C. Wong et al., 1987, *Nature*, 330:384-386), single stranded conformational polymorphism analyses (SSCP; M. Orita et al., 1989, *Proc. Natl. Acad. Sci. USA*, 86:2766-2770), heteroduplex analysis (T. J. Keen et al., 1991, *Genomics*, 11:199-205; D. J. Perry and R. W. Carrell, 1992), denaturing gradient gel electrophoresis (DGGE; R. M. Myers et al., 1985, *Nucl. Acids Res.*, 13:3131-3145), chemical mismatch cleavage (R. G. Cotton et al., 1988, *Proc. Natl. Acad. Sci. USA*, 85:4397-4401) and oligonucleotide hybridization (R. B. Wallace et al., 1981, *Nucl. Acids Res.*, 9:879-894; R. J. Lipshutz et al., 1995, *Biotechniques*, 19:442-447).

Diagnostic methods for the detection of RAI-3 gene-specific nucleic acid molecules, in patient samples or other appropriate cell sources, can involve the amplification of specific gene sequences, e.g., by PCR, followed by the analysis of the amplified molecules using techniques well known to those of skill in the art, such as, for example, those listed above. Utilizing analysis techniques such as these, the amplified sequences can be compared to those that would be expected if the nucleic acid being amplified contained only normal copies of the RAI-3 gene, in order to determine whether a RAI-3 gene mutation exists, for example, a mutation that correlates or associates with COPD, or susceptibility to, COPD or related disorders and conditions.

Further, well-known genotyping techniques can be performed to type polymorphisms that are in close proximity to mutations in the RAI-3 gene itself. These polymorphisms can be used to identify individuals in families likely to carry mutations. If a polymorphism exhibits linkage disequilibrium with mutations in the RAI-3 gene, it can also be used to identify individuals in the general population who are likely to carry mutations. Polymorphisms that can be used in this way include restriction fragment length polymorphisms (RFLPs), which involve sequence variations in restriction enzyme target sequences, single nucleotide polymorphisms (SNPs), (e.g., Examples 5-8), and simple sequence repeat polymorphisms (SSLPs). For example, U.S. Pat. No. 5,075,217 to Weber describes a DNA marker based on length polymorphisms in blocks of (dC-dA)n-(dG-dT)n short tandem repeats. The average separation of (dC-dA)n-(dG-dT)n blocks is estimated to be 30,000-60,000 bp. Markers which are so closely spaced exhibit a high frequency co-inheritance, and are extremely useful in the identification of genetic mutations, such as, for example, mutations within the RAI-3 gene, and the diagnosis of diseases and disorders related to RAI-3 mutations.

Also, U.S. Pat. No. 5,364,759 to Caskey et al. describes a DNA profiling assay for detecting short tri- and tetra-nucleotide repeat sequences. The process includes extracting the DNA of interest, e.g., the RAI-3 gene, amplifying the extracted DNA, and labeling the repeat sequences to form a genotypic map of an individual's DNA. An RAI-3 probe can also be used to directly identify restriction fragment polymorphisms (RFLPs) in an individual's DNA (gene). Further, an RAI-3 probe, or primers derived from the RAI-3 sequence, can be used to isolate genomic clones such as YACs, BACs, PACs, cosmids, phage or plasmids. The DNA contained in these clones can be screened for single nucleotide polymorphisms (SNPs) or simple sequence length polymorphisms (SSLPs) using standard hybridization or sequencing procedures.

Alternative diagnostic methods for the detection of RAI-3 gene-specific mutations or polymorphisms can include hybridization techniques which involve, for example, contacting and incubating nucleic acids including recombinant DNA molecules, cloned genes, or degenerate variants thereof, obtained from a sample, e.g., derived from a patient sample or other appropriate cellular source, with one or more labeled nucleic acid reagents, including RAI-3 nucleic acid molecules, such as recombinant DNA molecules, cloned genes or degenerate variants thereof, under conditions favorable for the specific annealing of these reagents to their complementary sequences within the RAI-3 gene. Preferably, the lengths of these nucleic acid reagents are at least 15 to 30 nucleotides. After incubation, all non-annealed nucleic acids are removed from the nucleic acid:RAI-3 molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled RAI-3 nucleic acid molecules are easily removed. Detection of the remaining annealed and labeled RAI-3 nucleic acid reagents is accomplished using standard techniques well-known to those in the art. The sequences to which the RAI-3 nucleic acid molecules have annealed can be compared to the annealing pattern expected from a normal RAI-3 gene sequence in order to determine whether an RAI-3 gene mutation or polymorphism is present.

Quantitative and qualitative aspects of RAI-3 gene expression can also be assayed. For example, RNA from a cell type or tissue known or suspected to express the RAI-3 gene can be isolated and tested utilizing hybridization or PCR techniques as described and known in the art. The isolated cells can be derived from cell culture or from a patient. The analysis of cells taken from culture may be a necessary step in the assessment of cells to be used as part of a cell-based gene therapy technique or, alternatively, to test the effect of compounds on the expression of the RAI-3 gene. Such analyses can reveal both quantitative and qualitative aspects of the expression pattern of the RAI-3 gene, including activation or inactivation of RAI-3 gene expression and presence of alternatively spliced RAI-3 transcripts.

In one aspect of such a detection scheme, a cDNA molecule is synthesized from an RNA molecule of interest (e.g., RAI-3, by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from the RAI-3 nucleic acid sequence. The preferred lengths of such nucleic acid reagents are at least 9-30 nucleotides.

For detection of the amplified product, the nucleic acid amplification can be performed using radioactively or non-radioactively labeled nucleotides. Alternatively, enough amplified product can be made so that the product can be visualized by standard ethidium bromide staining or by utilizing any other suitable nucleic acid staining protocol, or, for example, quantitative PCR. Such RT-PCR techniques can be utilized to detect differences in RAI-3 transcript size which may be due to normal or abnormal alternative splicing. In addition, such techniques can be utilized to detect quantitative differences between levels of full length and/or alternatively-spliced RAI-3 transcripts detected in normal individuals relative to those in individuals exhibiting COPD or COPD related conditions or disorders, or exhibiting a predisposition to COPD or COPD related disorders.

If detection of specific alternately-spliced species is desired, appropriate primers and/or hybridization probes can be used, such that, in the absence of such sequences, no amplification would occur. Alternatively, primer pairs can be chosen utilizing the RAI-3 nucleic acid sequence of SEQ ID NO:2 to choose primers which will yield fragments of differing size depending on whether a particular exon is present or absent from the RAI-3 transcript being utilized.

As an alternative to amplification techniques, standard Northern analyses can be performed if a sufficient quantity of the appropriate cells can be obtained. Utilizing such techniques, quantitative as well as size-related differences between RAI-3 transcripts can also be detected. In addition, it is possible to perform RAI-3 gene expression assays in situ, i.e., directly upon tissue sections (fixed and/or frozen) of patient tissue obtained from biopsies or resections, such that no nucleic acid purification is necessary. RAI-3 nucleic acid molecules can be used as probes and/or primers for such in situ procedures (see, for example, G. J. Nuovo, 1992, *PCR In Situ Hybridization: Protocols And Applications*, Raven Press, NY).

Detection of RAI-3 Gene Product/RAI-3 Protein or Polypeptide

Antibodies directed against wild type or mutant RAI-3 gene products, or conserved variants or peptide fragments thereof, as described above, can also be used for the diagnosis and prognosis of COPD or COPD related disorders. Such diagnostic methods can be used to detect abnormalities in the level of RAI-3 gene expression or abnormalities in the structure and/or temporal, tissue, cellular, or subcellular location of RAI-3 gene products. Antibodies, or fragments of antibodies, can be used to screen potentially therapeutic compounds in vitro to determine their effects on RAI-3 gene expression and RAI-3 peptide production. The compounds which have beneficial effects on COPD and COPD related disorders can be identified and a therapeutically effective dose determined.

In vitro immunoassays can be used, for example, to assess the efficacy of cell-based gene therapy for the treatment of COPD and COPD related disorders. For example, antibodies directed against RAI-3 peptides may be used in vitro to determine the level of RAI-3 gene expression found in cells that have been genetically engineered to produce RAI-3 peptides or protein. Such analysis allows for a determination of the number of transformed cells necessary to achieve therapeutic efficacy in vivo, as well as optimization of the gene replacement protocol.

The tissue or cell type to be analyzed generally includes those which are known, or suspected, to express the RAI-3 gene, preferably lung cells or lung tissue cells. Protein isolation methods employed can be those as described in Harlow, E. and Lane, D., 1988, *Antibodies: A Laboratory Manual*, Cold Spring Harbor Laboratory Press, Cold Spring Harbor, N.Y., for example. The isolated cells can be derived from cell culture or from a patient. The analysis of cells taken from culture may be a necessary step in the assessment of cells to be used as part of a cell-based gene therapy technique or, alternatively, to test the effect of compounds on the expression of the RAI-3 gene.

Preferred diagnostic methods for the detection of the RAI-3 gene products or conserved variants or peptide fragments thereof, may involve, for example, immunoassays wherein the RAI-3 gene product or conserved variants, including gene products which are the result of alternatively-spliced transcripts, or peptide fragments, are detected by their interaction with an anti-RAI-3-specific antibody. For example, antibodies, or fragments of antibodies, such as described above, can be used to detect both quantitatively or qualitatively the presence of the RAI-3 gene product or conserved variants or peptide fragments thereof. The antibodies (or fragments thereof) can also be employed histologically, for example, in immunofluorescence or immunoelectron microscopy, for in situ detection of the RAI-3 protein or conserved variants or peptide fragments thereof. In situ detection is carried out by removing a histological specimen from a patient, and applying thereto a labeled RAI-3 antibody according to this invention. The antibody (or antibody fragment) is preferably applied by overlaying the labeled antibody (or fragment) onto a biological sample. Through the use of such a procedure, it is possible to determine not only the presence of the RAI-3 gene product, or conserved variants or peptide fragments, but also its distribution in the examined tissue. The skilled practitioner will readily perceive that any of a wide variety of histological methods (such as staining procedures) can be modified in order to achieve such in situ detection.

Immunoassays for detecting RAI-3 or conserved variants or peptide fragments thereof typically comprise incubating a sample, such as a biological fluid, a tissue extract, freshly harvested cells, or lysates of cells which have been incubated in cell culture, in the presence of a detectably labeled antibody capable of binding RAI-3 protein or conserved variants or peptide fragments thereof, and detecting the bound antibody-RAI-3 complex by any of a number of techniques well-known in the art.

The biological sample can be brought into contact with and immobilized onto a solid phase support or carrier such as nitrocellulose, nylon membrane, PVDF membrane, or other solid support that is capable of immobilizing cells, cell particles or soluble proteins. The support can then be washed with suitable buffers followed by treatment with the detectably labeled anti-RAI-3 specific antibody. The solid phase support is washed with the buffer a second time to remove unbound antibody. The amount of bound label on the solid support is then detected by conventional means.

A "solid phase support or carrier" refers to any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

The binding activity of an anti-RAI-3 antibody can be determined according to well known methods. Those skilled in the art will be able to determine operative and optimal assay conditions for each determination by employing routine experimentation. One of the ways in which an RAI-3-specific antibody can be detectably labeled is by linking the antibody to an enzyme in an enzyme linked immunoassay (ELISA) (A. Voller "The Enzyme Linked Immunosorbent Assay (ELISA)", 1978, *Diagnostic Horizons* 2:1-7, Microbiological Associates Quarterly Publication, Walkersville, Md.); A. Voller et al., 1978, *J. Clin. Pathol.*, 31:507-520; J. E. Butler, 1981, *Meth. Enzymol.*, 73:482-523; E. Maggio (ed.), 1980, *Enzyme Immunoassay*, CRC Press, Boca Raton, Fla.; E. Ishikawa et al., (eds.), 1981, *Enzyme Immunoassay*, Kgaku Shoin, Tokyo). The enzyme which is bound to the antibody reacts with an appropriate substrate, preferably a chromogenic substrate, in such a manner as to produce a chemical moiety that can be detected, for example, by spectrophotometric, fluorometric or visual means. Examples of enzymes that can be used to detectably label an antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate compared with similarly prepared standards.

Detection can also be achieved using any of a variety of other immunoassays. For example, by radioactively labeling the antibodies or antibody fragments, it is possible to detect RAI-3 protein or peptides through the use of a radioimmunoassay (RIA) (see, for example, B. Weintraub, Principles of Radioimmunoassays, Seventh Training Course on Radioligand Assay Techniques, *The Endocrine Society*, March, 1986. The radioactive isotope can be detected by using a gamma counter or a scintillation counter or by autoradiography.

It is also possible to label the antibody with a fluorescent compound. When the fluorescently labeled antibody is exposed to light of the proper wavelength, its presence can then be detected due to fluorescence (emission of light of a different wavelength). Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Similarly, a bioluminescent compound can be used to label an anti-RAI-3 antibody. Bioluminescence is a type of chemiluminescence found in biological systems in which a catalytic protein increases the efficiency of the chemiluminescent reaction. The presence of a bioluminescent protein is determined by detecting the presence of luminescence. Illustrative bioluminescent compounds for the purposes of bioluminescent labeling include luciferin, luciferase and aequorin.

Screening Assays for Determining Compounds that Modulate RAI-3 and

Compositions Related Thereto

Screening assays can be used to identify compounds that modulate RAI-3 function or activity. Such compounds can include, but are not limited to, peptides, small organic or inorganic molecules or macromolecules such as nucleic acid molecules or proteins, e.g., antibodies and antibody fragments, and can be utilized, for example, in the control and/or treatment of COPD and COPD related disorders, in the modulation of second messenger or cellular molecules which are regulated or modulated by RAI-3, such as IκB, and which may affect COPD and its related conditions and disorders. These compounds may also be useful, e.g., in elaborating the biological functions of the RAI-3 gene product, i.e., the RAI-3 protein and its peptides, in modulating the RAI-3 biological functions and for preventing, treating, reducing, and/or ameliorating symptoms and/or physiological characteristics and effects of COPD or COPD related disorders.

The compositions of the invention include pharmaceutical compositions comprising one or more of the RAI-3 modulator compounds. Such pharmaceutical compositions can be formulated as discussed hereinbelow. More specifically, these compounds can include compounds that bind to RAI-3 and its peptide components, compounds that bind to other proteins or molecules that interact with an RAI-3 gene product and/or interfere with the interaction of the RAI-3 gene product with other proteins or molecules, and compounds that modulate the activity of the RAI-3 gene, i.e., modulate the level of RAI-3 gene expression and/or modulate the level of the RAI-3 gene product or protein activity.

In a related aspect, assays can be utilized that identify compounds that bind to RAI-3 gene regulatory sequences, e.g., promoter sequences (see e.g., K. A. Platt, 1994, *J. Biol. Chem.*, 269:28558-28562); such compounds may modulate the level of RAI-3 gene expression. In addition, functional assays can be used to screen for compounds that modulate RAI-3 gene product activity. In such assays, compounds are screened for agonistic or antagonistic activity with respect to the biological activity or function of the RAI-3 protein, polypeptide, or peptides, such as changes in the intracellular levels or activity of a molecule with which RAI-3 interacts or which is regulated by RAI-3, changes in regulatory factor release, or other activities or functions of the RAI-3 protein, polypeptide or peptides which are involved in causing or maintaining COPD and COPD related disorders according to this invention.

Figure 14A:
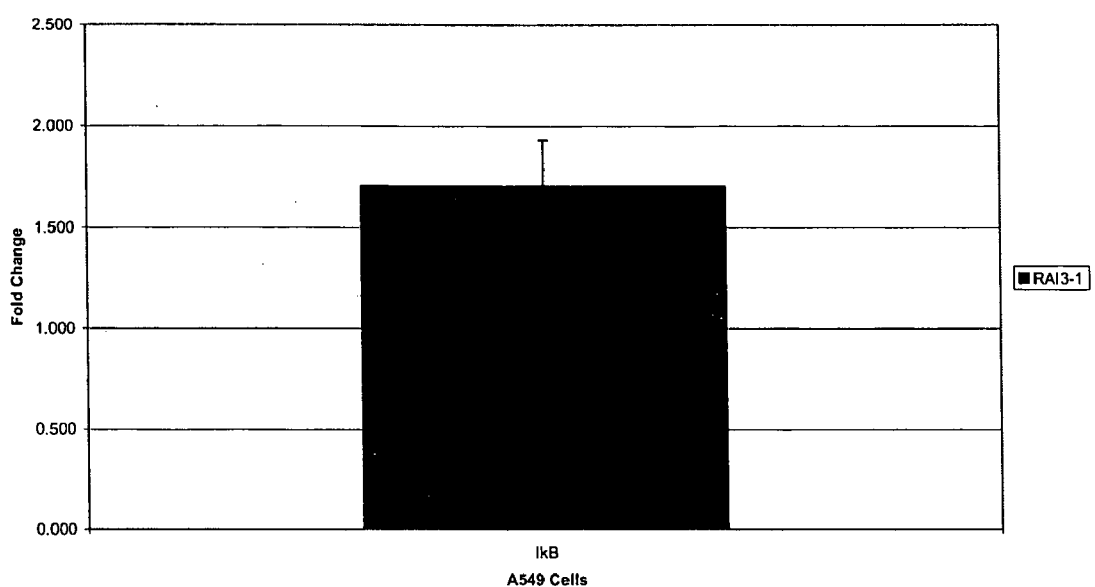
FIGS. 14A and 14B show the results of experiments in which antisense nucleic acid to RAI-3 was used to evaluate the outcome of IκB mRNA expression in A549 cells and E-selectin surface expression in human microvascular endothelial cells (HMVECs). Based on these experiments, it was found that antisense to RAI-3 increased the level of IκB mRNA in A549 cells that had been released from quiescence four hours prior to transfection with the RAI-3 ultramer antisense (FIG. 14A and Example 2). At sixteen to twenty-four hours post transfection, the mRNA was harvested and Taq-Man analysis was preformed for the expression of IκB and GAPDH. All samples were normalized to GAPDH and IκB values were reported as fold change relative to IκB in samples that were transfected with an ultramer control. Next, the RAI-3 ultramer was applied to primary HMVEC cells for 16-24 hours, followed by TNF-α treatment for 6 hours. Thereafter, E-selectin protein expression on the cell surface was evaluated. Knock down of RAI-3 mRNA decreased TNF-α induced E-selectin surface expression in HMVECs.
Figure 14B:
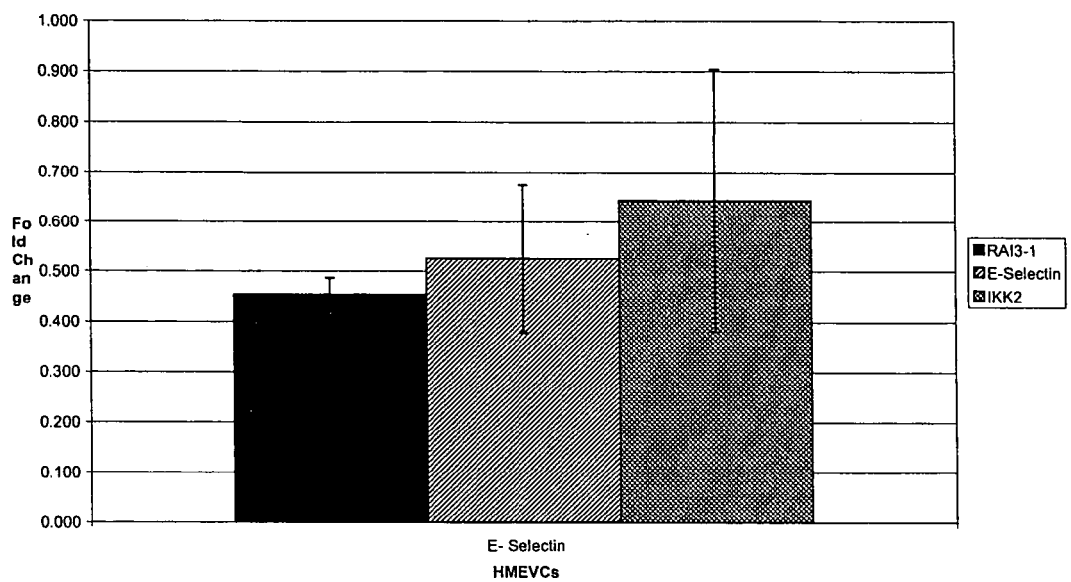

According to an embodiment of this invention, molecules that are affected, regulated, modulated, or which otherwise interact with RAI-3, particularly in cells affected by COPD, for example, molecules of the NF-κB pathway and/or E-selectin molecules, can be monitored or assayed in RAI-3-expressing host cells to determine if modulators of RAI-3 (e.g., antagonists such as antisense of RAI-3 as described further herein) affect the function of component molecules in the pathway. In a particular aspect of this embodiment, antisense to RAI-3 were used to evaluate the outcome of IκB niRNA expression in A549 cells, as well as E-selectin surface expression in human microvascular endothelial cells (HMVECs). It was found that antisense to RAI-3 increased the level of IκB mRNA in A549 cells and decreased TNF-α induced E-selectin surface expression in HMVECs. (FIGS. 14A and 14B and Examples 2 and 3).

With regard to the above findings, it has been shown that the IκB promoter is driven by NF-κB and by an NF-κB-independent arsenite/heat stress response (C. Y. Ito et al., 1994, *Nucleic Acids Res.*, 22:3787-3792; and H. R. Wong et al., 1997, *J. Clin. Invest.*, 99:2423-2428). In addition, the E-selectin promoter has been shown to be activated by NF-κB; however, elevated levels of cAMP can inhibit TNF-α stimulation of E-selectin expression on endothelial cells (V Ollivier et al., 1996, *J. Biol. Chem.*, 271:20828-20835; and L. G. De Luca et al., 1994, *J. Biol. Chem.*, 269:19193-19196). Similarly, LPS stimulation of TNF-α expression, a response that is also driven by NF-κB has been shown to be inhibited by elevated cAMP in RAW246.7 and THP-1 cells. (V Ollivier et al., 1996, *J. Biol. Chem.*, 271:20828-20835; and M Delgad et al., 1996, *J. Biol. Chem.*, 273:31427-31436). Stress induced by arsenite in PC12 cells has been shown to stimulate ATF/CREB family members (cAMP-responsive element-DNA binding proteins) to drive Gadd153 expression (T. W. Fawcet et al., 1999, *J. Biochem.*, 339:135-141). Taken together these data suggest that antisense to RAI-3 could increase cAMP pools that act to stimulate IκB expression, which, in turn, can drive down NF-κB nuclear location. Under this scenario, E-selectin expression would be decreased when RAI-3 is antagonized (either by antisense or small molecules) as a consequence of a decrease in NF-κB nuclear localization, as well as by increasing the cAMP pools.

The ability of RAI-3 to regulate NF-κB functions in RAI-3 expressing cells, endothelial cells and lung epithelial cells, supports the view that antagonist and agonists to RAI-3 would have an impact on many diseases, including autoimmune diseases, inflammation, asthma, COPD, rheumatoid arthritis (RA), cancers, such as, but not limited to, lung cancer, stomach cancer, breast cancer, testicular cancer, ovarian cancer, cervical cancer, genitourinary tract cancer, bladder cancer, prostate cancer, gastrointestinal cancer, colon cancer, esophageal cancer, head and neck cancer, cancer of the brain, thyroid cancer, liver cancer, pancreatic cancer, kidney cancer, etc., ischemia-reperfusion injury, atherosclerosis, thrombosis, and other vascular diseases. The results reported herein (Examples 2 and 3, FIGS. 14A and 14B) support the view that antagonists to RAI-3 can down regulate NF-κB-mediated functions, including reducing the expression of genes that control endothelial cell adhesion events and cytokine secretion (S. E. Meiler, 2002, *J. Mol. Cell. Cardiol.*, 34:349-359; S. Yoshimura et al., 2001, *Gene Ther.*, 8:1635-1642; M. Morigi et al., 1998, *J. Clin. Investigation*, 101:1905-1915; C. Sultana, 1998, *Blood*, 92:3924-3935; and G. Voraberger et al., 1991, *J. Immunol.*, 147:2777-2786).

The impact of blocking the binding of leukocytes and platelets to the endothelium is a reduction of inflammatory responses on the vessel wall, as well as entry of leukocytes into tissues involved in autoimmune diseases, sites of inflammation, and in diseases such as COPD where foreign substances (i.e., smoke, allergens, environmental pollutants, and pathogens) drive immune cell recruitment and activation (D. J. Lefer, 2000, *Ann. Rev. Pharmacology and Toxicology*, 40:283-294; M. P. Bevilacqua, 1994, *Ann. Rev. Med.*, 45:361-378; S. D. Rosen, 1993, *Seminars Immunol.* 5:237-247; A. J. Gearing and w. Newman, 1993, *Immunol. Today*, 14:506-512; and A. D. Blann and G. Y. Lip, 1997, *Clin. Cardiol.*, 20:822-824). Adhesion of metastatic cancer cells to endothelium is also believed to contribute to the metastatic process; accordingly, modulators such as antagonists to RAI-3 would be predicted to reduce endothelium-cancer cell interactions. (B. R. Zetter, 1993, *Semin. Cancer Biol.*, 4:219-229; T. Krause, 1999, *Clin. Exp. Metastasis*, 17:183-192).

The central role of NF-κB activation in bronchiolar epithelium in coordinating airway inflammation has been demonstrated in a number of mouse and cellular models where chemokine, eotaxin, IL-8, MMP-9, and iNOS synthase expression are enhanced leading to neutrophil and eosinophil infiltration and tissue damage (M. E. Poynter, 2002, *Am. J. Pathol.*, 160:1325-1334; D-W. Jeong, 2002, *J. Biol. Chem.*, 277:17871-17876; A. Hozumi et al., 2001, *Am. J. Physiol. Lung Cell Mol. Physiol.*, 281: L1444-L1452; R. S. Smith et al., 2001, *J. Immunol.*, 167:366-374; R. W. Ganster et al., 2001, *Proc. Natl. Acad. Sci. USA*, 98:8638-8643; and H. Takizawa, 1999, *J. Immunol.*, 162:4705-4711). In addition, NF-κB has been shown to regulate aquaporin 5, a major water channel that is expressed in alveolar, tracheal and upper bronchial epithelium, thereby contributing not only to lung inflammation, but also to airway edema (J. E. Towne et al., 2001, *J. Biol. Chem.*, 276:18657-18664). Mucin production by specialized epithelial cells has also been shown to be regulated by NF-κB (Seuningen et al., 2001. *Front. Biosci.*, 6: D1216-D1234; and J.-D. Li et al., 1998, *Proc. Natl. Acad. Sci. USA*, 95:5718-5723). Thus, using antagonist or agonist modulators of RAI-3 that target lung epithelial cells offers a novel utility as therapeutics for many diseases of the lung.

According to another embodiment of this invention, screening assays can be designed to identify compounds capable of binding to the RAI-3 gene product or peptides thereof. Such compounds can be useful, e.g., in modulating the activity of wild type and/or mutant RAI-3, in elaborating the biological function of the RAI-3 gene product, and in screens for identifying compounds that disrupt normal RAI-3 gene product interactions. Alternatively, such compounds may in themselves disrupt such interactions.

Screening assays to identify compounds that bind to RAI-3, and/or its composite peptides can involve preparing a reaction mixture of the RAI-3 protein or peptide and a test compound under conditions and for a time sufficient to allow the two components to interact with, i.e., bind to each other, and thus form a complex, which can represent a transient complex that can be removed and/or detected in the reaction mixture. For example, one type of assay involves anchoring an RAI-3 polypeptide or peptide, or the test substance, onto a solid phase and detecting the RAI-3 polypeptide or peptide/test compound complexes anchored on the solid phase at the end of the reaction. In one aspect of such a method, the RAI-3 polypeptide or peptide can be anchored onto a solid surface, and the test compound, which is not anchored, can be labeled, either directly or indirectly.

The detection of complexes anchored on the solid surface can be accomplished in a number of ways. In cases in which the previously non-immobilized component is pre-labeled, the detection of label immobilized on the surface indicates that complexes were formed. In cases in which the previously non-immobilized component is not pre-labeled, an indirect label can be used to detect complexes anchored on the surface; e.g., using a labeled antibody specific for the previously non-immobilized component (the antibody, in turn, can be directly labeled, or indirectly labeled with a labeled anti-Ig antibody).

Alternatively, a reaction can be conducted in a liquid phase, the reaction products separated from unreacted components, and complexes detected, e.g., using an immobilized antibody specific for the RAI-3 polypeptide or peptide, or the test compound, to anchor any complexes formed in solution, and a labeled antibody specific for the other component of the formed complex to detect anchored complexes.

Compounds that modulate RAI-3 protein activity can also include compounds that bind to proteins that interact with RAI-3. These modulatory compounds can be identified by first identifying those proteins, e.g., cellular proteins, that interact with the RAI-3 protein product, e.g., by standard techniques known in the art for detecting protein-protein interactions, such as co-immunoprecipitation, cross-linking and co-purification through gradients or chromatographic columns. Utilizing procedures such as these allows for the isolation of proteins that interact with the RAI-3 protein, polypeptide, or peptides.

Once isolated, such a protein can be identified and can, in turn, be used, in conjunction with standard techniques, to identify additional proteins with which that protein (and/or RAI-3) interacts. For example, at least a portion of the amino acid sequence of the protein that interacts with the RAI-3 gene product can be ascertained using techniques well known to those of skill in the art, such as via the Edman degradation technique (see, e.g., Creighton, 1983, *Proteins: Structures and Molecular Principles*, W.H. Freeman & Co., N.Y., pp. 34-49). The amino acid sequence thus obtained can be used as a guide for the generation of oligonucleotide mixtures that can, in turn, be used to screen for gene sequences encoding the interacting proteins. Screening is accomplished, for example, by standard hybridization or PCR techniques. Techniques for the generation of oligonucleotide mixtures and screening are well-known and practiced in the art (see, e.g., F. M. Ausubel, supra, and *PCR Protocols: A Guide to Methods and Applications*, 1990, M. Innis et al., eds. Academic Press, Inc., New York).

In addition, methods can be employed that result in the simultaneous identification of genes which encode proteins that interact with the RAI-3 polypeptide. These methods include, for example, probing expression libraries with labeled RAI-3 protein or polypeptide, using RAI-3 protein or polypeptide in a manner similar to the well known technique of antibody probing of λgt11 libraries. One method that detects protein interactions in vivo is the two-hybrid system. A version of this system is described by Chien et al., 1991, *Proc. Natl. Acad. Sci. USA*, 88:9578-9582 and is commercially available from Clontech (Palo Alto, Calif.).

Compounds that disrupt the interaction of RAI-3 with other molecules, or binding partners, as determined by techniques exemplified above, can be useful in regulating the activity of the RAI-3 protein, including mutant RAI-3 proteins. Such compounds can include, but are not limited to, molecules such as peptides, and the like, which bind to RAI-3 as described above. Illustrative assay systems used to identify compounds that interfere with the interaction between RAI-3 and its interacting molecule(s) involves preparing a reaction mixture containing the RAI-3 protein or peptide and the interacting molecule, under conditions and for a time sufficient to allow the two to interact (and bind), thus forming a complex. In order to test a compound for inhibitory activity, the reaction mixture is prepared in the presence and absence of the test compound. The test compound can be initially included in the reaction mixture, or it can be added at a time subsequent to the addition of RAI-3 and its interacting molecule. Control reaction mixtures are incubated without the test compound or with a placebo. Complexes formed between RAI-3 and the interacting molecule(s) are then detected. The formation of a complex in the control reaction, but not in the reaction mixture containing the test compound, indicates that the compound interferes with the interaction of RAI-3 and the interacting molecule. Further, complex formation within reaction mixtures containing the test compound and a normal RAI-3 protein or peptide product can also be compared with complex formation within reaction mixtures containing the test compound and a mutant RAI-3 protein or peptide product. This comparison could be particularly useful in those cases in which it is desirable to identify compounds that disrupt interactions of mutant but not normal RAI-3 proteins.

Assaying for compounds that interfere with the interaction of the RAI-3 protein or peptides and interacting (e.g., modulated or regulated) molecules can be conducted in a heterogeneous or homogeneous format. Heterogeneous assays involve anchoring either RAI-3 or the binding molecule onto a solid phase and detecting complexes anchored on the solid phase at the end of the reaction. In homogeneous assays, the entire reaction is carried out in a liquid phase. In either approach, the order of addition of the reaction components can be varied to obtain different information about the compounds being tested. For example, test compounds that interfere with the interaction between RAI-3 and its interacting molecules, e.g., by competition, can be identified by conducting the reaction in the presence of the test substance; i.e., by adding the test substance to the reaction mixture prior to, or simultaneously with, RAI-3 and the interacting molecule. Alternatively, test compounds that disrupt preformed complexes, e.g., compounds with higher binding constants that displace one of the components from the complex, can be tested by adding the test compound to the reaction mixture after the complexes between RAI-3 and another molecule or molecules have been formed. The various formats are described briefly below.

In a heterogeneous assay system, either RAI-3 or the interacting molecule, is anchored onto a solid surface, while the non-anchored molecule is labeled, either directly or indirectly. In practice, microtiter plates are conveniently utilized. The anchored species can be immobilized by non-covalent or covalent attachments. Non-covalent attachment can be achieved simply by coating the solid surface with a solution comprising RAI-3 or the interacting molecule and drying the surface. Alternatively, an immobilized antibody specific for the molecule to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed remain immobilized on the solid surface. The detection of complexes anchored on the solid surface is performed in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of adding the reaction components, test compounds which inhibit complex formation, or which disrupt preformed complexes, can be detected.

Alternatively, the reaction can be conducted in a liquid phase in the presence or absence of the test compound, the reaction products separated from unreacted components, and complexes detected; e.g., using an immobilized antibody specific for one of the interacting components, to anchor any complexes formed in solution, and a labeled antibody specific for the other partner to detect anchored complexes. Again, depending upon the order of addition of reaction components to the liquid phase, test compounds that inhibit complex formation or that disrupt preformed complexes can be identified.

In another aspect of such assays, a preformed complex of the RAI-3 protein or peptide and an interacting molecule is prepared in which either RAI-3 or its interacting partner molecule is labeled. However, the signal generated by the label is quenched due to complex formation between RAI-3 and the interacting molecule (see, e.g., U.S. Pat. No. 4,109,496 to Rubenstein which utilizes this approach for immunoassays). The addition of a test substance that competes with and displaces one of the species from the preformed complex will result in the generation of a signal above background. In this way, test substances that disrupt RAI-3 protein/interacting partner interactions can be identified.

Techniques as described above can be employed using RAI-3 peptide fragments that correspond to the binding domains of the RAI-3 protein and/or the interacting partner, instead of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interacting, e.g., binding. Alternatively, one protein can be anchored to a solid surface using methods as described above, and allowed to interact with, e.g., bind, to its labeled interacting partner, which has been treated with a proteolytic enzyme, such as trypsin. After washing, a short, labeled peptide comprising the interacting, e.g., binding, domain may remain associated with the solid material; the associated domain can be isolated and identified by amino acid sequencing. Also, once the gene coding for the intracellular binding partner is obtained, short gene segments can be engineered to express peptide fragments of the protein, which can then be tested for binding activity and purified or synthesized.

The human RAI-3 polypeptide and/or peptides, or immunogenic fragments or oligopeptides thereof, can be used for screening for therapeutic drugs or compounds for COPD or COPD related disorders in a variety of drug screening techniques. The fragment employed in such a screening assay can be free in solution, affixed to a solid support, borne on a cell surface, or located intracellularly. The reduction or elimination of activity in the formation of binding complexes between RAI-3 protein and the agent being tested can be measured. Thus, the present invention provides a method for screening or assessing a plurality of compounds for their specific binding affinity with the RAI-32 polypeptide, or a bindable peptide fragment, involving obtaining or providing or testing a plurality of compounds, combining the RAI-3 polypeptide, or a bindable peptide fragment, with each of the plurality of compounds for a time sufficient to allow binding under suitable conditions and detecting binding of the RAI-3 polypeptide or peptide to each of the plurality of test compounds, thereby identifying the compounds that specifically bind to the RAI-3 polypeptide or peptide.

Methods of identifying compounds that modulate the activity of the RAI-3 polypeptide and/or peptides comprise combining a potential or candidate compound or drug modulator with RAI-3 polypeptide or peptide, for example, the RAI-3 amino acid sequence as set forth in SEQ ID NO:3, or a peptide encoding sequence thereof, and measuring an effect of the candidate compound or drug modulator on the biological activity of the RAI-3 polypeptide or peptide. Such measurable effects include, for example, physical binding interaction; effects on native and cloned RAI-3-expressing cell lines; and effects on components of the NF-κB pathway which are regulated or modulated by RAI-3 either directly or indirectly via RAI-3 modulators as described herein.

Another method of identifying compounds that modulate the biological activity of the RAI-3 protein comprises combining a potential or candidate compound or drug modulator, e.g., of an NF-κB pathway component, such as IκB, with a host cell that expresses the RAI-3 polypeptide and measuring an effect of the candidate compound or drug modulator on the biological activity of the RAI-3 polypeptide. The host cell can also be capable of being induced to express the RAI-3 polypeptide, e.g., via inducible expression. Physiological effects of a given candidate modulator on the RAI-3 polypeptide can also be measured. Thus, cellular assays for particular NF-κB pathway modulators can be either direct measurement or quantification of the physical biological activity of RAI-3, or they can involve measurement or quantification of a physiological effect. Such methods preferably employ the RAI-3 polypeptide as described herein, or an overexpressed recombinant RAI-3 polypeptide in suitable host cells containing an expression vector as described herein, wherein the RAI-3 polypeptide is expressed, overexpressed, or undergoes up-regulated expression.

Another aspect of the present invention embraces a method of screening for a compound that is capable of modulating the biological activity of the RAI-3 polypeptide, comprising providing a host cell containing an expression vector harboring a nucleic acid sequence encoding a RAI-3 polypeptide, or a functional peptide or portion of the RAI-3 amino acid sequence (SEQ ID NO:3); determining the biological activity of the expressed RAI-3 polypeptide in the absence of a modulator compound; contacting the cell with the modulator compound; and determining the biological activity of the expressed RAI-3 polypeptide in the presence of the modulator compound. In such a method, a difference between the activity of the RAI-3 polypeptide in the presence of the modulator compound and in the absence of the modulator compound indicates a modulating effect of the compound.

Essentially any chemical compound can be employed as a potential modulator or ligand in the assays for determining or identifying RAI-3 modulators or effector molecules. Compounds tested as candidate modulators can be any small chemical compound, or biological entity (e.g., protein, sugar, nucleic acid, lipid). Test compounds are typically small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are routinely run in parallel, for example, in microtiter formats on microtiter plates in robotic assays, e.g., high throughput assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are especially envisioned for the detection of modulators or effectors of the RAI-3 polypeptide particularly for preventing, treating or ameliorating COPD and COPD related disorders as discussed herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

As is appreciated by the skilled practitioner, a combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487-493; and Houghton et al., 1991, *Nature,* 354:84-88). Other chemistries for generating chemical diversity libraries can also be used. Nonlimiting examples of chemical diversity library chemistries include, peptoids (PCT publication no. WO 91/019735), encoded peptides (PCT publication no. WO 93/20242), random bio-oligomers (PCT publication no. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909-6913), vinylogous polypeptides (Hagihara et al., 1992, *J. Amer. Chem. Soc.,* 114:6568), non-peptidal peptidomimetics with glucose scaffolding (Hirschmann et al., 1992, *J. Amer. Chem. Soc.*, 114:9217-9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309-314) and PCT/US96/10287), carbohydrate libraries (e.g., Liang et al., 1996, *Science*, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

Solid phase-based in vitro assays in a high throughput format are encompassed in which the cell or tissue expressing an RAI-3 polypeptide or an RAI-3 peptide is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

Also encompassed are screening and small molecule (e.g., drug) detection assays which involve the detection or identification of small molecules that can bind to the RAI-3 polypeptide or peptide. Particularly preferred are assays suitable for high throughput screening methodologies. In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, polypeptides such as RAI-3, based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify RAI-3 polypeptide or peptides for use in measuring or quantifying a biological binding or ligand binding activity, the source may be a whole cell lysate that can be prepared by successive freeze-thaw cycles (e.g., one to three) in the presence of standard protease inhibitors. The RAI-3 polypeptide can be partially or completely purified by standard protein purification methods, e.g., affinity chromatography using specific antibody as described, or by ligands specific for an epitope tag engineered into a recombinant RAI-3 polypeptide molecule. Binding activity can then be measured as described.

Compounds which are identified according to the methods provided herein, and which modulate or regulate the biological activity or physiology of the RAI-3 polypeptide are embraced as a preferred embodiment of this invention. It is contemplated that such modulatory compounds can be employed in treatment, prevention and therapeutic methods for treating or preventing COPD or COPD related disorders or conditions which are mediated by, associated with, regulated or modulated by RAI-3, by administering to an individual in need of such treatment a therapeutically effective amount of the compound identified by the methods described herein. In addition, the present invention provides methods for treating an individual in need of such treatment for COPD or a COPD related disease, disorder, or condition that is mediated by RAI-3, comprising administering to the individual a therapeutically effective amount of the RAI-3-modulating compound identified by a method provided herein.

Methods and Compositions for the Treatment of COPD and COPD Related Disorders, as Well as NF-κB-Mediated Diseases and Disorders, Associated with RAI-3 and/or Modulators Thereof The present invention also relates to methods and compositions for the treatment, amelioration, modulation and/or prevention of COPD and COPD related disorders that are mediated or regulated by RAI-3 expression or function, e.g., RAI-3 phosphorylation or activation, interaction with signal transduction molecules or cellular regulatory factor molecules or release, or by RAI-3 modulation, and the like. Further, RAI-3 effector functions can be modulated via such methods and compositions. Moreover, as described herein, the present invention relates to the treatment, amelioration, modulation, and/or prevention of a variety of other diseases or disorders involving the modulation of NF-κB activity or function, or the activity or function of NF-κB associated molecules, through RAI-3 or RAI-3 modulation.

That RAI-3 expression, function, and/or modulation have a direct involvement with COPD, the underlying symptoms of COPD, and COPD-related diseases, disorders, and/or conditions, is highly consistent with the finding that RAI-3 is overexpressed in the lung parenchyma (FIG. 15 and Example 10), since COPD is believed to originate in this part of the lung tissue. The parenchyma constitutes the terminal respiratory units, i.e., the most distal portions, of the lung, which are composed of alveolar ducts with the accompanying interconnected alveoli; the parenchyma also can contain very small caliber bronchi and bronchioles (such as terminal and respiratory bronchioles). It is well documented that emphysema is defined as an abnormal permanent enlargement of the air spaces distal to the terminal bronchioli, with concomitant destruction of the alveolar walls. In view of its connection with lung disease (and COPD), RAI-3 expression is consequently highest in parenchymal regions of the lung, which are known to be damaged in emphysema.

Moreover, it has been reported that increased airway resistance in COPD may also be due to disease of the small bronchioles just proximal to the alveolar regions. (W. M. Thurlbeck, 1991, Pathology of Chronic Airflow Obstruction, Ist Ed., W. B. Saunders, Philadelphia, Pa. pp 3-20). The main histopathological changes in these small airways involve inflammation, increased muscle mass and the abnormal appearance of goblet cells that produce increased amounts of mucin in the airway lumen, thereby resulting in airflow obstruction (M. G. Cosio et al., 1978, *New Engl. J. Med.*, 298:1277-1281; D. Lamb, 1995, Chronic Obstructive Pulmonary Disease, $2^{nd}$ ed. Chapman and Hall, London, pp. 9-34; and A. A. Glynn and L. Michaels, 1960, *Thorax*, 15:142-153). Because mucus overproduction is a hallmark of chronic bronchitis, it further correlates with the role of RAI-3 in lung pathobiology and disease states that RAI-3 is expressed in those regions of the lung where pathological changes contribute to bronchitis, as well as to emphysema.

The methods in accordance with this aspect of the invention include those that modulate RAI-3 gene and gene product activity. In certain instances, the treatment will require an increase, enhancement, upregulation or activation of RAI-3 activity, while in other instances, the treatment will require a decrease, reduction, down-regulation or suppression of RAI-3 activity. "Increase" and "decrease" refer to the differential levels of RAI-3 activity relative to RAI-3 activity in the cell type of interest in the absence of modulatory treatment. Methods for the decrease or increase of RAI-3 activity are described below. Methods which can either increase or decrease RAI-3 activity depending on the particular manner in which the method is practiced are further described below.

Methods Associated with a Decrease of RAI-3 Activity

Treatment of COPD and/or COPD related conditions and disorders can be achieved by methods which serve to decrease RAI-3 activity. Activity can be decreased directly, e.g., by decreasing the RAI-3 gene product, i.e., protein, activity and/or by decreasing the level of RAI-3 gene expression. For example, compounds such as those identified through the methods and assays described above that decrease RAI-3 protein activity can be used in accordance with the invention to ameliorate, reduce or abolish symptoms associated with COPD or COPD related conditions and disorders. Alternatively, compounds such as those identified through the methods and assays described above that decrease RAI-3 protein activity can be used in accordance with the invention to ameliorate, reduce or abolish symptoms associated with NFκB, IκBα, and/or E-selectin related conditions and disorders. As discussed above, such molecules can include, but are not limited to, peptides, including soluble peptides, and small organic or inorganic molecules, i.e., RAI-3 antagonists. Techniques for the determination of effective doses and administration of such compounds are described herein.

Antisense, siRNA, Ribozymes, and Triple Helix Formation

In addition, antisense and ribozyme molecules that inhibit RAI-3 gene expression can also be used to reduce the level of RAI-3 gene expression, thus effectively reducing the level of RAI-3 protein present in a cell, thereby decreasing the level of RAI-3 protein activity, or modulation that occurs in the cell as a result of smoke exposure. In addition, antisense molecules of RAI-3, and the like, can be used to modulate or affect the function of molecules which are regulated or mediated by, interact with, and/or are recipients of downstream effects of, RAI-3 in a cell. Still further, triple helix molecules can be utilized in reducing the level of RAI-3 gene expression. Such molecules can be designed to reduce or inhibit either wild type, or if appropriate, mutant RAI-3 target gene activity. Techniques for the production and use of such molecules are well known to those having skill in the art.

As is understood by the skilled practitioner, antisense approaches involve the design of oligonucleotides (either DNA or RNA) that are complementary to mRNA of the RAI-3 gene sequence or a portion thereof. The antisense oligonucleotides will bind to the complementary RAI-3 gene mRNA transcripts and prevent translation. Absolute complementarity, although preferred, is not required. A sequence "complementary" to a portion of an RNA, as referred to herein, means a sequence having sufficient complementarity to be able to hybridize with the RNA, and form a stable duplex. In the case of double-stranded antisense nucleic acids, a single strand of the duplex DNA may thus be tested, or triplex formation may be assayed. The ability to hybridize depends upon both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by using of standard procedures and practice to determine the melting point of the hybridized complex.

Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference. Antisense oligos, particularly siRNA reagents, may be used therapeutically by following the methods outlined Tiscornia et al (PNAS, 100(4):1844-1848 (2003); which is hereby incorporated by reference in its entirety). Other methods are known in the art and encompassed by the present invention.

Oligonucleotides that are complementary to the 5' end of the message, e.g., the 5' untranslated sequence up to and including the AUG initiation codon, typically work most efficiently at inhibiting translation. However, sequences complementary to the 3' untranslated sequences of mRNAs have recently been shown to be effective at inhibiting translation of mRNAs as well. (See, generally, R. Wagner, 1994, *Nature*, 372:333-335). Thus, oligonucleotides complementary to either the 5' or 3' untranslated (UTR), non-coding regions of the RAI-3 nucleic acid could be used in an antisense approach to inhibit translation of endogenous RAI-3 gene mRNA.

Oligonucleotides complementary to the 5' untranslated region of the mRNA preferably include the complement of the AUG start codon. Antisense oligonucleotides complementary to mRNA coding regions are less efficient inhibitors of translation, but can be used in accordance with the invention. Whether designed to hybridize to the 5' UTR, 3' UTR or coding region of a target or pathway gene mRNA, antisense nucleic acids are preferably at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, at least 26 nucleotides, or at least 50 nucleotides.

Regardless of the choice of target sequence, it is preferred that in vitro studies are first performed to quantify the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. In addition, results obtained using the antisense oligonucleotide are preferably compared with those obtained using a control oligonucleotide. It is also preferred that the control oligonucleotide is of approximately the same length as the antisense oligonucleotide and that the nucleotide sequence of the control oligonucleotide differs from the antisense sequence no more than is necessary to prevent specific hybridization to the target sequence.

The oligonucleotides can be DNA, RNA, or chimeric mixtures, derivatives, or modified versions thereof, single-stranded or double-stranded. The oligonucleotide can be modified at the base moiety, sugar moiety, or phosphate backbone, for example, to improve stability of the molecule, hybridization, etc. The oligonucleotide may also include other appended groups such as peptides (e.g., for targeting host cell receptors in vivo), or agents for facilitating transport across the cell membrane (see, e.g., Letsinger et al., 1989, Proc. Natl. Acad. Sci. USA., 86:6553-6556; Lemaitre et al., 1987, Proc. Natl. Acad. Sci. USA, 84:648-652; PCT Application No. WO 88/09810) or the blood-brain barrier (see, e.g., PCT Application No. WO 89/10134), or hybridization-triggered cleavage agents (see, e.g., Krol et al., 1988, Biotechniques, 6:958-976) or intercalating agents (see, e.g., Zon, 1988, Pharm. Res., 5:539-549). For example, the oligonucleotide can be conjugated to another molecule, e.g., a peptide, hybridization triggered cross-linking agent, transport agent, hybridization-triggered cleavage agent, etc.

Such oligonucleotides can be synthesized by standard methods known in the art, for example, by use of an automated DNA synthesizer (such as are commercially available from Biosearch, Applied Biosystems, etc.). As nonlimiting examples, phosphorothioate oligonucleotides can be synthesized by the method of Stein et al. (1988, Nucl. Acids Res., 16:3209) and methylphosphonate oligonucleotides can be prepared by use of controlled pore glass polymer supports (Sarin et al., 1988, Proc. Natl. Acad. Sci. USA, 85:7448-7451), etc.

The antisense molecules are preferably delivered to cells expressing the RAI-3 gene in vivo. A number of methods have been developed for delivering antisense DNA or RNA to cells; e.g., antisense molecules can be injected directly into the tissue site, or modified antisense molecules that are designed to target the desired cells (e.g., antisense linked to peptides or antibodies that specifically bind to receptors or antigens expressed on the target cell surface) can be administered systemically. Because it is often difficult to achieve intracellular concentrations of the antisense molecules that are sufficient to suppress translation of endogenous mRNAs, a particular approach utilizes a recombinant DNA construct in which the antisense oligonucleotide is placed under the control of a strong pol III or pol II promoter. The use of such a construct to transfect target cells, ex vivo, in vivo, or in vitro, will result in the transcription of sufficient amounts of single stranded RNAs that will form complementary base pairs with the endogenous RAI-3 gene transcripts and thereby prevent translation of the RAI-3 gene mRNA. For example, a vector can be introduced in vivo such that it is taken up by a cell and directs the transcription of an antisense RNA.

Ribozymes are enzymatic RNA molecules capable of catalyzing the specific cleavage of RNA (For a review, see, e.g., Rossi, J., 1994, Current Biology, 4:469-471). The mechanism of ribozyme action involves sequence-specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins. Ribozyme molecules designed to catalytically cleave RAI-3 gene mRNA transcripts can also be used to prevent translation of RAI-3 gene mRNA and expression of target or pathway genes. (See, e.g., PCT Application No. WO 90/11364; and Sarver et al., 1990, Science, 247:1222-1225).

The ribozymes for use in the present invention also include RNA endoribonucleases (hereinafter referred to as "Cech-type ribozymes") such as that which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; PCT Patent Application No. WO 88/04300; and Been and Cech, 1986, Cell, 47:207-216). The Cech-type ribozymes have an eight base pair active site which hybridizes to a target RNA sequence, after which cleavage of the target RNA takes place. Encompassed by the present invention are those Cech-type ribozymes which target eight base-pair active site sequences that are present in the RAI-3 gene.

As in the antisense approach, ribozymes can be composed of modified oligonucleotides (e.g. for improved stability, targeting, etc.) and should be delivered to cells which express the RAI-3 gene, in vivo, in vitro, or ex vivo. A preferred method of delivery involves using a DNA construct "encoding" the ribozyme under the control of a strong constitutive pol III or pol II promoter, so that transfected cells produce sufficient quantities of the ribozyme to destroy endogenous RAI-3 gene messages and inhibit RAI-3 mRNA translation. Because ribozymes, unlike antisense molecules, are catalytic, a lower intracellular concentration is required for efficiency.

Endogenous RAI-3 gene expression can also be reduced by inactivating or "knocking out" the target and/or pathway gene or its promoter using targeted homologous recombination (see, e.g., Smithies et al., 1985, Nature, 317:230-234; Thomas & Capecchi, 1987, Cell, 51:503-512; and Thompson et al., 1989 Cell, 5:313-321). For example, a mutant, non-functional RAI-3 gene (or a completely unrelated DNA sequence) flanked by DNA homologous to the endogenous RAI-3 gene (either the coding regions or regulatory regions of the RAI-3 gene) can be used, with or without a selectable marker and/or a negative selectable marker, to transfect cells that express the RAI-3 gene in vivo. Insertion of the DNA construct, via targeted homologous recombination, results in inactivation of the RAI-3 gene. Such techniques can also be utilized to generate COPD or COPD related disorders animal models. It should be noted that this approach can be adapted for use in humans provided that the recombinant DNA constructs are preferably directly administered or targeted to the required site in vivo using appropriate viral vectors, e.g., herpes virus vectors.

Alternatively, endogenous RAI-3 gene expression can be reduced by targeting deoxyribonucleotide sequences complementary to the regulatory region of the RAI-3 gene (i.e., the RAI-3 gene promoter and/or enhancers) to form triple helical structures that prevent transcription of the RAI-3 gene in target cells in the body (see generally, Helene, C., 1991, *Anticancer Drug Des.*, 6(6):569-84; Helene, C., et al., 1992, *Ann. N.Y. Acad. Sci.*, 660:27-36; and Maher, L. J., 1992, *Bioassays*, 14(12):807-15). Nucleic acid molecules for use in triple helix formation to inhibit transcription should be single stranded and composed of deoxynucleotides. The base composition of these oligonucleotides should be designed to promote triple helix formation via Hoogsteen base pairing rules, which generally require that sizeable stretches of either purines or pyrimidines are present on one strand of the duplex. Nucleotide sequences can be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules can be chosen that are purine-rich, for example, containing a stretch of G residues. These molecules form a triple helix with a DNA duplex that is rich in GC pairs, in which the majority of the purine residues are located on a single strand of the targeted duplex, resulting in GGC triplets across the three strands of the triplex.

Alternatively, the potential sequences that can be targeted for triple helix formation are increased by creating a "switchback" nucleic acid molecule. Switchback molecules are synthesized in an alternating 5'-3', 3'-5' manner, such that they base pair with first one strand of a duplex and then with the other, eliminating the necessity for a sizeable stretch of either purines or pyrimidines to be present on one strand of the duplex.

In instances in which the antisense, ribozyme, and/or triple helix molecules described herein are utilized to inhibit mutant RAI-3 gene expression, it is possible that the technique may so efficiently reduce or inhibit the transcription (triple helix) and/or translation (antisense, ribozyme) of mRNA produced by normal target gene alleles that the concentration of normal target gene product present may be lower than is necessary for a normal phenotype. In such cases, to ensure that substantially normal levels of RAI-3 gene activity are maintained, nucleic acid molecules that encode and express RAI-3 polypeptides exhibiting normal target gene activity can be introduced into cells via gene therapy methods that do not contain sequences susceptible to whatever antisense, ribozyme, or triple helix treatments are being utilized. In instances in which the target gene encodes an extracellular protein, it may be preferable to co-administer normal target gene protein in order to maintain the requisite level of target gene activity.

Antisense RNA and DNA, ribozyme, and triple helix molecules of the invention can be prepared by any method known in the art, e.g., methods for chemically synthesizing oligodeoxyribonucleotides and oligoribonucleotides that are practiced in the art such as solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters, such as the T7 or SP6 polymerase promoters. Alternatively, antisense cDNA constructs that synthesize antisense RNA constitutively or inducibly, depending on the promoter used, can be introduced into cell lines to form stable cell lines containing the construct.

In addition, well-known modifications to DNA molecules can be introduced into the RAI-3 nucleic acid molecule as a means of increasing intracellular stability and half-life. Illustrative modifications include, but are not limited to, the addition of flanking sequences of ribo- or deoxyribo-nucleotides to the 5' and/or 3' ends of the molecule, or the use of phosphorothioate or 2' O-methyl rather than phosphodiesterase linkages within the oligodeoxyribonucleotide backbone.

Methods for Increasing RAI-3 Activity

Successful treatment of COPD or COPD related conditions and disorders can also be effected, where appropriate, by techniques that result in an increase in the level of RAI-3 and/or RAI-3 activity. Activity can be increased by, for example, directly increasing RAI-3 protein activity and/or by increasing the level of RAI-3 gene expression. For example, modulatory compounds such as those identified through the assays and methods described above that increase RAI-3 activity can be used to treat COPD and/or COPD related conditions and disorders. Such molecules can include, but are not limited to peptides, including soluble peptides, and small organic or inorganic molecules, and are typically considered to be RAI-3 agonists. Such a modulatory compound can be administered to a patient exhibiting COPD or COPD related disorders and/or symptoms at a level sufficient to treat COPD or COPD related disorders and symptoms. Alternatively, such a modulatory compound can be administered to a patient exhibiting NFκB, IκBα, and/or E-selectin related disorders and/or symptoms at a level sufficient to treat the NFκB, IκBα, and/or E-selectin related disorders and/or symptoms. One of skill in the art will readily know how to determine the concentration of an effective non-toxic dose of the compound using procedures routinely practiced in the art.

Alternatively, in instances in which the compound to be administered is a peptide compound, DNA sequences encoding the peptide compound, i.e., a DNA molecule, can be directly administered to a patient exhibiting COPD or a COPD related disorder or symptoms, at a concentration sufficient to produce a level of peptide compound sufficient to ameliorate, reduce or abolish the symptoms of the disorder. Any of the techniques described herein which provide the intracellular administration of compounds, such as, for example, liposome administration, transfection, infection, or direct injection, can be utilized for the administration of such DNA molecules. In the case of peptide compounds which act extracellularly, the DNA molecules encoding such peptides can be taken up and expressed by any cell type, so long as a sufficient circulating concentration of peptide results for the elicitation of a reduction or elimination or amelioration of COPD or COPD related conditions or symptoms.

In cases in which COPD or a COPD related disorder or condition can be localized to a particular portion or region of the body, the DNA molecules encoding such modulatory peptides can be administered as part of a delivery complex. Such a delivery complex can comprise an appropriate nucleic acid molecule and a targeting means. Such targeting means can comprise, for example, sterols, lipids, viruses or target cell specific binding agents. Viral vectors can include, but are not limited to adenovirus, adeno-associated virus, and retrovirus vectors, in addition to other materials that introduce DNA into cells, such as liposomes. In instances in which COPD or a COPD related disorder or condition involves an aberrant RAI-3 gene or protein, patients can be treated by gene replacement therapy. One or more copies of a normal RAI-3 gene, or a portion of the gene that directs the production of a normal RAI-3 protein with normal RAI-3 protein function, can be inserted into cells by means of a delivery complex as described above. Such gene replacement techniques can be accomplished either in vivo or in vitro. Techniques which select for expression within the cell type of interest are preferred. For in vivo applications, such techniques can, for example, include appropriate local administration of RAI-3 gene sequences.

Additional methods that can be used to increase the overall level of RAI-3 activity, in appropriate conditions in which it is advantageous to do so, include the introduction of appropriate RAI-3 gene-expressing cells, preferably autologous cells, into a patient at sites and in amounts sufficient to ameliorate, reduce, or eliminate COPD or COPD related disorders, conditions, or symptoms. Such cells can be either recombinant or non-recombinant. Among the cell types that can be administered to increase the overall level of RAI-3 gene expression in an individual are normal cells, which express the RAI-3 gene. The cells can be administered at the anatomical site of expression, or as part of a tissue graft located at a different site in the body. Such cell-based gene therapy techniques are well known to those skilled in the art (see, e.g., Anderson, et al., U.S. Pat. No. 5,399,349; and Mulligan and Wilson, U.S. Pat. No. 5,460,959).

RAI-3 gene sequences can also be introduced into autologous cells in vitro. Cells expressing the RAI-3 gene sequence can then be reintroduced, preferably by intravenous administration, into the patient until the disorder is treated and symptoms of the disorder are ameliorated, reduced, or eliminated.

Additional Modulatory Techniques

The present invention also includes modulatory techniques which, depending on the specific application for which they are utilized, can yield either an increase or a decrease in RAI-3 activity levels leading to the amelioration, reduction, or elimination of COPD or COPD related disorders and conditions, such as those described above.

For example, antibodies exhibiting modulatory capability can be utilized according to the methods of this invention to treat COPD or COPD related disorders. Depending on the specific antibody, the modulatory effect can be an increase or decrease in RAI-3 activity, or in activity of a molecule regulated or modulated by RAI-3, e.g., IκB. Specific antibodies can be generated using standard techniques as described above against a full length wild type or mutant RAI-3 polypeptide, or against peptides corresponding to portions of the protein. The antibodies include, but are not limited to, polyclonal, monoclonal, Fab fragments, single chain antibodies, chimeric antibodies, etc.

Lipofectin or liposomes can be used to deliver the antibody or an antibody fragment comprising the Fab region, which binds to epitopic regions of the RAI-3 protein, to cells expressing RAI-3. Where fragments of the antibody are used, the smallest inhibitory fragment which binds to an RAI-3 binding domain is preferred. For example, peptides having an amino acid sequence corresponding to the domain of the variable region of an antibody that binds to the RAI-3 protein can be used. Such peptides can be synthesized chemically, or produced via recombinant DNA technology using methods well known in the art (e.g., see Creighton, 1983, supra and Sambrook et al., 1989, supra). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population using, for example, techniques such as those described in Marasco et al., 1993, Proc. Natl. Acad. Sci. USA, 90:7889-7893.

Pharmaceutical Preparations and Methods of Administration

The compounds, e.g., nucleic acid sequences, proteins, polypeptides, peptides, and recombinant cells, described above can be administered to a patient, or to an individual in need thereof, in therapeutically effective doses to treat or ameliorate COPD or COPD related conditions and disorders. Such compounds are preferably modulators of RAI-3, such as antagonists or agonists, more preferably, obtained by methods discussed herein. A therapeutically effective dose refers to that amount of a compound or cell population sufficient to result in amelioration, reduction, elimination, or treatment of the disorder or symptoms. Alternatively, a therapeutically effective amount is that amount of a nucleic acid sequence sufficient to express a concentration of the RAI-3 protein product which results in the amelioration of the disorder or symptoms.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, to reduce side effects. The data obtained from the cell culture assays and animal studies can be used in formulating a range of dosage for use in humans.

The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating blood or plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Pharmaceutical compositions for use in accordance with the present invention and methods can be formulated in a conventional manner using one or more physiologically acceptable and/or pharmaceutically acceptable carriers, diluents, or excipients. Thus, therapeutic (and preventative) compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pre-gelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods well known in the art. Liquid preparations for oral administration can take the form of, for example, solutions, syrups or suspensions, or they can be presented as a dry product for reconstitution with water or another suitable vehicle before use. Such liquid formulations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations and formulations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. It is preferred that RAI-3-expressing cells be introduced into patients via intravenous administration.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

Without intending to be in any way limiting, the following further embodiments are encompassed by the present invention:

EMBODIMENTS 1 AND 2

A method of diagnosing, ameliorating, treating, reducing, eliminating, and/or preventing a disease, disorder, and/or condition affected by modulation of the G-protein coupled receptor protein RAI-3 in cells expressing RAI-3, which comprises providing a modulator of RAI-3 in an amount effective to affect the function or activity of RAI-3, and/or to affect the function or activity of cellular molecules associated with modulated RAI-3 activity or function. In such a method, the modulation of RAI-3 activity and/or function can occur in cells stimulated by a variety of stimuli, including cytokines, factors and chemokines, such as TNF-alpha, EGF, LPS, eotaxin, RANTES, smoke from tobacco burning materials such as cigarettes, and the like. In addition, the modulation of RAI-3 activity and/or function can affect other cellular signaling molecules or mediators, such as, for example, cell adhesion molecules like I-CAM and E-selectin.

A method of diagnosing, ameliorating, treating, reducing, eliminating, and/or preventing a disease, disorder, and/or condition affected by modulation of the G-protein coupled receptor protein RAI-3 in cells expressing RAI-3, which comprises providing a modulator of RAI-3 in an amount effective to affect the function or activity of RAI-3, and/or to affect the function or activity of NF-κB activation associated with modulated RAI-3 activity or function. In such a method, the modulation of RAI-3 activity and/or function can occur in cells stimulated by a variety of stimuli, including cytokines, factors and chemokines, such as TNF-alpha, EGF, LPS, eotaxin, RANTES, smoke from tobacco burning materials such as cigarettes, and the like. In addition, the modulation of RAI-3 activity and/or function can affect other cellular signaling molecules or mediators, such as, for example, cell adhesion molecules like I-CAM and E-selectin.

The methods of embodiments 1 and 2, wherein the disease, disorder, and/or condition that can be diagnosed, ameliorated, treated, reduced, eliminated, or prevented includes COPD, the underlying symptoms of COPD, COPD-related disorders and/or conditions, autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, renal diseases, ischemia-reperfusion injury, heart disorders, disorders related to aberrant signal transduction, proliferation disorders, cancers, such as lung cancer, stomach cancer, testicular cancer, breast cancer, etc., metastases, HIV infection, or HIV propagation in cells infected with other viruses, asthma, cystic fibrosis and pulmonary fibrosis, ulcerative colitis, cerebral infarct, myocardial infarct, diabetic nephropathy, allergic rhinitis, Crohn's disease, atherosclerosis, rheumatoid arthritis, inflammatory/auto-immune disorders outside of the lung in addition to COPD, glioblastoma, pulmonary small cell undifferentiated carcinoma, carcinoma of the breast, colon, lung, ovary, pancreas, and prostate, and non-Hodgkin's lymphoma.

The methods of embodiments 1 and 2, wherein the modulator of RAI-3 function, activity and/or interaction is an antagonist.

The methods of embodiments 1 and 2, wherein the modulator of RAI-3 function, activity and/or interaction is an antagonist selected from drugs, chemical compounds, proteins, peptides, antibodies, ligand compounds, small molecules, antisense complementary nucleic acid molecules, siRNA molecules, ribozymes.

The methods of embodiments 1 and 2, wherein the modulator of RAI-3 function, activity and/or interaction is an RAI-3 antagonist which decreases NF-κB activity, decreases apoptotic events, and/or increases IκBα expression or activity levels.

The methods of embodiments 1 and 2, wherein the modulator of RAI-3 function, activity and/or interaction is an agonist.

The methods of embodiments 1 and 2, wherein the modulator of RAI-3 function, activity and/or interaction is an agonist selected from drugs, chemical compounds, proteins, peptides, antibodies, ligand compounds, or small molecules.

The methods of embodiments 1 and 2, wherein the modulator of RAI-3 function, activity and/or interaction is an RAI-3 agonist which increases NF-κB activity, increases apoptotic events, and/or decreases IκBα expression or activity levels.

EMBODIMENT 3

A method of identifying or screening for modulators of the G-protein coupled receptor protein RAI-3 for ameliorating, treating, reducing, eliminating, or preventing chronic obstructive pulmonary disease (COPD), or diseases, disorders and/or conditions related thereto, comprising testing a compound to determine if the test compound modulates or affects (i) the activity and/or function of RAI-3, (ii) the expression of RAI-3; and/or (iii) the interaction of RAI-3 with an associated cell molecule in cells exposed to smoke from tobacco burning products.

A method of identifying or screening for modulators of the G-protein coupled receptor protein RAI-3 for ameliorating, treating, reducing, eliminating, or preventing a disease, disorder and/or condition selected from autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, renal diseases, ischemia-reperfusion injury, heart disorders, disorders related to aberrant signal transduction, proliferation disorders, cancers, such as lung cancer, breast cancer, stomach cancer, testicular cancer, etc., metastases, HIV infection, or HIV propagation in cells infected with other viruses, asthma, cystic fibrosis, or pulmonary fibrosis, comprising testing a compound to determine if the test compound modulates or affects (i) the activity and/or function of RAI-3, (ii) the expression of RAI-3, and/or (iii) the interaction of RAI-3 with an associated cell molecule in cells in which NF-κB activation is affected.

A method of identifying or screening for modulators of the G-protein coupled receptor protein RAI-3, wherein modulators comprise compounds and drugs functioning as agonists and antagonists, comprising combining a candidate modulator compound with a host cell expressing the RAI-3 polypeptide having the sequence as set forth in SEQ ID NO:3; and measuring an effect of the candidate modulator compound on the activity or function of the expressed RAI-3 polypeptide. The method of this embodiment includes the use of the NFAT system, the CRE response element; host cells, e.g., CHO/NFAT-CRE cells and CHO/NFAT-G alpha 15 transfected with a vector containing a nucleic acid sequence encoding all or a functional part of the RAI-3 polypeptide, e.g., pcDNA3.1 Hygro™. The method further includes RAI-3-transfected cell lines, e.g., RAI-3-transfected CHO/NFAT-G alpha 15 having low, intermediate, and high levels of RAI-3 expression and/or low, intermediate and high levels of coupling to the beta lactamase response as described herein. (Example 1(L)).

A method of screening for or identifying compounds that can modulate the biological activity or function of the RAI-3 polypeptide, comprising determining the biological activity of the RAI-3 polypeptide in a cell expressing the RAI-3 polypeptide in the absence of a modulator compound; contacting the host cell expressing RAI-3 with the modulator compound; and determining the biological activity or function of RAI-3 in the presence of the modulator compound; wherein a difference between the activity of the RAI-3 polypeptide in the presence of the modulator compound and in the absence of the modulator compound is indicative of a modulating effect of the compound on RAI-3 activity or function. As in the above method, the NFAT system, the CRE response element; host cells, e.g., CHO/NFAT-CRE cells and CHO/NFAT-G alpha 15 transfected with a vector containing a nucleic acid sequence encoding all or a functional part of the RAI-3 polypeptide, e.g., pcDNA3.1 Hygro™ are envisioned for use as described herein. The method further includes RAI-3-transfected cell lines, e.g., RAI-3-transfected CHO NFAT-G alpha 15 having low, intermediate, and high levels of RAI-3 expression and/or low, intermediate and high levels of coupling to the beta lactamase response as described herein. (Example 1(L)).

A compound which is an RAI-3 modulator as identified by the methods of embodiment 3, as well as compositions, including pharmaceutical compositions, comprising the modulator compound.

FURTHER EMBODIMENTS

An isolated RAI-3 variant which has a sequence variation from that of SEQ ID NO:3. Such an RAI-3 variant has a sequence as defined in SEQ ID NO:19. (for example, as shown in Table 1 and FIGS. 25A-C).

An isolated nucleic acid variant of SEQ ID NO:2, wherein the variant contains a single nucleotide polymorphism (SNP) according to SEQ ID NO:18.

A polynucleotide sequence comprising at least 15 consecutive nucleotides, wherein the at least 15 consecutive nucleotides include a single nucleotide polymorphism (SNP) selected from Tables 1 and/or 10.

A polynucleotide sequence comprising at least about 15 consecutive nucleotides, wherein the at least about 15 consecutive nucleotides include a single nucleotide polymorphism (SNP) selected from Tables 1 and/or 10, and wherein the last nucleotide base of said nucleotide ends with a polymorphic allele at the polymorphic locus, wherein the term "about" is construed to equal either 1, 2, 3, 4, or 5 bases longer or shorter than the described nucleotide length.

An isolated polynucleotide encoding an RAI-3 polypeptide, said polynucleotide comprising the nucleic acid sequence set forth in SEQ ID NO:18.

An isolated polynucleotide encoding an RAI-3 polypeptide comprising the amino acid sequence set forth in SEQ ID NO:19.

Compositions, pharmaceutical compositions, vectors and host cells comprising the variant RAI-3 amino acid and nucleic acid sequences of these embodiments are encompassed by the invention.

An RAI-3 peptide of SEQ ID NO:1.

Antibodies, or fragments thereof, directed against RAI-3 polypeptides, peptides, variants, and fragments thereof. The antibodies can be directed against all or a portion of the RAI-3 peptides or polypeptides of one or more of SEQ ID NO:1, SEQ ID NO:3, SEQ ID NO:8, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:49, SEQ ID NO:50, SEQ ID NO:51, SEQ ID NO:91, or SEQ ID NO:92. The antibodies can be of any of the types described herein, including, for example, monoclonal, polyclonal, chimeric, and the like. Methods of utilizing the antibodies in screening assays, in diagnostic assays, as modulators, in detection assays, in purification techniques, and the like, are encompassed.

Compositions and pharmaceutical compositions comprising RAI-3 variant polypeptides, peptides and/or antibodies are encompassed by the invention. RAI-3 fusion polypeptides and peptides are also encompassed.

STILL FURTHER EMBODIMENTS

An isolated nucleic acid molecule that is complementary to all or a portion of the RAI-3 nucleic acid sequence of one or more of SEQ ID NO:2, SEQ ID NO:18, SEQ ID NO:30, SEQ ID NO:31, or SEQ ID NO:33.

An isolated nucleic acid molecule selected from SEQ ID NO:32, or SEQ ID NOS:52 through 61.

An isolated RAI-3 nucleic acid molecule selected from one or more of SEQ ID NO:18, SEQ ID NO:23, SEQ ID NO:18, SEQ ID NO:25, SEQ ID NO:27, SEQ ID NO:29, or SEQ ID NOS:65 through 70.

Compositions, pharmaceutical compositions, vectors and host cells comprising the above isolated nucleic acid molecules are encompassed. Probes and primer oligonucleotides as described in the Tables and disclosure herein are also encompassed.

A method of treating chronic obstructive pulmonary disease (COPD) and diseases, disorders and/or conditions related thereto, comprising providing an antisense nucleic acid molecule of G-protein coupled receptor protein RAI-3, or an oligomeric nucleic acid portion thereof, preferably, in a pharmaceutically acceptable formulation, in an amount effective to prevent expression of RAI-3 in cells exposed to smoke from tobacco burning products.

A method of treating a disease, disorder, and/or condition associated with NF-κB activation, or associated with activation of a molecule mediated by NF-κB activation, comprising providing a modulator of G-protein coupled receptor protein RAI-3, preferably, in a pharmaceutically acceptable formulation, in an amount effective to modulate the expression of RAI-3. In the method the modulator is an antagonist or an agonist.

ADDITIONAL EMBODIMENTS

A method of regulating second messenger pathways and molecules therein, wherein the second messenger pathways and molecules therein are associated with a pathobiological disease, disorder, and/or condition, such as the following: COPD, the underlying symptoms of COPD, COPD-related disorders and/or conditions, autoimmune disorders, disorders related to hyperimmune activity, inflammatory conditions, disorders related to aberrant acute phase responses, hypercongenital conditions, birth defects, necrotic lesions, wounds, organ transplant rejection, conditions related to organ transplant rejection, renal diseases, ischemia-reperfusion injury, heart disorders, disorders related to aberrant signal transduction, proliferation disorders, cancers, such as lung cancer, breast cancer, stomach cancer, testicular cancer, etc., metastases, HIV infection, or HIV propagation in cells infected with other viruses, asthma, cystic fibrosis and pulmonary fibrosis, comprising: modulating the function and/or activity of the G-protein coupled receptor RAI-3. The method comprises regulating, modulating, or affecting the activity of the NF-κB pathway and components thereof, e.g., IκB, by modulating, either by antagonizing or agonizing, the function and/or activity of RAI-3. RAI-3 modulation according to the method provides treatments for COPD, as well as for other diseases, disorders, and/or conditions that are mediated by NF-κB and/or other molecules related thereto. The method provides treatment, amelioration, or prevention of diseases that are caused by, or are associated with, NF-κB, the NF-κB pathway and/or its component molecules, wherein antagonist modulators of RAI-3 are preferably employed to suppress, inhibit, or reduce the activity of NF-κB, the NF-κb pathway and/or its component molecules, ulcerative colitis, cerebral infarct, myocardial infarct, diabetic nephropathy, allergic rhinitis, Crohn's disease, atherosclerosis, rheumatoid arthritis, inflammatory/auto-immune disorders outside of the lung in addition to COPD, glioblastoma, pulmonary small cell undifferentiated carcinoma, carcinoma of the breast, colon, lung, ovary, pancreas, and prostate, and non-Hodgkin's lymphoma.

A method of increasing IκB mRNA levels and/or decreasing tumor necrosis factor-alpha (TNF-alpha)-induced E-selectin expression in a cell, comprising: exposing the cell to a modulator of the G-protein coupled receptor protein RAI-3, or a functional portion thereof, wherein the modulator is preferably an RAI-3 antagonist.

EXAMPLES

The Examples herein are meant to exemplify the various aspects of carrying out the invention and are not intended to limit the scope of the invention in any way. The Examples do not include detailed descriptions for conventional methods employed, such as in the construction of vectors, the insertion of cDNA into such vectors, or the introduction of the resulting vectors into the appropriate host. Such methods are well known to those skilled in the art and are described in numerous publications, for example, Sambrook, Fritsch, and Maniatis, *Molecular Cloning: A Laboratory Manual*, $2^{nd}$ Edition, Cold Spring Harbor Laboratory Press, USA, (1989).

Example 1

Methods

A. Generation of Cigarette Smoke-bubbled Medium

Cigarette-smoke bubbled medium was generated using a cigarette smoking machine similar to that described by T. Müller, (1995, "Expression of c-fos in quiescent Swiss 3T3 cells exposed to aqueous cigarette smoke fractions", *Cancer*

Res., 55:1927-1932). The cigarettes used were the standard reference research cigarette 1R4F (Tobacco and Health Research Institute, University of Kentucky, Lexington, Ky.). For a concentration of CS-240 and CS-160, smoke from 240 and 160 cigarettes (10 puffs per cigarette), respectively, was bubbled through 500 ml of RPMI (Gibco/BRL/Invitrogen Corporation, Carlsbad, Calif.) medium and sterile filtered for use that same day.

B. Treatment of Cells with Cigarette Smoke-bubbled Medium

H292 lung airway epithelial cells (American Type Culture Collection (ATCC), Manassas, Va.) were grown in RPMI medium containing L-glutamine, 10% fetal bovine serum and 1% Penicillin-Streptomycin (Gibco/BRL/Invitrogen Corporation, Carlsbad, Calif.). When the cells reached confluency in the tissue culture plate, they were serum-starved for 24 hours and then treated with cigarette smoke-bubbled medium (serum-free) for various times as described above. Cells were lysed in 3 mL of Lysis Buffer containing 1% NP40, 50 mM Tris-HCl, 0.5% Na+ deoxycholate, 150 mM NaCl and 1 mM sodium orthovanadate in the presence of phosphatase inhibitors and protease inhibitors in the form of 1 tab (per 50 ml of Lysis Buffer) of Complete protease inhibitor cocktail (Roche, Basel, Switzerland).

Following the cigarette smoke treatment of cells and cell lysis, 15 µl of cell lysate were mixed with sample buffer and resolved by SDS-PAGE (4-20% gradient gel). Size-separated proteins from the gel were transferred to nitrocellulose membrane by standard Western Blotting techniques. The membrane were then probed with antiphosphotyrosine antibody: HRP-conjugated-4G10 antibody, #16-105, (Upstate Biotechnology, Inc., Lake Placid, N.Y.).

The optimum dose/concentration of cigarette smoke that resulted in a strong phosphorylation response was determined; in most experiments a concentration of CS-160 (equivalent to 240 cigarettes/500 ml of cell medium) was used. H292 cells were treated with CS-240 media for varying times. Cells were lysed and whole cell lysates were subjected to SDS PAGE to size-separate the phosphorylated proteins as described. The proteins were then analyzed by Western blot technique using an antiphosphotyrosine antibody (FIG. 1A). The tyrosine phosphorylation signal began to appear after about one hour of exposure and increased over the next hour.

C. EGFR Immunoprecipitation 1.5 ml of cell lysate (~½ of a confluent T75 flask) was pre-cleared twice with 50 µl of Protein A slurry, rotating at 4° C. Pre-cleared lysate was transferred to a new Eppendorf tube and 50 µl of Protein A and 2 µl of EGFR antisera (HER1/TWIB2, polyclonal rabbit antisera to human EGFR) were added. The precleared lysate, Protein A and EGFR antisera were mixed by rotating at 4° C. for one hour, and then were washed three times with Lysis Buffer, one time with 1×PBS (20 mM sodium phosphate, 150 mM NaCl, pH 7.4) followed by aspiration to dryness. 50 µl of sample buffer were added to the tubes and the samples were placed at 95° C. for 10 minutes before loading onto a gel (20 µl per lane).

Immunoprecipitation of EGFR showed that, upon exposure to cigarette smoke-bubbled media, EGFR is tyrosine phosphorylated (FIG. 1B). (K. Takeyama et al., 2001, Am. J. Physiol. Lung Cell Mol. Physiol., 280(1):L165-172). Based on these experiments and additional dosing experiments (FIGS. 2A and 2B), a dose of CS-160 for three hours was chosen for the proteomics experiments.

D. Proteomics Methods

H292 lung airway epithelial cells (ATCC) were grown in RPMI medium containing L-glutamine, 10% fetal bovine serum and 1% Penicillin-Streptomycin (Gibco/BRL). The cells were grown to a density of $3 \times 10^9$ cells in twenty-four 500 cm$^2$ plates and were serum-starved for another 24 hours prior to treatment with 1×PBS (for 3 hours), CS-160 cigarette smoke (for 3 hours) and 10 nM epidermal growth factor, EGF (Sigma-Aldrich, St. Louis, Mo.) for 2 hours. After treatment, the cells were washed with ice-cold PBS and lysed in 20 mL of Lysis Buffer containing 1% NP40, 50 mM Tris-HCl, 0.5% Na+ deoxycholate, 150 mM NaCl and 1 mM sodium orthovanadate in the presence of protease and phosphatase inhibitors. The lysates were then centrifuged at 100,000×g and the supernatants recovered. Protein concentration of an aliquot of the supernatant was determined by a BCA assay (P. K. Smith et al., 1985, Anal. Biochem., 150:76-85).

For immunoprecipitation of tyrosine phosphorylated proteins, cell lysates were first precleared with 500 µl each of Protein G agarose (Amersham Biosciences, Inc. Piscataway, N.J.), streptavidin-agarose and anti-mouse IgG agarose (Cappel/ICN, Aurora, Ohio) and were then incubated overnight at 4° C. with 100 µg each of the following five antibodies: PY20 Mouse/Biotin, (250 µg/mL), (Transduction Laboratories, Lexington, Ky., Catalog No. P11120); PY69 Mouse, (1 mg/mL), (Transduction Laboratories, Lexington, Ky., Catalog No. P39020); RC20-Biotin (250 µg/mL), (Transduction Laboratories, Lexington, Ky., Catalog No. E11230-150); Polyclonal Rabbit, 250 µg/mL), (Transduction Laboratories, Lexington, Ky., Catalog No. P11230-150); and 4G10 Mouse (1 mg/mL), (Upstate Biotechnology Inc. Lake Placid, N.Y., Catalog No. 05-321).

The bound proteins were incubated with a pre-washed cocktail of agarose beads conjugated to streptavidin, anti-mouse IgG and Protein G for two hours at 4° C. Precipitated immune complexes were then washed three times with 1 mL lysis buffer including inhibitors; washed another three times with TBS Wash buffer (1×TBS/150 mM NaCl, 10 mM Tris-HCl, pH 7.5. plus 0.025% NP40/1 mM sodium orthovanadate) and eluted overnight with 500 µl of 100 mM phenyl phosphate in TBS wash buffer. The eluted proteins were concentrated using chloroform methanol precipitation (D. Wessel and U. I. Flügge, 1984, Anal Biochem., 138:141-143) and dried in acetone. The dried pellets were resolubilized in 50 µl of 8M Urea, 400 mM ammonium bicarbonate, pH 8.5; reduced with 5 µl of 45 mM DTT at 56° C.; and alkylated with 5 µl 100 mM iodoacetamide at room temperature for 15 minutes. After a 4-fold dilution with water, each sample was digested overnight with 5 µg of modified porcine trypsin at 37° C. Contaminants were removed via solid phase extraction using C18 spin columns (Harvard Bioscience, Holliston, Mass.) according to the manufacturer's specifications. Residual acetonitrile was removed by lyophilization.

E. LC/LC/MS/MS (Biphasic Multidimensional Chromatography Linked to Tandem Mass Spectrometry)

Identification of the immunoprecipitated phosphorylated proteins was performed on the digested samples in a manner described by M. P. Washburn et al. (2001, Nature Biotechnology, 19:242-247). For the work performed herein, samples were manually loaded using an infusion pressure reservoir at 800 psi for ~30 minutes. The mobile phases used for reversed phase elution were termed A and B, where A=water with 0.2% isopropanol, 0.1% acetic acid, and 0.001% trifluoroacetic acid; and B=95% acetonitrile with 0.2% isopropanol, 0.1% acetic acid, and 0.001% trifluoroacetic acid in water. Gradients were binary in A and B, began with 0% B aqueous solvent, and moved to 50% B in 30 minutes. The on-column flow rates were estimated to be 1 µL per minute, and were generated by applying ~250 psi using a 249:1 split ratio emanating from a high-pressure pump (1100, Agilent, Wilmington, Del.). Mass spectrometry was performed on an ion trap instrument (LCQDeca/ThermoFinnigan, San Jose, Calif.) using data dependent scanning to choose the top three ions for fragmentation, and a 60 second exclude time. The strong cation exchange material used was Poros 20HS (Perkin Elmer/ABI, Weiterstadt, Germany) and the number of potassium chloride steps used was seven: i.e., 0 mM, 10 mM, 50 mM, 100 mM, 250 mM, 500 mM, and 2 M. Data were searched following acquisition using the SEQUEST algorithm (ThermoFinnigan, San Jose, Calif.) against a database of non-redundant protein sequences available from the National Center for Biotechnology Information (National Library of Medicine).

As described above, a number of in vitro experiments were carried out utilizing cultured epithelial (H292) cells, treated with either serum free medium (SFM), (control) or with CS-160. Cells were harvested following treatment and the phosphotyrosine containing proteins were immunoprecipitated using a cocktail of antibodies. The samples were then proteolyzed and analyzed by LC/LC/MS/MS.

Figure 3:
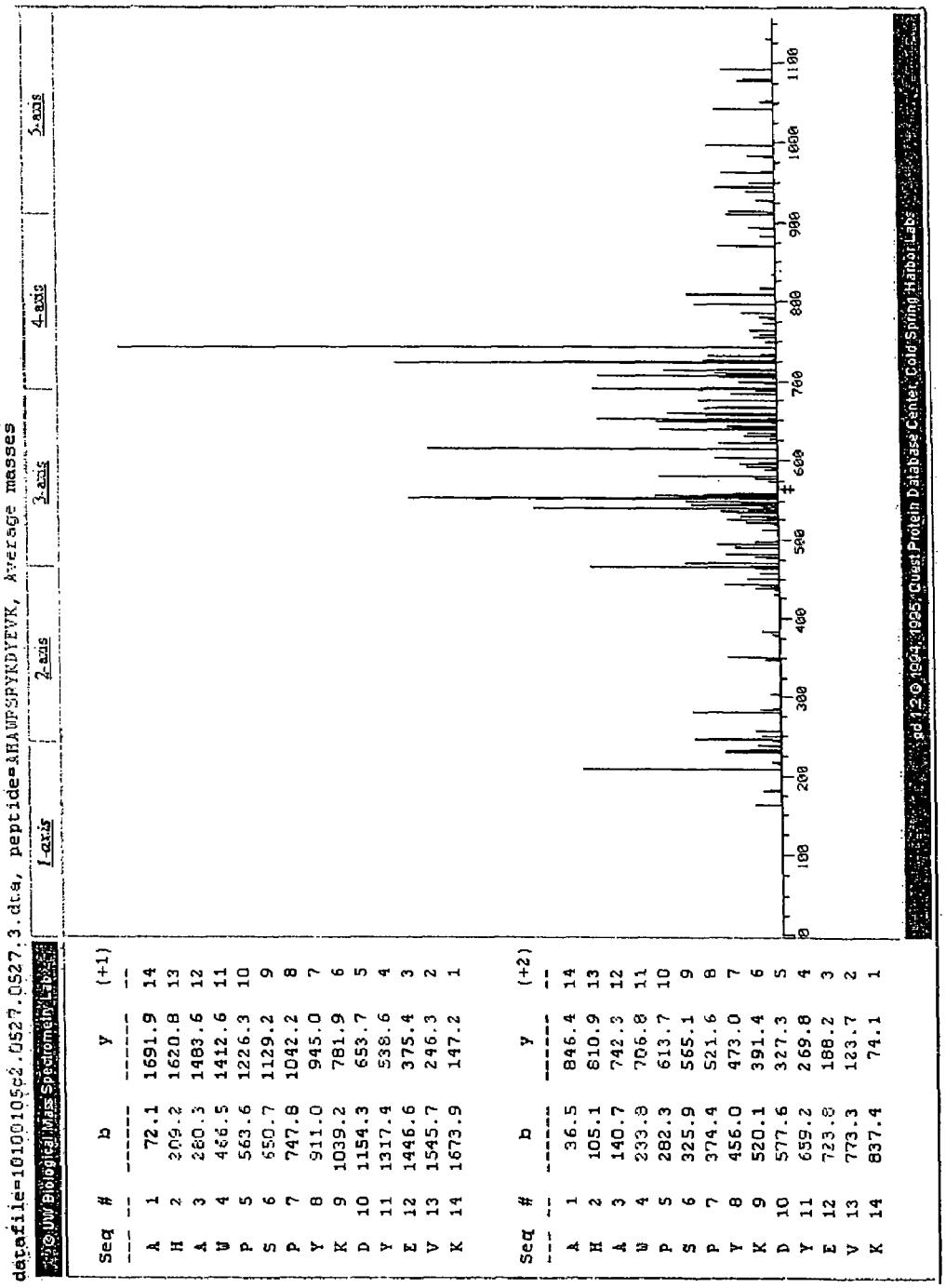
FIGS. 3 and 4 show the results of two LC/LC/MS/MS analyses. Identification of the immunoprecipitated proteins was performed on the digested samples as described in Example 1(E) herein below. A peptide having the amino acid sequence AHAWPSPYKDYEVK (SEQ ID NO:1) was identified and was determined to correspond to the RAI-3 protein (RefSeq NP_003970.1, amino acid sequence; RefSeq NM_003979, nucleic acid sequence).
Figure 4:
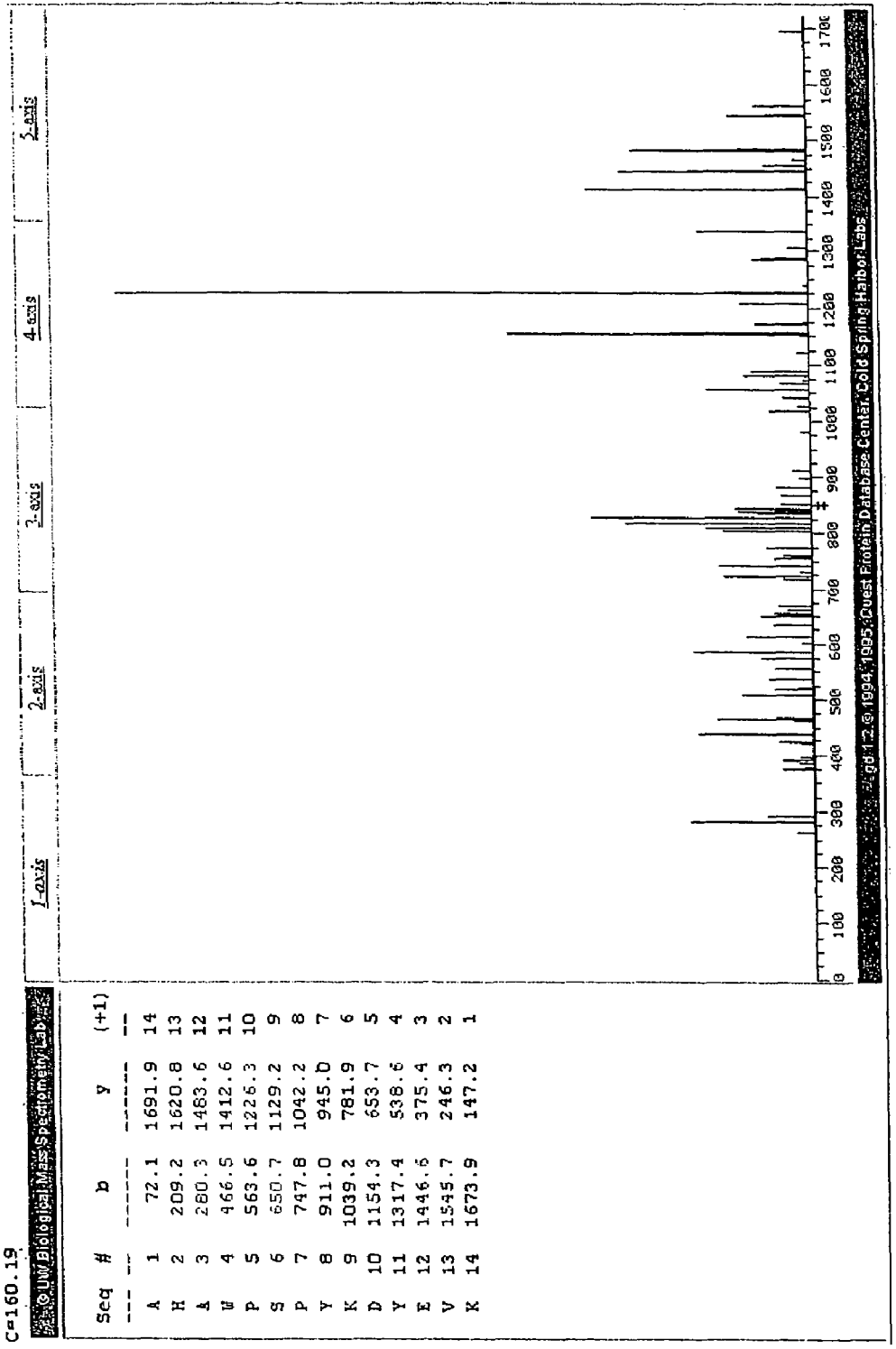

Approximately 350 proteins were identified as being tyrosine phosphorylated (or associated with tyrosine phosphorylated proteins) only from those cells that were exposed to cigarette smoke. Included among the 350 proteins identified were many signaling molecules and components of the EGFR pathway. Eighty four of the proteins present were identified from multiple peptides. One of the proteins identified was the lung-specific GPCR, RAI-3 (RefSeq NP_003970.1). The RAI-3 protein (RAI-3 peptide) was identified in two independent cigarette smoke experiments (FIGS. 3 and 4) and was not identified or present in the controls.

F. Western Blotting for Proteomics Experiments

Samples from each treatment, with and without immunoprecipitation, were boiled in Novex SDS-PAGE buffer and loaded onto 4-12% Bis-Tris gradient gels using MES buffer (Invitrogen Corporation, Carlsbad, Calif.). Separated proteins were transferred to PVDF membrane, blocked with 1% BSA for 1.0 hour, probed with 0.5 µg/mL monoclonal anti-phosphotyrosine antibody (Clone 4G10, Upstate Biotechnology Inc., Lake Placid, N.Y.) for 1.0 hour, followed by incubation with anti-mouse IgG coupled to HRP. (Upstate Biotechnology Inc., Lake Placid, N.Y.). The signal was detected using ECL Plus (Amersham Biosciences, Piscataway, N.J.) and then imaged using Fluor-S Max (BioRad Laboratories, Hercules, Calif.). Data were visualized with PDQuest software package (BioRad Laboratories, Hercules, Calif.).

G. RAI-3 Subcloning and Transfection

As described below, RAI-3 was amplified from H292 cDNA with appropriate restriction enzyme sites for cloning into mammalian expression vectors. Two expression constructs were made, one with a FLAG epitope tag at the amino terminus and one with a FLAG epitope tag at the carboxy terminus (see below). These constructs were transfected into A549, BEAS-2B, H292 and HEK 293 cell lines also as described.

H. Expression Constructs

To generate the HA-FLAG-RAI-3/pcDNA3.1 construct, human RAI-3 cDNA (Ref Seq NM_003979) was amplified by PCR from H292 cDNA using the following oligos:

```
RAI-3M254Forward:
                                      (SEQ ID NO:36)
gcg cgg ccc aat tgc atg gct aca aca gtc cct gat
gg,;
and RAI-3X1544Reverse:
                                      (SEQ ID NO:37)
gcg gcc ctc gag tta gct gcc ctc ttt ctt tac.
```

The initiating Methionine codon and stop codon are underlined. HA, i.e., a modified hemaglutinin signal sequence is described in X. M. Guan et al., 1992, *J. Biol. Chem.*, 267: 21995-21998; also, see below.

The oligos contained restriction sites for cloning into the expression vector, pcDNA3.1 (Invitrogen Corporation, Carlsbad, Calif.) and fusion to the HA leader sequence (MKTIIALSYIFCLVFA), (SEQ ID NO:38), and FLAG epitope tag (DYKDDDDARNS), (SEQ ID NO:39). The resulting amino acid sequence upstream from the RAI-3 initiating Methionine is MKTIIALSYIFCLVFADYKDDDDARNS (SEQ ID NO:40).

To generate the RAI-3-FLAG/pcDNA3.1Hygro construct, human RAI-3 cDNA (Ref Seq NM_003979.2) was amplified by PCR from a H292 cDNA using the following oligos:

```
RAI-3Bg254Forward:
                                      (SEQ ID NO:41)
gcg gcc aga tct gcc acc atg gct aca aca gtc cct
gat;
and RAI-3FLAGReverse:
                                      (SEQ ID NO:42)
gcg gcc ctc gag cta ctt gtc gtc gtc gtc ctt gta
gtc cat gct gcc ctc ttt ctt tac.
```

The initiating Methionine codon and stop codon are underlined. The oligos contained restriction sites for cloning into the expression vector, pcDNA3.1/Hygro (Invitrogen Corporation, Carlsbad, Calif.) and fusion to a FLAG epitope tag. (A. Einhauer and A. Jungbauer, 2001, "The FLAG peptide, a versatile fusion tag for the purification of recombinant proteins", *J. Biochem. Biophys. Methods,* 49(1-3):455-65). The resulting amino acid sequence after the last amino acid residue of RAI-3 is MDYKDDDDK*, (*=Stop codon), (SEQ ID NO:43). The DNA sequences of the constructs were confirmed by DNA sequencing using conventional methods.

I. Cell Transfections

HEK 293, H292, and BEAS-2B cell lines (available from the ATCC, Manassas, Va.) were plated in 100 mm cell culture dishes. When the cells were approximately 50% confluent, they were transfected with approximately 10 µg of DNA (See construct description above) using Lipofectamine and PLUS Reagents according to the manufacture's protocol (Invitrogen Corporation, Carlsbad, Calif.). After 24 hours the transfectants were passaged either 1:50 or 1:200 into 100 mM cell culture dishes containing the appropriate selection medium. For the HA-FLAG-RAI-3/pcDNA3.1 transfectants, the selection medium contained 600 µg/ml Geneticin/G-418 Sulfate (GibcoBRL/Invitrogen Corporation, Carlsbad, Calif.). For the cells transfected with the HA-FLAG-RAI-3/pcDNA3.1Hygro construct, the selection medium contained 500 μg/ml of Hygromycin B (Invitrogen Corporation, Carlsbad, Calif.). After approximately 10 days in selection medium, cell colonies were picked and placed into wells' of a 24-well plate and were maintained in the same concentrations of selective medium for expansion.

J. Characterization of RAI-3 Stable Cell Lines by Immunoprecipitation and Western Blotting Cell lines, e.g., human embryonic kidney cells (HEK 293), stably transfected with RAI-3 were maintained in complete RPMI medium containing L-glutamine, 10% fetal bovine serum and 1% Penicillin-Streptomycin (Gibco/BRL/Invitrogen Corporation, Carlsbad, Calif.) and 600 μg/ml Geneticin/G-418 Sulfate (GibcoBRL/Invitrogen Corporation, Carlsbad, Calif.). Each of 12 RAI-3 stably transfected cell line clones was plated in a 100 mM cell culture dish. Once the cells grew to confluence, the medium was aspirated to "dry" and 1.5 ml of ice-cold RIPA buffer (1% NP-40/0.5% deoxycholate/150 mM NaCl/50 mM Tris HCl, pH 7.5, plus protease inhibitors) were added. Cells were scraped off the dish with a cell scraper and the lysate was transferred to a 1.5 ml tube which was incubated on ice for 10 minutes. Cell debris was pelleted via centrifugation at 14,000 rpm at 4° C. for 10 minutes. The supernatant was transferred to a new tube and frozen at −80° C. until use.

For immunoprecipitations, cell lysates were thawed and pre-cleared three times (30 minutes with rotation at 4° C.; spin transfer to new tube) with 100 μl of Protein A. Lysates were immunoprecipitated with 2 μg of anti-FLAG M2 antibody Catalog # F-3165 (Sigma, Saint Louis, Mo.) overnight at 4° C. Thereafter, 40 μl of Protein A was added to the lysate/antibody mixture and rotated at 4° C. for 1.5 hours. The Protein A/lysate/antibody mixture was washed twice with RIPA buffer and twice with 1×PBS. After the final wash, Protein beads were aspirated "dry" and 30 μl of 2×SDS-PAGE sample buffer was added. After heating at 95° C. for 10 minutes, the samples were resolved by SDS-PAGE (4-20% gradient gel) and transferred to nitrocellulose by standard Western Blotting techniques. The membranes were blotted/probed with anti-FLAG-HRP antibody (Sigma, Saint Louis, Mo., Catalog # A8592).

The results of the above work was as follows: from the RAI-3 transfections of cells, twelve G418-selected, stable, FLAG-RAI-3/HEK 293 (Human Embryonic Kidney) clones were characterized for FLAG-RAI-3 expression. Anti-FLAG immunoprecipitation and Western blotting of clones 1-4 and 6-12 showed that the FLAG-RAI-3/HEK293 clones expressed a fusion protein near the expected molecular weight of RAI-3 alone, i.e., 40.251 kD (FIGS. 8A and 8B). The control lane (C) containing lysate from untransfected HEK293 cells showed staining of protein bands with the anti-FLAG antibody. Also included was a control of a purified FLAG-fusion protein of 58/48 kD. (FIG. 8B). Surface expression of the FLAG-RAI-3 clones 1-12 was detected using an anti-FLAG FITC-conjugated antibody. The clones had varying surface expression; clones 12 and 11 showed the most intense staining. (FIGS. 9A and 9B, and Example 1(K), below).

K. Characterization of RAI-3 Stable Cell Lines by FACS Analysis

Cells from confluent 100 mM cell culture plates (i.e., ~2×10$^6$ cells) were washed once with 1×PBS and then lifted from the plates with 2-3 ml of Cell Stripper (Cellgro/Mediatech, Herndon, Va.). 15 ml of 1×PBS was added to wash cells and then the cells were centrifuged at 1.5 K for 8 minutes at 4° C. to pellet. Cells were resuspended in 0.2 ml of binding buffer-DMEM (Gibco/BRL/Invitrogen Corporation, Carlsbad, Calif.) with 1% BSA final. Anti-FLAG FITC (Sigma, Saint Louis, Mo.; Catalog #F4049) was added at a dilution of 1:400. The cell and antibody mixture was incubated on ice for one hour. Cells were washed twice with 10 ml of binding buffer and resuspended in a final volume of 0.5 ml of binding buffer for FACS analysis. The cells were analyzed on a Becton Dickenson FACSort using Cell Quest software. (Becton-Dickenson, Franklin Lakes, N.J.). Cells were live gated and red/green color was compensated. The signal was compared to an untransfected HEK293 control.

L. Functional Coupling of Human GPCR, RAI-3

The use of mammalian cell reporter assays to demonstrate functional coupling of known GPCRs has been well documented in the literature (A. G. Gilman, 1987, *Annu. Rev. Biochem.*, 56, 615-649; V. Boss et al., 1996, *J. Biol. Chem.*, 271:10429-10432; J. Alam and J. L. Cook, 1990, *Anal. Biochem.*, 188:245-254; S. E. George et al., 1997, *J. Neurochem.*, 69:1278-1285; L. A. Selbie and S. J. Hill, 1998, *TIBS*, 19:87-93; and S. Rees et al., 1999, "Reporter gene systems for the study of G Protein Coupled Receptor signaling in mammalian cells", *In*: Milligan G. (ed.): *Signal Transduction: A practical approach*. Oxford, Oxford University Press, pp. 171-221). Moreover, reporter assays have been successfully used for identifying novel small molecule agonists or antagonists against GPCRs as a class of drug targets (G. Zlokarnik et al., 1998, *Science*, 279:84-88; S. E. George et al., 1997, Ibid.; V. Boss et al., 1996, Ibid.; and S. Rees et al., 1999, Ibid.). In such reporter assays, a promoter is regulated as a direct consequence of activation of specific signal transduction cascades following agonist binding to a GPCR (J. Alam and J. L. Cook, 1990, Ibid.; L. A. Selbie and S. J. Hill, 1998, Ibid.; V. Boss et al., 1996, Ibid.; S. E. George et al., 1997, Ibid.; and A. G. Gilman, 1987, Ibid.).

A number of response element-based reporter systems have been developed that enable the study of GPCR function. These include cAMP response element (CRE)-based reporter genes for G alpha i/o, G alpha s-coupled GPCRs, Nuclear Factor Activator of Transcription (NFAT)-based reporters for G alpha q/11-, or the promiscuous G protein G alpha 15/16-coupled receptors, and MAP kinase reporter genes for use in Galpha i/o coupled receptors (J. Blahos et al., 2001, *J. Biol. Chem.*, 275(5):3262-3269; L. A. Selbie and S. J. Hill, 1998, Ibid.; V. Boss et al., 1996, Ibid.; S. E. George et al., 1997, Ibid.; S. Offermanns and M. I. Simon, 1995, *J. Biol. Chem.*, 270(25):15175-15180; A. G. Gilman, 1987, Ibid.; and S. Rees et al., 1999, Ibid.). Transcriptional response elements that regulate the expression of Beta-Lactamase within a CHO K1 cell line (CHO/NFAT-CRE: Aurora Biosciences™) (G. Zlokarnik et al., 1998, Ibid.) have been implemented to characterize the function of the orphan RAI-3 polypeptide of the present invention. The system enables the demonstration of constitutive G-protein coupling to endogenous cellular signaling components upon intracellular overexpression of orphan receptors.

Receptor overexpression has been shown to represent a physiologically relevant event. For example, it has been shown that overexpression occurs in nature during metastatic carcinomas, wherein defective expression of the monocyte chemotactic protein 1 receptor, CCR2, in macrophages is associated with the incidence of human ovarian carcinoma (A. Sica et al., 2000, *J. Immunology*, 164:733-738 and R. Salcedo et al., 2000, *Blood*, 96(1):34-40). It has been shown that overproduction of the Beta 2 Adrenergic Receptor in transgenic mice leads to constitutive activation of the receptor signaling pathway such that these mice exhibit increased cardiac output (A. Kypson et al., 1999, *Gene Therapy*, 6:1298-304; G. W. Dom et al., 1999, *Proc. Natl. Acad. Sci. USA*, 96:6400-6405). The above are only a few of the many examples demonstrating constitutive activation of GPCRs in which many of these receptors are likely to be in the active, i.e., R*, conformation (J. Wess, 1997, *FASEB, J.*, 11(5):346-54).

The materials and methods involved in the RAI-3 coupling experiments are as follows:

DNA Constructs

GPCR RAI-3 cDNA was PCR amplified using PFU™ (Stratagene). The primers used in the PCR reaction were specific to the RAI-3 polynucleotide and were obtained from Gibco BRL, namely,

```
1. RAI-3Bg254Forward:
                                     (SEQ ID NO:41)
gcg gcc aga tct gcc acc atg gct aca aca gtc cct
gat;
and 2. RAI-3FLAGReverse:
                                     (SEQ ID NO:42)
gcg gcc ctc gag cta ctt gtc gtc gtc gtc ctt gta
gtc cat gct gcc ctc ttt ctt tac.
```

The following 3' primer sequence can be used to add a Flag-tag epitope to an RAI-3 nucleic acid sequence encoding an RAI-3 polypeptide for immunocytochemistry:

```
                                     (SEQ ID NO:44)
5'-cgggatcctacttgtcgtcgtcgtccttgtagtcgctgccctctttc tttacttc-3',
``` wherein the primer contains a BamHI site at the 5' end, an optimal Kozak sequence, in addition to a sequence encoding the FLAG tag epitope.

The product from the PCR reaction was isolated from a 0.8% Agarose gel (Invitrogen, Carlsbad, Calif.) and purified using a Gel Extraction Kit™ from Qiagen (Hilden, Germany). The purified product was then digested overnight along with the pcDNA3.1 Hygro™ mammalian expression vector (Invitrogen) using the HindIII and BamHI restriction enzymes (New England Biolabs (NEB), Beverly, Mass.). These digested products were then purified using the Gel Extraction Kit™ from Qiagen and subsequently ligated to the pcDNA3.1 Hygro™ mammalian expression vector (Invitrogen) using a DNA molar ratio of 4 parts insert to 1 part vector. All DNA modification enzymes were purchased from NEB. The ligation was incubated overnight at 16° C.; thereafter, one microliter of the mix was used to transform DH5 alpha cloning efficiency competent *E. coli*™ cells (Gibco BRL, Carlsbad Calif.). The plasmid DNA from the ampicillin resistant clones was isolated using the Wizard DNA Miniprep System™, commercially available from Promega (Madison, Wis.). Positive clones were confirmed and scaled up for purification using the Qiagen Maxiprep™ plasmid DNA purification kit.

Cell Line Generation

The pcDNA3.1 Hygro™ vector containing the orphan RAI-3 cDNA was used to transfect CHO/NFAT-CRE cells (Aurora Biosciences, San Diego, Calif.) using Lipofectamine 2000™ according to the manufacturer's specifications (Gibco BRL). After two days, the cells were passaged 1:3 into selective medium (DMEM 11056, 600 µg/ml Hygromycin, 200 µg/ml Zeocin, 10% FBS), (Gibco BRL-Invitrogen).

The CHO/NFAT-CRE cell lines, transiently or stably transfected with the orphan RAI-3 GPCR, were analyzed using the FACS Vantage SE™ (BD), fluorescence microscopy (Nikon), and the LJL Analyst™ (Molecular Devices). In this system, changes in real-time gene expression, as a consequence of constitutive G-protein coupling of the orphan RAI-3 GPCR, is examined by analyzing the fluorescence emission of the transformed cells at 447 nm and 518 nm. The changes in gene expression can be visualized using Beta-Lactamase as a reporter, which, when induced by the appropriate signaling cascade, hydrolyzes an intracellularly loaded, membrane-permeant ester substrate, i.e., Cephalosporin-Coumarin-Fluorescein-2/Acetoxymethyl™ (CCF2/AM™ Aurora Biosciences; G. Zlokarnik et al., 1998, Ibid.). The CCF2/AM™ substrate is a 7-hydroxycoumarin cephalosporin with a fluorescein attached through a stable thioether linkage. Induced expression of the Beta-Lactamase enzyme is readily apparent, since each enzyme molecule produced is capable of changing the fluorescence of many CCF2/AM™ substrate molecules.

In sum, CCF2/AM™ is a membrane permeant, intracellularly-trapped, fluorescent substrate with a cephalosporin core that links a 7-hydroxycoumarin to a fluorescein. For the intact molecule, excitation of the coumarin at 409 nm results in Fluorescence Resonance Energy Transfer (FRET) to the fluorescein which emits green light at 518 nm. Production of active Beta-Lactamase results in cleavage of the Beta-Lactam ring, leading to disruption of FRET, and excitation of the coumarin only—thus giving rise to blue fluorescent emission at 447 nm.

Fluorescent emissions were detected using a Nikon-TE300 microscope equipped with an excitation filter (D405/10X-25), dichroic reflector (430DCLP) and a barrier filter for dual DAPI/FITC (510 nM) to visually capture changes in Beta-Lactamase expression. The FACS Vantage SE is equipped with a Coherent Enterprise II Argon Laser and a Coherent 302C Krypton laser. In flow cytometry, UV excitation at 351-364 nm from the Argon Laser or violet excitation at 407 nm from the Krypton laser is used. The optical filters on the FACS Vantage SE are HQ460/50m and HQ535/40m bandpass separated by a 490 dichroic mirror.

Prior to analyzing the fluorescent emissions from the cell lines as described above, the cells were loaded with the CCF2/AM substrate. A 6×CCF2/AM loading buffer was prepared (1 mM CCF2/AM (Aurora Biosciences) dissolved in 100% DMSO (Sigma)). 12 µl of this stock solution was added to 60 µl of 100 mg/ml Pluronic F127 (Sigma) in DMSO containing 0.1% Acetic Acid (Sigma). This solution was added while vortexing to 1 mL of Sort Buffer (PBS minus calcium and magnesium, Gibco; 25 mM HEPES, Gibco, pH 7.4, 0.1% BSA). Cells were placed in serum-free medium and the 6×CCF2/AM was added to a final concentration of 1×. The cells were then loaded at room temperature for one to two hours, and then subjected to fluorescent emission analysis as described herein. Additional details relative to the cell loading methods and/or instrument settings are found in the following publications: G. Zlokarnik et al., 1998, Ibid.; M. Whitney et al., 1998, *Nature Biotech*, 16:1329-1333; and BD Biosciences, FACS Vantage SE Training Manual. Part Number 11-11020-00 Rev. A. August, 1999.

Immunocytochemistry

The cell lines transfected and selected for expression of Flag-epitope tagged orphan GPCRs were analyzed by immunocytochemistry. The cells were plated at $1 \times 10^3$ in each well of a glass slide (VWR) and were rinsed with PBS followed by acid fixation for 30 minutes at room temperature using a mixture of 5% Glacial Acetic Acid/90% EtOH. The cells were then blocked in 2% BSA and 0.1% Triton in PBS, and incubated for 2 hours at room temperature, or overnight at 4° C. A monoclonal anti-Flag FITC antibody was diluted at 1:50 in blocking solution and incubated with the cells for 2 hours at room temperature. The cells were then washed three times with 0.1% Triton in PBS for five minutes. The slides were overlayed dropwise with mounting medium (Biomedia-Gel Mount™; Biomedia; Containing Anti-Quenching Agent). Cells were examined at 10× magnification using a Nikon TE300 microscope equipped with FITC filter (535 nm).

Demonstration of RAI-3 Expression in Cells

Figure 23A:
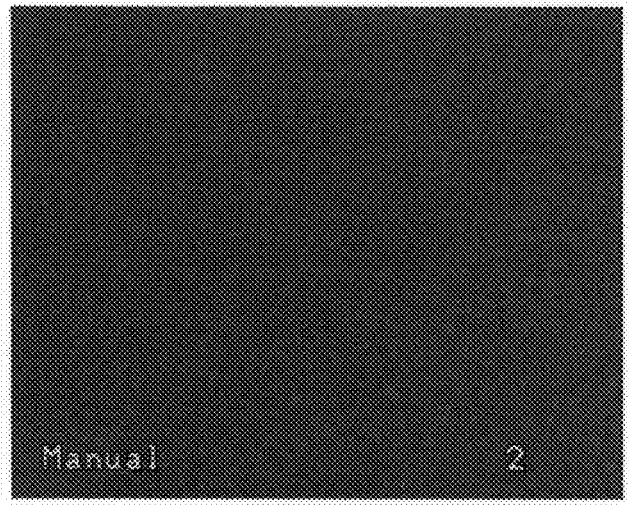
FIGS. 23A and 23B illustrate the expression of RAI-3 in transfected cells. For the experiments leading to these results, CHO/NFAT G alpha 15 cell lines were transfected with the pcDNA3.1 Hygro™/RAI-3-FLAG mammalian expression vector and were subjected to immunocytochemistry using a FITC-conjugated anti-Flag monoclonal antibody, as described herein. Untransfected control cells are shown in FIG. 23A. The image in FIG. 23B shows the fluorescent emission of the RAI-3-transfected cells at 530 nm, following illumination with a mercury light source. The cellular localization is clearly evident and is consistent with the expression of RAI-3.
Figure 23B:
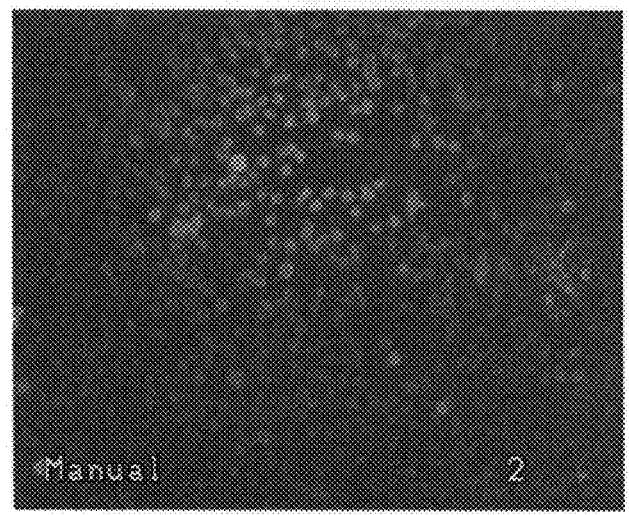

RAI-3 was tagged at the C-terminus using the Flag epitope and was inserted into the pcDNA3.1 Hygro™ expression vector, as described herein. Immunocytochemistry of CHO/NFAT G alpha 15 cell lines transfected with the Flag-tagged RAI-3 construct with FITC conjugated anti-Flag monoclonal antibody demonstrated that RAI-3 was indeed expressed in the cells. (FIG. 23B). Briefly, CHO/NFAT G alpha 15 cell lines were transfected with the pcDNA3.1 Hygro™/RAI-3-Flag vector, fixed with 70% methanol, and permeablized with 0.1% TritonX-100. The cells were then blocked with 1% Serum and incubated with a FITC-conjugated anti-Flag monoclonal antibody at 1:50 dilution in PBS-Triton. The cells were then washed several times with PBS-Triton, overlayed with mounting solution, and fluorescent images were captured. The control cell line, i.e., a non-transfected CHO/NFAT G alpha 15 cell line, exhibited no detectable background fluorescence. (FIG. 23A). The results showed that RAI-3 was expressed in these cells.

Screening Paradigm

The Aurora Beta-Lactamase technology provides a clear path for identifying agonists and antagonists of the RAI-3 polypeptide. Cell lines that exhibit a range of constitutive coupling activity can be identified by sorting RAI-3 transfected cell lines using the FACS Vantage SE. (See, FIGS. 23A-D). For example, cell lines that have been sorted as described herein were demonstrated to have an intermediate level of orphan GPCR expression, which also correlates with an intermediate coupling response, using the LJL analyst. Such cell lines can provide the opportunity to screen, indirectly, for both agonists and antagonists of RAI-3 by identifying either antagonists (inhibitors) that block the beta lactamase response, or agonists that increase the beta lactamase response. As described hereinabove, modulating the expression level of beta lactamase directly correlates with the level of cleaved CCR2 substrate. For example, this screening paradigm has been shown to work for the identification of modulators of a known GPCR, 5HT6, that couples through Adenylate Cyclase, in addition to the identification of modulators of the 5HT2c GPCR that couples through changes in $[Ca^{2+}]_i$.

Figure 24A:
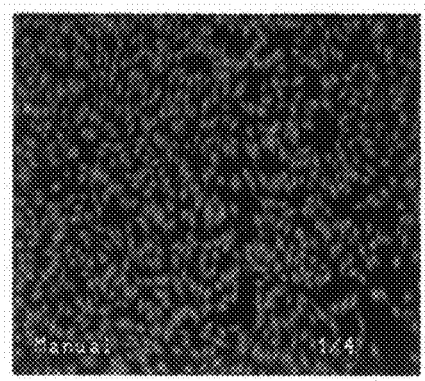
FIGS. 24A-24D shows that representative transfected CHO/NFAT G alpha 15 cell lines with intermediate and high beta lactamase expression levels are useful in screens to identify RAI-3 agonists and/or antagonists. Several CHO/NFAT G alpha 15 cell lines transfected with the pcDNA3.1 Hygro™/RAI-3 mammalian expression vector and having either intermediate or high beta lactamase expression levels of constitutive activation were isolated via FACS, as described herein.
Figure 24B:
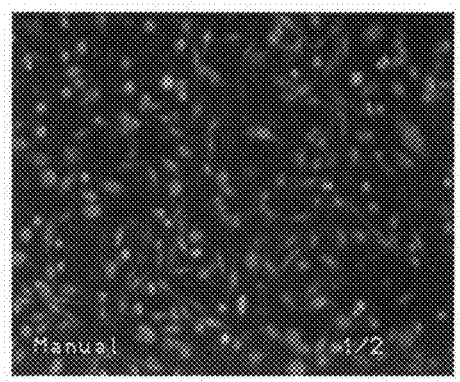
Figure 24C:
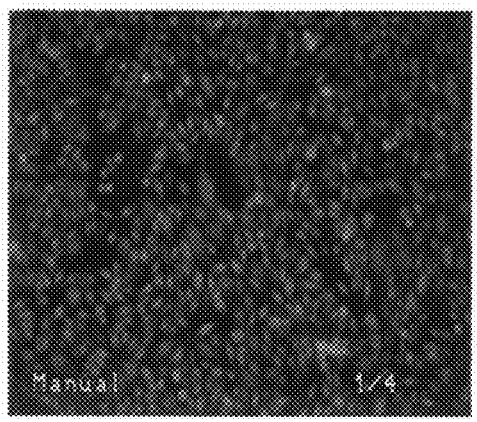
Figure 24D:
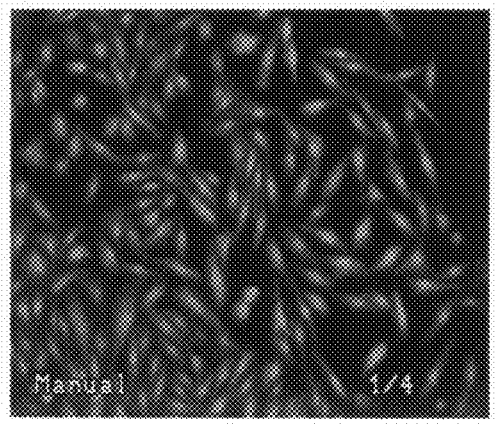

The data presented in FIGS. 23A-D represent cell lines that were engineered with the desired pattern of RAI-3 expression to enable the identification of potent small molecule agonists and antagonists. RAI-3 modulator screens can be carried out using a variety of high throughput methods known in the art. Preferred is the use of the fully automated Aurora UHTSS system. In FIG. 24A, the uninduced orphan transfected CHO/NFAT G alpha 15 cell line represents the relative background level of Beta Lactamase expression. Following treatment with a cocktail of 1 μM Thapsigargin, and 100 nM PMA (FIG. 24B; T/P), the cells fully activate the NFAT response element, thus demonstrating the dynamic range of the assay. FIG. 24C represents an orphan transfected CHO/NFAT G alpha 15 cell line that shows an intermediate level of beta lactamase expression post T/P stimulation, while FIG. 24D represents an orphan transfected CHOINFAT G alpha 15 cell line that shows a high level of beta lactamase expression post T/P stimulation.

M. Cell Staining

Surface expression of the of the FLAG-RAI-3 was detected by plating cells onto glass chamber slides (VWR Scientific, Bridgeport, N.J.) at ~75% confluency. Cells were washed four times with 1×TBS. Cell surface expression was detected after incubating the cells with an anti-FLAG M2 monoclonal antibody-FITC conjugate (Sigma, St. Louis, Mo.) at 0.5 μg/mL in TBS with 3% nonfat dry milk, and then washing five times with 1×TBS. Cells were visualized under the microscope using fluorescence illumination.

N. Treatment of Cells with All-Trans Retinoic Acid (ATRA)

$1 \times 10^6$ cells of each of the HEK 293, H292 and BEAS-2B cell lines were seeded into two (replicate) 100 mM cell culture dishes containing 20 ml of RPMI complete medium which contained L-glutamine, 10% fetal bovine serum and 1% Penicillin-Streptomycin (Gibco/BRL). To one 100 mM dish, 0.2 μl of DMSO were added. To the other 100 mM dish, 0.2 μl of 10 mM ATRA (Sigma R-2625, St. Louis, Mo.) were added to a final concentration of 1 nM. After 24 hours at 37° C. and 5% $CO_2$, cells were lysed with Buffer RLT (Qiagen, Hilden, Germany) and total RNA was harvested pursuant to the Rneasy Midi Kit protocol (Qiagen, Hilden, Germany). RAI-3 messenger RNA levels were measured by Real-time PCR as described below in Example 1(N).

O. Real-time PCR

After treatment of cells with ATRA for 24 hours as described above, real-time PCR was performed using the following primers:

```
Primer set #1
RAI-3-105F:  ccacacattttcagctgcaga    (SEQ ID NO:45)
and

RAI-3-158R:  gtgggatggagaattccttttg.  (SEQ ID NO:46)

Primer set #2
RAI-3-102F:  attccacacattttcagctgca;  (SEQ ID NO:47)
and

RAI-3-155R:  ggatggagaattccttttggg.   (SEQ ID NO:48)
```

SYBR Green PCR amplification was performed on an ABI PRISM 7700 Sequence Detection System (PE Applied Biosystems, Foster City, Calif.), and the reaction was carried out using SYBR Green PCR Core reagents (PE Applied Biosystems). Real time PCR was carried out at 40 cycles with the following parameters: 95° C. for 15 seconds and 60° C. for 60 seconds, with a pre-incubation period of 50° C. for 2 minutes, followed by 95° C. for 10 minutes. All amplification was normalized to β-actin gene amplification in the linear portion of the amplification curves. Data were then expressed as a fold increase over a reference tissue or cell type. RAI-3 message (mRNA) levels were found to increase in response to ATRA. In cells in which there was a high basal level of RAI-3 expression, e.g., H292 cells, there was also a modest, but measurable increase in RAI-3 mRNA levels.

P. Antibodies

For producing antibodies, the following RAI-3 peptides were synthesized (W. M. Keck Biotechnology Resource Center, New Haven, Conn.):

```
                                          (SEQ ID NO:49)
WHI5534: acetyl-CLTMNRTNVNVFSELSAPRRNEDFV-conh2,
(25 residues),;

(SEQ ID NO:50)
WHI5535: acetyl-CMLPDFDRRWDDTTLSSA-conh2,
(18 residues),;
and (SEQ ID NO:51)
WHI5536: acetyl-CKPQLVKKSYGVNERAYSQEE-conh2,
(21 residues),.
```

Peptides were conjugated to maleimide-activated KLH (keyhole limpet hemocyanin) carrier protein, (Pierce, Rockford, Ill.) via cysteine residues using methods conventionally known in the art. Conjugated peptides as immunogens are injected into rabbits to generate polyclonal anti-RAI-3 antibodies comprising antisera using conventional methods (e.g., as described by M. I. Becker et al., Antibodies: A Laboratory Manual, Ed. E. Harlow, Cold Spring Harbor (CSH) Laboratory, CSH, New York, Chapter 5, pp. 56-100, 1998) and into mice for the production of monoclonal antibodies by known methods (e.g., Kohler and Milstein, 1975, *Nature,* 256:495). In addition, phage display antibodies can be generated as known and practiced in the art (e.g., Tissue Antigens (2000) 56:1-9 and JMB (2000) 296:57-86).

Q. Antisense

Antisense oligonucleotides were determined and prepared by Sequitur (Natick, Mass.) based upon the RAI-3 nucleic acid sequence. Antisense oligos were tested in the A549 cell line (ATCC) and in HMVECs as described herein in Examples 2 and 3.

R. Gene Chip "Affy" Methods

The Affymetrix human U95v2 A, B, and C chips were probed with biotinylated in-vitro transcription product prepared from sample RNA as described (see: *Protocol for Affymetrix Gene Chip Expression*). Hybridization, wash, and Phycoerythrin streptavidin staining were performed using the Affymetrix hybridization oven and fluidics workstation per the manufacturer's protocols (Chapter 6 of Affymetrix Gene-Chip Expression Analysis Manual, revision 2). Stained chips were scanned on the Affymetrix GeneChip scanner, and data were analyzed using the Affymetrix GeneChip software to determine the specifically hybridizing signal for each gene.

Example 2

Method of Confirming the Functional Relevance of the RAI-3 Polynucleotide and Polypeptide to the IκB/NF-κB Pathway Through the Application of Antisense Oligonucleotide Methodology Antisense molecules or nucleic acid sequences complementary to the RAI-3 protein-encoding sequence, or any part thereof, were used to decrease or to inhibit the expression of naturally occurring RAI-3. Although the use of antisense or complementary oligonucleotides comprising about 15 to 35 base-pairs is described, essentially the same procedure is used with smaller or larger nucleic acid sequence fragments.

An oligonucleotide based on the coding sequence of RAI-3 protein, as shown in FIGS. 10A and 10B, 11B-C and/or as depicted in SEQ ID NO:2, for example, is used to inhibit expression of naturally occurring RAI-3. The complementary oligonucleotide is typically designed from the most unique 5' sequence and is used either to inhibit transcription by preventing promoter binding to the coding sequence, or to inhibit translation by preventing the ribosome from binding to the RAI-3 protein-encoding transcript. However, it is to be understood that other regions of the RAI-3 sequence may also be targeted.

Using an appropriate portion of a 5' sequence of SEQ ID NO:2, an effective antisense oligonucleotide includes any of about 15 to 35 nucleotides spanning the region which translates into the signal or 5' coding sequence, among other regions, encoding the RAI-3 polypeptide as shown in FIGS. 11A-11C (SEQ ID NO:3). Appropriate oligonucleotides were designed using OLIGO 4.06 software and the RAI-3 protein coding sequence (SEQ ID NO:2). Preferred oligonucleotides are deoxyribonucleotide-, or chimeric deoxyribonucleotide/ribonucleotide-based and are provided below. The oligonucleotides were synthesized using chemistry essentially as described in U.S. Pat. No. 5,849,902; which is hereby incorporated herein by reference in its entirety. RAI-3 antisense oligomers as used in the experiments described in this example are presented in Table 5 below:

TABLE 5

| Oligo ID# | Sequence | |
|---|---|---|
| 15689 | uuccaguuccacggcacuucaugcuu | (SEQ ID NO:52) |
| 15692 | guccaguccgaugaugaaggcgaagu | (SEQ ID NO:53) |
| 15694 ultramer | Contains equimolar concentrations of the following sequences: | |
| | 15689: uuccaguuccacggcacuucaugcuu; | (SEQ ID NO:52) |
| | 15692: guccaguccgaugaugaaggcgaagu; | (SEQ ID NO:53) |
| | 15696: caguuguuauaaaggcggcccucgcu; | (SEQ ID NO:54) |
| | 15697: uuguagccauucuggacccuagugcu; | (SEQ ID NO:55) and |
| | 15698: ucuuccagcccgugaaggaaccacau | (SEQ ID NO:56) |
| 15706 ultramer control* | Contains equimolar concentrations of the following sequences: | |
| | 15701: accuugaccuuaccgcacaggagau; | (SEQ ID NO:57) |
| | 15702: gagccucccgggaauauuguugacu; | (SEQ ID NO:58) |
| | 15703: gcugaucccaggucuuaccgauguuu; | (SEQ ID NO:59) |

TABLE 5-continued

| Oligo ID# | Sequence | |
|---|---|---|
| | 15704: acaccaaggaagugcccgaccuucu; | (SEQ ID NO:60) and |
| | 15705: gacugaaacuggcguccacccuacuu | (SEQ ID NO:61) |

*The initial fold change was compared to the average of 3 ultramer controls.
The fold change compared to the RAI-3 ultramer control was 0.55.

In accordance with this invention, the RAI-3 polypeptide has been shown to be involved in the regulation of mammalian NF-κB and apoptosis pathways. Subjecting cells to an effective amount of a pool of all five of the above-listed antisense oligonucleotides resulted in a significant increase in IκBα expression/activity, thus providing evidence that RAI-3 at least regulates the activity and/or expression of IκBα, either directly or indirectly. Moreover, the results suggest that RAI-3 is involved in the negative regulation of NF-κB/IκBα activity and/or expression, either directly or indirectly.

The IκBα assay used is described below and was based upon the analysis of IκBα activity as a downstream marker for proliferative signal transduction events.

Transfection of Post-quiescent A549 Cells with Antisense Oligonucleotides

The materials needed for this work include the following: A549 cells maintained in DMEM cell culture medium with high glucose (Gibco-BRL) supplemented with 10% Fetal Bovine Serum, 2 mM L-Glutamine, and 1× penicillin/streptomycin; Opti-MEM (Gibco-BRL); Lipofectamine 2000 (Invitrogen); Antisense oligomers (Sequitur); Polystyrene tubes; and Tissue culture treated plates.

Quiescent cells were prepared as follows:
On Day 0: 300,000 A549 cells were seeded in a T75 tissue culture flask in 10 ml of A549 cell culture medium and incubated in at 37° C., 5% $CO_2$ in a humidified incubator for 48 hours.

On Day 2: The T75 flasks were rocked to remove any loosely adherent cells, and the A549 growth medium was removed and replenished with 10 ml of fresh A549 medium. The cells were cultured for six days without changing the medium to create a quiescent cell population.

On Day 8: Quiescent cells were plated in multi-well format and transfected with antisense oligonucleotides.

A549 cells were transfected according to the following protocol:

The T75 flask containing quiescent population of A549 cells was trypsinized.

The cells were counted and seeded into 24-well plates with $6 \times 10^4$ quiescent A549 cells per well.

The cells were allowed to adhere to the tissue culture plate (approximately 4 hours).

The cells were transfected with antisense and control oligonucleotides according to the following protocol:

A 10× stock of lipofectamine 2000 (10 µg/ml is 10×) was prepared, and diluted lipid was allowed to stand at RT for 15 minutes. The stock solution of lipofectamine 2000 was 1 mg/ml. The 10× solution for transfection was 10 µg/ml. To prepare the 10× solution, 10 µl of lipofectamine 2000 stock were diluted per 1 ml of Opti-MEM (serum free medium).

A 10× stock of each oligomer was prepared to be used in the transfection. Stock solutions of oligomers were at 100 µM in 20 mM HEPES, pH 7.5. A 10× concentration of oligomer was 0.25 µM. To prepare the 10× solutions, 2.5 µl of oligomer were diluted per 1 ml of Opti-MEM. Equal volumes of the 10× lipofectamine 2000 stock and the 10× oligomer solutions were mixed well, and incubated for 15 minutes at room temperature to allow complexation of the oligomer and lipid. The resulting mixture was 5×. After the 15 minute complexation, 4 volumes of full growth medium was added to the oligomer/lipid complexes (solution was 1×). The medium was aspirated from the cells, and 0.5 ml of the 1× oligomer/lipid complexes were added to each well. The cells were incubated for 16-24 hours at 37° C. in a humidified $CO_2$ incubator. Thereafter, cell pellets were harvested for RNA isolation and TaqMan analysis of downstream marker genes.

TaqMan Reactions were carried out as follows:

Quantitative RT-PCR analysis was performed on total RNA preparations that had been treated with DNaseI or Poly A selected RNA. The DnaseI treatment can be performed using methods known in the art; preferably Qiagen's RNeasy kit is used to purify the RNA samples, in which DNAse I treatment is performed on the column. Briefly, a master mix of reagents was prepared according to the following Table 6:

TABLE 6

| Dnase I Treatment | |
|---|---|
| Reagent | Per r'xn (in µL) |
| 10× Buffer | 2.5 |
| Dnase I (1 unit/µl @ 1 unit per µg sample) | 2 |
| DEPC $H_2O$ | 0.5 |
| RNA sample @ 0.1 µg/ul (2-3 µg total) | 20 |
| Total | 25 |

Next, 5 µl of master mix was aliquoted into the wells of a 96-well PCR reaction plate (PE part # N801-0560). RNA samples were adjusted to 0.1 µg/µl with DEPC treated $H_2O$ (if necessary), and 20 µl were added to the aliquoted master mix for a final reaction volume of 25 µl. The wells were capped using strip well caps (PE part # N801-0935), placed in a plate centrifuge (Beckman Instruments), and briefly centrifuged to collect all volume in the bottom of the wells. Generally, a short spin up to 500 rpm in a Sorvall RT centrifuge was sufficient. The plates were incubated at 37° C. for 30 minutes. Thereafter, an equal volume of 0.1 mM EDTA in 10 mM Tris was added to each well, and heat inactivated at 70° C. for 5 minutes. The plates were stored at −80° C. following inactivation.

The reverse transcriptase (RT) reaction was carried out as follows:

A master mix of reagents was prepared according to the following Table 7:

TABLE 7

RT reaction

| Reagent | RT Per Rx'n (in μl) | No RT Per Rx'n (in μl) |
|---|---|---|
| 10x RT buffer | 5 | 2.5 |
| MgCl₂ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC H₂O | — | — |
| Total | 50 μL | 25 μL |

Samples were adjusted to a concentration such that 500 ng of RNA was added to each RT reaction (100 ng for the no RT). A maximum of 19 μl can be added to the RT reaction mixture (10.125 μl for the no RT.) Any remaining volume up to the maximum values was filled with DEPC treated H₂O, so that the total reaction volume was 50 μl (RT) or 25 μl (no RT). 37.5 μl of master mix (22.5 μl of no RT master mix) were aliquoted into the wells of a 96-well PCR reaction plate (PE part # N801-0560), and the RNA sample was added for a total reaction volume of 50 μl (25 μl, no RT) in each well. Control samples were loaded into two or even three different wells in order to have enough template for generation of a standard curve.

The wells were capped using strip well caps (PE part # N801-0935), placed in a plate centrifuge, and centrifuged briefly to collect all volume in the bottom of the wells. Generally, a short centrifugation (e.g., up to 500 rpm) in a Sorvall RT centrifuge was sufficient. For the RT-PCR reaction, the following thermal profile was used: 25° C. for 10 min.; 48° C. for 30 min.; 95° C. for 5 min.; 4° C. hold (for 1 hour). The plate was stored at −20° C. or lower upon completion.

The TaqMan reaction (Template comes from RT plate) was performed as follows: A master mix was prepared according to the following Table 8:

TABLE 8

TaqMan reaction (per well)

| Reagent | Per Rx'n (in μl) |
|---|---|
| TaqMan Master Mix | 4.17 |
| 100 μM Probe (SEQ ID NO: 64) | .025 |
| 100 μM Forward primer (SEQ ID NO: 62) | .05 |
| 100 μM Reverse primer (SEQ ID NO: 63) | .05 |
| Template | — |
| DEPC H₂O | 18.21 |
| Total | 22.5 |

The primers used for the RT-PCR reaction were as follows:

IκBα Primer and Probes

IκBα primer and probes

```
                         (SEQ ID NO:62)
Forward Primer:   gaggatgaggagagctatgacaca;

(SEQ ID NO:63)
Reverse Primer:   ccctttgcactcataacgtcag;
and (SEQ ID NO:64)
TaqMan Probe:     aaacacacagtcatcatagggcagctcgt.
```

Using a Gilson P-10 repeat pipettor, 22.5 μl of master mix was aliquoted into each well of a 96-well optical plate. Then, 2.5 μl of sample was added to individual wells using the P-10 pipettor. Generally, RT samples were run in triplicate with each primer/probe set used, and the "no RT" samples were run once with only one primer/probe set, often GAPDH (or other internal control). A standard curve was constructed and loaded onto the plate. The curve has five points plus one no template control (NTC, =DEPC treated H₂O). The curve was made with a high point of 50 ng of sample (twice the amount of the RNA in unknowns), and successive samples of 25, 10, 5, and 1 ng. The curve was made from a control sample(s) (see above).

The wells were capped using optical strip well caps (PE part # N801-0935), placed in a plate centrifuge, and centrifuged to collect all volume in the bottom of the wells. Generally, a short centrifugation (up to 500 rpm) in a Sorvall RT centrifuge was sufficient. The plates were loaded onto a PE 5700 sequence detector, taking precaution that the plate was aligned properly with the notch in the upper right hand corner. The lid was tightened down and run using the 5700 and 5700 quantification program and the SYBR probe using the following thermal profile: 50° C. for 2 min.; 95° C. for 10 min.; and the following profile for 40 cycles: 95° C. for 15 sec.; and 60° C. for 1 min., after which the reaction volume was changed to 25 μl.

Once the reaction was complete, a manual threshold of around 0.1 was set to minimize the background signal. Additional information relative to operation of the GeneAmp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Example 3

Method of Confirming the Functional Relevance of the RAI-3 Polynucleotide and Polypeptide to the NFκB Pathway Through the Application of Antisense Oligonucleotide Methodology Antisense molecules or nucleic acid sequences complementary to the RAI-3 protein-encoding sequence, or any part thereof, were used to decrease or to inhibit the expression of naturally occurring RAI-3. Although the use of antisense or complementary oligonucleotides comprising about 15 to 35 base-pairs is described, essentially the same procedure is used with smaller or larger nucleic acid sequence fragments.

An oligonucleotide based on the nucleic acid coding sequence of the RAI-3 protein, as shown in FIGS. 10A and 10B, 11B-11C, and/or as depicted in SEQ ID NO:2, for example, is used to inhibit expression of naturally occurring RAI-3. The complementary oligonucleotide is typically designed from the most unique 5' sequence and is used either to inhibit transcription by preventing promoter binding to the coding sequence, or to inhibit translation by preventing the ribosome from binding to the RAI-3 protein-encoding transcript. However, it is to be understood that other regions of the RAI-3 sequence may also be targeted.

Using an appropriate portion of a 5' sequence of SEQ ID NO:2, an effective antisense oligonucleotide includes any of about 15 to 35 nucleotides spanning the region which translates into the signal or 5' RAI-3 coding sequence, among other regions, of the RAI-3 polypeptide as shown in FIGS. 11A-11C, (SEQ ID NO:3). Appropriate oligonucleotides were designed using OLIGO 4.06 software and the RAI-3 protein coding sequence (SEQ ID NO:2). Preferred oligonucleotides are deoxyribonucleotide-, or chimeric deoxyribonucleotide/ribonucleotide-based and are provided below. The oligonucleotides were synthesized using chemistry essentially as described in U.S. Pat. No. 5,849,902; which is hereby incorporated herein by reference in its entirety. Antisense oligomers as used in the experiments described in this example are presented in Table 9 below:

plate is kept at 37° C. until read for use. HMVEC cells are then plated at $3 \times 10^4$ cells/well in 48 well plates.

On Day 1, HMVEC cells are transfected using 1 µg/ml of Lipofectamine 2000 lipid and 25 nM of antisense oligonucleotide according to the following protocol: The materials needed include: HMVEC cells maintained in EBM-2 (Clonetics) supplemented with EGM-2 MV (Clonetics); Opti-MEM (Gibco-BRL); Lipofectamine 2000 (Invitrogen); Antisense oligomers (Sequitur), see above; Polystyrene tubes; and tissue culture treated plates. A 10× stock of Lipofectamine 2000 (10 µg/ml is 10×) is prepared and the diluted lipid is allowed to stand at room temperature for 15 minutes. (Stock solution of Lipofectamine 2000 is 1 mg/ml; a 10× solution for transfection is 10 µg/ml). To prepare 10× solution, 10 µl of Lipofectamine 2000 stock is diluted per 1 ml of Opti-MEM (serum free medium). A 10× stock of each oligomer to be used in the transfection is then prepared. Stock

TABLE 9

| Oligo ID# | Sequence | |
|---|---|---|
| 15689 | uuccaguuccacggcacuucaugcuu | (SEQ ID NO:52) |
| 15692 | guccaguccgaugaugaaggcgaagu | (SEQ ID NO:53) |
| 15694 ultramer | Contains equimolar concentrations of the following sequences: | |
| | 15689: uuccaguuccacggcacuucaugcuu; | (SEQ ID NO:52) |
| | 15692: guccaguccgaugaugaaggcgaagu; | (SEQ ID NO:53) |
| | 15696: caguuguuauaaaggcggcccucgcu; | (SEQ ID NO:54) |
| | 15697: uuguagccauucuggacccuagugcu; | (SEQ ID NO:55) and |
| | 15698: ucuuccagcccgugaaggaaccacau; | (SEQ ID NO:56) |
| 15706 ultramer control | Contains equimolar concentrations of the following sequences: | |
| | 15701: accuugaccuuauccgcacaggagau; | (SEQ ID NO:57) |
| | 15702: gagccuccccgggaauauuguugacu; | (SEQ ID NO:58) |
| | 15703: gcugaucccaggucuuaccgauguuu; | (SEQ ID NO:59) |
| | 15704: acaccaaggaagugcccgaccuucu; | (SEQ ID NO:60) and |
| | 15705: gacugaaacuggcguccacccuacuu | (SEQ ID NO:61) |

*: The initial fold change was compared to the average of 3 ultramer controls. The fold change compared to the RAI-3 ultramer control was 0.55.

According to the present invention, the RAI-3 polypeptide has been shown to be involved in the regulation of mammalian NF-κB and apoptosis pathways. Subjecting cells to an effective amount of a pool of all five of the above-listed antisense oligonucleotides resulted in a significant decrease in E-selectin expression/activity in human microvascular endothelial cells (HMVECs), thus providing evidence that RAI-3 at least regulates the activity and/or expression of E-selectin, either directly, or indirectly. Moreover, the results suggest that RAI-3 is involved in the positive regulation of NF-κB/IκBα activity and/or expression, either directly or indirectly. The NF-kB/E-selectin assay used is described below and was based upon the analysis of E-selectin activity as a downstream marker for inflammatory/proliferative signal transduction events.

On Day 0, cell culture plates are coated with collagen. For one cell culture plate, collagen (0.4 mg/ml) is stored at 4° C. until needed. To prepare the collagen solution for adding to the plates, 112.5 µl of glacial acetic acid is added to 13.5 ml of $H_2O$, and then 84.35 µl of collagen is added to 13.5 ml of acetic acid. 250 µl of the collagen solution is added to each well of the plate and the plate is incubated for 2 hours at room temperature (final concentration of Type IV collagen (Sigma) is 2.5 µg/ml). Collagen is removed and wells of the plate (Costar) are rinsed with 500 µl of 2×PBS. 200 µl of cell culture medium (EBM-2 supplemented with EGM-2 MV, Clonetics, San Diego, Calif.) is added to the wells and the solutions of oligomers are at 100 µM in 20 mM HEPES, pH 7.5. A 10× concentration of oligomer is 0.25 µM. To prepare the 10× solutions, 2.5 µl of oligomer is diluted per 1 ml of Opti-MEM. Equal volumes of the 10× Lipofectamine 2000 stock and the 10× oligomer solutions are mixed well and incubated for 15 minutes at RT to allow complexation of the oligomer and lipid. The resulting mixture is 5×. After the 15 minute complexation, 4 volumes of full growth medium is added to the oligomer/lipid complexes (the solution is now 1×). The medium is then aspirated from the cells, and 0.5 ml of the 1× oligomer/lipid complexes is added to each well. The cells are incubated for 16-24 hours at 37° C. in a humidified $CO_2$ incubator. Oligomer update is evaluated by fluorescent microscopy. In addition, the cell viability is evaluated by performing staining analysis (CellTiter 96 Aqueous One, Promega, Madison, Wis.).

On Day 2, the TNF stimulation is carried out. TNF is stored at −70° C. in 10 µl aliquots at concentration of 50 µg/ml. Two fold dilutions of TNF are made by first adding 10 µl to 1 ml of EBM-2/EGM-2 MV medium to yield 500 ng/ml of the TNF aliquots. Then 300 µl are added to 15 ml of EBM-2/EGM-2 MV medium to yield a 10 ng/ml TNF solution. 250 µl of this final solution is added to each well containing HMVECs, and the cells are stimulated for 6 hours at 37° C. After stimulation, 100 µl of the cell supernatant is removed from each well and stored at −70° C. The remaining medium is then removed from each well. The cells are then titered, as follows: 200 µl of fresh medium is added to each well. 50 μl CTR (cell titer reagent) is added to each well. Two blank wells are included as controls with medium alone and CTR. The cells are incubated at 37° C. for about 90 minutes. Next, 100 μl of supernatant is removed from each well and placed in a 96 well plate. The absorbance is then read at 490 nm on spectrophotometer.

During the 90 minute incubation, a glutaraldehyde solution is prepared, as follows: 140 μl of glutaraldehyde is added to 14 ml of 1×PBS (0.5% glutaraldehyde). Blocking buffer is also prepared. For one plate, 50 ml is prepared, as follows: 46.5 ml 1×PBS is mixed with 1.5 ml of goat serum (Sigma-Aldrich), (stored at −20° C.) and 2 ml 0.5 M EDTA. After the cell titer is complete, the remaining medium is removed and 250 μl of glutaraldehyde solution is added to each well. A 10 minute incubation at 4° C. is performed. The plates are then flicked, and 500 μl of blocking buffer is added to each well. The plates are then Incubated at 4° C. overnight.

On Day 3, an E-selectin solution is prepared as follows: 22.5 μl of 100 μg/ml stock is added to 9 ml of blocking buffer. 150 μl of the resulting solution is added to each well, and incubated for 1 hour at 37° C. The wells are washed 4 times with cold PBS; the plates are flicked between washes; and then aspirated to remove remaining PBS. Horse radish peroxidase (HRP) solution is prepared by adding 2.25 μl of HRP (0.87 mg/ml, stored at 4° C.) to 9 ml of blocking buffer. 150 μl of the HRP solution is added to each well, and incubated for 1 hour at 37° C. The wells are washed 4 times with cold PBS; the plates are flicked between washes and then aspirated at the end to remove remaining PBS. 150 μl peroxidase color reagent is added to each well for development. The plates are allowed to develop for about 5 minutes and stopped with 150 μl of 1N $H_2SO_4$. 100 μl/well of solution is then transferred from each well to a 96 well plate, and the OD read at 450 nm. The positives are then noted. Antisense to RAI-3 was shown to result in inhibition of E-selectin expression in HMVEC cells in the above assay. (FIG. 14B).

Example 4

Method of Determining Alterations in a Gene Corresponding to an RAI-3 Polynucleotide RNA isolated from entire families or individual patients presenting with a phenotype of interest (such as a disease) is isolated. cDNA is then generated from these RNA samples using protocols known in the art. (See, e.g., J. Sambrook et al., *Molecular Cloning: A Laboratory Manual*, Cold Spring Harbor Laboratory, Cold Spring Harbor, N.Y., 1989). The cDNA is used as a template for PCR, employing primers surrounding the regions of interest in SEQ ID NO:2, or SEQ ID NO:18. Suggested PCR conditions consist of 35 cycles at 95° C. for 30 seconds; 60-120 seconds at 52° C.-58° C.; and 60-120 seconds at 70° C., using buffer solutions described, for example, in Sidransky et al., 1991, *Science*, 252:706.

PCR products are then sequenced using primers labeled at their 5' end with T4 polynucleotide kinase, employing SequiTherm Polymerase. (Epicentre Technologies, Madison, Wis.). The intron-exon borders of selected exons is also determined and genomic PCR products analyzed to confirm the results. PCR products harboring suspected mutations are then cloned and sequenced to validate the results of the direct sequencing. PCR products are cloned into T-tailed vectors as described in Holton et al., 1991, *Nucleic Acids Research*, 19:1156 and are sequenced with T7 polymerase (United States Biochemical). Affected individuals are identified by mutations not present in unaffected individuals.

Genomic rearrangements also serve as a method of determining alterations in a gene corresponding to a polynucleotide. Genomic clones are nick-translated with digoxigenindeoxy-uridine 5'-triphosphate (Boehringer Manheim), and FISH is performed as described in Johnson et al., 191, *Methods Cell Biol.*, 35:73-99. Hybridization with the labeled probe is carried out using a vast excess of human cot-1 DNA for specific hybridization to the corresponding genomic locus. Chromosomes are counter stained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., 1991, *Genet. Anal. Tech. Appl.*, 8:75). Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as diagnostic markers for an associated disease.

Example 5

Alternative Methods of Detecting Polymorphisms in an RAI-3 Polynucleotide

Preparation of Samples

Polymorphisms are detected in a target nucleic acid from an individual being analyzed. To assay genomic DNA, virtually any biological sample (other than pure red blood cells) is suitable. For example, convenient tissue samples include whole blood, semen, saliva, tears, urine, fecal material, sweat, buccal, skin and hair. To assay cDNA or mRNA, the tissue sample must be obtained from an organ in which the target nucleic acid is expressed. For example, if the target nucleic acid is a cytochrome P450, the liver is a suitable source.

Many of the methods described below require amplification of DNA from target samples. This can be accomplished by methods known in the art, particularly, for example, PCR. See generally, PCR Technology: Principles and Applications for DNA Amplification, (ed.) H. A. Erlich, Freeman Press, NY, N.Y., 1992; PCR Protocols: A Guide to Methods and Applications (eds.) Innis, et al., Academic Press, San Diego, Calif., 1990); Mattila et al., 1991, *Nucleic Acids Res.*, 19: 4967; Eckert et al., 1991, *PCR Methods and Applications* 1; PCR (eds.) McPherson et al., IRL Press, Oxford; and U.S. Pat. No. 4,683,202. Other suitable amplification methods include the ligase chain reaction (LCR) (See, e.g., Wu and Wallace, 1989, *Genomics*, 4:560; Landegren et al., 1988, *Science*, 241:1077); transcription amplification (Kwoh et al., 1989, *Proc. Natl. Acad. Sci. USA*, 86:1173); self-sustained sequence replication (Guatelli et al., 1990, *Proc. Nat. Acad. Sci. USA*, 87:1874); and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. Additional methods of amplification are known in the art or are described elsewhere herein.

Detection of Polymorphisms in Target DNA

There are two distinct types of analyses of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals with identify points of variation, i.e., polymorphic sites. By analyzing groups of individuals representing the greatest ethnic diversity among humans, and the greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described further herein.

The second type of analysis determines which form(s) of a characterized (known) polymorphism are present in individuals undergoing testing. Additional methods of analysis are known in the art or are described elsewhere herein.

Allele-Specific Probes

The design and use of allele-specific probes for analyzing polymorphisms is described, for example, by Saiki et al., 1986, Nature, 324:163-166; Dattagupta, E P 235,726; and Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, in which a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This type of probe design achieves good discrimination in hybridization between different allelic forms. Allele-specific probes are often used in pairs, with one member of the pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

Polymorphisms can also be identified by hybridization to nucleic acid arrays, some examples of which are described in WO 95/11995. The same arrays, or different arrays, can be used for the analysis of characterized polymorphisms. WO 95/11995 also describes sub-arrays that are optimized for the detection of a variant form of a pre-characterized polymorphism. Such a sub-array contains probes designed to be complementary to a second reference sequence, which is an allelic variant of the first reference sequence. The second group of probes is designed by the same principles as described, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 20 or more bases).

Allele-Specific Primers

An allele-specific primer hybridizes to a site on target DNA overlapping a polymorphism and only primes the amplification of an allelic form to which the primer exhibits perfect complementarity. See, e.g., Gibbs, 1989, Nucleic Acid Res., 17:2427-2448. An allele-specific primer is used in conjunction with a second primer which hybridizes at a distal site. Amplification proceeds from the two primers, resulting in a detectable product which indicates that the particular allelic form is present. A control is usually performed with a second pair of primers, one of which shows a single base mismatch at the polymorphic site, and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing elongation from the primer (see, e.g., WO 93/22456).

Direct-Sequencing

The direct analysis of the sequence of RAI-3 polymorphisms according to this invention can be accomplished using either the dideoxy chain termination method, or the Maxam—Gilbert method (see, e.g., J. Sambrook et al., Molecular Cloning, A Laboratory Manual (2nd Ed., CSHP, New York 1989); and Zyskind et al., 1988, Recombinant DNA Laboratory Manual, (Acad. Press).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and the electrophoretic migration of DNA in solution. (e.g., Chapter 7, PCR Technology. Principles and Applications for DNA Amplification, (ed.) Erlich, W. H. Freeman and Co, New York, 1992).

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., 1989, Proc. Nat. Acad. Sci. USA, 86:2766-2770. Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., 1997, *Proc. Natl. Acad. Sci. USA*, 94:10756-61, uses a locus-specific oligonucleotide primer labeled on the 5' terminus with 5-carboxyfluorescein (F AM). This labeled primer is designed so that the 3' end is immediately adjacent to the polymorphic site of interest. The labeled primer is hybridized to the locus, and single base extension of the labeled primer is performed with fluorescently-labeled dideoxyribonucleotides (ddNTPs) in dye-terminator sequencing fashion. An increase in fluorescence of the added ddNTP in response to excitation at the wavelength of the labeled primer is used to infer the identity of the added nucleotide.

Example 6

Method of Genotyping each RAI-3 SNP

Genomic DNA Preparation

Genomic DNA samples for genotyping are prepared using the Purigene™ DNA extraction kit from Gentra Systems (Gentra Systems, Inc., Minneapolis, Minn.). After preparation, DNA samples are diluted to a 2 ng/µl working concentration with TE buffer (10 mM Tris-Cl, pH 8.0, 0.1 mM EDTA, pH 8.0) and stored in 1 ml 96 deep-well plates (VWR) at −20° C. until use. Samples for genomic DNA preparation may be obtained from the Coriell Institute (Collingswood, N.J.), patients participating in a Bristol-Myers Squibb (BMS) clinical study, from other sources known in the art, or as otherwise described herein.

Genotyping

SNP genotyping reactions are performed using the SNP-Stream™ system (Orchid Biosience, Princeton, N.J.) based on genetic bit analysis (T. Nikiforov et al., 1994, *Nucl. Acids Res.*, 22:4167-4175). The regions including polymorphic sites are amplified by PCR using a pair of primers (OPERON Technologies), one of which can be phosphorothioated. 6 µl of a PCR cocktail containing 1.0 ng/µl of genomic DNA, 200 µM dNTPs, 0.5 µM forward PCR primer, 0.5 µM reverse PCR primer (phosphorothioated), 0.05 U/µl Platinum Taq DNA polymerase (LifeTechnologies), and 1.5 mM MgCl$_2$. The PCR primer pairs used for genotyping analysis can be designed using methods known in the art in conjunction with the teachings described herein.

PCR reactions are set up in 384-well plates (MJ Research) using a MiniTrak liquid handling station (Packard Bioscience). PCR thermocycling can be performed under the following conditions in a MJ Research Tetrad machine: step 1, 95 degrees for 2 min; step 2, 94 degrees for 30 min; step 3, 55 degrees for 2 min; step 4, 72 degrees for 30 sec; step 5, go back to step 2 for an additional 39 cycles; step 6, 72 degrees for 1 min; and step 7, 12 degrees indefinitely. After thermocycling, the amplified samples are placed in the SNPStream™ (Orchid Bioscience) machine, and the automated genetic bit analysis (GBA) reaction (T. Nikiforov et al., Ibid.) is performed. The first step of this reaction involves degradation of one of the strands of the PCR products by T7 gene 6 exonuclease to yield single-stranded products. The strand containing phosphorothioated primer is resistant to T7 gene 6 nuclease, and is not degraded by this enzyme. After digestion, the single-stranded PCR products are subjected to an annealing step in which the single stranded PCR products are annealed to the GBA primer on a solid phase, and then subjected to the GBA reaction (single base extension) using dideoxy-NTPs labeled with biotin or fluorescein. The GBA primers are designed using methods known in the art, in conjunction with the teachings of the present invention.

The present invention encompasses the substitution of certain polynucleotides within the GBA primers with a polynucleotide that can be substituted with a C3 linker (C3 spacer phosphoramidite) during synthesis of the primer. Such linkers can be obtained from Research Genetics; Sigma-Genosys; or Operon, for example. Incorporation of the dideoxynucleotides into a GBA primer is detected by use of a two color ELISA assay using anti-fluorescein alkaline phosphatase conjugate and anti-biotin horseradish peroxidase antibodies. Automated genotype calls are made by GenoPak software (Orchid Bioscience). Manual correction of automated calls can be performed upon inspection of the resulting allelogram of each SNP.

Example 7

Method of Genotyping RAI-3 SNPs

The genotypes of the RAI-3 SNPs described hereinabove (e.g., Tables 1 and 4) can be obtained by genomic PCR amplification followed by DNA sequencing. The PCR and sequencing primers are as described herein. (see, e.g., Table 9) The first step involves PCR amplification of the genomic DNA region containing the SNPs. The PCR reaction mixture contains the following components:

| 10x PCR II Buffer* | 2.5 µl |
| 25 mM MgCl$_2$ | 2.5 µl |
| 10 mM 4dNTP Mix | 0.4 µl |
| 5 U/µl Taq Gold | 0.4 µl |
| 20 µM primer mix** | 0.4 µl |
| 5 ng/µl Genomic DNA | 3 µl |
| PCR dH$_2$O | 16 µl |
| Total Volume | 25 µl |

*Purchased from PE Applied Biosystems (Foster City, CA)
**Contains PCR forward primer and PCR reverse primer. The names and sequences of these primers are described in Table 10 below.

PCR was performed in the Tetrad PCR machine (MJ Research) under the following conditions:

| Step 1 | 94° C., 10' |
| Step 2 | 94° C., 30" |
| Step 3 | 60° C., 30" |
| Step 4 | 72° C., 30" (steps 2-4 repeated 40 times) |
| Step 5 | 72° C., 7' |
| Step 6 | 12° C. |

After the PCR reaction, 0.25 µl of 10 units/µl exonuclease I and 4.8 µl of deionized water was added and the samples were incubated at 37° C. for 45 minutes, and at 95° C. for 15 minutes in succession.

After exonuclease I treatment, the samples were subjected to DNA sequencing reactions and capillary electrophoresis on a PRISM 3700 electrophoresis apparatus (PE Applied Biosystems, Foster City, Calif.) following the standard protocol as provided by the manufacturer. M13 forward (M13F) and M13 reverse (M13R) primers were used as DNA sequencing primers; the sequences of these M13 forward and reverse sequence primers are presented in Example 8 below. DNA sequencing results were analyzed by PolyPhred and Consed softwares. (D. A. Nickerson et al., 1997, "Polyphred: automating the detection and genotyping of single nucleotide substitutions using fluorescence-based resequencing", *Nucl. Acids Research,* 25:2745-2751; see Polyphred website at the following address: HyperText Transfer Protocol. (i.e., http) droog.mbt.washington.edu/Polyphred.HyperText Markup Language, i.e., html). The positions of these SNPs can be identified using the flanking sequence information provided in Table 10. The SNP genotype in each person can be identified by visually inspecting the DNA sequence trace of the corresponding SNP.

RAI-3 SNPs according to this invention, e.g., for use in the diagnosis of COPD and related disorders, are presented in Table 10. In Table 10, "Ref SEQ ID" refers to the identification (ID) of the GenBank reference genomic sequence that covers the SNP-containing region; "Ref SEQ Position" refers to the position of the SNP in the reference GenBank genomic sequence; "Ref NT" indicates the nucleotide at the SNP position in the GenBank genomic sequence; "Alt NT" indicates nucleotide at the SNP position in the variant form of the RAI-3 sequence; and "Ref AA" indicates amino acid residue at the SNP position based on the GenBank genomic sequence; "Alt. AA" refers to the amino acid residue at the SNP position based on the variant RAI-3 genomic sequence; "Mutation type" refers to the nature of the variation; "cDNA Ref. Seq. No." refers to the identification (ID) of the reference GenBank cDNA sequence covering the SNP-containing region; and "Protein Ref. Seq. No." refers to the identification (ID) of the reference GenBank amino acid sequence covering the SNP containing region.

The reference/SNP and flanking sequences in Table 10 are derived from a BAC genomic sequence according to the Ref. SEQ ID as shown in the table. As is appreciated by the skilled practitioner, these sequences are thus complementary in orientation to the RAI-3 coding sequence.

TABLE 10

| RAI-3 SNP ID; EXON # | Reference/SNP and Flanking Sequences | Ref. SEQ ID | Ref. SEQ. Position | Ref. NT | Alt. NT | Ref. AA | Alt. AA | Mutation Type | cDNA Ref. Seq No. | Protein Ref. Seq No. |
|---|---|---|---|---|---|---|---|---|---|---|
| RAI-3-s1; EXON 1 | 5'ctgagcagttgttataaagg[n] ggccctcgccggagggaggg3' (SEQ ID NO:65) [n] = c/t | AC007688.15 | 115864 | C | T | | | Non CDS | NM_003979.2 | NM_003970 |
| RAI-3-s7; INTRON 1 | 5'gccccagcgctctgggctcc[n] ggcgcctcacttaccctagt3' (SEQ ID NO:66) [n] = t/c | AC007688.15 | 115715 | T | C | | | Non CDS | NM_003979.2 | NM_003970 |
| RAI-3-s2; EXON 2 | 5'gccaccgaggtcacaacccc[n] gctgtggccaccgtttctag3' (SEQ ID NO:67) [n] = g/a | AC007688.15 | 99034 | G | A | | | Synonymous | NM_003979.2 | NM_003970 |
| RAI-3-s3; EXON 2 | 5'gtgctcccgtccagtccgat[n] atgaaggcgaaggtgaggcc3' (SEQ ID NO:68) [n] = g/a | AC007688.15 | 98887 | G | A | | | Synonymous | NM_003979.2 | NM_003970 |
| RAI-3-s4; EXON 2 | 5'cgtgtgggccctgtgctccc[n] tccagtccgatgatgaaggc3' (SEQ ID NO:69) [n] = g/a | AC007688.15 | 98875 | G | A | | | Synonymous | NM_003979.2 | NM_003970 |
| RAI-3-s5; EXON 2 | 5'catcaagaagaggacgtagg[n] gagcaggaggacaaagtctt3' (SEQ ID NO:70) [n] = t/c | AC007688.15 | 98601 | T | C | T | A | Non-synonymous | NM_003979.2 | NM_003970 |

The sequences of the primers as described for RAI-3 SNP genotyping in this example are shown in the following Table 11.

TABLE 11

| PCR Left (Forward) Primer Name | PCR Left Primer Sequence (5'→3') | PCR Right (Reverse) Primer Name | PCR Right Primer Sequence (5'→3') |
|---|---|---|---|
| RAI-3 Ex1_F | tgtaaaacgacggccagtgtcag acggtttttgggtcat (SEQ ID NO:71) | RAI-3 Ex1_R | caggaaacagctatgacccgctc tccccagacgattta (SEQ ID NO:77) |
| RAI-3 Ex1_F | tgtaaaacgacggccagtgtcag acggtttttgggtcat (SEQ ID NO:72) | RAI-3 Ex1_R | caggaaacagctatgacccgctc tccccagacgattta (SEQ ID NO:78) |
| RAI-3 Ex2-1_F | tgtaaaacgacggccagtaatac cttctccccactccaa (SEQ ID NO:73) | RAI-3 Ex2-1_R | caggaaacagctatgaccagatg gaaaagaggatcccaa (SEQ ID NO:79) |
| RAI-3 Ex2-1_F | tgtaaaacgacggccagtaatac cttctccccactccaa (SEQ ID NO:74) | RAI-3 Ex2-1_R | caggaaacagctatgaccagatg gaaaagaggatcccaa (SEQ ID NO:80) |
| RAI-3 Ex2-1_F | tgtaaaacgacggccagtaatac cttctccccactccaa (SEQ ID NO:75) | RAI-3 Ex2-1_R | caggaaacagctatgaccagatg gaaaagaggatcccaa (SEQ ID NO:81) |
| RAI-3 Ex2-3_F | tgtaaaacgacggccagtcctttc cctgttggtgattct (SEQ ID NO:76) | RAI-3 Ex2-3_R | caggaaacagctatgaccgccaa aactcgggactaacat (SEQ ID NO:82) |

The SNPs described in Table 4 hereinabove were further investigated to determine which DNA samples from individuals of a Caucasian population (CORIELLE CA, Coriell Cell Repositories, Collingswood, N.J.) contained the variations. The results are presented in Table 12 below.

TABLE 12

| | | SNP | | | | | | |
|---|---|---|---|---|---|---|---|---|
| Sample ID | SNP ID | RAI-3-s1 | RAI-3-s7 | RAI-3-s2 | RAI-3-s3 | RAI-3-s4 | RAI-3-s6 | RAI-3-s5 |
| NA17201 | CORIELL CA | | | homo* | | | | |
| NA17202 | CORIELL CA | | | | | | | |
| NA17203 | CORIELL CA | | | het | | het | | het |
| NA17204 | CORIELL CA | | | het | | | | |
| NA17205 | CORIELL CA | | | homo | | | | |
| NA17206 | CORIELL CA | het | | | | | | |
| NA17207 | CORIELL CA | | | homo | | | | |
| NA17208 | CORIELL CA | | | het | | | | |
| NA17209 | CORIELL CA | | | het | | | | |
| NA17210 | CORIELL CA | het | het | | | | | |

TABLE 12-continued

| Sample ID | SNP ID | SNP | | | | | | |
|---|---|---|---|---|---|---|---|---|
| | | RAI-3-s1 | RAI-3-s7 | RAI-3-s2 | RAI-3-s3 | RAI-3-s4 | RAI-3-s6 | RAI-3-s5 |
| NA17211 | CORIELL CA | | | ▓ | | | | |
| NA17212 | CORIELL CA | | | ▓ | | | | |
| NA17213 | CORIELL CA | | | | | | | |
| NA17214 | CORIELL CA | | | ▓ | | | | |
| NA17215 | CORIELL CA | | | | | | | |
| NA17216 | CORIELL CA | | | | | | | |
| NA17217 | CORIELL CA | | | ▓ | | | | |
| NA17218 | CORIELL CA | | | ▓ | | | | |
| NA17219 | CORIELL CA | | | homo | | | | |
| NA17220 | CORIELL CA | | | ▓ | | | | |
| NA17221 | CORIELL CA | | | | | | | |
| NA17222 | CORIELL CA | | | ▓ | | | | |
| NA17223 | CORIELL CA | | | | | | | |
| NA17224 | CORIELL CA | | | | | | | |
| NA17225 | CORIELL CA | | | homo | | | | |
| NA17226 | CORIELL CA | | | | | | | |
| NA17227 | CORIELL CA | | | ▓ | | | | |
| NA17228 | CORIELL CA | | | | | | | |
| NA17229 | CORIELL CA | | | ▓ | | | | |
| NA17230 | CORIELL CA | | | homo | | | | |
| NA17231 | CORIELL CA | | | ▓ | | | | |
| NA17232 | CORIELL CA | | | ▓ | | | | |
| NA17233 | CORIELL CA | | | ▓ | | | | |
| NA17234 | CORIELL CA | | | ▓ | | ▓ | | ▓ |
| NA17235 | CORIELL CA | | | ▓ | | | | |
| NA17236 | CORIELL CA | | | | | | | |

*"homo": homozygous;
**"het": heterozygous

In Table 12, the RAI-3-s6 SNP (118Gly allele) was not observed in the Caucasian samples. This is not surprising since this validated allele was found only in African Americans (TSC-Sanger Centre project, NCBI dbSNP website: hypertext transfer protocol, (i.e., http), world wide web (i.e., www), National Center for Biotechnology Information (ncbi) .National Library of Medicine (nlm).National Institutes of Health (nih).Government (gov)/single nucleotide polymorphism (snp)/.

The RAI-3-s5 SNP (182Ala allele) has a relatively low frequency in Coriell Caucasian samples (2/72=2.8%). Recently, a genetic linkage of several chromosomal regions with COPD phenotypes was discovered in the Caucasian population. (E. K. Silverman et al., 2002, *Am. J. Hum. Genet.*, 70(5):1229-1239). The RAI-3 gene is located in the chromosomal region that overlaps one of the linkage regions, namely, Chr12p13-p12.3. Since the RAI-3-s5 SNP is found in Caucasian samples and results in an amino acid substitution in the RAI-3 polypeptide, it is reasonably provided as a candidate for an underlying cause of COPD susceptibility in these patients and/or in a population, such as a Caucasian population. Thus, this SNP can exemplify a valuable genetic marker, for both diagnostic and prognostic utilization in COPD.

Example 8

Alternative Method of Genotyping RAI-3 SNPs

In addition to the method of genotyping described herein above, the skilled artisan can determine the genotype of the RAI-3 polymorphisms of the present invention using the below described alternative method. This method is referred to as the "GBS method" herein and can be performed as described in conjunction with the teachings as described elsewhere herein.

Briefly, the direct analysis of the sequence of RAI-3 polymorphisms of the present invention is accomplished by DNA sequencing of PCR products corresponding to the same PCR amplicons that are designed to be in close proximity to the polymorphisms of the present invention using the Primer3 program. The M13_SEQUENCE1 "tgtaaaacgacggccagt", (SEQ ID NO:83), is prepended to each forward PCR primer. The M13_SEQUENCE2 "caggaaacagctatgacc", (SEQ ID NO: 84), is prepended to each reverse PCR primer.

PCR amplification can be performed on genomic DNA samples amplified from (20 ng) in reactions (50 µl) containing 10 mM Tris-Cl pH 8.3, 50 mM KCl, 2.5 mM $MgCl_2$, 150 µM dNTPs, 3 µM PCR primers, and 3.75 U TaqGold DNA polymerase (PE Biosystems). PCR can be performed in MJ Research Tetrad machines under a set of cycling conditions comprising 94° C., 10 minutes, 30 cycles of 94° C., 30 seconds, 60° C., 30 seconds, and 72° C., 30 seconds, followed by 72° C, 7 minutes. PCR products are purified using QIAquick PCR purification kit (Qiagen) and are sequenced by the dye-terminator method using PRISM 3700 automated DNA sequencer (Applied Biosystems, Foster City, Calif.) following the manufacturer's instruction outlined in the Owner's Manual, which is hereby incorporated herein by reference in its entirety. PCR products are sequenced by the dye-terminator method using the M13_SEQUENCE1 (SEQ ID NO:83) and M13_SEQUENCE2 (SEQ ID NO:84) primers as described above. The genotype can be determined by analysis of the sequencing results at the polymorphic position.

Example 9

Additional Methods of Genotyping RAI-3 SNPs

The skilled practitioner appreciates that there are a number of methods suitable for genotyping a SNP of the present invention, aside from the preferred methods described herein. The present invention encompasses the following non-limiting types of genotype assays: PCR-free genotyping methods; Single-step homogeneous methods; Homogeneous detection with fluorescence polarization; Pyrosequencing; "Tag" based DNA chip system; Bead-based methods; fluorescent dye chemistry; Mass spectrometry based genotyping assays; TaqMan genotype assays; Invader genotype assays; and microfluidic genotype assays, among others. Also encompassed by the present invention are the following, non-limiting genotyping methods: U. Landegren et al., 1998, *Genome Res.* 8:769-776; P. Kwok, 2000, *Pharmacogenomics*, 1:95-100; I. Gut, 2001, *Hum Mutat.*, 17:475-492; D. Whitcombe et al., 1998, *Curr. Opin. Biotechnol.*, 9:602-608; S. Tillib and A. Mirzabekov, 2001, *Curr. Opin. Biotechnol.*, 12:53-58; E. Winzeler et al., 1998, *Science*, 281:1194-1197; V. Lyamichev et al., 1999, *Nat. Biotechnol.*, 17:292-296; J. Hall et al., 2000, *Proc. Natl. Acad. Sci. USA*, 97:8272-8277; C. Mein et al., 2000, *Genome Res.*, 10:333-343; Y. Ohnishi et al., 2001, *J. Hum. Genet.*, 46: 471-477; M. Nilsson et al., 1994, *Science*, 265:2085-2088; J. Baner et al., 1998, *Nucleic Acids Res.*, 26: 5073-5078; J. Baner et al., 2001, *Curr. Opin. Biotechnol.*, 12:11-15; A. Hatch et al., 1999, *Genet. Anal.*, 15:35-40; P. Lizardi et al., 1998, *Nat. Genet.*, 19(3):225-232; X. Zhong et al., 2001, *Proc. Natl. Acad. Sci. USA*, 98:3940-3945; F. Faruqi et al., 2001, *BMC Genomics* 2, 4; K. Livak, 1999, *Genet. Anal.*, 14:143-149; S. Marras et al., 1999, *Genet. Anal.*, 14:151-156; K. Ranade et al., 2001, *Genome Res.*, 11:1262-1268; M. Myakishev et al., 2001, *Genome Res.*, 11:163-169; L. Beaudet et al., 2001, *Genome Res.*, 11:600-608; X. Chen et al., 1999, *Genome Res.*, 9:492-498; N. Gibson et al., 1997, *Clin. Chem.*, 43:1336-1341; S. Latif et al., 2001, *Genome Res.*, 11: 436-440; T. Hsu et al., 2001, *Clin. Chem.*, 47:1373-1377; A. Alderborn et al., 2000, *Genome Res.*, 10:1249-1258; M. Ronaghi et al., 1998, *Science*, 281:363, 365; M. Ronaghi, 2001, *Genome Res.*, 11:3-11; A. Pease et al., 1994, *Proc. Natl. Acad. Sci. USA*, 91:5022-5026; E. Southern et al., 1993, *Genomics*, 13:1008-1017; D. Wang et al., 1998, *Science*, 280:1077-1082; P. Brown and D. Botstein, 1999, *Nat. Genet.*, 21:33-37; M. Cargill et al., 1999, *Nat. Genet.*, 22:231-238; S. Dong et al., 2001, *Genome Res.*, 11:1418-1424; M. Halushka et al., 1999, *Nat. Genet.*, 22:239-247; J. Hacia, 1999, *Nat. Genet.*, 21:42-47; R. Lipshutz et al., 1999, *Nat. Genet.*, 21:20-24; R. Sapolsky et al., 1999, *Genet. Anal.*, 14:187-192; Z. Tsuchihashi and P. Brown, 1994, *J. Virol.*, 68:5863; D. Herschlag, 1995, *J. Biol. Chem.*, 270:20871-20874; S. Head et al., 1997, *Nucleic Acids Res.*, 25:5065-5071; T. Nikiforov et al., 1994, *Nucleic Acids Res.*, 22:4167-4175; A. Syvanen et al., 1992, *Genomics*, 12:590-595; J. Shumaker et al., 1996, *Hum Mutat*, 7:346-354; K. Lindroos et al., 2001, *Nucleic Acids Res.*, 29:E69-9; K. Lindblad-Toh et al., 2000, *Nat. Genet.*, 24:381-386; T. Pastinen et al., 2000, *Genome Res.*, 10:1031-1042; J. Fan et al., 2000, *Genome Res*, 10:853-860; J. Hirschhorn et al., 2000, *Proc. Natl. Acad. Sci. USA*, 97:12164-12169; A. Bouchie, 2001, *Nature Biotechnol.*, 19:704; M. Hensel et al., 1995, *Science*, 269:400-403; D. Shoemaker et al., 1996, *Nature Genet.*, 14:450-456; N. Gerry et al., 1999, *J. Mol. Biol.*, 292:251-262; D. Ladner et al., 2001, Lab. Invest., 81:1079-1086; M. Iannone et al., 2000, *Cytometry*, 39:131-140; R. Fulton et al., 1997, *J. Clin. Chem.*, 43:1749-1756; B. Armstrong et al., 2000, *Cytometry*, 40:102-108 H. Cai et al., 2000, *Genomics*, 69:395; J. Chen et al., 2000, *Genome Res.*, 10:549-557; F. Ye et al., 2001, *Hum Mutat.*, 17:305-316; K. Michael et al., 1998, *Anal. Chem.*, 70:1242-1248; F. Steemers et al., 2000, *Nature Biotechnol.*, 18:91-94; W. Chan and S. Nie, 1998, *Science*, 281:2016-2018; M. Han et al., 2001, *Nature Biotechnol.*, 19:631-635; T. Griffin and L. Smith, 2000, *Trends Biotechnol.*, 18:77-84; P. Jackson et al., 2000, *Mol. Med. Today*, 6:271-276; L. Haff and I. Smirnov, 1997, *Genome Res.*, 7:378-388; P. Ross et al., 1998, *Nat. Biotechnol.*, 16:1347-1351; M. Bray et al., 2001, *Hum. Mutat.*, 17:296-304; S. Sauer et al., 2000, *Nucleic Acids Res.*, 28:E13; S. Sauer et al., 2000, *Nucleic Acids Res.*, 28:E100; X. Sun et al., 2000, *Nucleic Acids Res.*, 28:E68; K. Tang et al., 1999, *Proc. Natl. Acad. Sci. USA*, 91:10016-10020; J. Li et al., 1999, *Electrophoresis*, 20:1258-1265; D. Little et al., 1997, *Nat. Med.*, 3:1413-1416; D. Little et al., 1997, *Anal. Chem.*, 69:4540-4546; T. Griffin et al. 1997, *Nat. Biotechnol.*, 15:1368-1372; P. Ross et al., 1997, *Anal. Chem.*, 69:4197-4202; P. Jiang-Baucom et al., 1997, *Anal. Chem.*, 69:4894-4898; T. Griffin et al., 1999, *Proc. Natl. Acad. Sci. USA*, 96:6301-6306; M. Kokoris et al., 2000, *Mol. Diagnos.*, 5:329-340; C. Jurinke et al., 2001, *Methods Mol. Biol.*, 200: 170:103-16; and/or N. Taranenko et al., 1996, *Genet. Anal.*, 13:87-94.

Example 10

Site-Directed/Site-Specific Mutagenesis

In vitro site-directed/site-specific mutagenesis is an invaluable technique for studying protein structure-function relationships and gene expression, for example, as well as for vector modification. Site-directed mutagenesis can also be used for creating any of one or more of the RAI-3 mutants of the present invention, particularly conservative and/or non-conservative amino acid substitution RAI-3 mutants. Accordingly, site directed or site specific mutagenesis can be used to create and RAI-3 nucleic acid molecule encoding an RAI-3 allelic variant, e.g., an RAI-3 SNP as described herein above. Approaches utilizing single stranded DNA (ssDNA) as the template have been reported (e.g., T. A. Kunkel et al., 1985, *Proc. Natl. Acad. Sci. USA*, 82:488-492; M. A. Vandeyar et al., 1988, *Gene*, 65(1):129-133; M. Sugimoto et al., 1989, *Anal. Biochem.*, 179(2):309-311; and J. W. Taylor et al., 1985, *Nuc. Acids. Res.*, 13(24):8765-8785).

The use of PCR in site-directed mutagenesis accomplishes strand separation by using a denaturing step to separate the complementary strands and to allow efficient polymerization of the PCR primers. Accordingly, PCR site-directed mutagenesis methods permit site specific mutations to be incorporated in virtually any double stranded plasmid, thus eliminating the need for re-subcloning into M13-based bacteriophage vectors or single-stranded rescue. (M. P. Weiner et al., 1995, *Molecular Biology: Current Innovations and Future Trends*, Eds. A. M. Griffin and H. G. Griffin, Horizon Scientific Press, Norfolk, U K; and C. Papworth et al., 1996, *Strategies*, 9(3):3-4). A protocol for performing site-directed mutagenesis, particularly employing the QuikChange™ site-directed mutagenesis kit (Stratagene, La Jolla, Calif.; U.S. Pat. Nos. 5,789,166 and 5,923,419) is provided for making point mutations, to exchange, replace, or substitute amino acids, and to delete or insert single or multiple amino acids in the RAI-3 amino acid sequence.

Primer Design

For primer design using this protocol, the mutagenic oligonucleotide primers are designed individually according to the desired mutation. The following considerations are preferably made for designing mutagenic primers: 1) Both of the mutagenic primers preferably contain the desired mutation and anneal to the same sequence on opposite strands of the plasmid; 2) Primers should be between 25 and 45 bases in length, and the melting temperature ($T_m$) of the primers should be greater than, or equal to, 78° C. The following formula is commonly used for estimating the $T_m$ of primers: T=81.5+0.41 (% GC)−675/N−% mismatch. For calculating $T_m$, N is the primer length in bases; and values for % GC and % mismatch are whole numbers. For calculating $T_m$ for primers intended to introduce insertions or deletions, a modified version of the above formula is employed: T=81.5+0.41 (% GC)−675/N, where N does not include the bases which are being inserted or deleted; 3) The desired mutation (deletion or insertion) should be in the middle of the primer with approximately 10-15 bases of correct sequence on both sides; 4) The primers optimally should have a minimum GC content of 40%, and should terminate in one or more C or G bases; 5) Primers need not be 5'-phosphorylated, but are preferably purified either by fast polynucleotide liquid chromatography (FPLC) or by polyacrylamide gel electrophoresis (PAGE). Failure to purify the primers results in a significant decrease in mutation efficiency; and 6) It is important that primer concentration is in excess. It is suggested to vary the amount of template while keeping the concentration of the primers constantly in excess (QuikChange™ Site-Directed Mutagenesis Kit, Stratagene, La Jolla, Calif.).

Protocol for Setting Up the Reactions

Using the above-described primer design, two complementary oligonucleotides containing the desired mutation, flanked by unmodified nucleic acid sequence, are synthesized. The resulting oligonucleotide primers are purified. A control reaction is prepared using 5 µl 10× reaction buffer (100 mM KCl; 100 mM $(NH_4)_2SO_4$; 200 mM Tris-HCl, pH 8.8; 20 mM $MgSO_4$; 1% Triton® X-100; 1 mg/ml nuclease-free bovine serum albumin, BSA); 2 µl (10 ng) of pWhitescript™, 4.5-kb control plasmid (5 ng/µl); 1.25 µl (125 ng) of oligonucleotide control primer #1 (34-mer, 100 ng/µl); 1.25 µl (125 ng) of oligonucleotide control primer #2 (34-mer, 100 ng/µ); 1 µl of dNTP mix; double distilled $H_2O$; to a final volume of 50 µl. Thereafter, 1 µl of DNA polymerase (Pfu-Turbo® DNA Polymerase, Stratagene), (2.5 U/µl) is added. PfuTurbo® DNA Polymerase is stated to have 6-fold higher fidelity in DNA synthesis than does Taq polymerase. To maximize temperature cycling performance, use of thin-walled test tubes is preferred to ensure optimum contact with the heating blocks of the temperature cycler.

The sample reaction is prepared by combining 5 µl of 10× reaction buffer; 5-50 ng of dsDNA template; 125 ng of oligonucleotide primer #1; 5-50 ng of dsDNA template; 125 ng of oligonucleotide primer #2; 1 µl of dNTP mix; and dd$H_2O$ to a final volume of 50 µl. Thereafter, 1 µl of DNA polymerase (PfuTurbo DNA Polymerase, Stratagene), (2.5 U/µl), is added. If the thermal cycler does not have a hot-top assembly, each reaction should preferably be overlaid with approximately 30 µl of mineral oil.

Cycling the Reactions

Each reaction is cycled using the following cycling parameters:

| Segment | Cycles | Temperature | Time |
|---------|--------|-------------|------|
| 1 | 1 | 95° C. | 30 seconds |
| 2 | 12-18 | 95° C. | 30 seconds |
|   |       | 55° C. | 1 minute |
|   |       | 68° C. | 2 minutes/kb of plasmid length |

For the control reaction, a 12-minute extension time is used and the reaction is run for 12 cycles. Segment 2 of the above cycling parameters is adjusted in accordance with the type of mutation desired. For example, for point mutations, 12 cycles are used; for single amino acid changes, 16 cycles are used; and for multiple amino acid deletions or insertions, 18 cycles are used. Following the temperature cycling, the reaction is placed on ice for 2 minutes to cool the reaction to ≦37° C.

Digesting the Products and Transforming Competent Cells

One µl of the DpnI restriction enzyme (10 U/µl) is added directly (below mineral oil overlay) to each amplification reaction using a small, pointed pipette tip. The reaction mixture is gently and thoroughly mixed by pipetting the solution up and down several times. The reaction mixture is then centrifuged for 1 minute in a microcentrifuge. Immediately thereafter, each reaction is incubated at 37° C. for 1 hour to digest the parental (i.e., the non-mutated) supercoiled dsDNA. Competent cells (i.e., XL1-Blue supercompetent cells, Stratagene) are thawed gently on ice. For each control and sample reaction to be transformed, 50 µl of the supercompetent cells are aliquotted to a pre-chilled test tube (Falcon 2059 polypropylene). Next, 1 µl of the DpnI-digested DNA is transferred from the control and the sample reactions to separate aliquots of the supercompetent cells. The transformation reactions are gently swirled to mix and then are incubated for 30 minutes on ice. Thereafter, the transformation reactions are heat-pulsed for 45 seconds at 42° C. for 2 minutes. Next, 0.5 ml of NZY+ broth, preheated to 42° C., is added to the transformation reactions which are then incubated at 37° C. for 1 hour with shaking at 225-250 rpm. An aliquot of each transformation reaction is plated on agar plates containing the appropriate antibiotic for the vector. For the mutagenesis and transformation controls, cells are spread on LB-ampicillin agar plates containing 80 µg/ml of X-gal and 20 mM IPTG. Transformation plates are incubated for >16 hours at 37° C.

Example 11

TaqMan™ Quantitative PCR Analysis of RAI-3

Analysis of RAI-3 by TaqMan™ quantitative PCR on a large panel of normal tissue RNAs revealed that transcripts for this GPCR was found in tissues from all the major organ systems, with the highest amount found in the respiratory system and the lowest amount found in the nervous system. (FIG. 15). Within the lung, there is a gradient of expression from the parenchyma to the primary bronchus (all pulmonary related tissue RNAs obtained from non-smoking individuals). The level of expression found in the parenchyma of the lung is over 600,000 times higher then that observed in most the brain sub-regions. The expression in the lung parenchyma is, on average, about 6 times higher than that observed in the next highest organ system, the gastrointestinal tract. (FIG. 15). It is to be noted that some of gastrointestinal samples were obtained from smokers.

| Number | Tissue |
|--------|--------|
| 1 | DRG |
| 2 | adipose:mesenteric-ileum |
| 3 | bladder |
| 4 | bladder:trigone |
| 5 | blood-vessel:cerebral |
| 6 | blood-vessel:choroid-plexus |
| 7 | blood-vessel:coronary:artery |
| 8 | blood-vessel:mesenteric(colon) |
| 9 | blood-vessel:pulmonary |
| 10 | blood-vessel:renal |
| 11 | breast |
| 12 | caecum |
| 13 | colon |
| 14 | duodenum |
| 15 | fallopian-tube |
| 16 | gallbladder |
| 17 | heart:left-atria |
| 18 | heart:left-ventricle |
| 19 | ileum |
| 20 | jejunum |
| 21 | kidney:cortex |
| 22 | kidney:medulla |
| 23 | kidney: pelvis |
| 24 | lung:bronchus:primary |
| 25 | lung:bronchus:tertiary |
| 26 | lung:parenchyma |
| 27 | lymph-gland:tonsil |
| 28 | oesophagus |
| 29 | ovary |
| 30 | prostate |
| 31 | rectum |
| 32 | stomach:antrum |
| 33 | stomach:body |
| 34 | stomach:fundus |
| 35 | stomach:pyloric-canal |
| 36 | testis |
| 37 | thyroid-gland |

Figure 16:
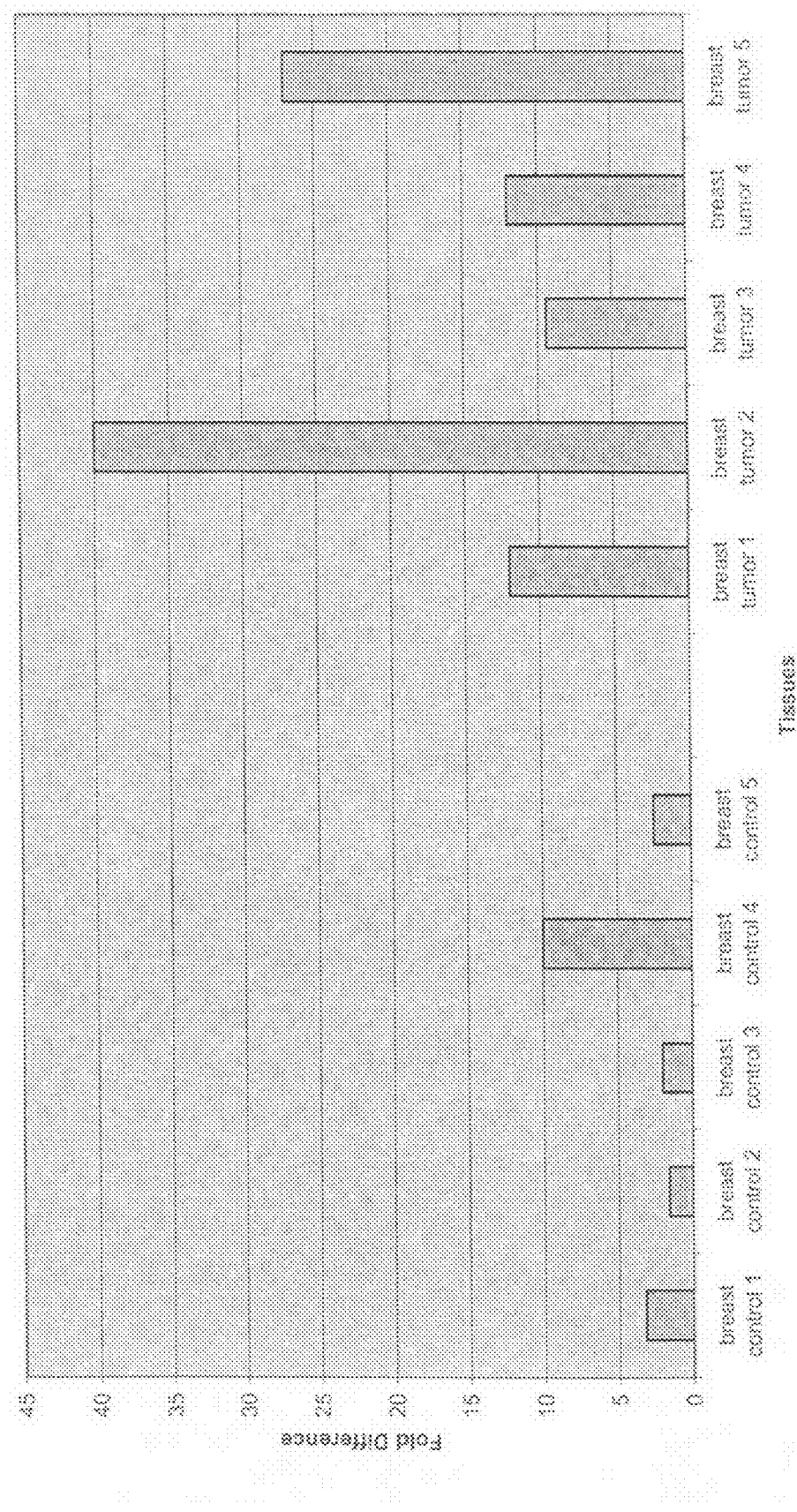
FIG. 16 shows the results of quantitative PCR analysis in breast tumors. (Example 10). Control breast tissue RNAs and breast tumor RNAs were evaluated. It was demonstrated that breast tumors (2 out of 5) have elevated steady-state RAI-3 RNA levels.
Figure 17:
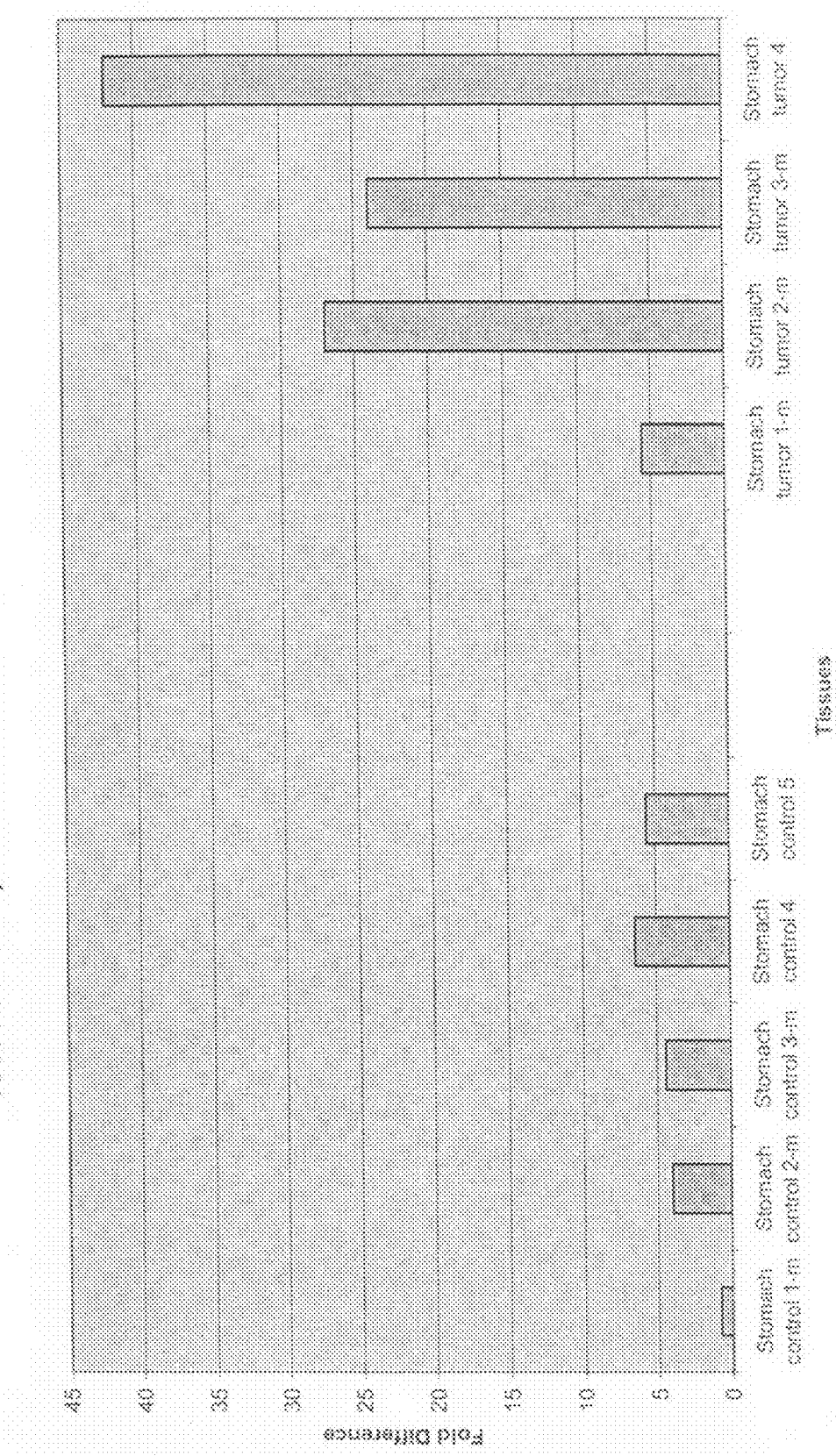
FIG. 17 shows the results of quantitative PCR analysis in stomach tumors. (Example 10). Control stomach tissue RNAs and stomach tumor RNAs were evaluated. It was demonstrated that stomach tumors (2 or 3 matched tissue samples and one additional non-matched sample for a total of 3 out 4) have elevated steady-state RAI-3 RNA levels.

Quantitative PCR analysis in a variety of control and tumor RNAs demonstrated that RAI-3 has elevated steady-state RNA levels in breast tumors (2 out of 5), (FIG. 16); in stomach tumors (2 or 3 matched tissue samples and one additional non-matched sample for a total of 3 out 4), (FIG. 17); and in testicular tumors (4 out 5 samples), (FIG. 18). These data suggest additional indications for which agonists and antagonists of RAI-3 can have utility in the treatment of a variety of human cancers. RAI-3 transcript levels can also be useful in the determination of tumor progression and diagnosis.

The sequences for the RAI-3 primer/probe set used in the above experiments in this Example include the following:

```
Forward Primer:
gcttcttcctctttgggatcct;      (SEQ ID NO:85)

Reverse Primer:
cttggtcagactgacagcatgag;     (SEQ ID NO:86)
and

Probe:
ttccatctgcttctcctgcctgctg.   (SEQ ID NO:87)
```

Example 12

Additional Methods Used in Assessing Functional of RAI-3 and its Association to COPD (Specific to FIGS. 26 to 28)

A. A549 Transient Transfection

The A549 cell line (American Type Culture Collection, Manassas, Va.) was plated in 100 mm petri dishes and transfected at about 75% confluency. Per plate each transfection was done with a mixture of 750 ul Opti-MEM media (Gibco-Invitrogen Corp, Grand Island N.Y.), 4 ug DNA and 20 ul Plus Reagent (Invitrogen Corp. Carlsbad, Calif.) combined with a mixture of 5 ml of Opti-MEM media and 30 ul Lipofectamine, as according to the manufacturer's specifications. The transfection mixture was left on the cells for 5 hours at 37° C., 5% CO2. At 5 hours, the transfection media was replaced with RPMI media containing 10% fetal bovine serum, 20 mM Glutamine, 1% Penicillin-Streptomycin (Gibco//Invitrogen Corporation, Carlsbad, Calif.).

B. Treatment of Cells with Cigarette Smoke-bubbled Medium

At 24 hours post-transfection, the media on the cells was changed to serum-free RPMI media containing only 20 mM Glutamine and 1% Penicillin-Streptomycin (Gibco/Invitrogen Corporation, Carlsbad, Calif.). At 48 hours, the cells were exposed to cigarette smoke-bubbled medium (see methods below, i.e., CS-160, the equivalent of 160 cigarettes per 500 ml of cell medium) for the periods of time shown (1 hr., 2 hr., and 3 hr.) and to EGF (10 nM) for 5 minutes.

C. Generation of Cell Lysates

Cells on each 100 mm plate were lysed in 3 mL of Lysis Buffer containing 1% NP40, 50 mM Tris-HCl, 0.5% Na+ deoxycholate, 150 mM NaCl and 1 mM sodium orthovanadate in the presence of phosphatase inhibitors and protease inhibitors in the form of 1 tab (per 50 ml of Lysis Buffer) of Complete protease inhibitor cocktail (Roche, Basel, Switzerland) and transferred to 2 Eppendorf tubes. Lysates were placed on ice for 10 min. and then spun in a microfuge at 4° C. at 14,000 rpm for 10 min. The lysate was transferred to a new tube and stored at −80 until immunoprecipitation.

D. Immunoprecipitation and Immunoblotting

Lysates were immunoprecipitated overnight at 4° C., rotating, with either 2 µg of anti-FLAG M2 antibody Catalog # F-3165 (Sigma, Saint Louis, Mo.) or 5 ul of rabbit antisera. Thereafter, 40 µl of Protein A was added to the lysate/antibody mixture and rotated at 4° C. for 1.5 hours. The Protein A/lysate/antibody mixture was washed twice with RIPA buffer and twice with 1×PBS. After the final wash the beads were aspirated "dry" and 60 µl of 2×SDS-PAGE sample buffer was added. After heating at 95° C. for 10 minutes, the samples were split (30 ul/gel) and resolved by SDS-PAGE (4-20% gradient gel) and transferred to nitrocellulose by standard Western Blotting techniques. The membranes were blotted/probed with either an anti-FLAG-HRP (Sigma, Saint Louis, Mo., Catalog # A8592), or an anti-phosphotyrosine-HRP antibody (HRP-conjugated-4G10 antibody, #16-105, Upstate Biotechnology, Inc., Lake Placid, N.Y.).

E. Generation of Cigarette Smoke-bubbled Medium

Cigarette-smoke bubbled medium was generated using a cigarette smoking machine similar to that described by T. Müller, (1995, "Expression of c-fos in quiescent Swiss 3T3 cells exposed to aqueous cigarette smoke fractions", *Cancer Res.*, 55:1927-1932). The cigarettes used were the standard reference research cigarette 1R4F (Tobacco and Health Research Institute, University of Kentucky, Lexington, Ky.). For a concentration of CS-160, smoke from 160 cigarettes (10 puffs per cigarette), respectively, was bubbled through 500 ml of RPMI (Gibco/BRL/Invitrogen Corporation, Carlsbad, Calif.) medium and sterile filtered for use that same day.

F. EGFR Immunoprecipitation 1.5 ml of cell lysate (~½ of a confluent T75 flask) was pre-cleared twice with 50 µl of Protein A slurry, rotating at 4° C. Pre-cleared lysate was transferred to a new Eppendorf tube and 50 µl of Protein A and 2 µl of EGFR antisera (HER1/TWIB2, polyclonal rabbit antisera to human EGFR) were added. The precleared lysate, Protein A and EGFR antisera were mixed by rotating at 4° C. for one hour, and then were washed three times with Lysis Buffer, one time with 1×PBS (20 mM sodium phosphate, 150 mM NaCl, pH 7.4) followed by aspiration to dryness. 30 µl of sample buffer were added to the tubes and the samples were placed at 95° C. for 10 minutes before loading onto a gel (30 µl per lane).

G. Generation of RAI-3 Antigen for Injection into Rabbits

An RAI-3 BglII/PstI restriction fragment (from the intitiating Methionine at amino acid position 1 to the Glutamine at amino acid position 328 of SEQ ID NO:3, deleting the last 30 amino acids) was cloned into the pEX34 expression system (Strebel, K., Beck, E., Strohamier, K., and Schaller, H. Characterization of foot-and-mouth disease virus gene products with antisera against bacterially synthesized fusion proteins. J. Virol., 57:983-991, 1986). PEX34 is a heat inducible lambda repressor-controlled expression system that uses a hydrophobic MS2 polymerase fragment as an N-terminal 10 kDa tag. The construct was then transfected into *E. coli* and the MS2-RAI-3 fusion protein was purified as described previously (J. Virol., 57:983-991, 1986).

H. Generation of RAI-3 Polyclonal Antisera in Rabbits

A rabbit antiserum specific for human RAI-3 was raised against the MS2 polymerase-RAI-3 fusion protein (as described above). Two rabbits were injected with 10 mg of MS2 polymerase-RAI-3 fusion protein for the initial immunization and 5 mg per boost for the 7 subsequent booster injections. Freund's Complete Adjuvant (FCA) was used for the initial immunization only and Freund's Incomplete Adjuvant (FIA) for all subsequent boosts. The sera was used directly as isolated from the rabbits and was not affinity purified to isolate antibodies.

I. Characterization of GW7, Rabbit RAI-3 Polyclonal Antisera by Immunoblotting

GW7, Post Boost #4, production bleed antisera was used to Western blot a stable RAI-3-expressing CHO K1 cell line (Cho/NFAT-CRE: Aurora Biosciences™) (G. Zlokarnik et al., 1998, Ibid.) The cells were immunoprecipitated with antiflag antibody and blotted with either Post Boost #4, production bleed antisera at a 1:500 dilution or 2 µg of anti-FLAG M2 antibody (Catalog # F-3165, Sigma, Saint Louis, Mo.)

J. Characterization of Rabbit RAI-3 Polyclonal Antisera, Immunoprecipitation

Lysates from ½ of a confluent T75 flask of either the stable Flag-RAI-3 CHO cell line or parental cell line were immunoprecipitated with 5 ul of rabbit RAI-3 antisera (GW7, Post Boost #4, production bleed antisera) and or 5 ul of rabbit pre-immune sera as an control and 40 µl of Protein A. The Protein A/lysate/antibody mixture was washed, aspirated "dry", and 30 µl of 2×SDS-PAGE sample buffer was added. After heating at 95° C for 10 minutes, the samples were loaded onto a 4-20% gradient gel, and resolved by SDS- PAGE and transferred to nitrocellulose by standard Western Blotting techniques. The membranes were blotted/probed a 1:1000 dilution of an anti-FLAG-HRP antibody (Catalog # A8592, Sigma, Saint Louis, Mo.).

Example 13

Additional Methods Used in Assessing Functional of RAI-3 and its Association to COPD (Specific to FIGS. 29 to 32)

A. Characterization of Rabbit RAI-3 Aantisera by Fluorescence-activated Cell Sorting (FACS) Analysis of CHO/Flag-RAI-3 Stable Cell Line and H292 and A549 Cell Lines The cells were suspended in binding buffer of DMEM (Gibco/Invitrogen Corporation, Carlsbad, Calif.) with 1% w/v bovine serum albumin and 0.1% sodium azide The mixture was incubated on ice for 1 hour followed by two washings with binding buffer. The cells were centrifuged at 500×G for 5 minutes between each wash. Ab were added on ice for 30 minutes. After further washing, the cells were analyzed on a Becton Dickenson FACSort using Cell Quest software. Cells were live gated and red/green color was compensated. Siglec)) Cells from confluent 100 mM cell culture plates (i.e., ~2×106.cells) were washed once with 1×PBS and then lifted from the plates with 2-3 ml of Cell Stripper (Cellgro/Mediatech, Herndon, Va.). 15 ml of 1×PBS was added to wash cells and then the cells were centrifuged at 1.5 K for 8 minutes at 4o C to pellet. Cells were resuspended in 0.2 ml of binding buffer-DMEM (Gibco/BRL/Invitrogen Corporation, Carlsbad, Calif.) with 1% BSA final and 0.02% azide. Anti-FLAG FITC (Sigma, Saint Louis, Mo.; Catalog #F4049) was added at a dilution of 1:400 or rabbit anti sera was added at a dilution of 1:250. The cells incubated with the rabbit antisera were centrifuged at 1.5 K for 8 minutes at 4° C. to pellet washed twice with 10 ml of binding buffer and resuspended in a final volume of 0.2 ml of binding buffer containing the 2° antibody a Fluorescein (FITC)-conjugated AffiniPure F(ab')$_2$ Goat Anti-Rabbit IgG.at a dilution of 1:200 (Jackson Immunoreseach Laboratories, Inc, West Grove, Pa.). The cell and antibody mixture was incubated on ice for one hour. Cells were washed twice with 10 ml of binding buffer and resuspended in a final volume of 0.5 ml of binding buffer for FACS analysis. The cells were analyzed on a Becton Dickenson FACSort using Cell Quest software. (Becton-Dickenson, Franklin Lakes, N.J.). Cells were live gated and red/green color was compensated.

B. Fluorescence-activated Cell Sorting (FACS) Analysis of siRNAi Transfected H292 Cell Line Cells (siRNA transfected as described above) from each well of the 12 well-culture plates (i.e., ~0.5×10$^6$ cells) were washed once with 1×PBS and then lifted from the plates with 0.5 ml of Cell Stripper (Cellgro/Mediatech, Herndon, Va.). 3 ml of 1×PBS was added to wash cells and then the cells were centrifuged at 1.5 K for 8 minutes at 4° C. to pellet. Cells were resuspended in 0.2 ml of binding buffer-DMEM (Gibco/BRL/Invitrogen Corporation, Carlsbad, Calif.) with 1% BSA final. Anti-FLAG FITC (Sigma, Saint Louis, Mo.; Catalog #F4049) was added at a dilution of 1:400. The cell and antibody mixture was incubated on ice for one hour. Cells were washed twice with 10 ml of binding buffer and resuspended in a final volume of 0.5 ml of binding buffer for FACS analysis. The cells were analyzed on a Becton Dickenson FACSort using Cell Quest software. (Becton-Dickenson, Franklin Lakes, N.J.). Cells were live gated and red/green color was compensated.

C. siRNA Oligo Sequences

For the RAI-3 siRNA oligos 1864+1865, the RAI-3 DNA target sequence is AAGGTGCAGGACTCCAACAGG (SEQ ID NO:93) and the annealed double stranded siRNA sequences are r(GGUGCAGGACUCCAACAGG)d(TT) (SEQ ID NO:94) and r(CCUGUUGGAGUCCUGCACC)d (TT) (SEQ ID NO:95). The target sequence for the Control siRNA oligos are AATTCTCCGAACGTGTCACGTTT (SEQ ID NO:96) Sense Oligo is UUCUCCGAACGUGU-CACGUUUTT (SEQ ID NO:97) and the Antisense Oligo is AAACGUGACACGUUCGGAGTT (SEQ ID NO:98). All siRNA oligos were purchased from Xeragon/Qiagen (Valencia, Calif.).

D. CHO/FlagRAI-3 Stable Cell Line RNAi Transfection

The day before transfection, 5×104 cells/well were seeded in 12 well-plates in RPMI media containing 10% fetal bovine serum, 20 mM Glutamine, 1% Penicillin-Streptomycin (Gibco//Invitrogen Corporation, Carlsbad, Calif.). On the day of the transfection, the cells were ~90% confluent. The media on the cells was replaced with 1 ml of RPMI media containing 10% fetal bovine serum and 20 mM Glutamine (minus antibiotics). For each well, 4 ul of a 20 uM stock of the siRNA was mixed with 100 ul Opti-MEM (Gibco/Invitrogen Corporation, Carlsbad, Calif.). In a separate tube, 4 ul of Lipofectamine 2000 (Invitrogen Corp., Carlsbad, Calif.) was diluted into 100 ul of Opti-MEM. The diluted siRNA and the diluted Lipofectamine 2000 solutions were mixed and left at room temperature for 20 minutes. The mixture was then added to the cells and incubated at 37o, 5% CO2 for 48 hours. The transfections were done in triplicates.

E. H292 siRNAi Transfection

The day before transfection, ~2.5×10$^4$ H292 cells/well were seeded into 24 well-plates in RPMI media containing 10% fetal bovine serum, 20 mM Glutamine, 1% Penicillin-Streptomycin (Gibco/Invitrogen Corporation, Carlsbad, Calif.). On the day of the transfection, the cells were ~90% confluent and the media was replaced with RPMI media containing 10% fetal bovine serum and 20 mM Glutamine and no antibiotics. For each well, 4 ul of a 20 uM stock of the siRNA was diluted into 50 ul Opti-MEM (Gibco/Invitrogen Corporation, Carlsbad, Calif.). In a separate tube, 2 ul of Lipofectamine 2000 (Invitrogen Corp., Carlsbad, Calif.) was diluted into 50 ul of Opti-MEM. The diluted siRNA and the diluted Lipofectamine 2000 solutions were mixed and left at room temperature for 20 minutes. The mixture was then added to the cells containing media without antibiotics and incubated at 37° C., 5% CO2, for 24 hours. The transfections were done in triplicates.

F. Treatment of H292/RAI-3 RNAi Transfectants with Cigarette Smoke-bubbled Media At 24 hours post siRNA transfection, the media was changed to serum-free RPMI media containing 20 mM Glutamine and 1% Penicillin-Streptomycin and *incubated at* 37° C., 5% CO2, for 24 hours. At 48 hours post transfection, the serum-free RPMI media was removed from the cells and replaced with 1.0 ml of cigarette smoke-bubbled medium (i.e., CS-10, the equivalent of 10 cigarettes per 500 ml of cell culture medium) for 72 hours (96 hours post-transfection) or control. At 72 hours (96 hours post-transfection), 100 ul×3 of supernatent from each well in the 24-well plate was transferred to 96-well plate for ELISA analysis. Untransfected controls (in triplicate) receiving CS-10 media showed a 7.73 fold increase in the levels of muc5AC protein in the supernatant when compared to the supernatant of cells with only serum-free RPMI media (CS-10: average 0.5927, StDev 0.1326, serum-free media: 0.0766, StDev 0.0339).

G. Fluorescence-activated Cell Sorting (FACS) Analysis of siRNAi Transfected H292 Cell Line Cells (siRNA transfected as described above) from each well of the 24 well-culture plates (i.e., ~0.5×10$^5$ cells) were washed once with 1×PBS and then lifted from the plates with 0.5 ml of Cell Stripper (Cellgro/Mediatech, Herndon, Va.). 3 ml of 1×PBS was added to wash cells and then the cells were centrifuged at 1.5 K for 8 minutes at 4° C. to pellet. Cells were resuspended in 0.2 ml of binding buffer which is composed from DMEM (Gibco/BRL/Invitrogen Corporation, Carlsbad, Calif.) with a final concentration of 1% BSA (Sigma-Aldrich Co. Saint Louis, Mo.) and 0.02% azide. Rabbit anti sera was added at a dilution of 1:250. The cells and antibody mixture was incubated for one hour on ice. The cells were centrifuged at 1.5 K for 8 minutes at 4° C. to pellet, washed twice with 10 ml of binding buffer and resuspended in a final volume of 0.2 ml of binding buffer containing the 2° antibody a Fluorescein (FITC)-conjugated AffiniPure F(ab')$_2$ Goat Anti-Rabbit IgG.at a dilution of 1:200 (Jackson Immunoreseach Laboratories, Inc, West Grove, Pa.). The cells and antibody mixture was incubated for 30 minutes on ice. The cells were centrifuged at 1.5 K for 8 minutes at 4° C. to pellet washed twice with 10 ml of binding buffer and resuspended in a final volume of 0.5 ml of binding buffer for FACS analysis. The cells were analyzed on a Becton Dickenson FACSort using Cell Quest software (Becton-Dickenson, Franklin Lakes, N.J.). Cells were live gated and red/green color was compensated.

H. muc5AC Enzyme-linked Immunosorbent Assays (ELISA)

A muc5AC coating antibody, Gastric Mucin Ab-1 45M1 (NeoMarkers, Fremont, Calif.) was diluted 1:1000 to 1 ug/ml final in 50 mM NaHCO3 pH 9 and coated onto a standard 96-well ELISA plate overnight at room temperature with rotating. The next day the plate was washed three times with 1×PBS/0.05% Tween 20 (PBS-T) and blocked with 200 ul of blocking buffer, 1×PBS/1% BSA final (30% solution, Sigma-Aldrich Co. Saint Louis, Mo.). Wells were blocked overnight at room temperature with rotating. Wells were washed three times with PBS-T and then 100 ul of the supernatant was added to each well. The supernatant was left on the plate overnight at room temperature with rotating. The next day the wells were washed three times with PBS-T. Muc5AC protein in the supernatent was detected with Peroxidase-Labeled Lectin from Glycine Max (Sigma-Aldrich, St. Louis, Mo.) diluted to 1ug/ml in 1×PBS/1% BSA final. Reactions were developed using 100 μl/well of 50:50 TMB Microwell Peroxidase Substrate System 2-C (Kirkegaard & Perry Laboratory, Gaithersburg, Md.). Color reactions were stopped with 100 μl/well 1 N. H$_2$SO$_4$ and the absorbency at 450 nm-650 nm was measured. Untransfected controls (in triplicate) receiving CS-10 media showed a 7.73 fold increase in the levels of muc5AC protein in the supernatant when compared to the supernatant of cells with only serum-free RPMI media (CS-10: average 0.5927, StDev 0.1326, serum-free media: 0.0766, StDev 0.0339).

Example 14

Method of Assessing the Expression of RAI-3 in Human Tissues by Immunohistochemical Staining Using ANTI-RAI-3 Rabbit Polyclonal Antibodies Immunohistochemistry expression of RAI-3, describes positive staining in pulmonary emphysema and chronic bronchitis samples when compared to normal (disease-free) lung samples (see FIGS. 33 and 34). The latter is consistent with the putative role of RAI-3 in the pathobiology of cigarette smoke-related pulmonary disease.

Immunohistochemical assay techniques are commonly known in the art and are described briefly herein. Briefly, immunocytochemical (ICC) experiments were performed on a DAKO autostainer following the procedures and reagents developed by DAKO. Specifically, the slides were blocked with avidin, rinsed, blocked with biotin, rinsed, protein blocked with DAKO universal protein block, machine blown dry, primary antibody, incubated, and the slides rinsed. Biotinylated secondary antibody was applied using the manufacturer's instructions (1 drop/10 ml, or approximately 0.75 μg/mL), incubated, rinsed slides, and applied Vectastain ABC-AP reagent for 30 minutes. Vector Red was used as substrate and prepared according to the manufacturer's instructions just prior to use. Slides containing paraffin sections (LifeSpan BioSciences, Inc.; Seattle, Wash.) were deparaffinized through xylene and alcohol, rehydrated, and then subjected to the steam method of target retrieval (#S1700; DAKO Corp.; Carpenteria, Calif.).

The following RAI-3 peptides were synthesized and used as antigens to create anti-RAI-3 antisera: peptide corresponding to amino acids 90 to 104 of SEQ ID NO:3 (DGSTGPTR-FFLFGIL SEQ ID NO:91); or a peptide corresponding to amino acids 269 to 284 of SEQ ID NO:3 (TKQRNPM-DYPVEDAFC SEQ ID NO:92). The staining patterns and conclusions described below and elsewhere herein were essentially the same when using polyclonal antibodies (LifeSpan Biosciences, Seattle, Wash.) directed against either a peptide (data not shown).

The results of the immunohistochemical staining pattern in human tissues of specific anti-RAI-3 rabbit polyclonal antibodies was assessed by a pathologist at LifeSpan Biosciences, Seattle WA. Consistent with the putative role of RAI-3 in the pathobiology of cigarette smoke-related pulmonary disease, increases in staining were identified in samples of pulmonary emphysema and chronic bronchitis when compared to normal (disease-free) lungs as shown in FIGS. 33 and 34. No significant changes in staining were identified in bronchial asthma compared to normal lung (data not shown). With the emphysematous tissue, the predominant staining was observed with pneumocytes and respiratory epithelial cells while the chronic bronchitis samples showed increased staining of respiratory epithelium, inflammatory cells, occasional endothelial cells and pneumocytes.

Interestingly, increased staining over normal tissue was observed in ulcerative colitis, cerebral infarct, myocardial infarct, diabetic nephropathy, allergic rhinitis, Crohn's disease, atherosclerosis and rheumatoid arthritis. This may suggest a role for RAI-3 in inflammatory/auto-immune disorders outside of the lung in addition to COPD. The most noteworthy staining of malignancies was observed in malignant melanoma in which tumor cells stained moderately to strongly, and, in one sample, many moderately to strongly positive tumor-associated lymphocytes were identified. In addition, at least faintly positive staining was identified in glioblastoma, pulmonary small cell undifferentiated carcinoma, carcinoma of the breast, colon, lung, ovary, pancreas, and prostate, and in non-Hodgkin's lymphoma. Increased staining was also observed in benign prostatic hyperplasia.

Example 15

Method of Testing the Ability of RAI-3 Modulators to Affect Lung Physiology In Vivo A number of methods may be employed to assess whether the RAI-3 modulators of the present invention (e.g., antisense compounds, siRNA compounds, anti-RAI-3 antibodies, small molecule compounds, etc.) are capable of affecting the physiology of lung cells, and in particular provide therapeutic efficacy in treating, ameliorating, and/or treating lung disorders, particularly inflammatory lung disordwers such as COPD. RAI-3 modulators can be characterized in vivo by measuring the effect of a compound (administered systemically or by inhalation) on neutrophilia, cytokine (e.g., TNFα), chemokine (e.g., KC or IL-8), and mucin production in either acutely or chronically-cigarette smoke-challenged mice (1). Similar endpoints can be measured in mice challenged by repeated intranasal administration of cigarette smoke-conditioned media (2). Alternatively, the effect of RAI-3 modulators can be investigated in mice that have received repeated intratracheal instillation of *Escherichia coli* LPS, with effects on many pulmonary endpoints being measured. These include effects on peribronchial and perivascular lymphocytic aggregates (CD4(+), CD8(+), and CD19(+)), parenchymal accumulation of macrophages and CD8(+) T cells, cytokine expression, as well as effects on airway and alveolar alterations such as mucus cell metaplasia, airway wall thickening, and irreversible alveolar enlargement (3).

The skilled artisan would appreciate that such methods are exemplary and that the methods may be modified to be specific to RAI-3, as applicable. The following publications are herein incorporated herein by reference in their entirety.

1. Churg A, Zay K, Shay S, Xie C, Shapiro S D, Hendricks R, Wright J L. Acute cigarette smoke-induced connective tissue breakdown requires both neutrophils and macrophage metalloelastase in mice. *Am J Respir Cell Mol Biol.* 2002, 27:368-74.

2. Miller L M, Foster W M, Dambach D M, Doebler D, McKinnon M, Killar L, Longphre M. A murine model of cigarette smoke-induced pulmonary inflammation using intranasally administered smoke-conditioned medium. *Exp. Lung Res.* 2002, 28:435-55.

3. Vernooy J H, Dentener M A, van Suylen R J, Buurman W A, Wouters E F. Long-term intratracheal lipopolysaccharide exposure in mice results in chronic lung inflammation and persistent pathology. *Am J Respir Cell Mol Biol.* 2002, 26:152-9.

Example 16

Method of Creating N- and C-Terminal Deletion Mutants Corresponding to the RAI-3 Polypeptide of the Present Invention As described elsewhere herein, the present invention encompasses the creation of N- and C-terminal deletion mutants, in addition to any combination of N- and C-terminal deletions thereof, corresponding to the RAI-3 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length RAI-3 polypeptide sequence (as described in herein, for example), appropriate primers of about 15-25 nucleotides derived from the desired 5' and 3' positions of SEQ ID NO:2 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

Representative PCR amplification conditions are provided below, although the skilled artisan would appreciate that other conditions may be required for efficient amplification. A 100 ul PCR reaction mixture may be prepared using 10 ng of the template DNA (cDNA clone of RAI-3), 200 uM 4dNTPs, 1 uM primers, 0.25U Taq DNA polymerase (PE), and standard Taq DNA polymerase buffer. Typical PCR cycling condition are as follows:

| 20-25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E.coli* cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of the RAI-3 gene (SEQ ID NO:2), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:2. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: $(S+(X*3))$ to $((S+(X*3))-25)$, wherein 'S' is equal to the nucleotide position of the initiating start codon of the RAI-3 gene (SEQ ID NO:2), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:2. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

In preferred embodiments, the following N-terminal RAI-3 deletion polypeptides are encompassed by the present invention: M1-S357, A2-S357, T3-S357, T4-S357, V5-S357, P6-S357, D7-S357, G8-S357, C9-S357, R10-S357, N11-S357, G12-S357, L13-S357, K14-S357, S15-S357, K16-S357, Y17-S357, Y18-S357, R19-S357, L20-S357, C21-S357, D22-S357, K23-S357, A24-S357, E25-S357, A26-S357, W27-S357, G28-S357, I29-S357, V30-S357, L31-S357, E32-S357, T33-S357, V34-S357, A35-S357, T36-S357, A37-S357, G38-S357, V39-S357, V40-S357, T41-S357, S42-S357, V43-S357, A44-S357, F45-S357, M46-S357, L47-S357, T48-S357, L49-S357, P50-S357, I51-S357, L52-S357, V53-S357, C54-S357, K55-S357, V56-S357, Q57-S357, D58-S357, S59-S357, N60-S357, R61-S357, R62-S357, K63-S357, M64-S357, L65-S357, P66-S357, T67-S357, Q68-S357, F69-S357, L70-S357, F71-S357, L72-S357, L73-S357, G74-S357, V75-S357, L76-S357, G77-S357, I78-S357, F79-S357, G80-S357, L81-S357, T82-S357, F83-S357, A84-S357, F85-S357, I86-S357, I87-S357, G88-S357, L89-S357, D90-S357, G91-S357, S92-S357, T93-S357, G94-S357, P95-S357, T96-S357, R97-S357, F98-S357, F99-S357, L100-S357, F101-S357, G102-S357, I103-S357, L104-S357, F105-S357, S106-S357, I107-S357, C108-S357, F109-S357, S110-S357, C111-S357, L112-S357, L113-S357, A114-S357, H115-S357, A116-S357, V117-S357, S118-S357, L119-S357, T120-S357, K121-S357, L122-S357, V123-S357, R124-S357, G125-S357, R126-S357, K127-S357, P128-S357, L129-S357, S130-S357, L131-S357, L132-S357, V133-S357, I134-S357, L135-S357, G136-S357, L137-S357, A138-S357, V139-S357, G140-S357, F141-S357, S142-S357, L143-S357, V144-S357, Q145-S357, D146-S357, V147-S357, I148-S357, A149-S357, I150-S357, E151-S357, Y152-S357, I153-S357, V154-S357, L155-S357, T156-S357, M157-S357, N158-S357, R159-S357, T160-S357, N161-S357, V162-S357, N163-S357, V164-S357, F165-S357, S166-S357, E167-S357, L168-S357, S169-S357, A170-S357, P171-S357, R172-S357, R173-S357, N174-S357, E175-S357, D176-S357, F177-S357, V178-S357, L179-S357, L180-S357, L181-S357, T182-S357, Y183-S357, V184-S357, L185-S357, F186-S357, L187-S357, M188-S357, A189-S357, L190-S357, T191-S357, F192-S357, L193-S357, M194-S357, S195-S357, S196-S357, F197-S357, T198-S357, F199-S357, C200-S357, G201-S357, S202-S357, F203-S357, T204-S357, G205-S357, W206-S357, K207-S357, R208-S357, H209-S357, G210-S357, A211-S357, H212-S357, I213-S357, Y214-S357, L215-S357, T216-S357, M217-S357, L218-S357, L219-S357, S220-S357, I221-S357, A222-S357, I223-S357, W224-S357, V225-S357, A226-S357, W227-S357, I228-S357, T229-S357, L230-S357, L231-S357, M232-S357, L233-S357, P234-S357, D235-S357, F236-S357, D237-S357, R238-S357, R239-S357, W240-S357, D241-S357, D242-S357, T243-S357, I244-S357, L245-S357, S246-S357, S247-S357, A248-S357, L249-S357, A250-S357, A251-S357, N252-S357, G253-S357, W254-S357, V255-S357, F256-S357, L257-S357, L258-S357, A259-S357, Y260-S357, V261-S357, S262-S357, P263-S357, E264-S357, F265-S357, W266-S357, L267-S357, L268-S357, T269-S357, K270-S357, Q271-S357, R272-S357, N273-S357, P274-S357, M275-S357, D276-S357, Y277-S357, P278-S357, V279-S357, E280-S357, D281-S357, A282-S357, F283-S357, C284-S357, K285-S357, P286-S357, Q287-S357, L288-S357, V289-S357, K290-S357, K291-S357, S292-S357, Y293-S357, G294-S357, V295-S357, E296-S357, N297-S357, R298-S357, A299-S357, Y300-S357, S301-S357, Q302-S357, E303-S357, E304-S357, I305-S357, T306-S357, Q307-S357, G308-S357, F309-S357, E310-S357, E311-S357, T312-S357, G313-S357, D314-S357, T315-S357, L316-S357, Y317-S357, A318-S357, P319-S357, Y320-S357, S321-S357, T322-S357, H323-S357, F324-S357, Q325-S357, L326-S357, Q327-S357, N328-S357, Q329-S357, P330-S357, P331-S357, Q332-S357, K333-S357, E334-S357, F335-S357, S336-S357, I337-S357, P338-S357, R339-S357, A340-S357, H341-S357, A342-S357, W343-S357, P344-S357, S345-S357, P346-S357, Y347-S357, K348-S357, D349-S357, Y350-S357, and/or E351-S357 of SEQ ID NO:3. Polynucleotide sequences encoding these polypeptides are also provided. The present invention also encompasses the use of these N-terminal RAI-3 deletion polypeptides as immunogenic and/or antigenic epitopes as described elsewhere herein.

In preferred embodiments, the following C-terminal RAI-3 deletion polypeptides are encompassed by the present invention: M1-S357, M1-G356, M1-E355, M1-K354, M1-K353, M1-V352, M1-E351, M1-Y350, M1-D349, M1-K348, M1-Y347, M1-P346, M1-S345, M1-P344, M1-W343, M1-A342, M1-H341, M1-A340, M1-R339, M1-P338, M1-I337, M1-S336, M1-F335, M1-E334, M1-K333, M1-Q332, M1-P331, M1-P330, M1-Q329, M1-N328, M1-Q327, M1-L326, M1-Q325, M1-F324, M1-H323, M1-T322, M1-S321, M1-Y320, M1-P319, M1-A318, M1-Y317, M1-L316, M1-T315, M1-D314, M1-G313, M1-T312, M1-E311, M1-E310, M1-F309, M1-G308, M1-Q307, M1-T306, M1-I305, M1-E304, M1-E303, M1-Q302, M1-S301, M1-Y300, M1-A299, M1-R298, M1-N297, M1-E296, M1-V295, M1-G294, M1-Y293, M1-S292, M1-K291, M1-K290, M1-V289, M1-L288, M1-Q287, M1-P286, M1-K285, M1-C284, M1-F283, M1-A282, M1-D281, M1-E280, M1-V279, M1-P278, M1-Y277, M1-D276, M1-M275, M1-P274, M1-N273, M1-R272, M1-Q271, M1-K270, M1-T269, M1-L268, M1-L267, M1-W266, M1-F265, M1-E264, M1-P263, M1-S262, M1-V261, M1-Y260, M1-A259, M1-L258, M1-L257, M1-F256, M1-V255, M1-W254, M1-G253, M1-N252, M1-A251, M1-A250, M1-L249, M1-A248, M1-S247, M1-S246, M1-L245, M1-I244, M1-T243, M1-D242, M1-D241, M1-W240, M1-R239, M1-R238, M1-D237, M1-F236, M1-D235, M1-P234, M1-L233, M1-M232, M1-L231, M1-L230, M1-T229, M1-I228, M1-W227, M1-A226, M1-V225, M1-W224, M1-I223, M1-A222, M1-I221, M1-S220, M1-L219, M1-L218, M1-M217, M1-T216, M1-L215, M1-Y214, M1-I213, M1-H212, M1-A211, M1-G210, M1-H209, M1-R208, M1-K207, M1-W206, M1-G205, M1-T204, M1-F203, M1-S202, M1-G201, M1-C200, M1-F199, M1-T198, M1-F197, M1-S196, M1-S195, M1-M194, M1-L193, M1-F192, M1-T191, M1-L190, M1-A189, M1-M188, M1-L187, M1-F186, M1-L185, M1-V184, M1-Y183, M1-T182, M1-L181, M1-L180, M1-L179, M1-V178, M1-F177, M1-D176, M1-E175, M1-N174, M1-R173, M1-R172, M1-P171, M1-A170, M1-S169, M1-L168, M1-E167, M1-S166, M1-F165, M1-V164, M1-N163, M1-V162, M1-N161, M1-T160, M1-R159, M1-N158, M1-M157, M1-T156, M1-L155, M1-V154, M1-I153, M1-Y152, M1-E151, M1-I150, M1-A149, M1-I148, M1-V147, M1-D146, M1-Q145, M1-V144, M1-L143, M1-S142, M1-F141, M1-G140, M1-V139, M1-A138, M1-L137, M1-G136, M1-L135, M1-I134, M1-V133, M1-L132, M1-L131, M1-S130, M1-L129, M1-P128, M1-K127, M1-R126, M1-G125, M1-R124, M1-V123, M1-L122, M1-K121, M1-T120, M1-L119, M1-S118, M1-V117, M1-A116, M1-H115, M1-A114, M1-L113, M1-L112, M1-C111, M1-S110, M1-F109, M1-C108, M1-I107, M1-S106, M1-F105, M1-L104, M1-I103, M1-G102, M1-F101, M1-L100, M1-F99, M1-F98, M1-R97, M1-T96, M1-P95, M1-G94, M1-T93, M1-S92, M1-G91, M1-D90, M1-L89, M1-G88, M1-I87, M1-I86, M1-F85, M1-A84, M1-F83, M1-T82, M1-L81, M1-G80, M1-F79, M1-I78, M1-G77, M1-L76, M1-V75, M1-G74, M1-L73, M1-L72, M1-F71, M1-L70, M1-F69, M1-Q68, M1-T67, M1-P66, M1-L65, M1-M64, M1-K63, M1-R62, M1-R61, M1-N60, M1-S59, M1-D58, M1-Q57, M1-V56, M1-K55, M1-C54, M1-V53, M1-L52, M1-I51, M1-P50, M1-L49, M1-T48, M1-L47, M1-M46, M1-F45, M1-A44, M1-V43, M1-S42, M1-T41, M1-V40, M1-V39, M1-G38, M1-A37, M1-T36, M1-A35, M1-V34, M1-T33, M1-E32, M1-L31, M1-V30, M1-I29, M1-G28, M1-W27, M1-A26, M1-E25, M1-A24, M1-K23, M1-D22, M1-C21, M1-L20, M1-R19, M1-Y18, M1-Y17, M1-K16, M1-S15, M1-K14, M1-L13, M1-G12, M1-N11, M1-R10, M1-C9, M1-G8, and/or M1-D7 of SEQ ID NO:3. Polynucleotide sequences encoding these polypeptides are also provided. The present invention also encompasses the use of these C-terminal RAI-3 deletion polypeptides as immunogenic and/or antigenic epitopes as described elsewhere herein.

Example 17

Method of Screening, In Vitro, Compounds that Bind to the RAI-3 Polypeptide

In vitro systems can be designed to identify compounds capable of binding the RAI-3 polypeptide of the invention. Compounds identified can be useful, for example, in modulating the activity of wild type and/or mutant RAI-3 polypeptide, preferably mutant RAI-3 polypeptide, can be useful in elaborating the biological function of the RAI-3 polypeptide, can be utilized in screens for identifying compounds that disrupt normal RAI-3 polypeptide interactions, or can in themselves disrupt such interactions.

The principle of the assays used to identify compounds that bind to the RAI-3 polypeptide involves preparing a reaction mixture of the RAI-3 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring RAI-3 polypeptide or the test substance onto a solid phase and detecting RAI-3 polypeptide/test compound complexes anchored on the solid phase at the end of the reaction. In one embodiment of such a method, the RAI-3 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for RAI-3 polypeptide or the test compound to anchor any complexes formed in solution, and a labeled antibody specific for the other component of the possible complex to detect anchored complexes.

Another example of a screening assay to identify compounds that bind to RAI-3, relates to the application of a cell membrane-based scintillation proximity assay ("SPA"). Such an assay would require the idenification of a ligand for RAI-3 polypeptide. Once identified, unlabeled ligand is added to assay-ready plates that would serve as a positive control. The SPA beads and membranes are added next, and then $^{125}$I-labeled ligand is added. After an equilibration period of 2-4 hours at room temperature, the plates can be counted in a scintillation counting machine, and the percent inhibition or stimulation calculated. Such an SPA assay may be based upon a manual, automated, or semi-automated platform, and encompass 96, 384, 1536-well plates or more. Any number of SPA beads may be used as applicable to each assay. Examples of SPA beads include, for example, Leadseeker WGA PS (Amersham cat # RPNQ 0260), and SPA Beads (PVT-PEI-WGA-TypeA; Amersham cat # RPNQ0003). The utilized membranes may also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference. The skilled artisan would acknowledge that certain modifications of known SPA assays may be required to adapt such assays to each respective polypeptide.

One such screening procedure involves the use of melanophores which are transfected to express the RAI-3 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i. e., inhibits activation of the receptor.

The technique may also be employed for screening of compounds which activate the receptor by contacting such cells with compounds to be screened and determining whether such compound generates a signal, i. e., activates the receptor. Other screening techniques include the use of cells which express the RAI-3 polypeptide (for example, transfected CHO cells) in a system which measures extracellular pH changes caused by receptor activation. In this technique, compounds may be contacted with cells expressing the receptor polypeptide of the present invention. A second messenger response, e. g., signal transduction or pH changes, is then measured to determine whether the potential compound activates or inhibits the receptor.

Another screening technique involves expressing the RAI-3 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the RAI-3 polypeptide such that the cell expresses the receptor on its surface. The cell is then contacted with a potential antagonist or agonist in the presence of a labeled form of a ligand, such as LPA. The ligand can be labeled, e. g., by radioactivity. The amount of labeled ligand bound to the receptors is measured, e. g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, *Xenopus Oocytes*, RBL-2H3, etc) which are transfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, *Xenopus Oocytes*, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as LPA, and the signal produced by the reporter gene is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonists involves introducing RNA encoding the RAI-3 polypeptide into *Xenopus oocytes* (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for RAI-3 polypeptide inhibitors by determining inhibition or stimulation of RAI-3 polypeptide-mediated cAMP and/or adenylate cyclase accumulation or diminution. Such a method involves transiently or stably transfecting a eukaryotic cell with RAI-3 polypeptide receptor to express the receptor on the cell surface.

The cell is then exposed to potential antagonists or agonists in the presence of RAI-3 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits RAI-3 polypeptide-ligand binding, the levels of RAI-3 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as RAI-3, along with a mixture comprised of mammalian expression plasmids cDNAs encoding GU15 (Wilkie T. M. et al Proc Natl Acad Sci USA 1991 88: 10049-10053), GU16 (Amatruda T. T. et al Proc Natl Acad Sci USA 1991 8: 5587-5591, and three chimeric G-proteins referred to as Gqi5, Gqs5, and Gqo5 (Conklin B R et al Nature 1993 363: 274-276, Conklin B. R. et al Mol Pharmacol 1996 50: 885-890). Following a 24 h incubation the trasfected HEK-293 cells are plated into poly-D-lysine coated 96 well black/clear plates (Becton Dickinson, Bedford, Mass.).

The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G015, GD16, GqiS, Gqs5, or Gqo5. If the GPCR requires the presence of one of the G-proteins for functional expression in HEK-293 cells, all subsequent experiments are performed with HEK-293 cell cotransfected with the GPCR and the G-protein which gives the best response. Alternatively, the receptor can be expressed in a different cell line, for example RBL-2H3, without additional Gproteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating type cells which triggers a MAP kinase cascade leading to G1 arrest as a prelude to cell fusion.

Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e. g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclindependent kinases leading to cell cycle arrest; and (iii) construction of reporter genes fused to the FUS 1 gene promoter (where FUS 1 encodes a membrane-anchored glycoprotein required for cell fusion). Downstream reporter genes can permit either a positive growth selection (e. g., histidine prototrophy using the FUS1-HIS3 reporter), or a colorimetric, fluorimetric or spectrophotometric readout, depending on the specific reporter construct used (e. g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J., Nature 384: 14-16, 1996; Manfredi et al., Mol. Cell. Biol. 16: 4700-4709,1996). This provides a rapid direct growth selection (e. g, using the FUS 1-HIS3 reporter) for surrogate peptide agonists that activate characterized or orphan receptors. Alternatively, yeast cells that functionally express human (or mammalian) G-protein coupled receptors linked to a reporter gene readout (e. g., FUS1-LacZ) can be used as a platform for high-throughput screening of known ligands, fractions of biological extracts and libraries of chemical compounds for either natural or surrogate ligands.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

Example 18

Method of Screening to Identify Modulators of the RAI-3 Polypeptide

Introduction

G protein-coupled receptors (GPCRs) are a superfamily of seven transmembrane-spanning proteins that are activated by a wide range of extracellular ligands, including small molecules such as biogenic amines, amino acids, ions, small and large peptides, and bioactive lipids. GPCRs are expressed in virtually all tissues and are involved in the regulation of a variety of cellular and physiological responses, such as neurotransmission, chemotaxis, inflammation, cell proliferation, cardiac and smooth muscle contractility, and visual and chemosensory perception (Bockaert et al., 2002; Pierce et al., 2002).

The sequencing of the human genome has led to predictions that as many as 1,000 of the 35,000-60,000 human genes encode G-protein coupled receptors (Lander et al., 2001; Venter et al., 2001). About 400 of these are non-chemosensory receptors and can therefore be considered as potential drug targets. More than half of the so-called "druggable" GPCRs are known receptors, in the sense that their activating ligands have been identified. The remaining ~155 receptors are "orphan receptors" (oGPCRs), for which the natural activating ligands remain unknown. While there has been recent success in identifying endogenous ligands for some oGPCRs, most remain without a cognate ligand despite substantial effort. This suggests that improvements to established deorphanizing methods can be made. The most common approach for de-orphanizing thus far is use "reverse pharmacology" to screen populations of mammalian cells transiently transfected with the oGPCR of interest. This reverse pharmacological strategy has resulted in the discovery of more than 50 ligands for orphan GPCRs (Szekeres, 2002). Candidate compounds for screening can be selected based on similarity of the orphan to receptors of known pharmacology. This approach is, however, ill-suited for those orphan receptors with little or no homology to known GPCRs. Alternatively, activating ligands can be identified using mixtures of fractionated tissue extracts, often prepared from tissues known to express the oGPCR in question (Civelli, 1998; Hinuma et al., 1999). Finally, diverse collections of known and presumptive GPCR signaling molecules can be assembled and screened in bulk for modulators of orphan receptor function. Also, since the signal transduction pathway(s) to which a given oGPCR naturally couples is unknown, orphan GPCRs are frequently screened in the presence of co-expressed promiscuous G protein alpha subunits, $G\alpha_{15}/G\alpha_{16}$, or various chimeric $G\alpha$ subunits in order to re-direct receptor signal output to pre-defined endpoints (Milligan et al., 1996; Milligan and Rees, 1999; Offermanns and Simon, 1995).

The inherent difficulty in identifying stable cell lines exhibiting expression and coupling of oGPCRs to signal transduction pathways in mammalian cell lines has forced most oGPCR screening to rely on transient transfection systems. Transient expression of an oGPCR has certain advantages, namely, that following transfection, oGPCRs are generally expressed at reasonably high levels at the cell surface. However, the logistical challenges involved in scaling transient transfection protocols to support high throughput screening (HTS) has necessitated smaller, more focused screening strategies for orphan GPCR ligand discovery (Howard et al., 2001). The screening decks of pharmaceutical companies, on the other hand, are large collections of very diverse drug-like molecules derived from medicinal chemistry, combinatorial synthesis, and natural products, and can exceed one million compounds. Successful integration of orphan receptors into the drug discovery pipeline would be greatly aided by methods and processes to support full deck high throughput or ultra-high throughput screening of these targets. Such integration would allow oGPCRs to be exposed to the entire chemical diversity contained within a large screening deck and is a complementary approach to the current endogenous ligand/focused screening paradigm.

Many GPCRs when overexpressed in heterologous systems (or when a mutant GPCR is expressed at endogenous levels), exhibit ligand independent, constitutive activity (de Ligt et al., 2000; Leurs et al., 2000). Constitutive receptor activity is generally understood as a spontaneous conversion of ligand-free receptors to an activated form that is capable of activating heterotrimeric G proteins and producing a measurable cellular response (Leurs et al., 1998). For orphan receptors, the presence of constitutive activity can provide a convenient indicator of receptor function and may reveal information about the receptor's signaling mechanism (Chalmers and Behan, 2002). Constitutive activity can also confer certain advantages during drug screening. For example, screening of cell lines expressing constitutively active receptors can result in an increased sensitivity toward agonists (Chen et al., 2000). In addition, since constitutively active receptors are sensitive to both agonists and inverse agonists, positive and negative modulators can be identified using the same cellular reagents or, possibly, during the same screening campaign (Chen et al., 2000).

Constitutive activity can be used, in conjunction with Aurora Biosciences' β-lactamase reporter system, to identify and select stable cell lines expressing functional oGPCRs for high-throughput screening. The bacterial β-lactamase reporter gene system has important features that make it ideally suited for orphan GPCR screening on an industrial scale. These include rapid assay development in conjunction with flow cytometry and compatibility with automated ultra-high throughput (uHTS) screening in highly miniaturized, cost-effective formats. Finally, screening cells that possess moderate to high constitutive receptor activity allows for identification of functional antagonists (inverse agonists), an ability that is absent from most deorphanizing assays in current use.

The orphan GPCR RAI-3 was first isolated as a retinoic-acid inducible transcript from the squamous carcinoma cell line, UMSCC-22B (Cheng and Lotan, 1998). Expression analysis revealed that RAI-3 transcripts were abundant in fetal and adult lung tissue, although expression is detected in other peripheral tissues as well. Based on sequence homologies to other G protein coupled receptors, RAI-3, and the closely related receptors GPCR5B, GPCR5C, and GPCR5D (Brauner-Osborne et al., 2001; Brauner-Osborne and Krogsgaard-Larsen, 2000; Robbins et al., 2000) define a Group 5 within the Family C family of GPCRs. In addition to the RAI-3 related receptors, Family C contains the metabotropic glutamate receptors, the metabotropic GABA-B receptors, and the calcium-sensing receptor. Most Family C receptors, which are typified by the presence of extremely long extracellular amino-terminal extensions. These amino-terminal regions have been proposed to form so-called "Venus Flytrap" structures and define the ligand binding domains and participate in heterodimerization of Family C receptors. RAI-3 and the other Group 5 receptors, however, possess relatively short amino-terminal extensions, making speculation about the endogenous RAI-3 ligand(s) difficult (Brauner-Osborne et al., 2001).

Both fully automated ultra-high throughput full-deck screening and focused screening deorphanizing methods to the identification of modulatory ligands for the orphan GPCR, RAI-3, is described.

Materials and Methods

Compounds and Compound Screening Plates

The orphan receptor deorphanizing ligand library was constructed from commercially available GPCR compound libraries. The Neurotransmitter, Bioactive Lipid, and Orphan Ligand Libraries were obtained from BIOMOL Research Laboratories (Plymouth Meeting, Pa.), and the GPCR Peptide Ligand Library was purchased from Phoenix Pharmaceuticals (Belmont, Calif.). All other compounds were purchased from Sigma-Aldrich (St. Louis, Mo.). Prior to use, the peptides in the GPCR Peptide Ligand Library were diluted to 10 μM final concentration using the manufacturer's peptide storage buffer. The concentration and storage buffer of the molecules in the commercial libraries varied but was typically 10 mM in DMSO. The commercially obtained 96 well compound plates were reformatted into 384 well storage plates. For screening, GPCR compound libraries containing in-house synthesized molecules, along with several hundred known GPCR agonists present in the Bristol-Myers Squibb compound screening deck, were added to the deorphanizing ligand library (in-house compound concentration 1 mM in 100% DMSO). All compound plates destined for primary screening were replica plated and stored at −80° C. until use. Ten-point 1:3 serial dilutions of compounds for concentration-response testing were prepared in 100% DMSO using a Matrix Technologies SerialMate (Hudson, N.H.).

Cell Culture

All cell culture media and supplements were purchased from Invitrogen Life Technologies (Grand Island, N.Y.). The parental CHO-NFAT/G15-BLam cells were obtained from Aurora Biosciences (La Jolla, Calif.) (described herein) and maintained in Dulbecco's modified Eagle's medium supplemented with 10% heat-inactivated fetal bovine serum (FBS), 1 mM sodium pyruvate, 1×MEM nonessential amino acids, 200 μg/ml Zeocin™ and 3 μg/ml blasticidin. Cell lines stably expressing orphan GPCRs cells were maintained in the same media with the addition of 600 μg/ml Hygromycin B. Cells were routinely propagated by subculturing on a biweekly schedule.

Transient Transfection

HEK293 cells were cultured in modified Eagle's medium supplemented with 10% FBS and seeded at $8 \times 10^6$ cells per T-175 $cm^2$ tissue culture flask one day prior to transfections. Transfections were performed with 12 μg of total DNA per flask using the Lipofectamine Plus™ reagent (Invitrogen Life Technologies, Grand Island, N.Y.) according to the manufacturer's instructions. Cells were transfected with a 50:50 mixture of pcDNA3-Gα15 and pcDNA3.1-RAI-3 FLAG plasmids, pcDNA3.1 (mock transfections) or pcDNA3.1-Topaz (evaluation of transfection efficiency). Twenty-four hours after transfection, cells co-transfected with RAI-3+Gα15, and the mock transfected cells, were harvested, counted and seeded into 384 well plates for the calcium imaging assay (see below). Cells transfected with Topaz were harvested and transfection efficiency was determined by FACS using the

Beta-Lactamase Assay

The day before the assay, cell lines displaying RAI-3 expression were plated into 384-well assay plates at a density of 15,000 cells/well in Dulbecco's modified Eagle's medium containing 2.5% heat-inactivated FBS, 25 mM HEPES, 1 mM sodium pyruvate, and 1×MEM nonessential amino acids. Plates were incubated overnight at 37° C. in an atmosphere containing 5% $CO_2$. The day of the assay, cells were treated with a positive control stimulus (1 µM thapsigargin and 10 nM phorbol 12-myristate 13-acetate (PMA) in cell culture medium), a negative control stimulus (cell culture medium), or test compound. The final concentration of DMSO in the assay wells was 0.5%. For concentration-response testing, the highest concentration of compound in the assay was 50 µM. All concentration-response assays were performed in triplicate. Following a 4 hour incubation at 37° C. to allow for expression of the β-lactamase enzyme, ⅙ volume of a cell loading solution containing 12 µM CCF2-AM (PanVera LLC, Madison, Wis.), 6 mg/ml pluronic F127 (prepared as a 100 mg/ml stock in DMSO containing 10% acetic acid), and 15 mM probenecid was added and the cells incubated for 1-2 hours at room temperature. Beta-lactamase activity was measured on an LJL fluorescence plate reader fitted with a 425 nm long-pass dichroic mirror, a 405±10 nm excitation filter, and 460±20 nm and 530±25 nm emission filters. Compound responses, either stimulatory or inhibitory, were determined by comparing the cell-associated fluorescence in the test well to that of the negative control (medium only) wells.

Ultra-High Throughput Screening

Ultra-high throughput screening (uHTS) was performed using an Aurora Ultra High Throughput Screening System (UHTSS™, Aurora Instruments, LLC, La Jolla). Assay-ready 3456-well screening plates were prepared by predispensing 7.5 nL of test compound (1 mM in 100% DMSO) per well with the Piezo Sample Dispensing Robot™ (PSDR). Assay-ready screening plates were stored at 4° C. for no more than 30 days. On each screening day, cells were harvested from ~90% confluent T-175 tissue culture flasks using non-enzymatic cell dissociation buffer. Cells were resuspended in fresh culture medium (containing 2.5% heat-inactivated FBS, 25 mM HEPES, 1 mM sodium pyruvate, and 1×MEM nonessential amino acids), and 0.75 µL of the cell suspension was dispensed into the assay plates. An additional 0.75 µl of media or the thapsigargin/PMA cocktail was added to compound wells and control wells, respectively. Following a 4 hr incubation at 37° C./5% $CO_2$, 0.3 µL of the cell loading solution containing 12 uM CCF2/AM and probenecid was added. All cell and reagent additions were performed by the 3456-well Reagent Dispensing Robot™ (RDR). After a one hour incubation at room temperature, the assay plates were read on the Topology Compensating Plate Reader™ (TcPR) set for 400 nM excitation and dual emission reads of 460 and 535 nM. A flow chart of the process is presented in FIG. 3. The TcPR photomultiplier gain was set to 900 volts per channel. This procedure was followed for each of the cell lines and repeated on each day that the screen was to be run. Hits were defined as compounds displaying activities greater than 3 standard deviations above (for agonists) or below (for inverse agonists) the sample mean. Compounds selected as hits were subsequently hit-picked from the original source plate utilizing the Hit Picking Robot™ (HPR) in a fully automated manner on the UHTSS. Briefly, 6-point serial dilutions for each compound were prepared in intermediate 384-well storage plates. The intermediate CRC source plates were reformatted into 3456-well plates by the PSDR, which also prepared 5 separate dilutions from each of the original dilutions. The highest concentration of compound in the UHTSS concentration-response assay was typically 12 µM. The final DMSO concentration ranged from 1.2%-0.33%. All concentration-response assays were performed simultaneously against the original RAI-3 clonal line and its constitutive activity matched comparison line. Primary hits displaying selective activity at the RAI-3 cell line were considered to be confirmed hits.

Calcium Imaging Assay

Transiently transfected HEK293 cells were detached with Cell Dissociation Buffer, resuspended in phenol red-free Dulbecco's modified Eagle's medium supplemented with 20 mM HEPES, pH 7.2, and plated at 15,000 cells per well in poly-d-lysine coated 384 well assay plates (Coming Life Sciences, Acton, Mass.). Following an overnight incubation at 37° C./5% $CO_2$, cells were loaded for 90 minutes with the cell-permeable calcium indicator, Fluo-4 (TEF Labs, Austin, Tex.). The loading solution (3×) contained 10 µg/ml Fluo-4 and 0.5 mg/ml pluronic F127 in Hanks Balanced Salt Solution supplemented with 20 mM HEPES. Stable RAI-3 cell lines in the CHO-NFAT/G15 background were processed identically except that the cells were plated overnight in medium containing 1% HI-FBS, and the loading solution contained 7.5 mM probenecid (final concentration 2.5 mM). The assay was initiated by the addition of 20 µL of a 2.5× compound solution, diluted in the HEPES-buffered Hanks solution. Control wells received dilution buffer only (negative controls) or a challenge dose of either carbachol or ATP at 100 µM final concentration, both of which activate endogenous HEK293 GPCRs that are coupled to calcium mobilization. Changes in intracellular calcium concentration in response to compound addition were imaged using a Molecular Devices FLIPR™. The final compound concentrations in the FLIPR primary screening assay was 160 µM, 16 µM, and 160 nM for the commercial compounds, in-house library compounds, and commercial peptides, respectively. All primary screening hits were analyzed by retesting in duplicate at the same compound concentrations used for primary screening. Confirmed positives (those active during retest) were further analyzed by concentration-response testing, and the highest compound concentration in this assay was 160 µM. All concentration-response assays were performed in triplicate.

Statistical Calculations

The following statistical measures were used to calculate assay robustness ($x_1$ and $x_3$ are the means of the minimum and maximum signals, and $s_1$ and $s_3$ are the respective standard deviations):

$$Z' = 1 - \left( \frac{3s_3 + 3s_1}{\overline{x}_3 - \overline{x}_1} \right)$$

$$\text{Signal Window} = \frac{(\overline{x}_3 - 3s_3) - (\overline{x}_1 + 3s_1)}{\sqrt{\frac{(s_1^2 + s_3^2)}{2}}}$$

-continued $$\text{Signal-to-Noise} = \frac{(\bar{x}_3 - \bar{x}_1)}{\sqrt{s_3^2 + s_1^2}}$$

Selection of Cell Lines for Ultra-High Throughput Screening

Candidate stable β-lactamase reporter cell lines expressing the orphan GPCR, RAI-3, were tested to determine their suitability for HTS. Beta-lactamase activity is assessed by monitoring changes in the fluorescence resonance energy transfer (FRET) between the β-lactam-linked coumarin and fluorescein dye pairs of CCF2. In conditions of low β-lactamase expression, excitation of the coumarin results in efficient FRET, strong emission at 530 nm and a low $em_{460}/em_{530}$ ratio. Expression of β-lactamase enzyme results in cleavage of the β-lactam moiety and disruption of FRET, leading to increased coumarin emission at 460 nm, and a resulting increase in the $em_{460}/em_{530}$ ratio (Zlokarnik et al., 1998). The constitutive β-lactamase activity of each cell line was estimated by comparing the observed β-lactamase activity of the orphan cell lines to that of the CHO-G15/NFAT parental cell line. The ability of each of the cell lines to produce a positive response was determined by the activity obtained following exposure of the cells to the PMA cocktail. Statistical measures were calculated for each orphan in "agonist mode" (using the basal and PMA-inducible activities of the orphan cell line as the minimum and maximum) and in "inverse-agonist mode" (using the basal orphan activity as the maximum signal, and the parental basal activity as the minimum signal). Cell lines with an assay Z' of at least 0.5 in either agonist or antagonist mode were selected for screening. Two cell lines stably expressing RAI-3 were selected for parallel screening on the Aurora Ultra High Throughput Screening System (UHTSS™). One RAI-3 cell line (RAI-3 Clone E8) possessed very low constitutive activity, thereby permitting the identification of agonists only. The other RAI-3 cell line (Clone B8) possessed sufficient constitutive activity to permit the detection of both agonists and inverse agonists. Both cell lines displayed acceptable assay performance during validation and testing (Tables 1 and 2). During assay validation, the Z' for RAI-3 Clone B8 was below 0.5. However, since this clone, unlike the other RAI-3 cell lines investigated, had moderately high constitutive activity, it also was selected for screening. Two additional orphan receptor cell lines were validated and screened at the same time. Both of these other orphans receptors belong to GPCR Family A (rhodopsin-like). One is a putative peptide receptor while the other has the greatest similarity to receptors for biogenic amines. These cell lines were chosen in part because their constitutive activities roughly corresponded to the constitutive activities displayed by the RAI-3 cell lines. This allowed for selectivity comparisons to be made for the primary screening hits. All four cell lines were derived from the same parental cells, CHO NFAT/Gα$_{15}$, and utilized the β-lactamase reporter. All the clones were previously confirmed to express the appropriate orphan receptor at the mRNA and protein levels (described elsewhere herein).

Compound Identification—UHTSS™

Approximately 290,000 compounds were screened in triplicate against the four cell lines, with almost 4 million data points and 3,000 concentration-response curves generated in 8 weeks. During screening, the assay Z' for both cell lines was typically greater than 0.5 (data not shown). A total of thirty-three hits were identified for the two RAI-3 cell lines. Approximately half ($^{16}/_{33}$) appeared to possess agonist activity in the UHTSS beta-lactamase screen, and of these six compounds were active at both the RAI-3 Clone B8 and RAI-3 Clone E8 cell lines. By comparison, there were 27 and 12 hits for the orphan cell lines with moderate and low constitutive activity, respectively. All of the RAI-3 primary hits were tested in concentration-response experiments for agonist activity using a 384-well β-lactamase assay and a 384-well calcium imaging assay. Both these follow-up assays permitted the use of higher starting compound concentrations than did the closed-loop UHTSS process. In addition, the calcium imaging assay employed transiently transfected HEK293, permitting confirmation in an independent assay. The follow-up testing confirmed three of the original 33 UHTSS hits as potential surrogate agonists for RAI-3 (Table 2). One of these three compounds showed selective agonist activity for RAI-3 in the 384-well β-lactamase assay and in the HEK293 transient calcium assay. A second compound was a selective agonist in the HEK293 transient calcium assay but was a nonselective agonist in the 384-well β-lactamase assay. The third compound, while a selective agonist in the HEK293 transient calcium assay, was inactive in the 384-well β-lactamase assay.

TABLE 2

| Compound | Clone B8 uHTSS | Clone E8 uHTSS | HEK FLIPR | 384-Well Lactamase |
|---|---|---|---|---|
| 1 | Agonist | Agonist | Selective agonist | Selective agonist |
| 2 | Agonist | Agonist | Selective agonist | Nonselective agonist |
| 3 | Agonist | Agonist | Selective agonist | Inactive |

Thirty substances of interest from the RAI-3 ultra-high throughput screening campaign, were identified. These were followed up using 384-well β-lactamase and calcium imaging assays. Three substances displayed some degree of selectivity in the follow-up assays: Compound 1 was selectively active in the 384 well lactamase assay and the HEK transient FLIPR assay; Compound 2 was selectively active in the HEK transient FLIPR assay but was active in all CHO lines tested; and Compound 3 was inactive in all CHO cell assays but was selectively active in the HEK transient FLIPR assay.

A response curve for Compound 1 measuring the level of modulation of RAI-3 constitutive activity is provided in FIG. 35A. A response curve for Compound 1 measuring the level of modulation of the constitutive activity of another G-protein coupled receptor, HGPRBMY7 is provided in FIG. 35B. The data demonstrates that the screening method for RAI-3 is capable of identifying selective modulators of RAI-3.

LITERATURE CITED

Bockaert, J., Claeysen, S., Becamel, C., Pinloche, S., and Dumuis, A. (2002). G protein-coupled receptors: dominant players in cell-cell communication. Int Rev Cytol 212, 63-132.

Brauner-Osborne, H., Jensen, A. A., Sheppard, P. O., Brodin, B., Krogsgaard-Larsen, P., and O'Hara, P. (2001). Cloning and characterization of a human orphan family C G-protein coupled receptor GPRC5D. Biochim Biophys Acta 1518, 237-248.

Brauner-Osborne, H., and Krogsgaard-Larsen, P. (2000). Sequence and expression pattern of a novel human orphan G-protein-coupled receptor, GPRC5B, a family C receptor with a short amino-terminal domain. Genomics 65, 121-128.

Chalmers, D. T., and Behan, D. P. (2002). The use of constitutively active GPCRs in drug discovery and functional genomics. Nat Rev Drug Discovery 1, 599-608.

Chen, G., Way, J., Armour, S., Watson, C., Queen, K., Jayawickreme, C. K., Chen, W. J., and Kenakin, T. (2000). Use of constitutive G protein-coupled receptor activity for drug discovery. Mol Pharmacol 57, 125-134.

Cheng, Y., and Lotan, R. (1998). Molecular cloning and characterization of a novel retinoic acid-inducible gene that encodes a putative G protein-coupled receptor. J Biol Chem 273, 35008-35015.

Civelli, O. (1998). Functional genomics, the search for novel neurotransmitters and neuropeptides. FEBS Letters 430, 55-58.

de Ligt, R. A., Kourounakis, A. P., and A P, I. J. (2000). Inverse agonism at G protein-coupled receptors: (patho) physiological relevance and implications for drug discovery. Br J Pharmacol 130, 1-12.

Hinuma, S., Onda, H., and Fujino, M. (1999). The quest for novel bioactive peptides utilizing orphan seven-transmembrane-domain receptors. J Mol Med 77, 495-504.

Howard, A. D., McAllister, G., Feighner, S. D., Liu, Q., Nargund, R. P., Van der Ploeg, L. H., and Patchett, A. A. (2001). Orphan G-protein-coupled receptors and natural ligand discovery. Trends Pharmacol Sci 22, 132-140.

Lander, E. S., Linton, L. M., Birren, B., Nusbaum, C., Zody, M. C., Baldwin, J., Devon, K., Dewar, K., Doyle, M., FitzHugh, W., et al. (2001). Initial sequencing and analysis of the human genome. Nature 409, 860-921.

Leurs, R., Rodriguez Pena, M. S., Bakker, R. A., Alewijnse, A. E., and Timmerman, H. (2000). Constitutive activity of G protein coupled receptors and drug action. Pharm Acta Helv 74, 327-331.

Leurs, R., Smit, M. J., Alewijnse, A. E., and Timmerman, H. (1998). Agonist-independent regulation of constitutively active G-protein-coupled receptors. Trends Biochem Sci 23, 418-422.

Milligan, G., Marshall, F., and Rees, S. (1996). G(16) as a universal G protein adapter: implications for agonist screening strategies. Trends Pharmacol Sci 17, 235-237.

Milligan, G., and Rees, S. (1999). Chimaeric G alpha proteins: their potential use in drug discovery. Trends Pharmacol Sci 20, 118-124.

Offermanns, S., and Simon, M. I. (1995). G alpha 15 and G alpha 16 couple a wide variety of receptors to phospholipase C. J Biol Chem 270, 15175-15180.

Pierce, K. L., Premont, R. T., and Lefkowitz, R. J. (2002). Seven-transmembrane receptors. Nature Reviews Mol Cell Biol 3, 639-650.

Robbins, M. J., Michalovich, D., Hill, J., Calver, A. R., Medhurst, A. D., Gloger, I., Sims, M., Middlemiss, D. N., and Pangalos, M. N. (2000). Molecular cloning and characterization of two novel retinoic acid-inducible orphan G-protein-coupled receptors (GPRC5B and GPRC5C). Genomics 67, 8-18.

Sambrook, J., and Russell, D. W. (2001). Molecular Cloning: A Laboratory Manual, 3rd Edition (Cold Spring Harbor, Cold Spring Harbor Laboratory Press).

Szekeres, P. G. (2002). Functional assays for identifying ligands at orphan G protein-coupled receptors. Receptors and Channels 8, 297-308.

Venter, J. C., Adams, M. D., Myers, E. W., Li, P. W., Mural, R. J., Sutton, G. G., Smith, H. O., Yandell, M., Evans, C. A., Holt, R. A., et al. (2001). The sequence of the human genome. Science 291, 1304-1351.

Zlokarnik, G., Negulescu, P. A., Knapp, T. E., Mere, L., Burres, N., Feng, L., Whitney, M., Roemer, K., and Tsien, R. Y. (1998). Quantitation of transcription and clonal selection of single living cells with beta-lactamase as reporter. Science 279, 84-88.

The contents of all patents, patent applications, published PCT applications and articles, books, references, reference manuals, abstracts, the Sequence Listing and internet websites cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

SEQUENCE LISTING

```
<160> NUMBER OF SEQ ID NOS: 98

<210> SEQ ID NO 1
<211> LENGTH: 14
<212> TYPE: PRT
<213> ORGANISM: Homo sapiens

<400> SEQUENCE: 1

Ala His Ala Trp Pro Ser Pro Tyr Lys Asp Tyr Glu Val Lys
1               5                   10

<210> SEQ ID NO 2
<211> LENGTH: 2456
<212> TYPE: DNA
<213> ORGANISM: Homo sapiens

<400> SEQUENCE: 2
ataacagcat gaagtgccgt ggaactggaa taggcgtgtc ctctccctcg accctccccc      60
```

-continued

```
tccttgtccc tctgctcacc cctcgctcgt tccctccctc cggcgagggc cgccttata    120 acaactgctc agagtgcgag ggcgggatag ctgtccaagg tctcccccag cactgaggag    180
ctcgcctgct gccctcttgc gcgcgggaag cagcaccaag ttcacggcca acgccttggc    240
actagggtcc agaatggcta caacagtccc tgatggttgc cgcaatggcc tgaaatccaa    300
gtactacaga ctttgtgata aggctgaagc ttggggcatc gtcctagaaa cggtggccac    360
agccggggtt gtgacctcgg tggccttcat gctcactctc ccgatcctcg tctgcaaggt    420
gcaggactcc aacaggcgaa aaatgctgcc tactcagttt ctcttcctcc tgggtgtgtt    480
gggcatcttt ggcctcacct tcgccttcat catcggactg gacgggagca cagggcccac    540
acgcttcttc ctctttggga tcctcttttc catctgcttc cctgcctgc tggctcatgc     600 tgtcagtctg accaagctcg tccggggag gaagccccctt tccctgttgg tgattctggg    660
tctggccgtg ggcttcagcc tagtccagga tgttatcgct attgaatata ttgtcctgac    720
catgaatagg accaacgtca atgtcttttc tgagctttcc gctcctcgtc gcaatgaaga    780 cttttgtcctc ctgctcacct acgtcctctt cttgatggcg ctgaccttcc tcatgtcctc    840
cttcaccttc tgtggttcct tcacgggctg gaagagacat ggggcccaca tctacctcac    900
gatgctcctc tccattgcca tctgggtggc ctggatcacc ctgctcatgc ttcctgactt    960
tgaccgcagg tgggatgaca ccatcctcag ctccgccttg gctgccaatg gctgggtgtt   1020
cctgttggct tatgttagtc ccgagttttg gctgctcaca aagcaacgaa accccatgga   1080
ttatcctgtt gaggatgctt tctgtaaacc tcaactcgtg aagaagagct atggtgtgga   1140
gaacagagcc tactctcaag aggaaatcac tcaaggtttt gaagagacag gggacacgct   1200
ctatgccccc tattccacac attttcagct gcagaaccag cctcccccaaa aggaattctc   1260 catcccacgg gcccacgctt ggccgagccc ttacaaagac tatgaagtaa agaaagaggg   1320
cagctaactc tgtcctgaag agtgggacaa atgcagccgg gcggcagatc tagcgggagc   1380
tcaaagggat gtgggcgaaa tcttgagtct tctgagaaaa ctgtacaaga cactacggga   1440
acagtttgcc tccctcccag cctcaaccac aattcttcca tgctggggct gatgtgggct   1500
agtaagactc cagttcttag aggcgctgta gtattttttt tttttgtct catcctttgg    1560 atacttcttt taagtgggag tctcaggcaa ctcaagttta gacccttact ctttttgttt   1620
gttttttgaa acaggatctt gctctgtcac ccaggcttga gtgcagtggt gcgatcacag   1680
cccagtgcag cctcgaccac ctgtgctcaa gcaatcctcc catctccatc tcccaaagtg   1740
ctgggatgac aggcgtgagc cacagctccc agcctaggcc cttaatcttg ctgttattt    1800 ccatggacta aaggtctggt catctgagct cacgctggct cacacagctc tagggggcctg  1860 ctcctctaac tcacagtggg ttttgtgagg ctctgtggcc cagagcagac ctgcatatct   1920
gagcaaaaat agcaaaagcc tctctcagcc cactggcctg aatctacact ggaagccaac   1980
ttgctggcac ccccgctccc caaccttct tgcctgggta ggagaggcta aagatcaccc     2040
taaatttact catctctcta gtgctgcctc acattgggcc tcagcagctc cccagcacca   2100
attcacaggt caccctctc ttcttgcact gtccccaaac ttgctgtcaa ttccgagatc     2160
taatctcccc ctacgctctg ccaggaattc tttcagacct cactagcaca agcccggttg   2220
ctccttgtca ggagaatttg tagatcattc tcacttcaaa ttcctggggc tgatacttct   2280
ctcatcttgc accccaacct ctgtaaatag atttaccgca tttacggctg cattctgtaa   2340
gtgggcatgg tctcctaatg gaggagtgtt cattgtataa taagttattc acctgagtat   2400
```
gcaataaaga tgtggtggcc actctttcat ggtggtggca gcaaaaaaaa aaaaaa    2456

<210> SEQ ID NO 3
<211> LENGTH: 357
<212> TYPE: PRT
<213> ORGANISM: Homo sapiens

<400> SEQUENCE: 3

```
Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
50                  55                  60

Leu Pro Thr Gln Phe Leu Phe Leu Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
            100                 105                 110

Leu Ala His Ala Val Ser Leu Thr Lys Leu Val Arg Gly Arg Lys Pro
        115                 120                 125

Leu Ser Leu Leu Val Ile Leu Gly Leu Ala Val Gly Phe Ser Leu Val
130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Thr Tyr Val Leu Phe Leu Met Ala Leu Thr Phe
            180                 185                 190

Leu Met Ser Ser Phe Thr Phe Cys Gly Ser Phe Thr Gly Trp Lys Arg
        195                 200                 205

His Gly Ala His Ile Tyr Leu Thr Met Leu Leu Ser Ile Ala Ile Trp
210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
            260                 265                 270

Asn Pro Met Asp Tyr Pro Val Glu Asp Ala Phe Cys Lys Pro Gln Leu
        275                 280                 285

Val Lys Lys Ser Tyr Gly Val Glu Asn Arg Ala Tyr Ser Gln Glu Glu
290                 295                 300

Ile Thr Gln Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
                325                 330                 335

Ile Pro Arg Ala His Ala Trp Pro Ser Pro Tyr Lys Asp Tyr Glu Val
            340                 345                 350

Lys Lys Glu Gly Ser
        355
```

<210> SEQ ID NO 4
<211> LENGTH: 345
<212> TYPE: PRT
<213> ORGANISM: Homo sapiens

<400> SEQUENCE: 4

```
Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
        115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
            260                 265                 270

Cys Pro Leu Gln Gly Asn Ala Cys Pro Val Thr Ala Tyr Gln His Ser
        275                 280                 285

Phe Gln Val Glu Asn Gln Glu Leu Ser Arg Ala Arg Asp Ser Asp Gly
    290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345
```

<210> SEQ ID NO 5
<211> LENGTH: 300
<212> TYPE: PRT
<213> ORGANISM: Mus musculus -continued

<400> SEQUENCE: 5

Met Tyr Glu Asp Cys Val Lys Ser Thr Glu Asp Tyr Tyr Leu Phe Cys
1               5                   10                  15

Asp Asn Glu Gly Pro Trp Ala Ile Val Leu Glu Ser Leu Ala Val Ile
            20                  25                  30

Gly Ile Val Val Thr Ile Leu Leu Leu Ala Phe Leu Phe Leu Met
        35                  40                  45

Arg Lys Val Gln Asp Cys Ser Gln Trp Asn Val Leu Pro Thr Gln Phe
50                  55                  60

Leu Phe Leu Leu Ala Val Leu Gly Leu Phe Gly Leu Thr Phe Ala Phe
65                  70                  75                  80

Ile Ile Gln Leu Asn His Gln Thr Ala Pro Val Arg Tyr Phe Leu Phe
                85                  90                  95

Gly Val Leu Phe Ala Ile Cys Phe Ser Cys Leu Leu Ala His Ala Ser
            100                 105                 110

Asn Leu Val Lys Leu Val Arg Gly Arg Val Ser Phe Cys Trp Thr Thr
        115                 120                 125

Ile Leu Phe Ile Ala Ile Gly Val Ser Leu Leu Gln Thr Ile Ile Ala
130                 135                 140

Ile Glu Tyr Val Thr Leu Ile Met Thr Arg Gly Leu Met Phe Glu His
145                 150                 155                 160

Met Thr Pro Tyr Gln Leu Asn Val Asp Phe Val Cys Leu Leu Ile Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ala
        195                 200                 205

Thr Val Leu Val Ser Ile Ile Trp Val Val Trp Ile Ser Met Leu
210                 215                 220

Leu Arg Gly Asn Pro Gln Leu Gln Arg Gln Pro His Trp Asp Asp Ala
225                 230                 235                 240

Val Ile Cys Ile Gly Leu Val Thr Asn Ala Trp Val Phe Leu Leu Ile
                245                 250                 255

Tyr Ile Ile Pro Glu Leu Ser Ile Leu Tyr Arg Ser Cys Arg Gln Glu
            260                 265                 270

Cys Pro Thr Gln Gly Asn Val Cys Gln Val Pro Val Tyr Gln Arg Ser
        275                 280                 285

Phe Arg Met Asp Thr Gln Glu Pro Thr Arg Glu Cys
290                 295                 300

<210> SEQ ID NO 6
<211> LENGTH: 403
<212> TYPE: PRT
<213> ORGANISM: Homo sapiens

<400> SEQUENCE: 6

Met Phe Val Ala Ser Glu Arg Lys Met Arg Ala His Gln Val Leu Thr
1               5                   10                  15

Phe Leu Leu Leu Phe Val Ile Thr Ser Val Ala Ser Glu Asn Ala Ser
            20                  25                  30

Thr Ser Arg Gly Cys Gly Leu Asp Leu Leu Pro Gln Tyr Val Ser Leu
        35                  40                  45

Cys Asp Leu Asp Ala Ile Trp Gly Ile Val Val Glu Ala Val Ala Gly
50                  55                  60

Ala Gly Ala Leu Ile Thr Leu Leu Leu Met Leu Ile Leu Leu Val Arg
65                  70                  75                  80

Leu Pro Phe Ile Lys Glu Lys Glu Lys Lys Ser Pro Val Gly Leu His
                85                  90                  95

Phe Leu Phe Leu Leu Gly Thr Leu Gly Leu Phe Gly Leu Thr Phe Ala
            100                 105                 110

Phe Ile Ile Gln Glu Asp Glu Thr Ile Cys Ser Val Arg Arg Phe Leu
            115                 120                 125

Trp Gly Val Leu Phe Ala Leu Cys Phe Ser Cys Leu Leu Ser Gln Ala
        130                 135                 140

Trp Arg Val Arg Arg Leu Val Arg His Gly Thr Gly Pro Ala Gly Trp
145                 150                 155                 160

Gln Leu Val Gly Leu Ala Leu Cys Leu Met Leu Val Gln Val Ile Ile
                165                 170                 175

Ala Val Glu Trp Leu Val Leu Thr Val Leu Arg Asp Thr Arg Pro Ala
            180                 185                 190

Cys Ala Tyr Glu Pro Met Asp Phe Val Met Ala Leu Ile Tyr Asp Met
            195                 200                 205

Val Leu Leu Val Val Thr Leu Gly Leu Ala Leu Phe Thr Leu Cys Gly
210                 215                 220

Lys Phe Lys Arg Trp Lys Leu Asn Gly Ala Phe Leu Leu Ile Thr Ala
225                 230                 235                 240

Phe Leu Ser Val Leu Ile Trp Val Ala Trp Met Thr Met Tyr Leu Phe
            245                 250                 255

Gly Asn Val Lys Leu Gln Gln Gly Asp Ala Trp Asn Asp Pro Thr Leu
            260                 265                 270

Ala Ile Thr Leu Ala Ala Ser Gly Trp Val Phe Val Ile Phe His Ala
        275                 280                 285

Ile Pro Glu Ile His Cys Thr Leu Leu Pro Ala Leu Gln Glu Asn Thr
        290                 295                 300

Pro Asn Tyr Phe Asp Thr Ser Gln Pro Arg Met Arg Glu Thr Ala Phe
305                 310                 315                 320

Glu Glu Asp Val Gln Leu Pro Arg Ala Tyr Met Glu Asn Lys Ala Phe
            325                 330                 335

Ser Met Asp Glu His Asn Ala Ala Leu Arg Thr Ala Gly Phe Pro Asn
            340                 345                 350

Gly Ser Leu Gly Lys Arg Pro Ser Gly Ser Leu Gly Lys Arg Pro Ser
        355                 360                 365

Ala Pro Phe Arg Ser Asn Val Tyr Gln Pro Thr Glu Met Ala Val Val
        370                 375                 380

Leu Asn Gly Gly Thr Ile Pro Thr Ala Pro Pro Ser His Thr Gly Arg
385                 390                 395                 400

His Leu Trp

<210> SEQ ID NO 7
<211> LENGTH: 498
<212> TYPE: PRT
<213> ORGANISM: Homo sapiens

<400> SEQUENCE: 7

Met Phe Val Ala Ser Glu Arg Lys Met Arg Ala His Gln Val Leu Thr
1               5                   10                  15

Phe Leu Leu Leu Phe Val Ile Thr Ser Val Ala Ser Glu Asn Ala Ser
            20                  25                  30

-continued

Thr Ser Arg Gly Cys Gly Leu Asp Leu Leu Pro Gln Tyr Val Ser Leu
         35                  40                  45

Cys Asp Leu Asp Ala Ile Trp Gly Ile Met Ala Ile His Lys Ala Leu
 50                  55                  60

Val Met Cys Leu Gly Leu Pro Leu Phe Leu Phe Pro Gly Ala Trp Ala
 65                  70                  75                  80

Gln Gly His Val Pro Pro Gly Cys Ser Gln Gly Leu Asn Pro Leu Tyr
                 85                  90                  95

Tyr Asn Leu Cys Asp Arg Ser Gly Ala Trp Gly Ile Val Leu Glu Ala
                100                 105                 110

Val Ala Gly Ala Gly Ile Val Thr Thr Phe Val Leu Thr Ile Ile Leu
             115                 120                 125

Val Ala Ser Leu Pro Phe Val Gln Asp Thr Lys Lys Arg Ser Leu Leu
 130                 135                 140

Gly Thr Gln Val Phe Phe Leu Leu Gly Thr Leu Gly Leu Phe Cys Leu
145                 150                 155                 160

Val Phe Ala Cys Val Val Lys Pro Asp Phe Ser Thr Cys Ala Ser Arg
                 165                 170                 175

Arg Phe Leu Phe Gly Val Leu Phe Ala Ile Cys Phe Ser Cys Leu Ala
                 180                 185                 190

Ala His Val Phe Ala Leu Asn Phe Leu Ala Arg Lys Asn His Gly Pro
            195                 200                 205

Arg Gly Trp Val Ile Phe Thr Val Ala Leu Leu Leu Thr Leu Val Glu
        210                 215                 220

Val Ile Ile Asn Thr Glu Trp Leu Ile Ile Thr Leu Val Arg Gly Ser
225                 230                 235                 240

Gly Glu Gly Gly Pro Gln Gly Asn Ser Ser Ala Gly Trp Ala Val Ala
                245                 250                 255

Ser Pro Cys Ala Val Ala Asn Met Asp Phe Val Met Ala Leu Ile Tyr
                260                 265                 270

Val Met Leu Leu Leu Leu Gly Ala Phe Leu Gly Ala Trp Pro Ala Leu
            275                 280                 285

Cys Gly Arg Tyr Lys Arg Trp Arg Lys His Gly Val Phe Val Leu Leu
        290                 295                 300

Thr Thr Ala Thr Ser Val Ala Ile Trp Val Val Trp Ile Val Met Tyr
305                 310                 315                 320

Thr Tyr Gly Asn Lys Gln His Asn Ser Pro Thr Trp Asp Asp Pro Thr
                325                 330                 335

Leu Ala Ile Ala Leu Ala Ala Asn Ala Trp Ala Phe Val Leu Phe Tyr
            340                 345                 350

Val Ile Pro Glu Val Ser Gln Val Thr Lys Ser Ser Pro Glu Gln Ser
        355                 360                 365

Tyr Gln Gly Asp Met Tyr Pro Thr Arg Gly Val Gly Tyr Glu Thr Ile
    370                 375                 380

Leu Lys Glu Gln Lys Gly Gln Ser Met Phe Val Glu Asn Lys Ala Phe
385                 390                 395                 400

Ser Met Asp Glu Pro Val Ala Ala Lys Arg Pro Val Ser Pro Tyr Ser
                405                 410                 415

Gly Tyr Asn Gly Gln Leu Leu Thr Ser Val Tyr Gln Pro Thr Glu Met
            420                 425                 430

Ala Leu Met His Lys Val Pro Ser Glu Gly Ala Tyr Asp Ile Ile Leu
        435                 440                 445

```
Pro Arg Ala Thr Ala Asn Ser Gln Val Met Gly Ser Ala Asn Ser Thr
    450                 455                 460

Leu Arg Ala Glu Asp Met Tyr Ser Ala Gln Ser His Gln Ala Ala Thr
465                 470                 475                 480

Pro Pro Lys Asp Gly Lys Asn Ser Gln Val Phe Arg Asn Pro Tyr Val
                485                 490                 495

Trp Asp

<210> SEQ ID NO 8
<211> LENGTH: 357
<212> TYPE: PRT
<213> ORGANISM: Homo sapiens

<400> SEQUENCE: 8

Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
                20                  25                  30

Thr Val Ala Thr Ala Gly Val Val Thr Ser Val Ala Phe Met Leu Thr
                35                  40                  45

Leu Pro Ile Leu Val Cys Lys Val Gln Asp Ser Asn Arg Arg Lys Met
            50                  55                  60

Leu Pro Thr Gln Phe Leu Phe Leu Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
                100                 105                 110

Leu Ala His Ala Val Gly Leu Thr Lys Leu Val Arg Gly Arg Lys Pro
            115                 120                 125

Leu Ser Leu Leu Val Ile Leu Gly Leu Ala Val Gly Phe Ser Leu Val
            130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Thr Tyr Val Leu Phe Leu Met Ala Leu Thr Phe
                180                 185                 190

Leu Met Ser Ser Phe Thr Phe Cys Gly Ser Phe Thr Gly Trp Lys Arg
            195                 200                 205

His Gly Ala His Ile Tyr Leu Thr Met Leu Leu Ser Ile Ala Ile Trp
            210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
                260                 265                 270

Asn Pro Met Asp Tyr Pro Val Glu Asp Ala Phe Cys Lys Pro Gln Leu
            275                 280                 285

Val Lys Lys Ser Tyr Gly Val Glu Asn Arg Ala Tyr Ser Gln Glu Glu
            290                 295                 300

Ile Thr Gln Gly Phe Glu Glu Thr Gly Asp Thr Leu Tyr Ala Pro Tyr
305                 310                 315                 320
```

```
Ser Thr His Phe Gln Leu Gln Asn Gln Pro Pro Gln Lys Glu Phe Ser
            325                 330                 335

Ile Pro Arg Ala His Ala Trp Pro Ser Pro Tyr Lys Asp Tyr Glu Val
            340                 345                 350

Lys Lys Glu Gly Ser
        355

<210> SEQ ID NO 9
<211> LENGTH: 357
<212> TYPE: PRT
<213> ORGANISM: Homo sapiens

<400> SEQUENCE: 9

Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
50                  55                  60

Leu Pro Thr Gln Phe Leu Phe Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
            100                 105                 110

Leu Ala His Ala Val Ser Leu Thr Lys Leu Val Arg Gly Arg Lys Pro
        115                 120                 125

Leu Ser Leu Leu Val Ile Leu Gly Leu Ala Val Gly Phe Ser Leu Val
130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Thr Tyr Val Leu Phe Leu Met Ala Leu Thr Phe
            180                 185                 190

Leu Met Ser Ser Phe Thr Phe Cys Gly Ser Phe Thr Gly Trp Lys Arg
        195                 200                 205

His Gly Ala His Ile Tyr Leu Thr Met Leu Leu Ser Ile Ala Ile Trp
    210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
            260                 265                 270

Asn Pro Met Asp Tyr Pro Val Glu Asp Ala Phe Cys Lys Pro Gln Leu
        275                 280                 285

Val Lys Lys Ser Tyr Gly Val Glu Asn Arg Ala Tyr Ser Gln Glu Glu
    290                 295                 300

Ile Thr Arg Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
                325                 330                 335
```

```
Ile Pro Arg Ala His Ala Trp Pro Ser Pro Tyr Lys Asp Tyr Glu Val
            340                 345                 350

Lys Lys Glu Gly Ser
        355

<210> SEQ ID NO 10
<211> LENGTH: 59
<212> TYPE: PRT
<213> ORGANISM: Mus musculus

<400> SEQUENCE: 10

Asp Gly Ala Thr Gly Pro Thr Arg Phe Phe Leu Phe Gly Val Leu Phe
1               5                   10                  15

Ala Ile Cys Phe Ser Cys Leu Leu Ala His Ala Phe Asn Leu Ile Lys
            20                  25                  30

Leu Val Arg Gly Arg Lys Pro Leu Ser Trp Leu Val Ile Leu Ser Leu
        35                  40                  45

Ala Val Gly Phe Ser Leu Val Gln Asp Val Ile
    50                  55

<210> SEQ ID NO 11
<211> LENGTH: 59
<212> TYPE: PRT
<213> ORGANISM: Rattus norvetigus

<400> SEQUENCE: 11

Asp Arg Ala Thr Gly Pro Thr Arg Phe Phe Leu Phe Gly Val Leu Phe
1               5                   10                  15

Ala Leu Cys Phe Ser Cys Leu Leu Ala His Ala Phe Asn Leu Ile Lys
            20                  25                  30

Leu Val Arg Gly Arg Lys Pro Leu Ser Trp Leu Val Ile Leu Ser Leu
        35                  40                  45

Ala Val Gly Phe Ser Leu Val Gln Asp Val Ile
    50                  55

<210> SEQ ID NO 12
<211> LENGTH: 59
<212> TYPE: PRT
<213> ORGANISM: Bos taurus

<400> SEQUENCE: 12

Asn Gly Gly Thr Gly Pro Thr Arg Phe Phe Leu Phe Gly Val Leu Phe
1               5                   10                  15

Ala Leu Cys Phe Ser Cys Leu Leu Val His Ala Phe Asn Leu Thr Lys
            20                  25                  30

Leu Val Arg Gly Arg Gln Pro Leu Ser Met Leu Val Met Leu Gly Leu
        35                  40                  45

Ala Leu Gly Phe Ser Leu Val Gln Asp Ile Ile
    50                  55

<210> SEQ ID NO 13
<211> LENGTH: 59
<212> TYPE: PRT
<213> ORGANISM: Homo sapiens

<400> SEQUENCE: 13

Asp Gly Ser Thr Gly Pro Thr Arg Phe Phe Leu Phe Gly Ile Leu Phe
1               5                   10                  15

Ser Ile Cys Phe Ser Cys Leu Leu Ala His Ala Val Gly Leu Thr Lys
```

```
                20                  25                  30
Leu Val Arg Gly Arg Lys Pro Leu Ser Leu Leu Val Ile Leu Gly Leu
         35                  40                  45

Ala Val Gly Phe Ser Leu Val Gln Asp Val Ile
     50                  55

<210> SEQ ID NO 14
<211> LENGTH: 54
<212> TYPE: PRT
<213> ORGANISM: Homo sapiens

<400> SEQUENCE: 14

Glu Ile Thr Gln Gly Phe Glu Thr Gly Asp Thr Leu Tyr Ala Pro
1               5                   10                  15

Tyr Ser Thr His Phe Gln Leu Gln Asn Gln Pro Pro Gln Lys Glu Phe
                20                  25                  30

Ser Ile Pro Arg Ala His Ala Trp Pro Ser Pro Tyr Lys Asp Tyr Glu
             35                  40                  45

Val Lys Lys Glu Gly Ser
     50

<210> SEQ ID NO 15
<211> LENGTH: 54
<212> TYPE: PRT
<213> ORGANISM: Homo sapiens

<400> SEQUENCE: 15

Glu Ile Thr Arg Gly Phe Glu Thr Gly Asp Thr Leu Tyr Ala Pro
1               5                   10                  15

Tyr Ser Thr His Phe Gln Leu Gln Asn Gln Pro Pro Gln Lys Glu Phe
                20                  25                  30

Ser Ile Pro Arg Ala His Ala Trp Pro Ser Pro Tyr Lys Asp Tyr Glu
             35                  40                  45

Val Lys Lys Glu Gly Ser
     50

<210> SEQ ID NO 16
<211> LENGTH: 51
<212> TYPE: PRT
<213> ORGANISM: Mus musculus

<400> SEQUENCE: 16

Glu Ile Thr Gln Gly Leu Glu Met Gly Asp Thr Leu Tyr Ala Pro Tyr
1               5                   10                  15

Ser Thr His Phe Gln Leu Gln Asn His Gln Lys Asp Phe Ser Ile Pro
                20                  25                  30

Arg Ala Gln Ala Pro Ala Ser Pro Tyr Asn Asp Tyr Glu Gly Arg Lys
             35                  40                  45

Gly Asp Ser
     50

<210> SEQ ID NO 17
<211> LENGTH: 357
<212> TYPE: PRT
<213> ORGANISM: Homo sapiens

<400> SEQUENCE: 17

Met Ala Thr Thr Val Pro Asp Gly Cys Arg Asn Gly Leu Lys Ser Lys
1               5                   10                  15
```

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
 50                  55                  60

Leu Pro Thr Gln Phe Leu Phe Leu Leu Gly Val Leu Gly Ile Phe Gly
 65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
                100                 105                 110

Leu Ala His Ala Val Ser Leu Thr Lys Leu Val Arg Gly Arg Lys Pro
                115                 120                 125

Leu Ser Leu Leu Val Ile Leu Gly Leu Ala Val Gly Phe Ser Leu Val
130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Ala Tyr Val Leu Phe Leu Met Ala Leu Thr Phe
                180                 185                 190

Leu Met Ser Ser Phe Thr Phe Cys Gly Ser Phe Thr Gly Trp Lys Arg
                195                 200                 205

His Gly Ala His Ile Tyr Leu Thr Met Leu Leu Ser Ile Ala Ile Trp
                210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
                260                 265                 270

Asn Pro Met Asp Tyr Pro Val Glu Asp Ala Phe Cys Lys Pro Gln Leu
                275                 280                 285

Val Lys Lys Ser Tyr Gly Val Glu Asn Arg Ala Tyr Ser Gln Glu Glu
290                 295                 300

Ile Thr Gln Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
                325                 330                 335

Ile Pro Arg Ala His Ala Trp Pro Ser Pro Tyr Lys Asp Tyr Glu Val
                340                 345                 350

Lys Lys Glu Gly Ser
        355

<210> SEQ ID NO 18
<211> LENGTH: 2456
<212> TYPE: DNA
<213> ORGANISM: Artificial Sequence
<220> FEATURE:
<223> OTHER INFORMATION: RAI3 Polymorphic Allele Summary Sequence.
<220> FEATURE:
<221> NAME/KEY: misc_feature
<222> LOCATION: (112)..(112)
<223> OTHER INFORMATION: wherein "n" equals either G or A.
<220> FEATURE:
<221> NAME/KEY: misc_feature
<222> LOCATION: (364)..(364)
<223> OTHER INFORMATION: wherein "n" equals either C or T.
<220> FEATURE:
<221> NAME/KEY: misc_feature
<222> LOCATION: (511)..(511)
<223> OTHER INFORMATION: wherein "n" equals either C or T.
<220> FEATURE:
<221> NAME/KEY: misc_feature
<222> LOCATION: (523)..(523)
<223> OTHER INFORMATION: wherein "n" equals either C or T.
<220> FEATURE:
<221> NAME/KEY: misc_feature
<222> LOCATION: (605)..(605)
<223> OTHER INFORMATION: wherein "n" equals either A or G.
<220> FEATURE:
<221> NAME/KEY: misc_feature
<222> LOCATION: (797)..(797)
<223> OTHER INFORMATION: wherein "n" equals either A or G.
<220> FEATURE:
<221> NAME/KEY: misc_feature
<222> LOCATION: (1111)..(1111)
<223> OTHER INFORMATION: wherein "n" equals either T or C.
<220> FEATURE:
<221> NAME/KEY: misc_feature
<222> LOCATION: (1173)..(1173)
<223> OTHER INFORMATION: wherein "n" equals either A or G.

<400> SEQUENCE: 18

| | | | | | |
|---|---|---|---|---|---|
| ataacagcat | gaagtgccgt | ggaactggaa | taggcgtgtc | ctctccctcg | acctcccc      60 |
| tccttgtccc | tctgctcacc | cctcgctcgt | tccctccctc | cggcgagggc | cnccttata    120 |
| acaactgctc | agagtgcgag | ggcgggatag | ctgtccaagg | tctcccccag | cactgaggag   180 |
| ctcgcctgct | gccctcttgc | gcgcgggaag | cagcaccaag | ttcacggcca | acgccttggc   240 |
| actagggtcc | agaatggcta | caacagtccc | tgatggttgc | cgcaatggcc | tgaaatccaa   300 |
| gtactacaga | ctttgtgata | aggctgaagc | ttggggcatc | gtcctagaaa | cggtggccac   360 |
| agcngggggtt | gtgacctcgg | tggccttcat | gctcactctc | ccgatcctcg | tctgcaaggt   420 |
| gcaggactcc | aacaggcgaa | aaatgctgcc | tactcagttt | ctcttcctcc | tgggtgtgtt   480 |
| gggcatcttt | ggcctcacct | tcgccttcat | natcggactg | gangggagca | cagggcccac   540 |
| acgcttcttc | ctctttggga | tcctcttttc | catctgcttc | tcctgcctgc | tggctcatgc   600 |
| tgtcngtctg | accaagctcg | tccggggggag | gaagcccctt | tccctgttgg | tgattctggg   660 |
| tctggccgtg | ggcttcagcc | tagtccagga | tgttatcgct | attgaatata | ttgtcctgac   720 |
| catgaatagg | accaacgtca | atgtcttttc | tgagctttcc | gctcctcgtc | gcaatgaaga   780 |
| cttttgtcctc | ctgctcncct | acgtcctctt | cttgatggcg | ctgaccttcc | tcatgtcctc   840 |
| cttcaccttc | tgtggttcct | tcacgggctg | gaagagacat | ggggcccaca | tctacctcac   900 |
| gatgctcctc | tccattgcca | tctgggtggc | ctggatcacc | ctgctcatgc | ttcctgactt   960 |
| tgaccgcagg | tgggatgaca | ccatcctcag | ctccgccttg | gctgccaatg | gctgggtgtt  1020 |
| cctgttggct | tatgttagtc | ccgagttttg | gctgctcaca | aagcaacgaa | acccatgga   1080 |
| ttatcctgtt | gaggatgctt | tctgtaaacc | ncaactcgtg | aagaagagct | atggtgtgga  1140 |
| gaacagagcc | tactctcaag | aggaaatcac | tcnaggtttt | gaagacag | gggacacgct  1200 |
| ctatgccccc | tattccacac | attttcagct | gcagaaccag | cctccccaaa | aggaattctc  1260 |
| catcccacgg | gccacgcttt | ggccgagccc | ttacaaagac | tatgaagtaa | agaaagaggg  1320 |
| cagctaactc | tgtcctgaag | agtgggacaa | atgcagccgg | gcggcagatc | tagcgggagc  1380 |
| tcaaagggat | gtgggcgaaa | tcttgagtct | tctgagaaaa | ctgtacaaga | cactacggga  1440 |
| acagtttgcc | tccctcccag | cctcaaccac | aattcttcca | tgctggggct | gatgtgggct  1500 |

-continued

```
agtaagactc cagttcttag aggcgctgta gtatttttt tttttttgtct catcctttgg    1560 atacttcttt taagtgggag tctcaggcaa ctcaagttta gacccttact cttttttgttt   1620 gtttttttgaa acaggatctt gctctgtcac ccaggcttga gtgcagtggt gcgatcacag   1680
cccagtgcag cctcgaccac ctgtgctcaa gcaatcctcc catctccatc tcccaaagtg   1740
ctgggatgac aggcgtgagc cacagctccc agcctaggcc cttaatcttg ctgttatttt   1800
ccatggacta aaggtctggt catctgagct cacgctggct cacacagctc taggggcctg   1860
ctcctctaac tcacagtggg ttttgtgagg ctctgtggcc cagagcagac ctgcatatct   1920
gagcaaaaat agcaaaagcc tctctcagcc cactggcctg aatctacact ggaagccaac   1980
ttgctggcac ccccgctccc caacccttct tgcctgggta ggagaggcta aagatcaccc   2040
taaatttact catctctcta gtgctgcctc acattgggcc tcagcagctc cccagcacca   2100
attcacaggt caccctctc ttcttgcact gtccccaaac ttgctgtcaa ttccgagatc    2160
taatctcccc ctacgctctg ccaggaattc tttcagacct cactagcaca agcccggttg   2220
ctccttgtca ggagaatttg tagatcattc tcacttcaaa ttcctggggc tgatacttct   2280
ctcatcttgc accccaacct ctgtaaatag atttaccgca tttacggctg cattctgtaa   2340
gtgggcatgg tctcctaatg gaggagtgtt cattgtataa taagttattc acctgagtat   2400
gcaataaaga tgtggtggcc actctttcat ggtggtggca gcaaaaaaaa aaaaaa      2456
```

<210> SEQ ID NO 19
<211> LENGTH: 357
<212> TYPE: PRT
<213> ORGANISM: Artificial Sequence
<220> FEATURE:
<223> OTHER INFORMATION: RAI3 Polymorphic Allele Summary Sequence.
<220> FEATURE:
<221> NAME/KEY: MISC_FEATURE
<222> LOCATION: (118)..(118)
<223> OTHER INFORMATION: wherein "Xaa" equals either 'Ser' or 'Gly'.
<220> FEATURE:
<221> NAME/KEY: MISC_FEATURE
<222> LOCATION: (182)..(182)
<223> OTHER INFORMATION: wherein "Xaa" equals either 'Thr' or 'Ala'.
<220> FEATURE:
<221> NAME/KEY: MISC_FEATURE
<222> LOCATION: (307)..(307)
<223> OTHER INFORMATION: wherein "Xaa" equals either 'Gln' or 'Arg'.

<400> SEQUENCE: 19

```
Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
    50                  55                  60

Leu Pro Thr Gln Phe Leu Phe Leu Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
            100                 105                 110

Leu Ala His Ala Val Xaa Leu Thr Lys Leu Val Arg Gly Arg Lys Pro
        115                 120                 125

Leu Ser Leu Leu Val Ile Leu Gly Leu Ala Val Gly Phe Ser Leu Val
```

```
                130             135             140
Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Xaa Tyr Val Leu Phe Leu Met Ala Leu Thr Phe
                180                 185                 190

Leu Met Ser Ser Phe Thr Phe Cys Gly Ser Phe Thr Gly Trp Lys Arg
                195                 200                 205

His Gly Ala His Ile Tyr Leu Thr Met Leu Leu Ser Ile Ala Ile Trp
210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
                260                 265                 270

Asn Pro Met Asp Tyr Pro Val Glu Asp Ala Phe Cys Lys Pro Gln Leu
                275                 280                 285

Val Lys Lys Ser Tyr Gly Val Glu Asn Arg Ala Tyr Ser Gln Glu Glu
                290                 295                 300

Ile Thr Xaa Gly Phe Glu Glu Thr Gly Asp Thr Leu Tyr Ala Pro Tyr
305                 310                 315                 320

Ser Thr His Phe Gln Leu Gln Asn Gln Pro Gln Lys Glu Phe Ser
                325                 330                 335

Ile Pro Arg Ala His Ala Trp Pro Ser Pro Tyr Lys Asp Tyr Glu Val
                340                 345                 350

Lys Lys Glu Gly Ser
                355

<210> SEQ ID NO 20
<211> LENGTH: 357
<212> TYPE: PRT
<213> ORGANISM: Homo sapiens

<400> SEQUENCE: 20

Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
                20                  25                  30

Thr Val Ala Thr Ala Gly Val Val Thr Ser Val Ala Phe Met Leu Thr
                35                  40                  45

Leu Pro Ile Leu Val Cys Lys Val Gln Asp Ser Asn Arg Arg Lys Met
            50                  55                  60

Leu Pro Thr Gln Phe Leu Phe Leu Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
                100                 105                 110

Leu Ala His Ala Val Ser Leu Thr Lys Leu Val Arg Gly Arg Lys Pro
                115                 120                 125

Leu Ser Leu Leu Val Ile Leu Gly Leu Ala Val Gly Phe Ser Leu Val
            130                 135                 140
```

```
Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
            165                 170                 175

Phe Val Leu Leu Leu Thr Tyr Val Leu Phe Leu Met Ala Leu Thr Phe
        180                 185                 190

Leu Met Ser Ser Phe Thr Phe Cys Gly Ser Phe Thr Gly Trp Lys Arg
            195                 200                 205

His Gly Ala His Ile Tyr Leu Thr Met Leu Leu Ser Ile Ala Ile Trp
        210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
            245                 250                 255

Leu Leu Ala Tyr Val Ser Pro Glu Phe Trp Leu Leu Thr Lys Gln Arg
        260                 265                 270

Asn Pro Met Asp Tyr Pro Val Glu Asp Ala Phe Cys Lys Pro Gln Leu
            275                 280                 285

Val Lys Lys Ser Tyr Gly Val Glu Asn Arg Ala Tyr Ser Gln Glu Glu
        290                 295                 300

Ile Thr Gln Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
            325                 330                 335

Ile Pro Arg Ala His Ala Trp Pro Ser Pro Tyr Lys Asp Tyr Glu Val
        340                 345                 350

Lys Lys Glu Gly Ser
        355

<210> SEQ ID NO 21
<211> LENGTH: 357
<212> TYPE: PRT
<213> ORGANISM: Homo sapiens

<400> SEQUENCE: 21

Met Ala Thr Thr Val Pro Asp Gly Cys Arg Asn Gly Leu Lys Ser Lys
1               5                   10                  15

Tyr Tyr Arg Leu Cys Asp Lys Ala Glu Ala Trp Gly Ile Val Leu Glu
            20                  25                  30

Thr Val Ala Thr Ala Gly Val Val Thr Ser Val Ala Phe Met Leu Thr
        35                  40                  45

Leu Pro Ile Leu Val Cys Lys Val Gln Asp Ser Asn Arg Arg Lys Met
    50                  55                  60

Leu Pro Thr Gln Phe Leu Phe Leu Gly Val Leu Gly Ile Phe Gly
65                  70                  75                  80

Leu Thr Phe Ala Phe Ile Ile Gly Leu Asp Gly Ser Thr Gly Pro Thr
            85                  90                  95

Arg Phe Phe Leu Phe Gly Ile Leu Phe Ser Ile Cys Phe Ser Cys Leu
        100                 105                 110

Leu Ala His Ala Val Ser Leu Thr Lys Leu Val Arg Gly Arg Lys Pro
    115                 120                 125

Leu Ser Leu Leu Val Ile Leu Gly Leu Ala Val Gly Phe Ser Leu Val
        130                 135                 140

Gln Asp Val Ile Ala Ile Glu Tyr Ile Val Leu Thr Met Asn Arg Thr
145                 150                 155                 160
```

```
Asn Val Asn Val Phe Ser Glu Leu Ser Ala Pro Arg Arg Asn Glu Asp
            165                 170                 175
Phe Val Leu Leu Leu Thr Tyr Val Leu Phe Leu Met Ala Leu Thr Phe
            180                 185                 190
Leu Met Ser Ser Phe Thr Phe Cys Gly Ser Phe Thr Gly Trp Lys Arg
            195                 200                 205
His Gly Ala His Ile Tyr Leu Thr Met Leu Leu Ser Ile Ala Ile Trp
            210                 215                 220
Val Ala Trp Ile Thr Leu Leu Met Leu Pro Asp Phe Asp Arg Arg Trp
225                 230                 235                 240
Asp Asp Thr Ile Leu Ser Ser Ala Leu Ala Ala Asn Gly Trp Val Phe
            245                 250                 255
Leu Leu Ala Tyr Val Ser Pro Glu Phe Trp Leu Leu Thr Lys Gln Arg
            260                 265                 270
Asn Pro Met Asp Tyr Pro Val Glu Asp Ala Phe Cys Lys Pro Gln Leu
            275                 280                 285
Val Lys Lys Ser Tyr Gly Val Glu Asn Arg Ala Tyr Ser Gln Glu Glu
            290                 295                 300
Ile Thr Gln Gly Phe Glu Glu Thr Gly Asp Thr Leu Tyr Ala Pro Tyr
305                 310                 315                 320
Ser Thr His Phe Gln Leu Gln Asn Gln Pro Gln Lys Glu Phe Ser
            325                 330                 335
Ile Pro Arg Ala His Ala Trp Pro Ser Pro Tyr Lys Asp Tyr Glu Val
            340                 345                 350
Lys Lys Glu Gly Ser
            355

<210> SEQ ID NO 22
<211> LENGTH: 40
<212> TYPE: DNA
<213> ORGANISM: Homo sapiens

<400> SEQUENCE: 22
ctagaaacgg tggccacagc cggggttgtg acctcggtgg                              40

<210> SEQ ID NO 23
<211> LENGTH: 40
<212> TYPE: DNA
<213> ORGANISM: Homo sapiens

<400> SEQUENCE: 23
ctagaaacgg tggccacagc tggggttgtg acctcggtgg                              40

<210> SEQ ID NO 24
<211> LENGTH: 44
<212> TYPE: DNA
<213> ORGANISM: Homo sapiens

<400> SEQUENCE: 24
tgcctgctgg ctcatgctgt cagtctgacc aagctcgtcc gggg                         44

<210> SEQ ID NO 25
<211> LENGTH: 44
<212> TYPE: DNA
<213> ORGANISM: Homo sapiens

<400> SEQUENCE: 25
tgcctgctgg ctcatgctgt cggtctgacc aagctcgtcc gggg                         44
```

<210> SEQ ID NO 26
<211> LENGTH: 50
<212> TYPE: DNA
<213> ORGANISM: Homo sapiens

<400> SEQUENCE: 26
tcctgttgag gatgctttct gtaaacctca actcgtgaag aagagctatg          50

<210> SEQ ID NO 27
<211> LENGTH: 50
<212> TYPE: DNA
<213> ORGANISM: Homo sapiens

<400> SEQUENCE: 27
tcctgttgag gatgctttct gtaaacccca actcgtgaag aagagctatg          50

<210> SEQ ID NO 28
<211> LENGTH: 40
<212> TYPE: DNA
<213> ORGANISM: Homo sapiens

<400> SEQUENCE: 28
tctcaagagg aaatcactca aggttttgaa gagacagggg                     40

<210> SEQ ID NO 29
<211> LENGTH: 40
<212> TYPE: DNA
<213> ORGANISM: Homo sapiens

<400> SEQUENCE: 29
tctcaagagg aaatcactcg aggttttgaa gagacagggg                     40

<210> SEQ ID NO 30
<211> LENGTH: 42
<212> TYPE: DNA
<213> ORGANISM: Homo sapiens

<400> SEQUENCE: 30
gcccacgctt ggccgagccc ttacaaagac tatgaagtaa ag                  42

<210> SEQ ID NO 31
<211> LENGTH: 17
<212> TYPE: DNA
<213> ORGANISM: Homo sapiens

<400> SEQUENCE: 31
gcccacgctt ggccgag                                              17

<210> SEQ ID NO 32
<211> LENGTH: 19
<212> TYPE: DNA
<213> ORGANISM: Homo sapiens

<400> SEQUENCE: 32
ctttacttca tagtctttg                                            19

<210> SEQ ID NO 33
<211> LENGTH: 42
<212> TYPE: DNA
<213> ORGANISM: Artificial Sequence
<220> FEATURE:
<223> OTHER INFORMATION: Degenerate Oligonucleotide.
<220> FEATURE:

```
<221> NAME/KEY: misc_feature
<222> LOCATION: (3)..(39)
<223> OTHER INFORMATION: wherein "n" equals A, C, G, or T.
<220> FEATURE:
<221> NAME/KEY: misc_feature
<222> LOCATION: (6)..(33)
<223> OTHER INFORMATION: wherein "y" equals C, or T.
<220> FEATURE:
<221> NAME/KEY: misc_feature
<222> LOCATION: (27)..(42)
<223> OTHER INFORMATION: wherein "r" equals A, or G.

<400> SEQUENCE: 33
gcncaygcnt ggccntcncc ntayaargay taygargtna ar                         42

<210> SEQ ID NO 34
<211> LENGTH: 17
<212> TYPE: DNA
<213> ORGANISM: Artificial Sequence
<220> FEATURE:
<223> OTHER INFORMATION: Degenerate Oligonucleotide.
<220> FEATURE:
<221> NAME/KEY: misc_feature
<222> LOCATION: (3)..(15)
<223> OTHER INFORMATION: wherein "n" equals A, C, G, or T.
<220> FEATURE:
<221> NAME/KEY: misc_feature
<222> LOCATION: (6)..(6)
<223> OTHER INFORMATION: wherein "y" equals C, or T.

<400> SEQUENCE: 34
gcncaygcnt ggccntc                                                    17

<210> SEQ ID NO 35
<211> LENGTH: 23
<212> TYPE: DNA
<213> ORGANISM: Artificial Sequence
<220> FEATURE:
<223> OTHER INFORMATION: Degenerate Oligonucleotide.
<220> FEATURE:
<221> NAME/KEY: misc_feature
<222> LOCATION: (1)..(16)
<223> OTHER INFORMATION: wherein "y" equals C, or T.
<220> FEATURE:
<221> NAME/KEY: misc_feature
<222> LOCATION: (4)..(22)
<223> OTHER INFORMATION: wherein "n" equals A, C, G, or T.
<220> FEATURE:
<221> NAME/KEY: misc_feature
<222> LOCATION: (10)..(19)
<223> OTHER INFORMATION: wherein "r" equals A, or G.

<400> SEQUENCE: 35
yttnacytcr tartcyttrt ang                                             23

<210> SEQ ID NO 36
<211> LENGTH: 38
<212> TYPE: DNA
<213> ORGANISM: Homo sapiens

<400> SEQUENCE: 36
gcgcggccca attgcatggc tacaacagtc cctgatgg                             38

<210> SEQ ID NO 37
<211> LENGTH: 33
<212> TYPE: DNA
<213> ORGANISM: Homo sapiens

<400> SEQUENCE: 37
gcggccctcg agttagctgc cctctttctt tac                                  33
```

<210> SEQ ID NO 38
<211> LENGTH: 16
<212> TYPE: PRT
<213> ORGANISM: Homo sapiens

<400> SEQUENCE: 38

Met Lys Thr Ile Ile Ala Leu Ser Tyr Ile Phe Cys Leu Val Phe Ala
1               5                   10                  15

<210> SEQ ID NO 39
<211> LENGTH: 11
<212> TYPE: PRT
<213> ORGANISM: Bacteriophage T7

<400> SEQUENCE: 39

Asp Tyr Lys Asp Asp Asp Asp Ala Arg Asn Ser
1               5                   10

<210> SEQ ID NO 40
<211> LENGTH: 27
<212> TYPE: PRT
<213> ORGANISM: Homo sapiens

<400> SEQUENCE: 40

Met Lys Thr Ile Ile Ala Leu Ser Tyr Ile Phe Cys Leu Val Phe Ala
1               5                   10                  15

Asp Tyr Lys Asp Asp Asp Asp Ala Arg Asn Ser
                20                  25

<210> SEQ ID NO 41
<211> LENGTH: 39
<212> TYPE: DNA
<213> ORGANISM: Homo sapiens

<400> SEQUENCE: 41
gcggccagat ctgccaccat ggctacaaca gtccctgat                       39

<210> SEQ ID NO 42
<211> LENGTH: 60
<212> TYPE: DNA
<213> ORGANISM: Homo sapiens

<400> SEQUENCE: 42
gcggccctcg agctacttgt cgtcgtcgtc cttgtagtcc atgctgccct ctttctttac   60

<210> SEQ ID NO 43
<211> LENGTH: 9
<212> TYPE: PRT
<213> ORGANISM: Homo sapiens

<400> SEQUENCE: 43

Met Asp Tyr Lys Asp Asp Asp Asp Lys
1               5

<210> SEQ ID NO 44
<211> LENGTH: 55
<212> TYPE: DNA
<213> ORGANISM: Homo sapiens

<400> SEQUENCE: 44
cgggatccta cttgtcgtcg tcgtccttgt agtcgctgcc ctctttcttt acttc         55

```
<210> SEQ ID NO 45
<211> LENGTH: 21
<212> TYPE: DNA
<213> ORGANISM: Homo sapiens

<400> SEQUENCE: 45
ccacacattt tcagctgcag a                                              21

<210> SEQ ID NO 46
<211> LENGTH: 22
<212> TYPE: DNA
<213> ORGANISM: Homo sapiens

<400> SEQUENCE: 46
gtgggatgga gaattccttt tg                                             22

<210> SEQ ID NO 47
<211> LENGTH: 22
<212> TYPE: DNA
<213> ORGANISM: Homo sapiens

<400> SEQUENCE: 47
attccacaca ttttcagctg ca                                             22

<210> SEQ ID NO 48
<211> LENGTH: 21
<212> TYPE: DNA
<213> ORGANISM: Homo sapiens

<400> SEQUENCE: 48
ggatggagaa ttccttttgg g                                              21

<210> SEQ ID NO 49
<211> LENGTH: 25
<212> TYPE: PRT
<213> ORGANISM: Homo sapiens

<400> SEQUENCE: 49

Cys Leu Thr Met Asn Arg Thr Asn Val Asn Val Phe Ser Glu Leu Ser
1               5                   10                  15

Ala Pro Arg Arg Asn Glu Asp Phe Val
            20                  25

<210> SEQ ID NO 50
<211> LENGTH: 18
<212> TYPE: PRT
<213> ORGANISM: Homo sapiens

<400> SEQUENCE: 50

Cys Met Leu Pro Asp Phe Asp Arg Arg Trp Asp Asp Thr Thr Leu Ser
1               5                   10                  15

Ser Ala

<210> SEQ ID NO 51
<211> LENGTH: 21
<212> TYPE: PRT
<213> ORGANISM: Homo sapiens

<400> SEQUENCE: 51

Cys Lys Pro Gln Leu Val Lys Lys Ser Tyr Gly Val Asn Glu Arg Ala
1               5                   10                  15

Tyr Ser Gln Glu Glu
            20
```

<210> SEQ ID NO 52
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 52
uuccaguucc acggcacuuc augcuu                                              26

<210> SEQ ID NO 53
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 53
guccaguccg augaugaagg cgaagu                                              26

<210> SEQ ID NO 54
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 54
caguuguuau aaaggcggcc cucgcu                                              26

<210> SEQ ID NO 55
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 55
uuguagccau ucuggacccu agugcu                                              26

<210> SEQ ID NO 56
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 56
ucuuccagcc cgugaaggaa ccacau                                              26

<210> SEQ ID NO 57
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 57
accuugaccu uauccgcaca ggagau                                              26

<210> SEQ ID NO 58
<211> LENGTH: 26
<212> TYPE: DNA
<213> ORGANISM: Artificial Sequence
<220> FEATURE:

<223> OTHER INFORMATION: Synthesized Antisense Oligonucleotide.

<400> SEQUENCE: 58
gagccucccc gggaauauug uugacu                                       26

<210> SEQ ID NO 59
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 59
gcugauccca ggucuuaccg auguuu                                       26

<210> SEQ ID NO 60
<211> LENGTH: 25
<212> TYPE: DNA
<213> ORGANISM: Artificial Sequence
<220> FEATURE:
<223> OTHER INFORMATION: Synthesized Antisense Oligonucleotide.

<400> SEQUENCE: 60
acaccaagga agugcccgac cuucu                                        25

<210> SEQ ID NO 61
<211> LENGTH: 26
<212> TYPE: DNA
<213> ORGANISM: Artificial Sequence
<220> FEATURE:
<223> OTHER INFORMATION: Synthesized Antisense Oligonucleotide.

<400> SEQUENCE: 61
gacugaaacu ggcguccacc cuacuu                                       26

<210> SEQ ID NO 62
<211> LENGTH: 24
<212> TYPE: DNA
<213> ORGANISM: Homo sapiens

<400> SEQUENCE: 62
gaggatgagg agagctatga caca                                         24

<210> SEQ ID NO 63
<211> LENGTH: 22
<212> TYPE: DNA
<213> ORGANISM: Homo sapiens

<400> SEQUENCE: 63
ccctttgcac tcataacgtc ag                                           22

<210> SEQ ID NO 64
<211> LENGTH: 29
<212> TYPE: DNA
<213> ORGANISM: Homo sapiens

<400> SEQUENCE: 64
aaacacacag tcatcatagg gcagctcgt                                    29

<210> SEQ ID NO 65
<211> LENGTH: 41
<212> TYPE: DNA
<213> ORGANISM: Homo sapiens
<220> FEATURE:
<221> NAME/KEY: misc_feature

```
<222> LOCATION: (21)..(21)
<223> OTHER INFORMATION: wherein "n" equals either C, or T.

<400> SEQUENCE: 65
ctgagcagtt gttataaagg nggccctcgc cggagggagg g                          41

<210> SEQ ID NO 66
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: wherein "n" equals either T, or C.

<400> SEQUENCE: 66
gccccagcgc tctgggctcc nggcgcctca cttaccctag t                          41

<210> SEQ ID NO 67
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: wherein "n" equals either G, or A.

<400> SEQUENCE: 67
gccaccgagg tcacaacccc ngctgtggcc accgtttcta g                          41

<210> SEQ ID NO 68
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: wherein "n" equals either G, or A.

<400> SEQUENCE: 68
gtgctcccgt ccagtccgat natgaaggcg aaggtgaggc c                          41

<210> SEQ ID NO 69
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: wherein "n" equals either G, or A.

<400> SEQUENCE: 69
cgtgtgggcc ctgtgctccc ntccagtccg atgatgaagg c                          41

<210> SEQ ID NO 70
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: wherein "n" equals either T, or C.

<400> SEQUENCE: 70
catcaagaag aggacgtagg ngagcaggag gacaaagtct t                          41

<210> SEQ ID NO 71
```

```
<211> LENGTH: 39
<212> TYPE: DNA
<213> ORGANISM: Homo sapiens

<400> SEQUENCE: 71
tgtaaaacga cggccagtgt cagacggttt ttgggtcat                              39

<210> SEQ ID NO 72
<211> LENGTH: 39
<212> TYPE: DNA
<213> ORGANISM: Homo sapiens

<400> SEQUENCE: 72
tgtaaaacga cggccagtgt cagacggttt ttgggtcat                              39

<210> SEQ ID NO 73
<211> LENGTH: 39
<212> TYPE: DNA
<213> ORGANISM: Homo sapiens

<400> SEQUENCE: 73
tgtaaaacga cggccagtaa taccttctcc ccactccaa                              39

<210> SEQ ID NO 74
<211> LENGTH: 39
<212> TYPE: DNA
<213> ORGANISM: Homo sapiens

<400> SEQUENCE: 74
tgtaaaacga cggccagtaa taccttctcc ccactccaa                              39

<210> SEQ ID NO 75
<211> LENGTH: 39
<212> TYPE: DNA
<213> ORGANISM: Homo sapiens

<400> SEQUENCE: 75
tgtaaaacga cggccagtaa taccttctcc ccactccaa                              39

<210> SEQ ID NO 76
<211> LENGTH: 39
<212> TYPE: DNA
<213> ORGANISM: Homo sapiens

<400> SEQUENCE: 76
tgtaaaacga cggccagtcc tttccctgtt ggtgattct                              39

<210> SEQ ID NO 77
<211> LENGTH: 38
<212> TYPE: DNA
<213> ORGANISM: Homo sapiens

<400> SEQUENCE: 77
caggaaacag ctatgacccg ctctccccag acgattta                               38

<210> SEQ ID NO 78
<211> LENGTH: 38
<212> TYPE: DNA
<213> ORGANISM: Homo sapiens

<400> SEQUENCE: 78
caggaaacag ctatgacccg ctctccccag acgattta                               38
```

```
<210> SEQ ID NO 79
<211> LENGTH: 39
<212> TYPE: DNA
<213> ORGANISM: Homo sapiens

<400> SEQUENCE: 79
caggaaacag ctatgaccag atggaaaaga ggatcccaa                          39

<210> SEQ ID NO 80
<211> LENGTH: 39
<212> TYPE: DNA
<213> ORGANISM: Homo sapiens

<400> SEQUENCE: 80
caggaaacag ctatgaccag atggaaaaga ggatcccaa                          39

<210> SEQ ID NO 81
<211> LENGTH: 39
<212> TYPE: DNA
<213> ORGANISM: Homo sapiens

<400> SEQUENCE: 81
caggaaacag ctatgaccag atggaaaaga ggatcccaa                          39

<210> SEQ ID NO 82
<211> LENGTH: 39
<212> TYPE: DNA
<213> ORGANISM: Homo sapiens

<400> SEQUENCE: 82
caggaaacag ctatgaccgc caaaactcgg gactaacat                          39

<210> SEQ ID NO 83
<211> LENGTH: 18
<212> TYPE: DNA
<213> ORGANISM: Homo sapiens

<400> SEQUENCE: 83
tgtaaaacga cggccagt                                                 18

<210> SEQ ID NO 84
<211> LENGTH: 18
<212> TYPE: DNA
<213> ORGANISM: Homo sapiens

<400> SEQUENCE: 84
caggaaacag ctatgacc                                                 18

<210> SEQ ID NO 85
<211> LENGTH: 22
<212> TYPE: DNA
<213> ORGANISM: Homo sapiens

<400> SEQUENCE: 85
gcttcttcct ctttgggatc ct                                            22

<210> SEQ ID NO 86
<211> LENGTH: 23
<212> TYPE: DNA
<213> ORGANISM: Homo sapiens

<400> SEQUENCE: 86
cttggtcaga ctgacagcat gag                                           23
```

<210> SEQ ID NO 87
<211> LENGTH: 25
<212> TYPE: DNA
<213> ORGANISM: Homo sapiens

<400> SEQUENCE: 87
ttccatctgc ttctcctgcc tgctg    25

<210> SEQ ID NO 88
<211> LENGTH: 59
<212> TYPE: PRT
<213> ORGANISM: Homo sapiens

<400> SEQUENCE: 88

Asn Gln Gln Thr Ala Pro Val Arg Tyr Phe Leu Phe Gly Val Leu Phe
1               5                   10                  15

Ala Leu Cys Phe Ser Cys Leu Leu Ala His Ala Ser Asn Leu Val Lys
            20                  25                  30

Leu Val Arg Gly Cys Val Ser Phe Ser Trp Thr Thr Ile Leu Cys Ile
        35                  40                  45

Ala Ile Gly Cys Ser Leu Leu Gln Ile Ile Ile
    50                  55

<210> SEQ ID NO 89
<211> LENGTH: 59
<212> TYPE: PRT
<213> ORGANISM: Mus musculus

<400> SEQUENCE: 89

Asn His Gln Thr Ala Pro Val Arg Tyr Phe Leu Phe Gly Val Leu Phe
1               5                   10                  15

Ala Ile Cys Phe Ser Cys Leu Leu Ala His Ala Ser Asn Leu Val Lys
            20                  25                  30

Leu Val Arg Gly Arg Val Ser Phe Cys Trp Thr Thr Ile Leu Phe Ile
        35                  40                  45

Ala Ile Gly Val Ser Leu Leu Gln Thr Ile Ile
    50                  55

<210> SEQ ID NO 90
<211> LENGTH: 46
<212> TYPE: PRT
<213> ORGANISM: Homo sapiens

<400> SEQUENCE: 90

Arg Asp Ser Asp Gly Ala Glu Glu Asp Val Ala Leu Thr Ser Tyr Gly
1               5                   10                  15

Thr Pro Ile Gln Pro Gln Thr Val Asp Pro Thr Gln Glu Cys Phe Ile
            20                  25                  30

Pro Gln Ala Lys Leu Ser Pro Gln Gln Asp Ala Gly Gly Val
        35                  40                  45

<210> SEQ ID NO 91
<211> LENGTH: 15
<212> TYPE: PRT
<213> ORGANISM: Artificial Sequence
<220> FEATURE:
<223> OTHER INFORMATION: Synthesized Polypeptide.

<400> SEQUENCE: 91

Asp Gly Ser Thr Gly Pro Thr Arg Phe Phe Leu Phe Gly Ile Leu
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Synthesized Polypeptide.

<400> SEQUENCE: 92

Thr Lys Gln Arg Asn Pro Met Asp Tyr Pro Val Glu Asp Ala Phe Cys
1               5                   10                  15

<210> SEQ ID NO 93
<211> LENGTH: 21
<212> TYPE: DNA
<213> ORGANISM: Homo sapiens

<400> SEQUENCE: 93
aaggtgcagg actccaacag g                                         21

<210> SEQ ID NO 94
<211> LENGTH: 21
<212> TYPE: DNA
<213> ORGANISM: Artificial Sequence
<220> FEATURE:
<223> OTHER INFORMATION: Synthesized Oligonucleotide.

<400> SEQUENCE: 94
ggugcaggac uccaacaggt t                                         21

<210> SEQ ID NO 95
<211> LENGTH: 21
<212> TYPE: DNA
<213> ORGANISM: Artificial Sequence
<220> FEATURE:
<223> OTHER INFORMATION: Synthesized Oligonucleotide.

<400> SEQUENCE: 95
ccuguuggag uccugcacct t                                         21

<210> SEQ ID NO 96
<211> LENGTH: 23
<212> TYPE: DNA
<213> ORGANISM: Homo sapiens

<400> SEQUENCE: 96
aattctccga acgtgtcacg ttt                                       23

<210> SEQ ID NO 97
<211> LENGTH: 23
<212> TYPE: DNA
<213> ORGANISM: Artificial Sequence
<220> FEATURE:
<223> OTHER INFORMATION: Synthesized Oligonucleotide.

<400> SEQUENCE: 97
uucuccgaac gugucacguu utt                                       23

<210> SEQ ID NO 98
<211> LENGTH: 21
<212> TYPE: DNA
<213> ORGANISM: Artificial Sequence
<220> FEATURE:
<223> OTHER INFORMATION: Synthesized Oligonucleotide.

-continued

```
<400> SEQUENCE: 98
aaacgugaca cguucggagt t                                              21
```

What is claimed is:

1. A method of diagnosing the presence of a stomach tumor or predisposition to a stomach tumor in a sample comprising:
   a) determining the expression level of RNA encoding a polypeptide consisting of the sequence of amino acids 1 to 357 of SEQ ID NO:3 in a normal stomach tissue sample and in a test stomach tissue sample by measuring RNA of said polypeptide; and
   b) comparing said expression level of said RNA from said test stomach tissue sample with said expression level of said RNA from said normal stomach test sample; wherein an elevated expression level of said RNA in said test stomach tissue sample relative to the expression level of said RNA in said normal stomach tissue sample is indicative of the presence of a stomach tumor or a predisposition to a stomach tumor.

2. The method according to claim 1, wherein said RNA measurement comprises specific hybridization between said RNA to the complete complementary sequence of a member of the group consisting of:
   a) an isolated nucleic acid consisting of a polynucleotide provided as SEQ ID NO:2;
   b) an isolated nucleic acid consisting of nucleotides 251 to 1324 of SEQ ID NQ:2;
   c) an isolated nucleic acid consisting of nucleotides 254 to 1324 of SEQ ID NO:2;
   d) an isolated nucleic acid consisting of nucleotides 521 to 565 of SEQ ID NO:2;
   e) an isolated nucleic acid consisting of nucleotides 1055 to 1105 of SEQ ID NO:2;
   f) an isolated nucleic acid consisting of nucleotides 1271 to 1312 of SEQ ID NO:2;
   g) an isolated nucleic acid consisting of nucleotides 716 to 787 of SEQ ID NO:2;
   h) an isolated nucleic acid consisting of nucleotides 947 to 997 of SEQ ID NO:2;
   i) an isolated nucleic acid consisting of nucleotides 1106 to 1165 of SEQ ID NO:2;
   j) an isolated nucleic acid consisting of the polynucleotide sequence provided as SEQ ID NO:30;
   k) an isolated nucleic acid consisting of the polynucleotide sequence provided as SEQ ID NO:31;
   l) an isolated nucleic acid consisting of the polynucleotide sequence provided as SEQ ID NO:32; and
   m) an isolated nucleic acid consisting of the polynucleotide sequence provided as SEQ ID NO:33,
   wherein said hybridization is performed under conditions at least as stringent as hybridization in 6× sodium chloride/sodium citrate (SSC) at about 45° C. followed by one or more washes in 0.2×SSC/0.1% SDS at about 50-65° C.

* * * * *

UNITED STATES PATENT AND TRADEMARK OFFICE
CERTIFICATE OF CORRECTION

PATENT NO. : 7,517,652 B2
APPLICATION NO. : 11/809905
DATED : April 14, 2009
INVENTOR(S) : Gena S. Whitney et al.

Page 1 of 1

It is certified that error appears in the above-identified patent and that said Letters Patent is hereby corrected as shown below:

On the title page, item [56]:
Column 2 (Other Publications)

Line 13, "RA13" should read -- RAI3 --

Column 225

Line 33, "NQ:2;" should read -- NO:2; --

Signed and Sealed this

Eighth Day of September, 2009

David J. Kappos
*Director of the United States Patent and Trademark Office*